United States Patent
McSwiggen et al.

(10) Patent No.: US 7,662,952 B2
(45) Date of Patent: Feb. 16, 2010

(54) RNA INTERFERENCE MEDIATED INHIBITION OF GRB2 ASSOCIATED BINDING PROTEIN (GAB2) GENE EXPRESSION USING SHORT INTERFERING NUCLEIC ACID (SINA)

(75) Inventors: James McSwiggen, Boulder, CO (US); Leonid Beigelman, Brisbane, CA (US)

(73) Assignee: Sirna Therapeutics, Inc., San Francisco, CA (US)

(*) Notice: Subject to any disclaimer, the term of this patent is extended or adjusted under 35 U.S.C. 154(b) by 0 days.

(21) Appl. No.: 12/203,029

(22) Filed: Sep. 2, 2008

(65) Prior Publication Data
US 2009/0093435 A1    Apr. 9, 2009

Related U.S. Application Data

(63) Continuation of application No. 10/923,380, filed on Aug. 20, 2004, now abandoned, which is a continua- (Continued)

(60) Provisional application No. 60/358,580, filed on Feb. 20, 2002, provisional application No. 60/363,124, filed on Mar. 11, 2002, provisional application No. 60/386,782, filed on Jun. 6, 2002, provisional application No. 60/406,784, filed on Aug. 29, 2002, provisional application No. 60/408,378, filed on Sep. 5, 2002, provisional application No. 60/409,293, filed on Sep. 9, 2002, provisional application No. 60/440,129, filed on Jan. 15, 2003.

(51) Int. Cl.
*C07H 21/04* (2006.01)
(52) U.S. Cl. ............... 536/24.5; 536/24.31; 536/24.1; 435/6; 435/325; 435/375; 514/44
(58) Field of Classification Search .............. None
See application file for complete search history.

(56) References Cited

U.S. PATENT DOCUMENTS 5,814,620 A    9/1998 Robinson et al.

(Continued)

FOREIGN PATENT DOCUMENTS

CA    2359180 A1    3/2000

(Continued)

OTHER PUBLICATIONS

Lynch et al. PKB-mediated negative feedback tightly regulates mitogenic signalling via Gab2. EMBO Journal 2002, vol. 21 Nos. 1 &2: 72-82.*

(Continued)

*Primary Examiner*—Kimberly Chong
(74) *Attorney, Agent, or Firm*—Elaine C. Stracker

(57) ABSTRACT

This invention relates to compounds, compositions, and methods useful for modulating GRB2 associated binding protein (GAB2) gene expression using short interfering nucleic acid (siNA) molecules. This invention also relates to compounds, compositions, and methods useful for modulating the expression and activity of other genes involved in pathways of GRB2 associated binding protein (GAB2) gene expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of GAB2 genes. The small nucleic acid molecules are useful in the treatment of cancer, malignant blood disease (leukemia), inflammatory diseases or conditions, allergic diseases or conditions, or proliferative diseases or conditions.

19 Claims, 25 Drawing Sheets

Related U.S. Application Data

(63) tion-in-part of application No. PCT/US03/04909, filed on Feb. 18, 2003, and a continuation-in-part of application No. PCT/US2004/016390, filed on May 24, 2004, which is a continuation-in-part of application No. 10/826,966, filed on Apr. 16, 2004, now abandoned, which is a continuation-in-part of application No. 10/757,803, filed on Jan. 14, 2004, which is a continuation-in-part of application No. 10/720,448, filed on Nov. 24, 2003, which is a continuation-in-part of application No. 10/693,059, filed on Oct. 23, 2003, which is a continuation-in-part of application No. 10/444,853, filed on May 23, 2003, which is a continuation-in-part of application No. PCT/US03/05346, filed on Feb. 20, 2003, and a continuation-in-part of application No. PCT/US03/05028, filed on Feb. 20, 2003.

(56) References Cited

U.S. PATENT DOCUMENTS

| | | | |
|---|---|---|---|
| 5,998,203 A * | 12/1999 | Matulic-Adamic et al. | 435/325 |
| 5,998,206 A | 12/1999 | Cowsert | |
| 6,506,559 B1 | 1/2003 | Fire et al. | |
| 2002/0151693 A1 | 10/2002 | Breaker et al. | |
| 2003/0083294 A1* | 5/2003 | Sullenger et al. | 514/44 |
| 2004/0259247 A1* | 12/2004 | Tuschl et al. | 435/375 |
| 2005/0020521 A1* | 1/2005 | Rana | 514/44 |
| 2005/0080246 A1 | 4/2005 | Allerson et al. | |
| 2005/0246794 A1 | 11/2005 | Khvorova et al. | |

FOREIGN PATENT DOCUMENTS

| | | |
|---|---|---|
| WO | WO-90/14090 A1 | 11/1990 |
| WO | WO-94/01550 A1 | 1/1994 |
| WO | WO-99/32619 A1 | 7/1999 |
| WO | WO-99/49029 A1 | 9/1999 |
| WO | WO-00/44895 A1 | 8/2000 |
| WO | WO-00/44914 A1 | 8/2000 |
| WO | WO-01/36646 A1 | 5/2001 |
| WO | WO-01/96584 A2 | 12/2001 |
| WO | WO-01/96584 A3 | 12/2001 |
| WO | WO 02/22636 A1 | 3/2002 |
| WO | WO-02/44321 A2 | 6/2002 |
| WO | WO-02/44321 A3 | 6/2002 |
| WO | WO-03/064626 A2 | 8/2003 |
| WO | WO-03/064626 A3 | 8/2003 |

OTHER PUBLICATIONS

Caplen NJ. RNAi as a Gene Therapy Approach. Expert Opinon. Biol. Thera. (2003) vol. 3(4) 575-586. Ashley Publications Ltd.*
Parrish et al. Functional Anatomy of a dsRNA trigger: differential requirements for the two trigger strands in RNA interference. Molecular Cell, 2000, vol. 6: 1077-1087.*
Braasch et al. Novel Antisense and Peptide Nucleic Acid Strategies for Controlling Gene Expression. Biochemistry 2002, Vo. 41(14): 4503-4510.*
Pieken et al. Kinetic Characterization of Ribonuclease-Resistant 2'-Modified Hammerhead Ribozymes. Science, 1991, vol. 253: pp. 314-317.*
Anderson et al. "Bispecific Short Hairpin siRNA Constructs Targeted to CD4, CXCR4, and CCR5 Confer HIV-1 Resistance," *Oligonucleotides* 13(5):303-312 (2003).
Bass "The Short Answer," Nature 411:428-429 (2001).
Caplen et al. "RNAi as a Gene Therapy Approach," *Expert Opinion. Biol. Thera*. 3(4):575-586 (2003), Ashley Publications Ltd.
Elbashir et al. "Analysis of Gene Function in Somatic Mammalian Cells Using Small Interfering RNAs," *Methods* 26(2):199-213 (2002).
Elbashir et al. "Duplexes of 21-Nucleotide RNAs Mediate RNA Interference in Cultured Mammalian Cells," *Nature* 411(6836):494-498 (2001).
Elbashir et al. "Functional Anatomy of siRNAs for Mediating Efficient RNAi in Drosophila melanogaster Embryo Lysate," *EMBO J.* 20(23):6877-6888 (2001).
Elbashir et al. "RNA Interference is Mediated by 21- and 22-Nucleotide RNAs," *Genes Dev*. 15(2):188-200 (2001).
Fire et al. "Potent and Specific Genetic Interference by Double-Stranded RNA in *Caenorhabditis elegans*," Nature 391:806-811 (1998).
Futami et al. "Induction of Apoptosis in HeLa Cells with siRNA Expression Vector Targeted Against Bcl-2," *Nucleic Acids Research Supplement* 2:251-252 (2002).
Hammond et al. "Post-Transcriptional Gene Silencing by Double-Stranded RNA," *Nature Reviews* 2:110-119 (2001).
International Search Report mailed on Mar. 18, 2005 for PCT/US03/04909, 2 pages.
International Search Report mailed on Mar. 31, 2005 for PCT/US04/16390, 2 pages.
International Search Report mailed on Oct. 17, 2003 for PCT/US03/05028, 2 pages.
International Search Report mailed on Oct. 17, 2003 for PCT/US03/05346, 1 page.
Jiang "Grb2 Regulates Internalization of EGF Receptors through Clathrin-coated Pits," Mol. Biol. Of The Cell. 14:858-870 (2003).
Leirdal et al. "Gene Silencing in Mammalian Cells by Preformed Small RNA Duplexes," *Biochemical and Biophysical Research Communications* 295:744-748 (2002).
Lin et al. "A Novel mRNA-cDNA Interference Phenomenon for Silencing Bcl-2 Expression in Human LNCaP Cells," *Biochemical and Biophysical Research Communications* 281:639-644 (2001).
Lynch et al. "PKB-Mediated Negative Feedback Tightly Regulates Mitogenic Signaling via Gab2," *EMBO Journal* 21:72-82 (2002).
Nishida "Gab-Family Adapter Proteins Act Downstream of Cytokine and Growth Factor Receptors and T- and B-Cell Antigen Receptors," Blood 93(6):1809-1816 (1999).
Olie et al. "Analysis of Ribosyl-Modified, Mixed Backbone Analogs of bcl-2/bcl-xL Antisense Oligonucleotide," *Biochimica et Biophysica Acta* 1576:101-109 (2002).
Parrish "Functional Anatomy of a dsRNA Trigger: Diferential Requirement for the Two Trigger Strands in RNA Interference," Mol. Cell. 6:1077-1087 (2000).
Tari "Growth Inhibition of Breast Cancer Cells by Grb2 Downregulation is Correlated with Inactivation of Mitogen-Activated Protein Kinase in EGFR, but Not in ErbB2 cells," Oncogene 18:1325-1332 (1999).
Tuschl et al. "Small Interfering RNAs: A Revolutionary Tool for the Analysis of Gene Function and Gene Therapy," *Molecular Interventions* 295(3):158-167 (2002).
Tuschl et al. "Targeted mRNA Degradation by Double-Stranded RNA In Vitro," *Genes and Development* 13(24):3191-3197 (1999).
Vickers et al. "Efficient Reduction of Target RNAs by Small Interfering RNa and RNase H-dependent Antisense Agents," J. Biol. Chem. 278(9):7108-7118 (2003).
Office Action mailed on Oct. 20, 2006 for U.S. Appl. No. 10/923,380, 20 pages.
Office Action mailed on Jul. 3, 2007 for U.S. Appl. No. 10/923,380, 22 pages.
Office Action mailed on Feb. 4, 2008 for U.S. Appl. No. 10/444,853, 37 pages.
Office Action mailed on Jun. 26, 2008 for U.S. Appl. No. 10/923,380, 21 pages.
Office Action mailed on Jul. 1, 2008 for U.S. Appl. No. 11/499,520, 13 pages.
Office Action mailed on Jul. 2, 2008 for U.S. Appl. No. 10/757,803, 26 pages.
Office Action mailed on Oct. 8, 2008 for U.S. Appl. No. 11/499,529, 34 pages.

Office Action mailed on Nov. 14, 2008 for U.S. Appl. No. 11/502,875, 14 pages.
Office Action mailed on Jan. 26, 2009 for U.S. Appl. No. 11/676,124, 15 pages.
Office Action mailed on Feb. 3, 2009 for U.S. Appl. No. 10/693,059, 7 pages.
Office Action mailed on Apr. 8, 2009 for U.S. Appl. No. 11/502,876, 31 pages.
Office Action mailed on Apr. 16, 2009 for U.S. Appl. No. 12/105,010, 24 pages.

* cited by examiner

Figure 1
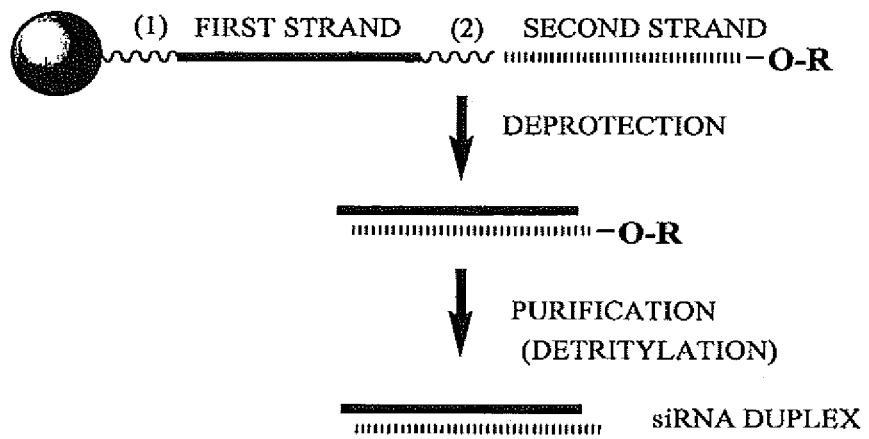
 = SOLID SUPPORT
R = TERMINAL PROTECTING GROUP
FOR EXAMPLE:
DIMETHOXYTRITYL (DMT)
(1) 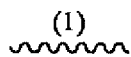 = CLEAVABLE LINKER
(FOR EXAMPLE: NUCLEOTIDE SUCCINATE OR
INVERTED DEOXYABASIC SUCCINATE)
(2) 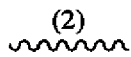 = CLEAVABLE LINKER
(FOR EXAMPLE: NUCLEOTIDE SUCCINATE OR
INVERTED DEOXYABASIC SUCCINATE)
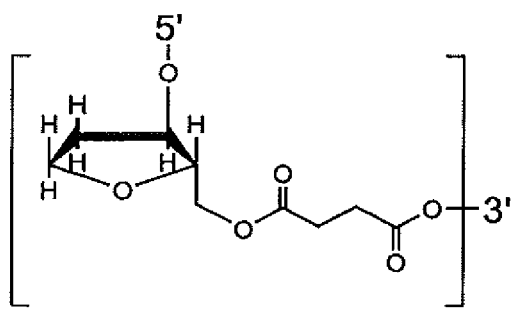
INVERTED DEOXYABASIC SUCCINATE LINKAGE
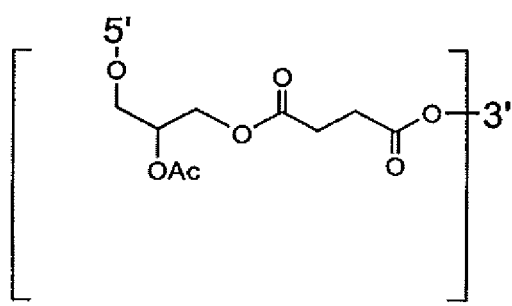
GLYCERYL SUCCINATE LINKAGE Figure 9: Target site Selection using siRNA

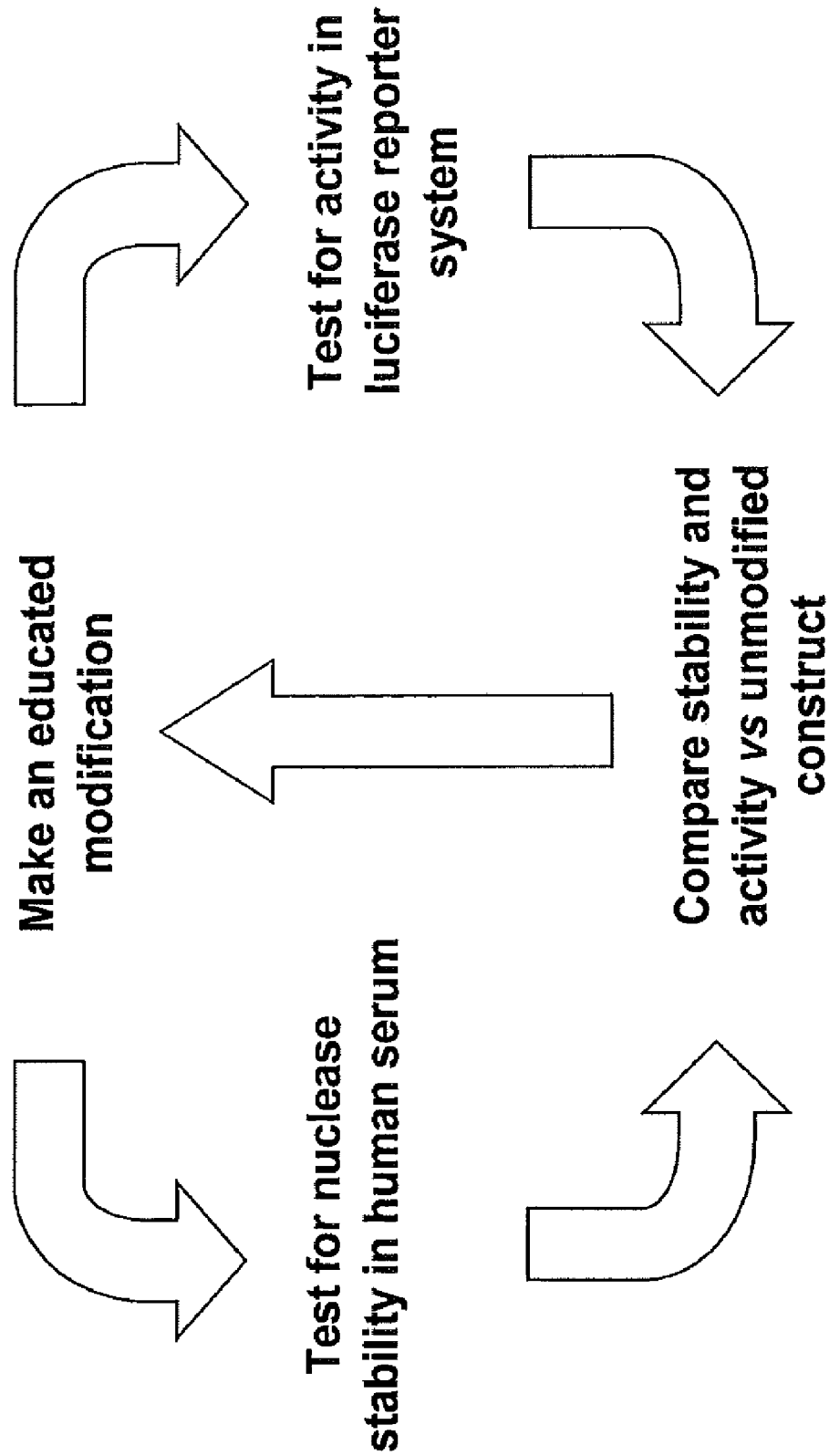
Figure 11: Modification Strategy

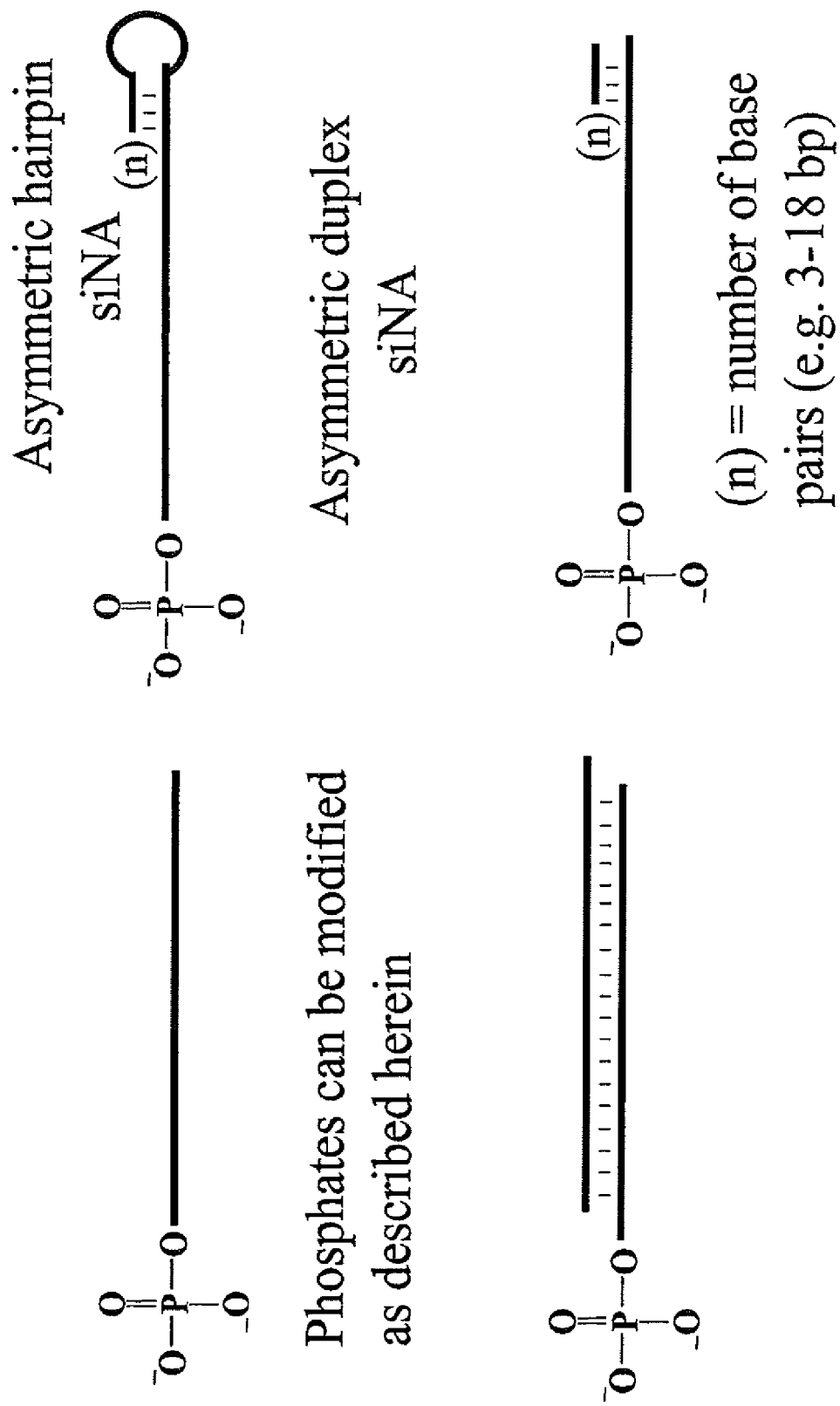

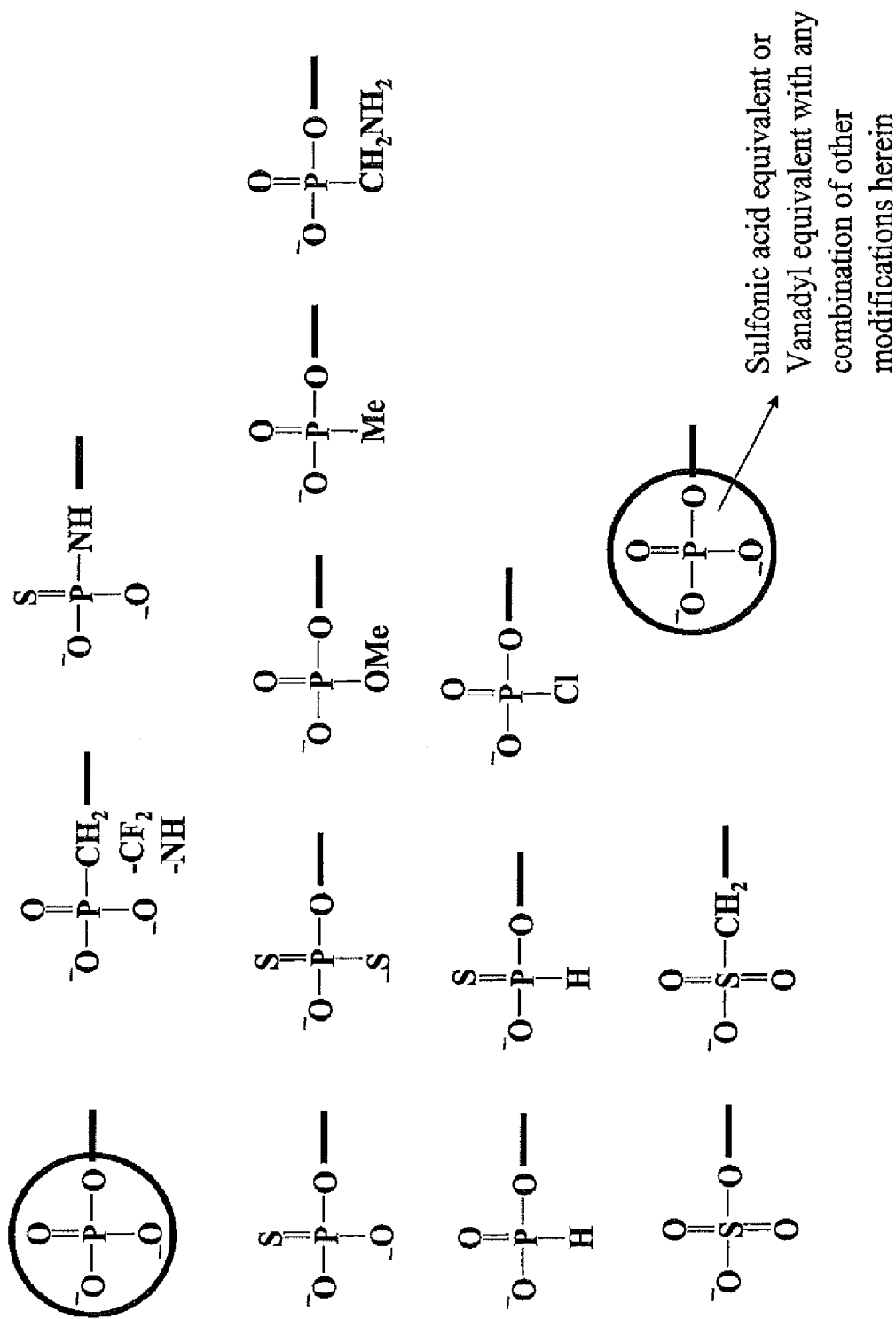
Figure 13: 5'-phosphate modifications

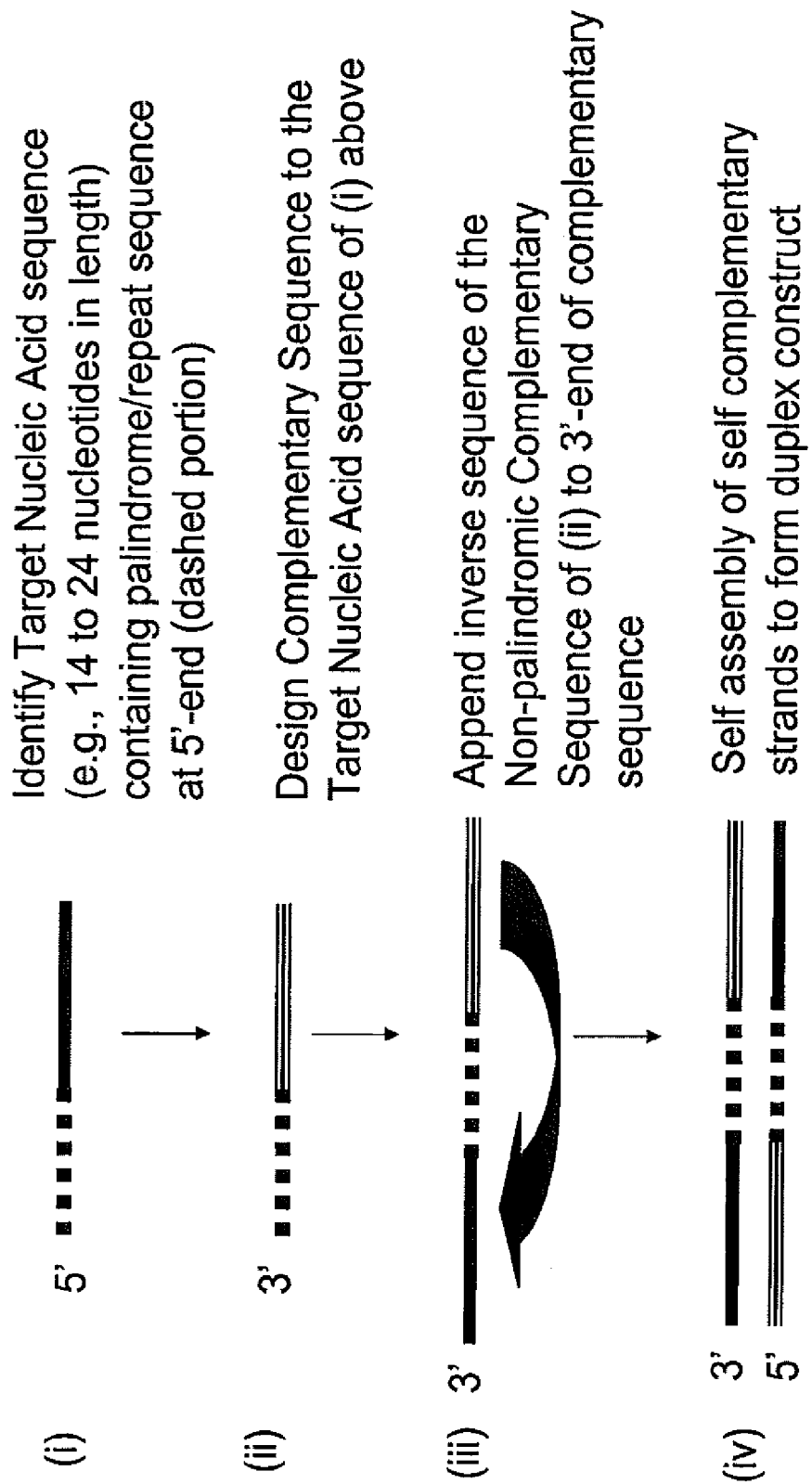
Figure 14A: Duplex forming oligonucleotide constructs that utilize Palindrome or repeat sequences

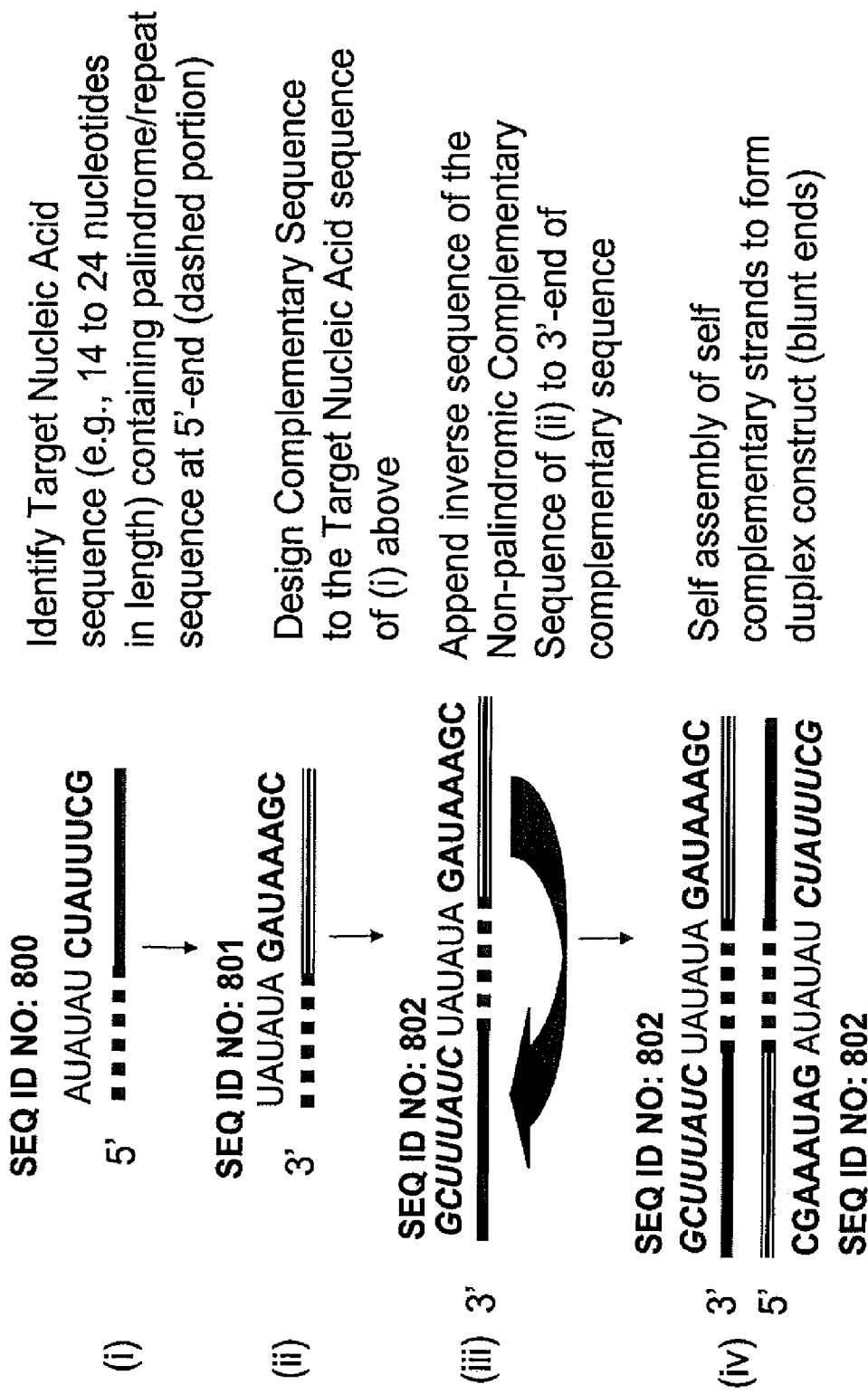
Figure 14B: Example of a duplex forming oligonucleotide sequence that utilizes a palindrome or repeat sequence

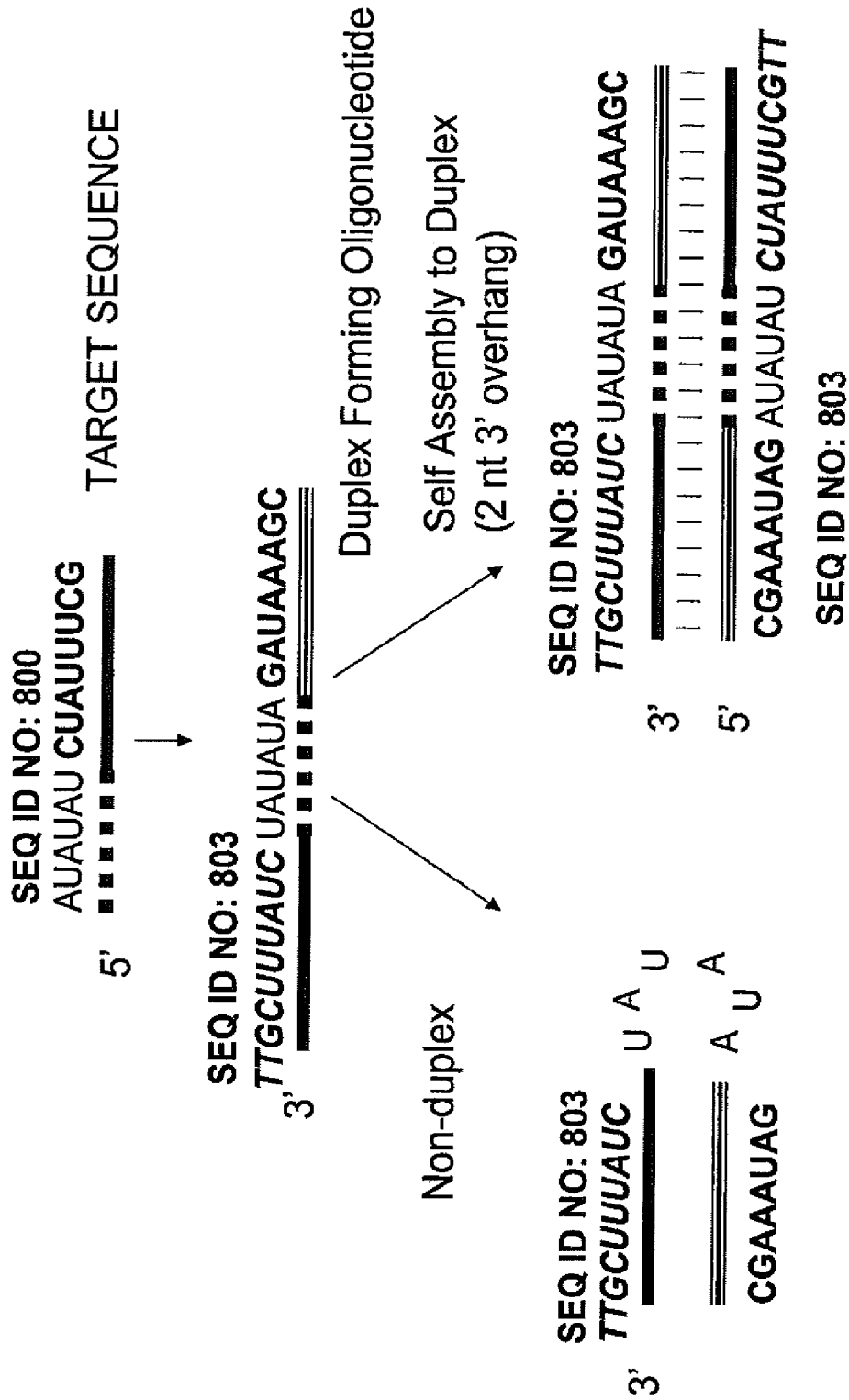
Figure 14C: Example of a duplex forming oligonucleotide sequence that utilizes a palindrome or repeat sequence, self assembly

Figure 14D: Example of a duplex forming oligonucleotide sequence that utilizes a palindrome or repeat sequence, self assembly and inhibition of Target Sequence Expression

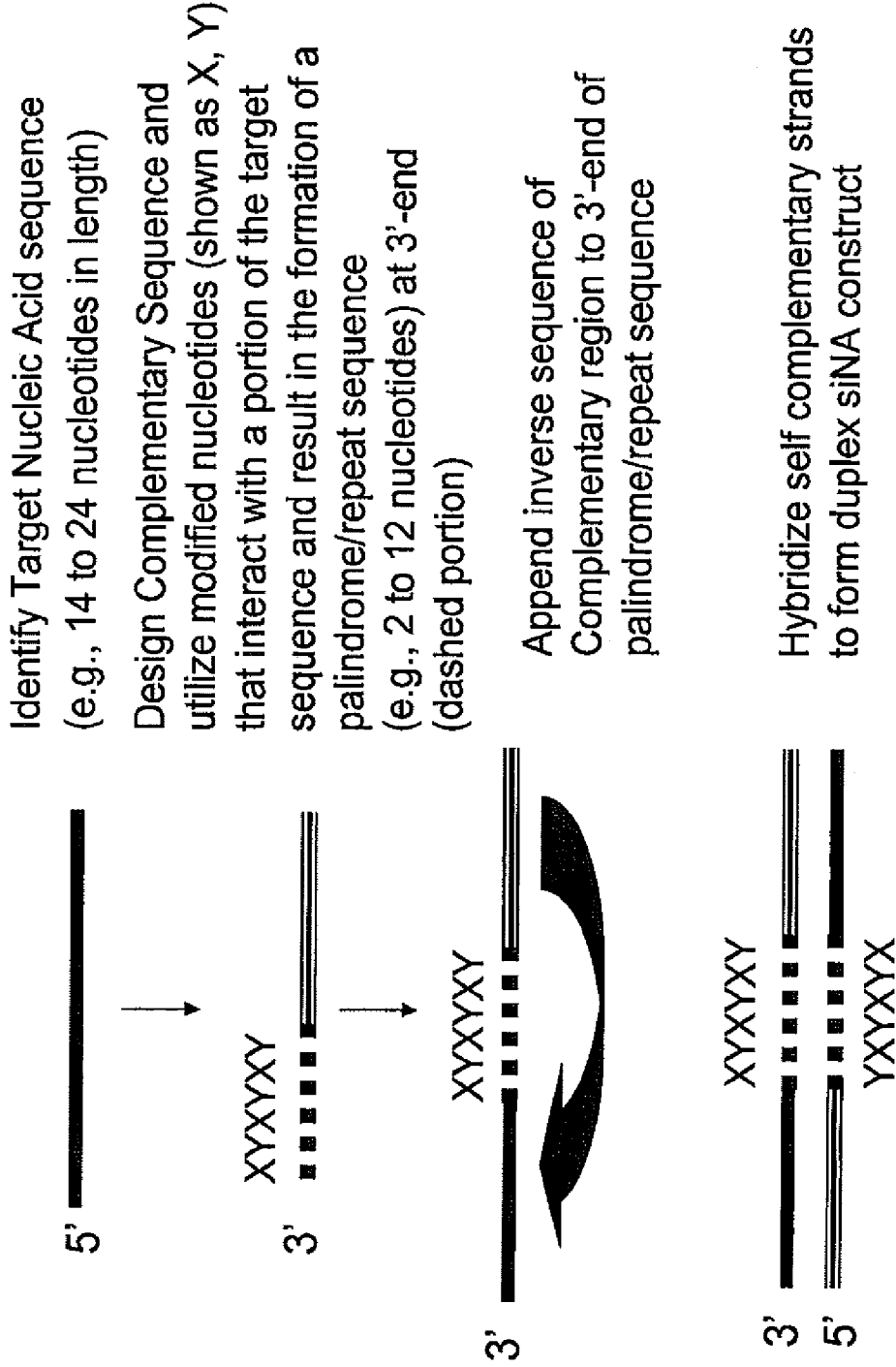
Figure 15: Duplex forming oligonucleotide constructs that utilize artificial palindrome or repeat sequences

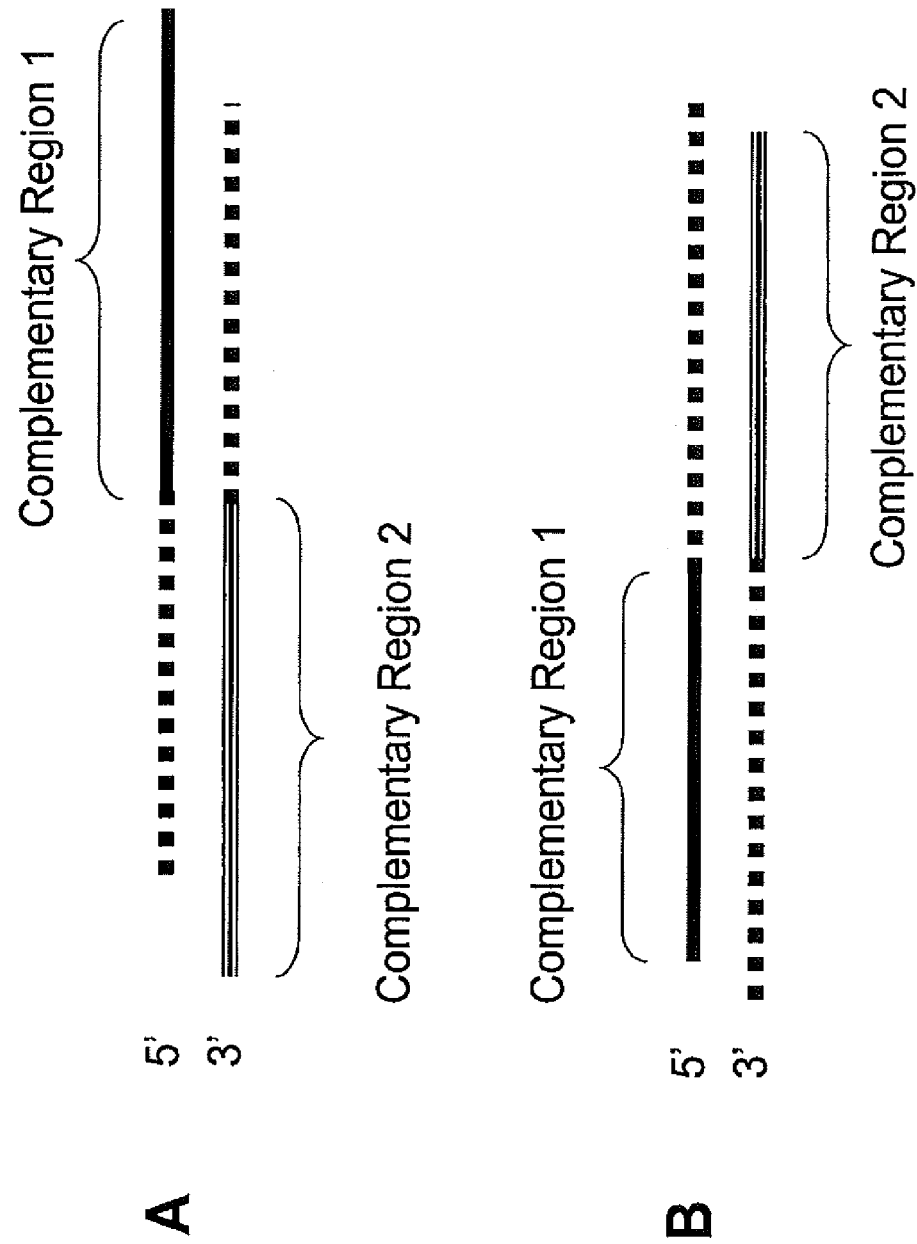
Figure 16: Examples of double stranded multifunctional siNA constructs with distinct complementary regions

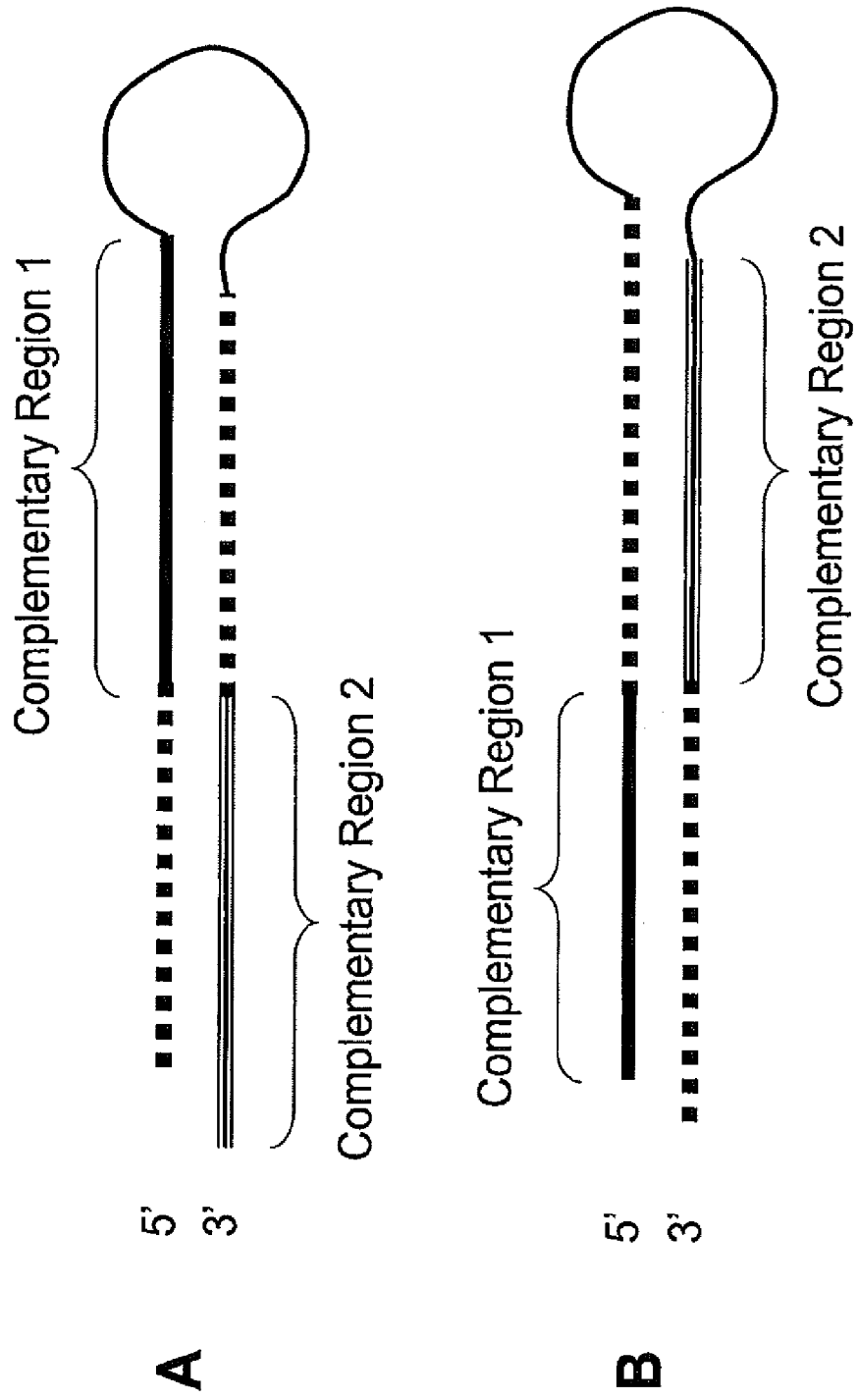
Figure 17: Examples of hairpin multifunctional siNA constructs with distinct complementary regions

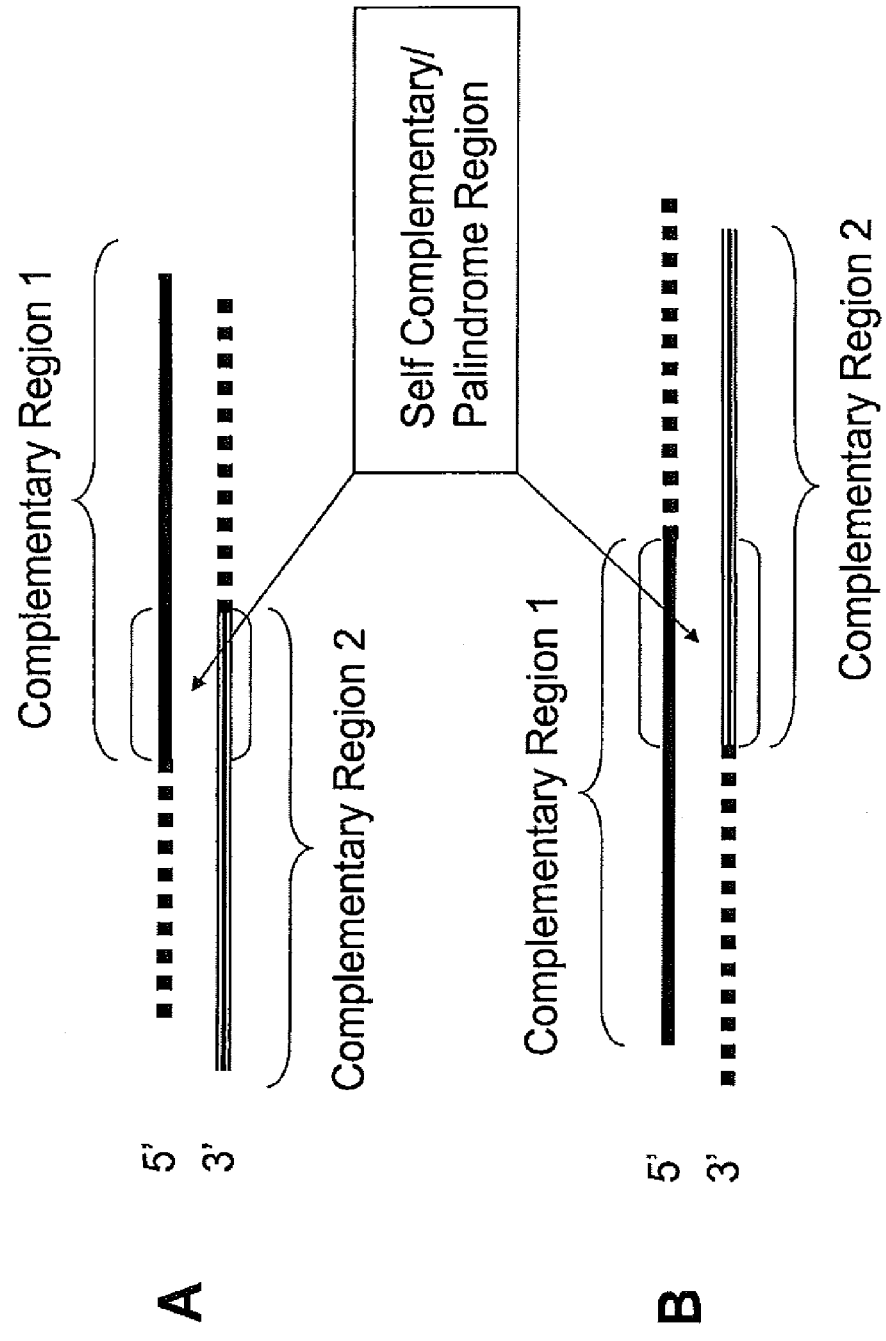
Figure 18: Examples of double stranded multifunctional siNA constructs with distinct complementary regions and a self complementary/palindrome region

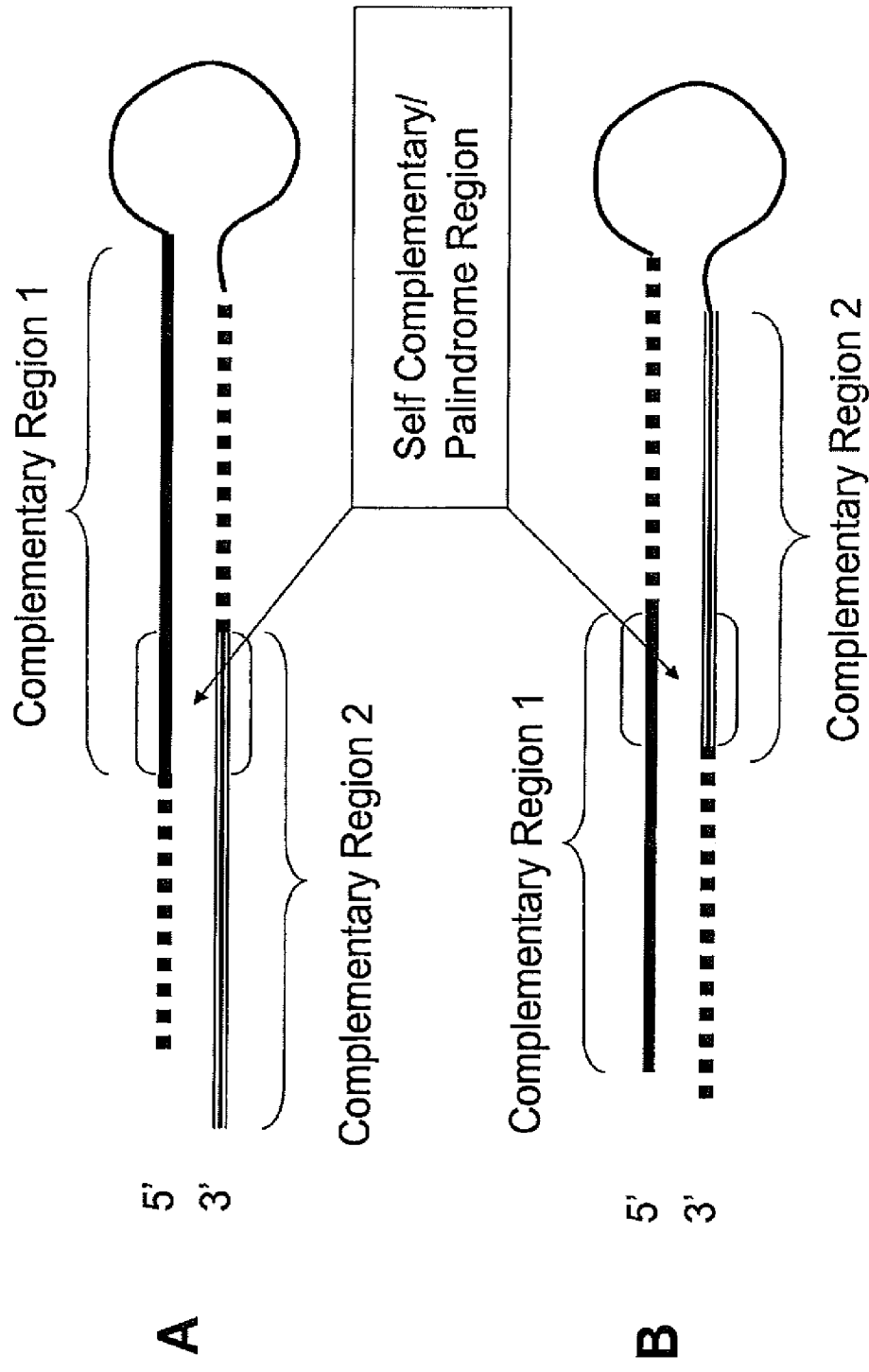
Figure 19: Examples of hairpin multifunctional siNA constructs with distinct complementary regions and a self complementary/palindrome region

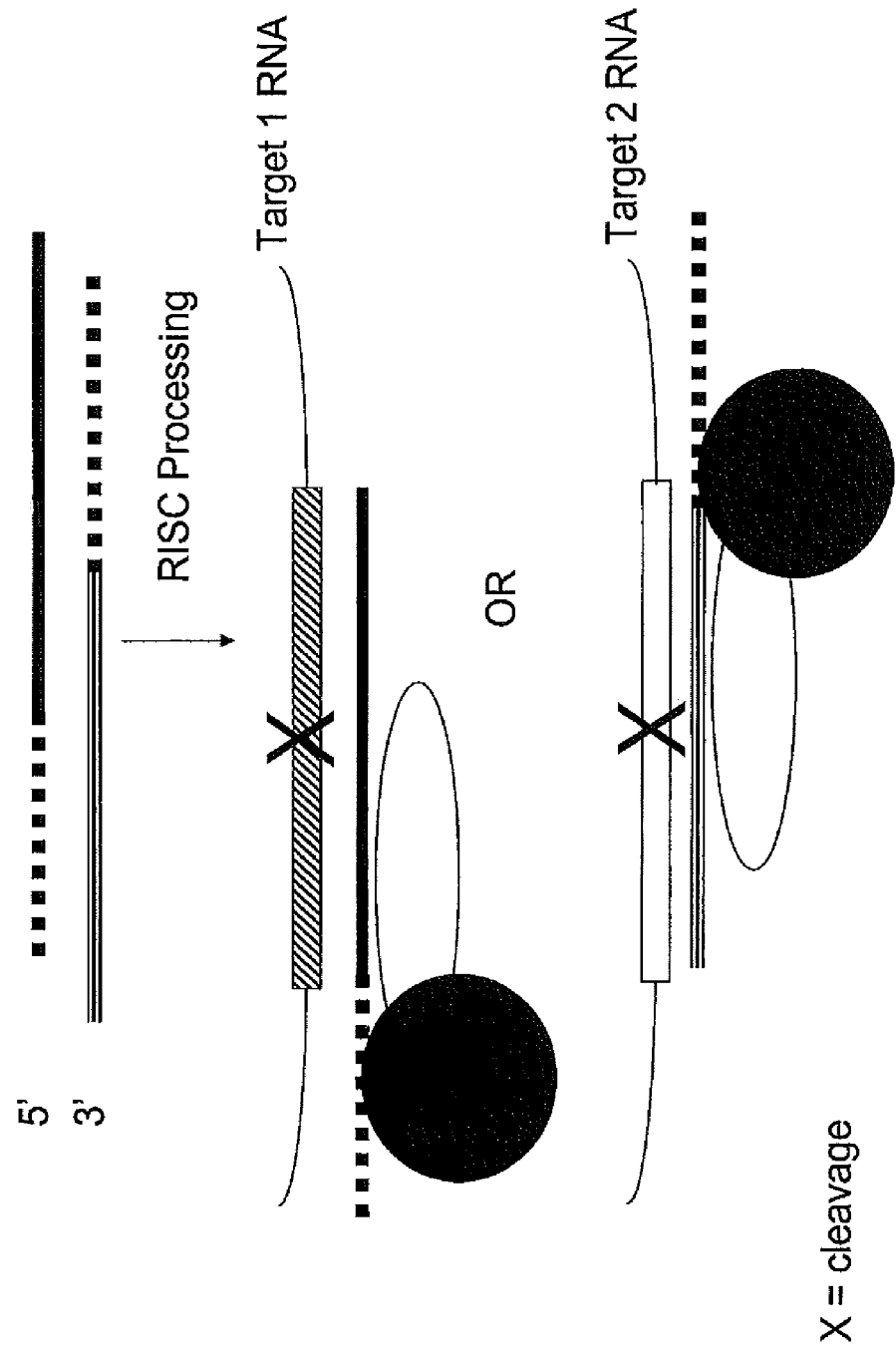
Figure 20: Example of multifunctional siNA targeting two Separate Target nucleic acid sequences

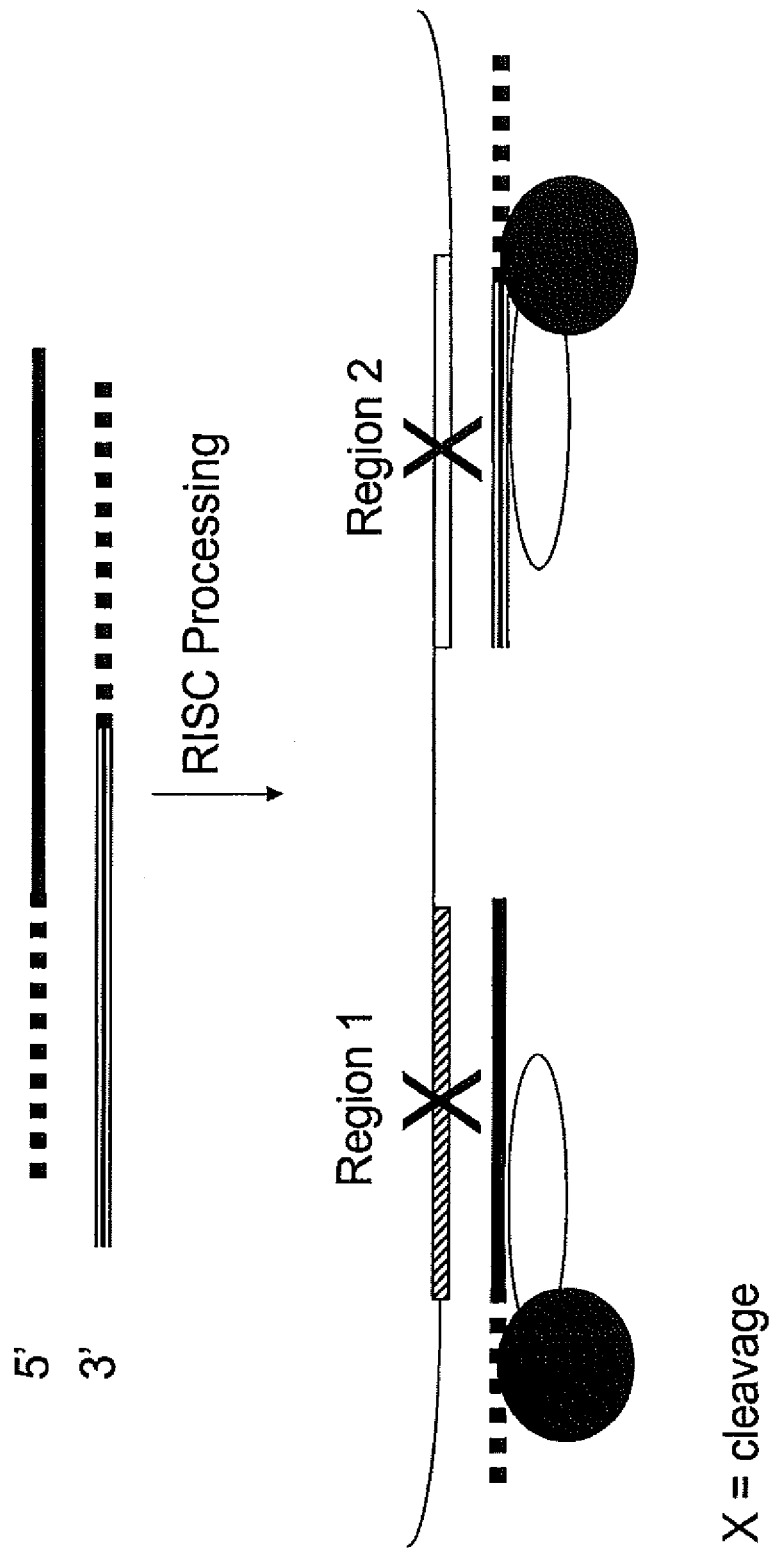
Figure 21: Example of multifunctional siNA targeting two regions within the same target nucleic acid sequence

SEQUENCE LISTING

<160> NUMBER OF SEQ ID NOS: 804

<210> SEQ ID NO 1
<211> LENGTH: 19
<212> TYPE: RNA
<213> ORGANISM: Artificial Sequence
<220> FEATURE:
<223> OTHER INFOR~ION: Synthetic

<400> SEQUENCE: 1
aauuuugaga agugguggg                                                19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
gaugaagaag aucccugaa                                                19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
agagaggagu aacugagac                                                19

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
caaaggcgag gcuagcaau                                                19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
uagagagaca agugaggga                                                19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
aauuagaccu uugguauca                                                19

<210> SEQ ID NO 7
<211> LENGTH: 19

```
<212> TYPE: RNA
<213> ORGANISM: Artificial Sequence
<220> FEATURE:
<223> OTHER INFORMATION: Synthetic

<400> SEQUENCE: 7
aucaugaaaa ggccuggaa                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
agaaacgcug guuuauccu                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
ugcggagugg ccggaugag                                                  19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
gcggugaccc agauguucu                                                  19

<210> SEQ ID NO 11
<211> LENGTH: 19
<212> TYPE: RNA
<213> ORGANISM: Artificial Sequence
<220> FEATURE:
<223> OTHER INFORMATION: Synthetic

<400> SEQUENCE: 11
uggaauacua caagaacga                                                  19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
aucacuccaa gaagccucu                                                  19

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
```

-continued ugcggaucau caaccugaa                                   19

<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
acuucuguga gcagguaga                                   19

<210> SEQ ID NO 15
<211> LENGTH: 19
<212> TYPE: RNA
<213> ORGANISM: Artificial Sequence
<220> FEATURE:
<223> OTHER INFORMATION: Synthetic

<400> SEQUENCE: 15
augcaggccu gaccuuuaa                                   19

<210> SEQ ID NO 16
<211> LENGTH: 19
<212> TYPE: RNA
<213> ORGANISM: Artificial Sequence
<220> FEATURE:
<223> OTHER INFORMATION: Synthetic

<400> SEQUENCE: 16
acaagaagga gcugcagga                                   19

<210> SEQ ID NO 17
<211> LENGTH: 19
<212> TYPE: RNA
<213> ORGANISM: Artificial Sequence
<220> FEATURE:
<223> OTHER INFORMATION: Synthetic

<400> SEQUENCE: 17
auaguuuugu guuugacau                                   19

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
ucaagaccag ugaacgcac                                   19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
ccuuuuaccu gguggcuga                                   19

<210> SEQ ID NO 20
<211> LENGTH: 19
<212> TYPE: RNA
<213> ORGANISM: Artificial Sequence

```
<220> FEATURE:
<223> OTHER INFORMATION: Synthetic

<400> SEQUENCE: 20
agacagaaga ggacaugaa                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
auaagugggu ccagagcau                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
ucugccagau cuguggcuu                                                    19

<210> SEQ ID NO 23
<211> LENGTH: 19
<212> TYPE: RNA
<213> ORGANISM: Artificial Sequence
<220> FEATURE:
<223> OTHER INFORMATION: Synthetic

<400> SEQUENCE: 23
ucaaucaggc ugaggagag                                                    19

<210> SEQ ID NO 24
<211> LENGTH: 19
<212> TYPE: RNA
<213> ORGANISM: Artificial Sequence
<220> FEATURE:
<223> OTHER INFORMATION: Synthetic

<400> SEQUENCE: 24
gcacagacuc ccugagaaa                                                    19

<210> SEQ ID NO 25
<211> LENGTH: 19
<212> TYPE: RNA
<213> ORGANISM: Artificial Sequence
<220> FEATURE:
<223> OTHER INFORMATION: Synthetic

<400> SEQUENCE: 25 auguuccuc agccgguca                                                     19

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26 auggccccg cucuucucc                                                     19
```

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27
cagcugagcu cagcagcuc                                              19

<210> SEQ ID NO 28
<211> LENGTH: 19
<212> TYPE: RNA
<213> ORGANISM: Artificial Sequence
<220> FEATURE:
<223> OTHER INFORMATION: Synthetic

<400> SEQUENCE: 28
cuagccagca ccuucuccg                                              19

<210> SEQ ID NO 29
<211> LENGTH: 19
<212> TYPE: RNA
<213> ORGANISM: Artificial Sequence
<220> FEATURE:
<223> OTHER INFORMATION: Synthetic

<400> SEQUENCE: 29
gagagcgcaa guccucagc                                              19

<210> SEQ ID NO 30
<211> LENGTH: 19
<212> TYPE: RNA
<213> ORGANISM: Artificial Sequence
<220> FEATURE:
<223> OTHER INFORMATION: Synthetic

<400> SEQUENCE: 30
ccccaucaca cuccagcca                                              19

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
agccaacucu guucacguu                                              19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32 uugaacccc ugugucaaa                                               19

<210> SEQ ID NO 33
<211> LENGTH: 19
<212> TYPE: RNA
<213> ORGANISM: Artificial Sequence
<220> FEATURE:
<223> OTHER INFORMATION: Synthetic

```
<400> SEQUENCE: 33
accacaugca gcccaccuu                                               19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
uguccaccag cgcaccuca                                               19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
aggaguaucu cuacuugca                                               19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
accagugcau aagccgaag                                               19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
gagcagaaaa ugcaaggag                                               19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
gugccagcuu cucucaggg                                               19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
gcaccagagc cucuuuucu                                               19

<210> SEQ ID NO 40
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 40
ucaugaggag ugacacagc                                              19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
cuguacaaaa acuugccca                                              19

<210> SEQ ID NO 42
<211> LENGTH: 19
<212> TYPE: RNA
<213> ORGANISM: Artificial Sequence
<220> FEATURE:
<223> OTHER INFORMATION: Synthetic

<400> SEQUENCE: 42
agggcaaugg acacugugu                                              19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
ucaacgggau cagugguca                                              19

<210> SEQ ID NO 44
<211> LENGTH: 19
<212> TYPE: RNA
<213> ORGANISM: Artificial Sequence
<220> FEATURE:
<223> OTHER INFORMATION: Synthetic

<400> SEQUENCE: 44
aaguccaugg cuucuauag                                              19

<210> SEQ ID NO 45
<211> LENGTH: 19
<212> TYPE: RNA
<213> ORGANISM: Artificial Sequence
<220> FEATURE:
<223> OTHER INFORMATION: Synthetic

<400> SEQUENCE: 45
gccuucccaa gccgagccg                                              19

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
```
ggcacaauac agaauucag                                                19

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
gagacaguac cuacgaccu                                                19

<210> SEQ ID NO 48
<211> LENGTH: 19
<212> TYPE: RNA
<213> ORGANISM: Artificial Sequence
<220> FEATURE:
<223> OTHER INFORMATION: Synthetic

<400> SEQUENCE: 48 uccccccgcag ccuggccuc                                               19

<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
cccauggcca caccaaggg                                                19

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
gcagccucac aggcuccga                                                19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
agacagauaa ugaggaugu                                                19

<210> SEQ ID NO 52
<211> LENGTH: 19
<212> TYPE: RNA
<213> ORGANISM: Artificial Sequence
<220> FEATURE:
<223> OTHER INFORMATION: Synthetic

<400> SEQUENCE: 52
uguacaccuu caagacgcc                                                19

<210> SEQ ID NO 53
<211> LENGTH: 19
<212> TYPE: RNA

<213> ORGANISM: Artificial Sequence
<220> FEATURE:
<223> OTHER INFORMATION: Synthetic

<400> SEQUENCE: 53
ccagcaacac ccugugcag                                                        19

<210> SEQ ID NO 54
<211> LENGTH: 19
<212> TYPE: RNA
<213> ORGANISM: Artificial Sequence
<220> FEATURE:
<223> OTHER INFORMATION: Synthetic

<400> SEQUENCE: 54
gggaguucgg ggaccuccu                                                        19

<210> SEQ ID NO 55
<211> LENGTH: 19
<212> TYPE: RNA
<213> ORGANISM: Artificial Sequence
<220> FEATURE:
<223> OTHER INFORMATION: Synthetic

<400> SEQUENCE: 55
ugguagacaa uauggaugu                                                        19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
uuccggccac cccacucuc                                                        19

<210> SEQ ID NO 57
<211> LENGTH: 19
<212> TYPE: RNA
<213> ORGANISM: Artificial Sequence
<220> FEATURE:
<223> OTHER INFORMATION: Synthetic

<400> SEQUENCE: 57
cagccuacca gaucccuag                                                        19

<210> SEQ ID NO 58
<211> LENGTH: 19
<212> TYPE: RNA
<213> ORGANISM: Artificial Sequence
<220> FEATURE:
<223> OTHER INFORMATION: Synthetic

<400> SEQUENCE: 58
ggacauucac ucuggacaa                                                        19

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
aaaaccacaa ugccaugac                                                        19

```
<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
caguggccac uccugggga                                                  19

<210> SEQ ID NO 61
<211> LENGTH: 19
<212> TYPE: RNA
<213> ORGANISM: Artificial Sequence
<220> FEATURE:
<223> OTHER INFORMATION: Synthetic

<400> SEQUENCE: 61
acucagccau agcuccccc                                                  19

<210> SEQ ID NO 62
<211> LENGTH: 19
<212> TYPE: RNA
<213> ORGANISM: Artificial Sequence
<220> FEATURE:
<223> OTHER INFORMATION: Synthetic

<400> SEQUENCE: 62
caccccgccc ccccaagcc                                                  19

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
caagucaggc agaaacacc                                                  19

<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
cucgaugggg caguccuca                                                  19

<210> SEQ ID NO 65
<211> LENGTH: 19
<212> TYPE: RNA
<213> ORGANISM: Artificial Sequence
<220> FEATURE:
<223> OTHER INFORMATION: Synthetic

<400> SEQUENCE: 65
agcagagacc gccaaucag                                                  19

<210> SEQ ID NO 66
<211> LENGTH: 19
<212> TYPE: RNA
<213> ORGANISM: Artificial Sequence
<220> FEATURE:
```

-continued

<223> OTHER INFORMATION: Synthetic

<400> SEQUENCE: 66
gugaaaauag cagaucugu                                                19

<210> SEQ ID NO 67
<211> LENGTH: 19
<212> TYPE: RNA
<213> ORGANISM: Artificial Sequence
<220> FEATURE:
<223> OTHER INFORMATION: Synthetic

<400> SEQUENCE: 67
ucgcugccac caucccag                                                 19

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68
gacgcaacac ccucccugc                                                19

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69
caauggacaa cagccgacu                                                19

<210> SEQ ID NO 70
<211> LENGTH: 19
<212> TYPE: RNA
<213> ORGANISM: Artificial Sequence
<220> FEATURE:
<223> OTHER INFORMATION: Synthetic

<400> SEQUENCE: 70
uucaccgagc uucuuccug                                                19

<210> SEQ ID NO 71
<211> LENGTH: 19
<212> TYPE: RNA
<213> ORGANISM: Artificial Sequence
<220> FEATURE:
<223> OTHER INFORMATION: Synthetic

<400> SEQUENCE: 71
gugagaccua cgaguaccc                                                19

<210> SEQ ID NO 72
<211> LENGTH: 19
<212> TYPE: RNA
<213> ORGANISM: Artificial Sequence
<220> FEATURE:
<223> OTHER INFORMATION: Synthetic

<400> SEQUENCE: 72
cacagcgugg uggagagag                                                19

```
<210> SEQ ID NO 73
<211> LENGTH: 19
<212> TYPE: RNA
<213> ORGANISM: Artificial Sequence
<220> FEATURE:
<223> OTHER INFORMATION: Synthetic

<400> SEQUENCE: 73
gugcaggccg gucugcuga                                              19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74
aauccaugag ugauggagu                                              19

<210> SEQ ID NO 75
<211> LENGTH: 19
<212> TYPE: RNA
<213> ORGANISM: Artificial Sequence
<220> FEATURE:
<223> OTHER INFORMATION: Synthetic

<400> SEQUENCE: 75
uuggcucuuu ccugccagg                                              19

<210> SEQ ID NO 76
<211> LENGTH: 19
<212> TYPE: RNA
<213> ORGANISM: Artificial Sequence
<220> FEATURE:
<223> OTHER INFORMATION: Synthetic

<400> SEQUENCE: 76
ggaaaaugau ugugggccg                                              19

<210> SEQ ID NO 77
<211> LENGTH: 19
<212> TYPE: RNA
<213> ORGANISM: Artificial Sequence
<220> FEATURE:
<223> OTHER INFORMATION: Synthetic

<400> SEQUENCE: 77
gaucggacag caccaauuc                                              19

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
cugaagacaa cuaugugcc                                              19

<210> SEQ ID NO 79
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 79
ccaugaaucc agguucuuc                                              19

<210> SEQ ID NO 80
<211> LENGTH: 19
<212> TYPE: RNA
<213> ORGANISM: Artificial Sequence
<220> FEATURE:
<223> OTHER INFORMATION: Synthetic

<400> SEQUENCE: 80
ccacccuguu ggccaugga                                              19

<210> SEQ ID NO 81
<211> LENGTH: 19
<212> TYPE: RNA
<213> ORGANISM: Artificial Sequence
<220> FEATURE:
<223> OTHER INFORMATION: Synthetic

<400> SEQUENCE: 81
aacgagcagg ugauaauuc                                              19

<210> SEQ ID NO 82
<211> LENGTH: 19
<212> TYPE: RNA
<213> ORGANISM: Artificial Sequence
<220> FEATURE:
<223> OTHER INFORMATION: Synthetic

<400> SEQUENCE: 82
cccagagcgu cuacauccc                                              19

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
caaugagccc aggggccca                                              19

<210> SEQ ID NO 84
<211> LENGTH: 19
<212> TYPE: RNA
<213> ORGANISM: Artificial Sequence
<220> FEATURE:
<223> OTHER INFORMATION: Synthetic

<400> SEQUENCE: 84
aucacuuuga cucacuugg                                              19

<210> SEQ ID NO 85
<211> LENGTH: 19
<212> TYPE: RNA
<213> ORGANISM: Artificial Sequence
<220> FEATURE:
<223> OTHER INFORMATION: Synthetic

<400> SEQUENCE: 85
gcuacccauc aacaacccu                                              19

<210> SEQ ID NO 86
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 86
uuccugugca ccgaggccc                                                      19

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87
ccagcagagg aagugagau                                                      19

<210> SEQ ID NO 88
<211> LENGTH: 19
<212> TYPE: RNA
<213> ORGANISM: Artificial Sequence
<220> FEATURE:
<223> OTHER INFORMATION: Synthetic

<400> SEQUENCE: 88
uucagccacc cccugucaa                                                      19

<210> SEQ ID NO 89
<211> LENGTH: 19
<212> TYPE: RNA
<213> ORGANISM: Artificial Sequence
<220> FEATURE:
<223> OTHER INFORMATION: Synthetic

<400> SEQUENCE: 89
accgcaaccu caaaccuga                                                      19

<210> SEQ ID NO 90
<211> LENGTH: 19
<212> TYPE: RNA
<213> ORGANISM: Artificial Sequence
<220> FEATURE:
<223> OTHER INFORMATION: Synthetic

<400> SEQUENCE: 90
aucggaaagc aaagccaac                                                      19

<210> SEQ ID NO 91
<211> LENGTH: 19
<212> TYPE: RNA
<213> ORGANISM: Artificial Sequence
<220> FEATURE:
<223> OTHER INFORMATION: Synthetic

<400> SEQUENCE: 91
caccacuuga ccugaggaa                                                      19

<210> SEQ ID NO 92
<211> LENGTH: 19
<212> TYPE: RNA
<213> ORGANISM: Artificial Sequence
<220> FEATURE:
<223> OTHER INFORMATION: Synthetic

<400> SEQUENCE: 92
```

-continued acaacaccgu caucgauga                                           19

<210> SEQ ID NO 93
<211> LENGTH: 19
<212> TYPE: RNA
<213> ORGANISM: Artificial Sequence
<220> FEATURE:
<223> OTHER INFORMATION: Synthetic

<400> SEQUENCE: 93
aacuccccuu caagucacc                                           19

<210> SEQ ID NO 94
<211> LENGTH: 19
<212> TYPE: RNA
<213> ORGANISM: Artificial Sequence
<220> FEATURE:
<223> OTHER INFORMATION: Synthetic

<400> SEQUENCE: 94
cuaucaccaa gucuugguc                                           19

<210> SEQ ID NO 95
<211> LENGTH: 19
<212> TYPE: RNA
<213> ORGANISM: Artificial Sequence
<220> FEATURE:
<223> OTHER INFORMATION: Synthetic

<400> SEQUENCE: 95
cuagggccaa ccacaccuu                                           19

<210> SEQ ID NO 96
<211> LENGTH: 19
<212> TYPE: RNA
<213> ORGANISM: Artificial Sequence
<220> FEATURE:
<223> OTHER INFORMATION: Synthetic

<400> SEQUENCE: 96
ucaacuccag cuccuccca                                           19

<210> SEQ ID NO 97
<211> LENGTH: 19
<212> TYPE: RNA
<213> ORGANISM: Artificial Sequence
<220> FEATURE:
<223> OTHER INFORMATION: Synthetic

<400> SEQUENCE: 97
aguacugccg ccccaucuc                                           19

<210> SEQ ID NO 98
<211> LENGTH: 19
<212> TYPE: RNA
<213> ORGANISM: Artificial Sequence
<220> FEATURE:
<223> OTHER INFORMATION: Synthetic

<400> SEQUENCE: 98
ccacccagag caucaccag                                           19

<210> SEQ ID NO 99
<211> LENGTH: 19
<212> TYPE: RNA
<213> ORGANISM: Artificial Sequence

```
<220> FEATURE:
<223> OTHER INFORMATION: Synthetic

<400> SEQUENCE: 99
gcacagacuc aggagacag                                                  19

<210> SEQ ID NO 100
<211> LENGTH: 19
<212> TYPE: RNA
<213> ORGANISM: Artificial Sequence
<220> FEATURE:
<223> OTHER INFORMATION: Synthetic

<400> SEQUENCE: 100
gcgaagagaa cuauguccc                                                  19

<210> SEQ ID NO 101
<211> LENGTH: 19
<212> TYPE: RNA
<213> ORGANISM: Artificial Sequence
<220> FEATURE:
<223> OTHER INFORMATION: Synthetic

<400> SEQUENCE: 101
cuaugcaaaa cccaguguc                                                  19

<210> SEQ ID NO 102
<211> LENGTH: 19
<212> TYPE: RNA
<213> ORGANISM: Artificial Sequence
<220> FEATURE:
<223> OTHER INFORMATION: Synthetic

<400> SEQUENCE: 102
cugcaucucc cguucccag                                                  19

<210> SEQ ID NO 103
<211> LENGTH: 19
<212> TYPE: RNA
<213> ORGANISM: Artificial Sequence
<220> FEATURE:
<223> OTHER INFORMATION: Synthetic

<400> SEQUENCE: 103
guggcacgaa caguccugc                                                  19

<210> SEQ ID NO 104
<211> LENGTH: 19
<212> TYPE: RNA
<213> ORGANISM: Artificial Sequence
<220> FEATURE:
<223> OTHER INFORMATION: Synthetic

<400> SEQUENCE: 104
ccccuaagaa gagcaccgg                                                  19

<210> SEQ ID NO 105
<211> LENGTH: 19
<212> TYPE: RNA
<213> ORGANISM: Artificial Sequence
<220> FEATURE:
<223> OTHER INFORMATION: Synthetic

<400> SEQUENCE: 105
gcagcguuga uuaucuggc                                                  19
```

<210> SEQ ID NO 106
<211> LENGTH: 19
<212> TYPE: RNA
<213> ORGANISM: Artificial Sequence
<220> FEATURE:
<223> OTHER INFORMATION: Synthetic

<400> SEQUENCE: 106
cccuggacuu ccagccgag                                               19

<210> SEQ ID NO 107
<211> LENGTH: 19
<212> TYPE: RNA
<213> ORGANISM: Artificial Sequence
<220> FEATURE:
<223> OTHER INFORMATION: Synthetic

<400> SEQUENCE: 107
gcuccccaag cccccaccg                                               19

<210> SEQ ID NO 108
<211> LENGTH: 19
<212> TYPE: RNA
<213> ORGANISM: Artificial Sequence
<220> FEATURE:
<223> OTHER INFORMATION: Synthetic

<400> SEQUENCE: 108
gcaagccauc uacuucauc                                               19

<210> SEQ ID NO 109
<211> LENGTH: 19
<212> TYPE: RNA
<213> ORGANISM: Artificial Sequence
<220> FEATURE:
<223> OTHER INFORMATION: Synthetic

<400> SEQUENCE: 109
ccgucaccuc ugaugagaa                                               19

<210> SEQ ID NO 110
<211> LENGTH: 19
<212> TYPE: RNA
<213> ORGANISM: Artificial Sequence
<220> FEATURE:
<223> OTHER INFORMATION: Synthetic

<400> SEQUENCE: 110
agguggacua cguucaggu                                               19

<210> SEQ ID NO 111
<211> LENGTH: 19
<212> TYPE: RNA
<213> ORGANISM: Artificial Sequence
<220> FEATURE:
<223> OTHER INFORMATION: Synthetic

<400> SEQUENCE: 111
uggacaagga gaagaccca                                               19

<210> SEQ ID NO 112
<211> LENGTH: 19
<212> TYPE: RNA
<213> ORGANISM: Artificial Sequence
<220> FEATURE:
<223> OTHER INFORMATION: Synthetic

```
<400> SEQUENCE: 112
aggcccugca gaacaccau                                          19

<210> SEQ ID NO 113
<211> LENGTH: 19
<212> TYPE: RNA
<213> ORGANISM: Artificial Sequence
<220> FEATURE:
<223> OTHER INFORMATION: Synthetic

<400> SEQUENCE: 113
ugcaggagug gacagacgu                                          19

<210> SEQ ID NO 114
<211> LENGTH: 19
<212> TYPE: RNA
<213> ORGANISM: Artificial Sequence
<220> FEATURE:
<223> OTHER INFORMATION: Synthetic

<400> SEQUENCE: 114
ugcggcaguc cucagagcc                                          19

<210> SEQ ID NO 115
<211> LENGTH: 19
<212> TYPE: RNA
<213> ORGANISM: Artificial Sequence
<220> FEATURE:
<223> OTHER INFORMATION: Synthetic

<400> SEQUENCE: 115
cuuccaaggg ugccaagcu                                          19

<210> SEQ ID NO 116
<211> LENGTH: 19
<212> TYPE: RNA
<213> ORGANISM: Artificial Sequence
<220> FEATURE:
<223> OTHER INFORMATION: Synthetic

<400> SEQUENCE: 116
ugugaugaga gggccaccg                                          19

<210> SEQ ID NO 117
<211> LENGTH: 19
<212> TYPE: RNA
<213> ORGANISM: Artificial Sequence
<220> FEATURE:
<223> OTHER INFORMATION: Synthetic

<400> SEQUENCE: 117
gcagagccca ggaggcagc                                          19

<210> SEQ ID NO 118
<211> LENGTH: 19
<212> TYPE: RNA
<213> ORGANISM: Artificial Sequence
<220> FEATURE:
<223> OTHER INFORMATION: Synthetic

<400> SEQUENCE: 118
caucuccaga gcuggcccu                                          19

<210> SEQ ID NO 119
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 119
uucccaucuc cccucuccc                                                      19

<210> SEQ ID NO 120
<211> LENGTH: 19
<212> TYPE: RNA
<213> ORGANISM: Artificial Sequence
<220> FEATURE:
<223> OTHER INFORMATION: Synthetic

<400> SEQUENCE: 120
ccucucccgu ucuuccucc                                                      19

<210> SEQ ID NO 121
<211> LENGTH: 19
<212> TYPE: RNA
<213> ORGANISM: Artificial Sequence
<220> FEATURE:
<223> OTHER INFORMATION: Synthetic

<400> SEQUENCE: 121
ccauccaccu ccucucuac                                                      19

<210> SEQ ID NO 122
<211> LENGTH: 19
<212> TYPE: RNA
<213> ORGANISM: Artificial Sequence
<220> FEATURE:
<223> OTHER INFORMATION: Synthetic

<400> SEQUENCE: 122
cucugccagu cucagccuu                                                      19

<210> SEQ ID NO 123
<211> LENGTH: 19
<212> TYPE: RNA
<213> ORGANISM: Artificial Sequence
<220> FEATURE:
<223> OTHER INFORMATION: Synthetic

<400> SEQUENCE: 123
ucaaagcacu ugacaucag                                                      19

<210> SEQ ID NO 124
<211> LENGTH: 19
<212> TYPE: RNA
<213> ORGANISM: Artificial Sequence
<220> FEATURE:
<223> OTHER INFORMATION: Synthetic

<400> SEQUENCE: 124
gggacccuga acccuuccc                                                      19

<210> SEQ ID NO 125
<211> LENGTH: 19
<212> TYPE: RNA
<213> ORGANISM: Artificial Sequence
<220> FEATURE:
<223> OTHER INFORMATION: Synthetic

<400> SEQUENCE: 125
```
ccugggaggu gagggccug         19

<210> SEQ ID NO 126
<211> LENGTH: 19
<212> TYPE: RNA
<213> ORGANISM: Artificial Sequence
<220> FEATURE:
<223> OTHER INFORMATION: Synthetic

<400> SEQUENCE: 126
gaucaaggca ccuccucug         19

<210> SEQ ID NO 127
<211> LENGTH: 19
<212> TYPE: RNA
<213> ORGANISM: Artificial Sequence
<220> FEATURE:
<223> OTHER INFORMATION: Synthetic

<400> SEQUENCE: 127
gcccacucgg ggcccagcu         19

<210> SEQ ID NO 128
<211> LENGTH: 19
<212> TYPE: RNA
<213> ORGANISM: Artificial Sequence
<220> FEATURE:
<223> OTHER INFORMATION: Synthetic

<400> SEQUENCE: 128
ugugauuuuu aucaguaau         19

<210> SEQ ID NO 129
<211> LENGTH: 19
<212> TYPE: RNA
<213> ORGANISM: Artificial Sequence
<220> FEATURE:
<223> OTHER INFORMATION: Synthetic

<400> SEQUENCE: 129
uggccaugcc uccacccac         19

<210> SEQ ID NO 130
<211> LENGTH: 19
<212> TYPE: RNA
<213> ORGANISM: Artificial Sequence
<220> FEATURE:
<223> OTHER INFORMATION: Synthetic

<400> SEQUENCE: 130
ccuuaguuag gagcuacuu         19

<210> SEQ ID NO 131
<211> LENGTH: 19
<212> TYPE: RNA
<213> ORGANISM: Artificial Sequence
<220> FEATURE:
<223> OTHER INFORMATION: Synthetic

<400> SEQUENCE: 131
uccaaaaagc auccuucag         19

<210> SEQ ID NO 132
<211> LENGTH: 19
<212> TYPE: RNA

```
<213> ORGANISM: Artificial Sequence
<220> FEATURE:
<223> OTHER INFORMATION: Synthetic

<400> SEQUENCE: 132
gccucuuccu guccuuuag                                                    19

<210> SEQ ID NO 133
<211> LENGTH: 19
<212> TYPE: RNA
<213> ORGANISM: Artificial Sequence
<220> FEATURE:
<223> OTHER INFORMATION: Synthetic

<400> SEQUENCE: 133
gaccugacuc ucuaccaga                                                    19

<210> SEQ ID NO 134
<211> LENGTH: 19
<212> TYPE: RNA
<213> ORGANISM: Artificial Sequence
<220> FEATURE:
<223> OTHER INFORMATION: Synthetic

<400> SEQUENCE: 134
auguuuggag ggaagggcu                                                    19

<210> SEQ ID NO 135
<211> LENGTH: 19
<212> TYPE: RNA
<213> ORGANISM: Artificial Sequence
<220> FEATURE:
<223> OTHER INFORMATION: Synthetic

<400> SEQUENCE: 135
uggggcucug agccagauu                                                    19

<210> SEQ ID NO 136
<211> LENGTH: 19
<212> TYPE: RNA
<213> ORGANISM: Artificial Sequence
<220> FEATURE:
<223> OTHER INFORMATION: Synthetic

<400> SEQUENCE: 136
uccacaccuc acguucagu                                                    19

<210> SEQ ID NO 137
<211> LENGTH: 19
<212> TYPE: RNA
<213> ORGANISM: Artificial Sequence
<220> FEATURE:
<223> OTHER INFORMATION: Synthetic

<400> SEQUENCE: 137
ucacagcccu cagcuaucu                                                    19

<210> SEQ ID NO 138
<211> LENGTH: 19
<212> TYPE: RNA
<213> ORGANISM: Artificial Sequence
<220> FEATURE:
<223> OTHER INFORMATION: Synthetic

<400> SEQUENCE: 138
uucccuccgg ccacugggc                                                    19
```

-continued

```
<210> SEQ ID NO 139
<211> LENGTH: 19
<212> TYPE: RNA
<213> ORGANISM: Artificial Sequence
<220> FEATURE:
<223> OTHER INFORMATION: Synthetic

<400> SEQUENCE: 139
cuaccucucc uucaguccc                                                  19

<210> SEQ ID NO 140
<211> LENGTH: 19
<212> TYPE: RNA
<213> ORGANISM: Artificial Sequence
<220> FEATURE:
<223> OTHER INFORMATION: Synthetic

<400> SEQUENCE: 140
cagaagacaa gucucacca                                                  19

<210> SEQ ID NO 141
<211> LENGTH: 19
<212> TYPE: RNA
<213> ORGANISM: Artificial Sequence
<220> FEATURE:
<223> OTHER INFORMATION: Synthetic

<400> SEQUENCE: 141
aacccaggga gucaaggac                                                  19

<210> SEQ ID NO 142
<211> LENGTH: 19
<212> TYPE: RNA
<213> ORGANISM: Artificial Sequence
<220> FEATURE:
<223> OTHER INFORMATION: Synthetic

<400> SEQUENCE: 142
ccagcaaacc aaaguggau                                                  19

<210> SEQ ID NO 143
<211> LENGTH: 19
<212> TYPE: RNA
<213> ORGANISM: Artificial Sequence
<220> FEATURE:
<223> OTHER INFORMATION: Synthetic

<400> SEQUENCE: 143
uaauggacuu uuucauucc                                                  19

<210> SEQ ID NO 144
<211> LENGTH: 19
<212> TYPE: RNA
<213> ORGANISM: Artificial Sequence
<220> FEATURE:
<223> OTHER INFORMATION: Synthetic

<400> SEQUENCE: 144
cuguuuuucu uggcaggag                                                  19

<210> SEQ ID NO 145
<211> LENGTH: 19
<212> TYPE: RNA
<213> ORGANISM: Artificial Sequence
<220> FEATURE:
```

<223> OTHER INFORMATION: Synthetic

<400> SEQUENCE: 145
gagaagcaag gccacuaaa					19

<210> SEQ ID NO 146
<211> LENGTH: 19
<212> TYPE: RNA
<213> ORGANISM: Artificial Sequence
<220> FEATURE:
<223> OTHER INFORMATION: Synthetic

<400> SEQUENCE: 146
aagaggagau gguggagac					19

<210> SEQ ID NO 147
<211> LENGTH: 19
<212> TYPE: RNA
<213> ORGANISM: Artificial Sequence
<220> FEATURE:
<223> OTHER INFORMATION: Synthetic

<400> SEQUENCE: 147
cggaggcuca gcagugguc					19

<210> SEQ ID NO 148
<211> LENGTH: 19
<212> TYPE: RNA
<213> ORGANISM: Artificial Sequence
<220> FEATURE:
<223> OTHER INFORMATION: Synthetic

<400> SEQUENCE: 148
cuugaggggu aaaggacuu					19

<210> SEQ ID NO 149
<211> LENGTH: 19
<212> TYPE: RNA
<213> ORGANISM: Artificial Sequence
<220> FEATURE:
<223> OTHER INFORMATION: Synthetic

<400> SEQUENCE: 149
uagaugccca gaugaagag					19

<210> SEQ ID NO 150
<211> LENGTH: 19
<212> TYPE: RNA
<213> ORGANISM: Artificial Sequence
<220> FEATURE:
<223> OTHER INFORMATION: Synthetic

<400> SEQUENCE: 150
gggaaagcug acaucugca					19

<210> SEQ ID NO 151
<211> LENGTH: 19
<212> TYPE: RNA
<213> ORGANISM: Artificial Sequence
<220> FEATURE:
<223> OTHER INFORMATION: Synthetic

<400> SEQUENCE: 151
agggaaccca cuuugaggc					19

```
<210> SEQ ID NO 152
<211> LENGTH: 19
<212> TYPE: RNA
<213> ORGANISM: Artificial Sequence
<220> FEATURE:
<223> OTHER INFORMATION: Synthetic

<400> SEQUENCE: 152
cugaggccau ggcaggaca                                              19

<210> SEQ ID NO 153
<211> LENGTH: 19
<212> TYPE: RNA
<213> ORGANISM: Artificial Sequence
<220> FEATURE:
<223> OTHER INFORMATION: Synthetic

<400> SEQUENCE: 153
agcugcugug gggugcaga                                              19

<210> SEQ ID NO 154
<211> LENGTH: 19
<212> TYPE: RNA
<213> ORGANISM: Artificial Sequence
<220> FEATURE:
<223> OTHER INFORMATION: Synthetic

<400> SEQUENCE: 154
aggcagaaga ugaaggaca                                              19

<210> SEQ ID NO 155
<211> LENGTH: 19
<212> TYPE: RNA
<213> ORGANISM: Artificial Sequence
<220> FEATURE:
<223> OTHER INFORMATION: Synthetic

<400> SEQUENCE: 155
aaaaggaagg gaaaacuga                                              19

<210> SEQ ID NO 156
<211> LENGTH: 19
<212> TYPE: RNA
<213> ORGANISM: Artificial Sequence
<220> FEATURE:
<223> OTHER INFORMATION: Synthetic

<400> SEQUENCE: 156
auggccaacc uagagcagc                                              19

<210> SEQ ID NO 157
<211> LENGTH: 19
<212> TYPE: RNA
<213> ORGANISM: Artificial Sequence
<220> FEATURE:
<223> OTHER INFORMATION: Synthetic

<400> SEQUENCE: 157
caaggagcag ggcuuggag                                              19

<210> SEQ ID NO 158
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 158
gcucgggugg uggagauga                                               19

<210> SEQ ID NO 159
<211> LENGTH: 19
<212> TYPE: RNA
<213> ORGANISM: Artificial Sequence
<220> FEATURE:
<223> OTHER INFORMATION: Synthetic

<400> SEQUENCE: 159
acaaggacac uguggguc                                                19

<210> SEQ ID NO 160
<211> LENGTH: 19
<212> TYPE: RNA
<213> ORGANISM: Artificial Sequence
<220> FEATURE:
<223> OTHER INFORMATION: Synthetic

<400> SEQUENCE: 160 cuggucccc agaacucug                                                19

<210> SEQ ID NO 161
<211> LENGTH: 19
<212> TYPE: RNA
<213> ORGANISM: Artificial Sequence
<220> FEATURE:
<223> OTHER INFORMATION: Synthetic

<400> SEQUENCE: 161
ggagcuacag gccacucua                                               19

<210> SEQ ID NO 162
<211> LENGTH: 19
<212> TYPE: RNA
<213> ORGANISM: Artificial Sequence
<220> FEATURE:
<223> OTHER INFORMATION: Synthetic

<400> SEQUENCE: 162
aggcccaagg gcuaguccu                                               19

<210> SEQ ID NO 163
<211> LENGTH: 19
<212> TYPE: RNA
<213> ORGANISM: Artificial Sequence
<220> FEATURE:
<223> OTHER INFORMATION: Synthetic

<400> SEQUENCE: 163
ucuuccccag uccccucag                                               19

<210> SEQ ID NO 164
<211> LENGTH: 19
<212> TYPE: RNA
<213> ORGANISM: Artificial Sequence
<220> FEATURE:
<223> OTHER INFORMATION: Synthetic

<400> SEQUENCE: 164 gaggccccg ccagcccca                                                19

<210> SEQ ID NO 165
<211> LENGTH: 19
```

<212> TYPE: RNA
<213> ORGANISM: Artificial Sequence
<220> FEATURE:
<223> OTHER INFORMATION: Synthetic

<400> SEQUENCE: 165
accuugaaag cagcauaca                                                19

<210> SEQ ID NO 166
<211> LENGTH: 19
<212> TYPE: RNA
<213> ORGANISM: Artificial Sequence
<220> FEATURE:
<223> OTHER INFORMATION: Synthetic

<400> SEQUENCE: 166
aggggaaggc uuggaccaa                                                19

<210> SEQ ID NO 167
<211> LENGTH: 19
<212> TYPE: RNA
<213> ORGANISM: Artificial Sequence
<220> FEATURE:
<223> OTHER INFORMATION: Synthetic

<400> SEQUENCE: 167
agcugggcga ccaagcaca                                                19

<210> SEQ ID NO 168
<211> LENGTH: 19
<212> TYPE: RNA
<213> ORGANISM: Artificial Sequence
<220> FEATURE:
<223> OTHER INFORMATION: Synthetic

<400> SEQUENCE: 168
auggggcagg aacacaugg                                                19

<210> SEQ ID NO 169
<211> LENGTH: 19
<212> TYPE: RNA
<213> ORGANISM: Artificial Sequence
<220> FEATURE:
<223> OTHER INFORMATION: Synthetic

<400> SEQUENCE: 169
guaaaggggu ggggaauau                                                19

<210> SEQ ID NO 170
<211> LENGTH: 19
<212> TYPE: RNA
<213> ORGANISM: Artificial Sequence
<220> FEATURE:
<223> OTHER INFORMATION: Synthetic

<400> SEQUENCE: 170
ugggagggag uguggugug                                                19

<210> SEQ ID NO 171
<211> LENGTH: 19
<212> TYPE: RNA
<213> ORGANISM: Artificial Sequence
<220> FEATURE:
<223> OTHER INFORMATION: Synthetic

<400> SEQUENCE: 171 ggauggggu gaugcaggg　　　　　　　　　　　　　　　　　　　　19

<210> SEQ ID NO 172
<211> LENGTH: 19
<212> TYPE: RNA
<213> ORGANISM: Artificial Sequence
<220> FEATURE:
<223> OTHER INFORMATION: Synthetic

<400> SEQUENCE: 172
gacugagggg aacccuggg　　　　　　　　　　　　　　　　　　　　19

<210> SEQ ID NO 173
<211> LENGTH: 19
<212> TYPE: RNA
<213> ORGANISM: Artificial Sequence
<220> FEATURE:
<223> OTHER INFORMATION: Synthetic

<400> SEQUENCE: 173
gacaggcaca ggcugggca　　　　　　　　　　　　　　　　　　　　19

<210> SEQ ID NO 174
<211> LENGTH: 19
<212> TYPE: RNA
<213> ORGANISM: Artificial Sequence
<220> FEATURE:
<223> OTHER INFORMATION: Synthetic

<400> SEQUENCE: 174
agaggcacag ggcagugca　　　　　　　　　　　　　　　　　　　　19

<210> SEQ ID NO 175
<211> LENGTH: 19
<212> TYPE: RNA
<213> ORGANISM: Artificial Sequence
<220> FEATURE:
<223> OTHER INFORMATION: Synthetic

<400> SEQUENCE: 175
aggggacucu gcagugggg　　　　　　　　　　　　　　　　　　　　19

<210> SEQ ID NO 176
<211> LENGTH: 19
<212> TYPE: RNA
<213> ORGANISM: Artificial Sequence
<220> FEATURE:
<223> OTHER INFORMATION: Synthetic

<400> SEQUENCE: 176
gucgggaagu gaguuucuu　　　　　　　　　　　　　　　　　　　　19

<210> SEQ ID NO 177
<211> LENGTH: 19
<212> TYPE: RNA
<213> ORGANISM: Artificial Sequence
<220> FEATURE:
<223> OTHER INFORMATION: Synthetic

<400> SEQUENCE: 177
uugcagugag cagugcagu　　　　　　　　　　　　　　　　　　　　19

<210> SEQ ID NO 178
<211> LENGTH: 19
<212> TYPE: RNA
<213> ORGANISM: Artificial Sequence

```
<220> FEATURE:
<223> OTHER INFORMATION: Synthetic

<400> SEQUENCE: 178
uggaagucgg gcacagagg                                                19

<210> SEQ ID NO 179
<211> LENGTH: 19
<212> TYPE: RNA
<213> ORGANISM: Artificial Sequence
<220> FEATURE:
<223> OTHER INFORMATION: Synthetic

<400> SEQUENCE: 179
guagcagaca gaugugaag                                                19

<210> SEQ ID NO 180
<211> LENGTH: 19
<212> TYPE: RNA
<213> ORGANISM: Artificial Sequence
<220> FEATURE:
<223> OTHER INFORMATION: Synthetic

<400> SEQUENCE: 180
gcagugguga aggccaugu                                                19

<210> SEQ ID NO 181
<211> LENGTH: 19
<212> TYPE: RNA
<213> ORGANISM: Artificial Sequence
<220> FEATURE:
<223> OTHER INFORMATION: Synthetic

<400> SEQUENCE: 181
uagcaagugg ggaaauaca                                                19

<210> SEQ ID NO 182
<211> LENGTH: 19
<212> TYPE: RNA
<213> ORGANISM: Artificial Sequence
<220> FEATURE:
<223> OTHER INFORMATION: Synthetic

<400> SEQUENCE: 182
auccaaaggg ccugggagu                                                19

<210> SEQ ID NO 183
<211> LENGTH: 19
<212> TYPE: RNA
<213> ORGANISM: Artificial Sequence
<220> FEATURE:
<223> OTHER INFORMATION: Synthetic

<400> SEQUENCE: 183 uugggggug cccaacgca                                                 19

<210> SEQ ID NO 184
<211> LENGTH: 19
<212> TYPE: RNA
<213> ORGANISM: Artificial Sequence
<220> FEATURE:
<223> OTHER INFORMATION: Synthetic

<400> SEQUENCE: 184
aauccuuggg ggugcaggg                                                19
```

```
<210> SEQ ID NO 185
<211> LENGTH: 19
<212> TYPE: RNA
<213> ORGANISM: Artificial Sequence
<220> FEATURE:
<223> OTHER INFORMATION: Synthetic

<400> SEQUENCE: 185
guggagcaga aagugaagg                                                 19

<210> SEQ ID NO 186
<211> LENGTH: 19
<212> TYPE: RNA
<213> ORGANISM: Artificial Sequence
<220> FEATURE:
<223> OTHER INFORMATION: Synthetic

<400> SEQUENCE: 186
gagggacacg ugcaagagu                                                 19

<210> SEQ ID NO 187
<211> LENGTH: 19
<212> TYPE: RNA
<213> ORGANISM: Artificial Sequence
<220> FEATURE:
<223> OTHER INFORMATION: Synthetic

<400> SEQUENCE: 187
uggugugcau ggugguguyg                                                19

<210> SEQ ID NO 188
<211> LENGTH: 19
<212> TYPE: RNA
<213> ORGANISM: Artificial Sequence
<220> FEATURE:
<223> OTHER INFORMATION: Synthetic

<400> SEQUENCE: 188
gacaugagga ccguuccua                                                 19

<210> SEQ ID NO 189
<211> LENGTH: 19
<212> TYPE: RNA
<213> ORGANISM: Artificial Sequence
<220> FEATURE:
<223> OTHER INFORMATION: Synthetic

<400> SEQUENCE: 189
aggaugggac aguggguca                                                 19

<210> SEQ ID NO 190
<211> LENGTH: 19
<212> TYPE: RNA
<213> ORGANISM: Artificial Sequence
<220> FEATURE:
<223> OTHER INFORMATION: Synthetic

<400> SEQUENCE: 190
aggcaggaca aggagaaag                                                 19

<210> SEQ ID NO 191
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 191
gcagggcaga augaugccu                                              19

<210> SEQ ID NO 192
<211> LENGTH: 19
<212> TYPE: RNA
<213> ORGANISM: Artificial Sequence
<220> FEATURE:
<223> OTHER INFORMATION: Synthetic

<400> SEQUENCE: 192
uagaggacca caucaggca                                              19

<210> SEQ ID NO 193
<211> LENGTH: 19
<212> TYPE: RNA
<213> ORGANISM: Artificial Sequence
<220> FEATURE:
<223> OTHER INFORMATION: Synthetic

<400> SEQUENCE: 193
auggcugaca gcuugugcc                                              19

<210> SEQ ID NO 194
<211> LENGTH: 19
<212> TYPE: RNA
<213> ORGANISM: Artificial Sequence
<220> FEATURE:
<223> OTHER INFORMATION: Synthetic

<400> SEQUENCE: 194
ccaugggcug uggcguaug                                              19

<210> SEQ ID NO 195
<211> LENGTH: 19
<212> TYPE: RNA
<213> ORGANISM: Artificial Sequence
<220> FEATURE:
<223> OTHER INFORMATION: Synthetic

<400> SEQUENCE: 195
gucagaucgc aggguagga                                              19

<210> SEQ ID NO 196
<211> LENGTH: 19
<212> TYPE: RNA
<213> ORGANISM: Artificial Sequence
<220> FEATURE:
<223> OTHER INFORMATION: Synthetic

<400> SEQUENCE: 196
aacgagucug gccuggugc                                              19

<210> SEQ ID NO 197
<211> LENGTH: 19
<212> TYPE: RNA
<213> ORGANISM: Artificial Sequence
<220> FEATURE:
<223> OTHER INFORMATION: Synthetic

<400> SEQUENCE: 197
ccggcccagu guuccuca                                               19

<210> SEQ ID NO 198
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 198
agcucauccg cccucuguu                                                   19

<210> SEQ ID NO 199
<211> LENGTH: 19
<212> TYPE: RNA
<213> ORGANISM: Artificial Sequence
<220> FEATURE:
<223> OTHER INFORMATION: Synthetic

<400> SEQUENCE: 199
ugcucccuag cauuccagg                                                   19

<210> SEQ ID NO 200
<211> LENGTH: 19
<212> TYPE: RNA
<213> ORGANISM: Artificial Sequence
<220> FEATURE:
<223> OTHER INFORMATION: Synthetic

<400> SEQUENCE: 200
gagccaucuu ggacucucc                                                   19

<210> SEQ ID NO 201
<211> LENGTH: 19
<212> TYPE: RNA
<213> ORGANISM: Artificial Sequence
<220> FEATURE:
<223> OTHER INFORMATION: Synthetic

<400> SEQUENCE: 201
cuccccaggu uugaaaggc                                                   19

<210> SEQ ID NO 202
<211> LENGTH: 19
<212> TYPE: RNA
<213> ORGANISM: Artificial Sequence
<220> FEATURE:
<223> OTHER INFORMATION: Synthetic

<400> SEQUENCE: 202
ccaucagauu agcagggac                                                   19

<210> SEQ ID NO 203
<211> LENGTH: 19
<212> TYPE: RNA
<213> ORGANISM: Artificial Sequence
<220> FEATURE:
<223> OTHER INFORMATION: Synthetic

<400> SEQUENCE: 203 cggggguguag ggcaucacc                                                  19

<210> SEQ ID NO 204
<211> LENGTH: 19
<212> TYPE: RNA
<213> ORGANISM: Artificial Sequence
<220> FEATURE:
<223> OTHER INFORMATION: Synthetic

<400> SEQUENCE: 204
```

```
ccaagguucc uucucuuaa                                              19

<210> SEQ ID NO 205
<211> LENGTH: 19
<212> TYPE: RNA
<213> ORGANISM: Artificial Sequence
<220> FEATURE:
<223> OTHER INFORMATION: Synthetic

<400> SEQUENCE: 205
aacuaagggu gggggaucu                                              19

<210> SEQ ID NO 206
<211> LENGTH: 19
<212> TYPE: RNA
<213> ORGANISM: Artificial Sequence
<220> FEATURE:
<223> OTHER INFORMATION: Synthetic

<400> SEQUENCE: 206
ugaauguuuu uauguugac                                              19

<210> SEQ ID NO 207
<211> LENGTH: 19
<212> TYPE: RNA
<213> ORGANISM: Artificial Sequence
<220> FEATURE:
<223> OTHER INFORMATION: Synthetic

<400> SEQUENCE: 207
cuguucuuga cuaaauuuu                                              19

<210> SEQ ID NO 208
<211> LENGTH: 19
<212> TYPE: RNA
<213> ORGANISM: Artificial Sequence
<220> FEATURE:
<223> OTHER INFORMATION: Synthetic

<400> SEQUENCE: 208
ucaagaguuu cagaagcaa                                              19

<210> SEQ ID NO 209
<211> LENGTH: 19
<212> TYPE: RNA
<213> ORGANISM: Artificial Sequence
<220> FEATURE:
<223> OTHER INFORMATION: Synthetic

<400> SEQUENCE: 209
acaggacaga ccagacguu                                              19

<210> SEQ ID NO 210
<211> LENGTH: 19
<212> TYPE: RNA
<213> ORGANISM: Artificial Sequence
<220> FEATURE:
<223> OTHER INFORMATION: Synthetic

<400> SEQUENCE: 210
uucauucuac ccuggggcg                                              19

<210> SEQ ID NO 211
<211> LENGTH: 19
<212> TYPE: RNA
```

<213> ORGANISM: Artificial Sequence
<220> FEATURE:
<223> OTHER INFORMATION: Synthetic

<400> SEQUENCE: 211
gaacagaacu ucuuccucc                                                    19

<210> SEQ ID NO 212
<211> LENGTH: 19
<212> TYPE: RNA
<213> ORGANISM: Artificial Sequence
<220> FEATURE:
<223> OTHER INFORMATION: Synthetic

<400> SEQUENCE: 212
ccaaacaaug acuuccugc                                                    19

<210> SEQ ID NO 213
<211> LENGTH: 19
<212> TYPE: RNA
<213> ORGANISM: Artificial Sequence
<220> FEATURE:
<223> OTHER INFORMATION: Synthetic

<400> SEQUENCE: 213
ccauguuuga ugggacag                                                     19

<210> SEQ ID NO 214
<211> LENGTH: 19
<212> TYPE: RNA
<213> ORGANISM: Artificial Sequence
<220> FEATURE:
<223> OTHER INFORMATION: Synthetic

<400> SEQUENCE: 214
gcuaccacug uccucugcc                                                    19

<210> SEQ ID NO 215
<211> LENGTH: 19
<212> TYPE: RNA
<213> ORGANISM: Artificial Sequence
<220> FEATURE:
<223> OTHER INFORMATION: Synthetic

<400> SEQUENCE: 215
ccccauuccc cuuucagcu                                                    19

<210> SEQ ID NO 216
<211> LENGTH: 19
<212> TYPE: RNA
<213> ORGANISM: Artificial Sequence
<220> FEATURE:
<223> OTHER INFORMATION: Synthetic

<400> SEQUENCE: 216
ucccaugagc augcauagu                                                    19

<210> SEQ ID NO 217
<211> LENGTH: 19
<212> TYPE: RNA
<213> ORGANISM: Artificial Sequence
<220> FEATURE:
<223> OTHER INFORMATION: Synthetic

<400> SEQUENCE: 217
uucaccagac caauggccu                                                    19

-continued

<210> SEQ ID NO 218
<211> LENGTH: 19
<212> TYPE: RNA
<213> ORGANISM: Artificial Sequence
<220> FEATURE:
<223> OTHER INFORMATION: Synthetic

<400> SEQUENCE: 218
uagccauucu cuaaguccc                                                19

<210> SEQ ID NO 219
<211> LENGTH: 19
<212> TYPE: RNA
<213> ORGANISM: Artificial Sequence
<220> FEATURE:
<223> OTHER INFORMATION: Synthetic

<400> SEQUENCE: 219
cauccuggaa gaaguuauu                                                19

<210> SEQ ID NO 220
<211> LENGTH: 19
<212> TYPE: RNA
<213> ORGANISM: Artificial Sequence
<220> FEATURE:
<223> OTHER INFORMATION: Synthetic

<400> SEQUENCE: 220
uucuucaaga gcugcaccu                                                19

<210> SEQ ID NO 221
<211> LENGTH: 19
<212> TYPE: RNA
<213> ORGANISM: Artificial Sequence
<220> FEATURE:
<223> OTHER INFORMATION: Synthetic

<400> SEQUENCE: 221
ucuccuccua gcauuaguu                                                19

<210> SEQ ID NO 222
<211> LENGTH: 19
<212> TYPE: RNA
<213> ORGANISM: Artificial Sequence
<220> FEATURE:
<223> OTHER INFORMATION: Synthetic

<400> SEQUENCE: 222
uuagaucaac ucaaggagu                                                19

<210> SEQ ID NO 223
<211> LENGTH: 19
<212> TYPE: RNA
<213> ORGANISM: Artificial Sequence
<220> FEATURE:
<223> OTHER INFORMATION: Synthetic

<400> SEQUENCE: 223
uauuuauuaa uggcugcug                                                19

<210> SEQ ID NO 224
<211> LENGTH: 19
<212> TYPE: RNA
<213> ORGANISM: Artificial Sequence
<220> FEATURE:

```
<223> OTHER INFORMATION: Synthetic

<400> SEQUENCE: 224
gucuccaguu ucugggguu                                                  19

<210> SEQ ID NO 225
<211> LENGTH: 19
<212> TYPE: RNA
<213> ORGANISM: Artificial Sequence
<220> FEATURE:
<223> OTHER INFORMATION: Synthetic

<400> SEQUENCE: 225
uaagcacuaa ggacacaag                                                  19

<210> SEQ ID NO 226
<211> LENGTH: 19
<212> TYPE: RNA
<213> ORGANISM: Artificial Sequence
<220> FEATURE:
<223> OTHER INFORMATION: Synthetic

<400> SEQUENCE: 226
gaaucaauca gaccuucuc                                                  19

<210> SEQ ID NO 227
<211> LENGTH: 19
<212> TYPE: RNA
<213> ORGANISM: Artificial Sequence
<220> FEATURE:
<223> OTHER INFORMATION: Synthetic

<400> SEQUENCE: 227
cccugaacuu aagauagcc                                                  19

<210> SEQ ID NO 228
<211> LENGTH: 19
<212> TYPE: RNA
<213> ORGANISM: Artificial Sequence
<220> FEATURE:
<223> OTHER INFORMATION: Synthetic

<400> SEQUENCE: 228
cacaaucaga aaaggaca                                                   19

<210> SEQ ID NO 229
<211> LENGTH: 19
<212> TYPE: RNA
<213> ORGANISM: Artificial Sequence
<220> FEATURE:
<223> OTHER INFORMATION: Synthetic

<400> SEQUENCE: 229
aaggacauga gacaguggu                                                  19

<210> SEQ ID NO 230
<211> LENGTH: 19
<212> TYPE: RNA
<213> ORGANISM: Artificial Sequence
<220> FEATURE:
<223> OTHER INFORMATION: Synthetic

<400> SEQUENCE: 230
ugauggccau cagacagag                                                  19
```

```
<210> SEQ ID NO 231
<211> LENGTH: 19
<212> TYPE: RNA
<213> ORGANISM: Artificial Sequence
<220> FEATURE:
<223> OTHER INFORMATION: Synthetic

<400> SEQUENCE: 231
gacuucaaau gcugaugga                                                      19

<210> SEQ ID NO 232
<211> LENGTH: 19
<212> TYPE: RNA
<213> ORGANISM: Artificial Sequence
<220> FEATURE:
<223> OTHER INFORMATION: Synthetic

<400> SEQUENCE: 232
agggcagagg aaguacuua                                                      19

<210> SEQ ID NO 233
<211> LENGTH: 19
<212> TYPE: RNA
<213> ORGANISM: Artificial Sequence
<220> FEATURE:
<223> OTHER INFORMATION: Synthetic

<400> SEQUENCE: 233
agggagguug gugucagag                                                      19

<210> SEQ ID NO 234
<211> LENGTH: 19
<212> TYPE: RNA
<213> ORGANISM: Artificial Sequence
<220> FEATURE:
<223> OTHER INFORMATION: Synthetic

<400> SEQUENCE: 234
ggcaggagug ggggaucag                                                      19

<210> SEQ ID NO 235
<211> LENGTH: 19
<212> TYPE: RNA
<213> ORGANISM: Artificial Sequence
<220> FEATURE:
<223> OTHER INFORMATION: Synthetic

<400> SEQUENCE: 235
gggaaggugg auucuagga                                                      19

<210> SEQ ID NO 236
<211> LENGTH: 19
<212> TYPE: RNA
<213> ORGANISM: Artificial Sequence
<220> FEATURE:
<223> OTHER INFORMATION: Synthetic

<400> SEQUENCE: 236
aaaagggagu gccugaggu                                                      19

<210> SEQ ID NO 237
<211> LENGTH: 19
<212> TYPE: RNA
<213> ORGANISM: Artificial Sequence
<220> FEATURE:
<223> OTHER INFORMATION: Synthetic
```

-continued

```
<400> SEQUENCE: 237
uaggccuuag aagggggaug                                              19

<210> SEQ ID NO 238
<211> LENGTH: 19
<212> TYPE: RNA
<213> ORGANISM: Artificial Sequence
<220> FEATURE:
<223> OTHER INFORMATION: Synthetic

<400> SEQUENCE: 238
gagucagauu uuuacagag                                               19

<210> SEQ ID NO 239
<211> LENGTH: 19
<212> TYPE: RNA
<213> ORGANISM: Artificial Sequence
<220> FEATURE:
<223> OTHER INFORMATION: Synthetic

<400> SEQUENCE: 239
ggaggagggc agggcuugg                                               19

<210> SEQ ID NO 240
<211> LENGTH: 19
<212> TYPE: RNA
<213> ORGANISM: Artificial Sequence
<220> FEATURE:
<223> OTHER INFORMATION: Synthetic

<400> SEQUENCE: 240
gguccagugg aggaagaag                                               19

<210> SEQ ID NO 241
<211> LENGTH: 19
<212> TYPE: RNA
<213> ORGANISM: Artificial Sequence
<220> FEATURE:
<223> OTHER INFORMATION: Synthetic

<400> SEQUENCE: 241
ggaaggagag gcuuggaaa                                               19

<210> SEQ ID NO 242
<211> LENGTH: 19
<212> TYPE: RNA
<213> ORGANISM: Artificial Sequence
<220> FEATURE:
<223> OTHER INFORMATION: Synthetic

<400> SEQUENCE: 242
agccuugugu cuugggaaa                                               19

<210> SEQ ID NO 243
<211> LENGTH: 19
<212> TYPE: RNA
<213> ORGANISM: Artificial Sequence
<220> FEATURE:
<223> OTHER INFORMATION: Synthetic

<400> SEQUENCE: 243
aaaaaggccu uugagcaua                                               19

<210> SEQ ID NO 244
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 244 augguccag ccacucaga                                                    19

<210> SEQ ID NO 245
<211> LENGTH: 19
<212> TYPE: RNA
<213> ORGANISM: Artificial Sequence
<220> FEATURE:
<223> OTHER INFORMATION: Synthetic

<400> SEQUENCE: 245
aagugcaggg gccaugccu                                                   19

<210> SEQ ID NO 246
<211> LENGTH: 19
<212> TYPE: RNA
<213> ORGANISM: Artificial Sequence
<220> FEATURE:
<223> OTHER INFORMATION: Synthetic

<400> SEQUENCE: 246
uugguguucc aauaaguga                                                   19

<210> SEQ ID NO 247
<211> LENGTH: 19
<212> TYPE: RNA
<213> ORGANISM: Artificial Sequence
<220> FEATURE:
<223> OTHER INFORMATION: Synthetic

<400> SEQUENCE: 247
aauggaagca gugguggua                                                   19

<210> SEQ ID NO 248
<211> LENGTH: 19
<212> TYPE: RNA
<213> ORGANISM: Artificial Sequence
<220> FEATURE:
<223> OTHER INFORMATION: Synthetic

<400> SEQUENCE: 248
agcuacacug ggcagaguu                                                   19

<210> SEQ ID NO 249
<211> LENGTH: 19
<212> TYPE: RNA
<213> ORGANISM: Artificial Sequence
<220> FEATURE:
<223> OTHER INFORMATION: Synthetic

<400> SEQUENCE: 249
uggcagggug cugguucac                                                   19

<210> SEQ ID NO 250
<211> LENGTH: 19
<212> TYPE: RNA
<213> ORGANISM: Artificial Sequence
<220> FEATURE:
<223> OTHER INFORMATION: Synthetic

<400> SEQUENCE: 250
```

| | |
|---|---|
| cucugcccag cccugaaug | 19 |

```
<210> SEQ ID NO 251
<211> LENGTH: 19
<212> TYPE: RNA
<213> ORGANISM: Artificial Sequence
<220> FEATURE:
<223> OTHER INFORMATION: Synthetic

<400> SEQUENCE: 251
```

| | |
|---|---|
| gugugccuua aaggccccc | 19 |

```
<210> SEQ ID NO 252
<211> LENGTH: 19
<212> TYPE: RNA
<213> ORGANISM: Artificial Sequence
<220> FEATURE:
<223> OTHER INFORMATION: Synthetic

<400> SEQUENCE: 252
```

| | |
|---|---|
| cuacaagggg ccccauacg | 19 |

```
<210> SEQ ID NO 253
<211> LENGTH: 19
<212> TYPE: RNA
<213> ORGANISM: Artificial Sequence
<220> FEATURE:
<223> OTHER INFORMATION: Synthetic

<400> SEQUENCE: 253
```

| | |
|---|---|
| gacagagcuu uuaacuggu | 19 |

```
<210> SEQ ID NO 254
<211> LENGTH: 19
<212> TYPE: RNA
<213> ORGANISM: Artificial Sequence
<220> FEATURE:
<223> OTHER INFORMATION: Synthetic

<400> SEQUENCE: 254
```

| | |
|---|---|
| ugccuucccu guacccgca | 19 |

```
<210> SEQ ID NO 255
<211> LENGTH: 19
<212> TYPE: RNA
<213> ORGANISM: Artificial Sequence
<220> FEATURE:
<223> OTHER INFORMATION: Synthetic

<400> SEQUENCE: 255
```

| | |
|---|---|
| agcagccaca agugggccc | 19 |

```
<210> SEQ ID NO 256
<211> LENGTH: 19
<212> TYPE: RNA
<213> ORGANISM: Artificial Sequence
<220> FEATURE:
<223> OTHER INFORMATION: Synthetic

<400> SEQUENCE: 256
```

| | |
|---|---|
| cagacuauug cagccuccc | 19 |

```
<210> SEQ ID NO 257
<211> LENGTH: 19
<212> TYPE: RNA
<213> ORGANISM: Artificial Sequence
```

```
<220> FEATURE:
<223> OTHER INFORMATION: Synthetic

<400> SEQUENCE: 257
cauaaacaug ugagcaugu                                                        19

<210> SEQ ID NO 258
<211> LENGTH: 19
<212> TYPE: RNA
<213> ORGANISM: Artificial Sequence
<220> FEATURE:
<223> OTHER INFORMATION: Synthetic

<400> SEQUENCE: 258
uucugagugu gccaugaug                                                        19

<210> SEQ ID NO 259
<211> LENGTH: 19
<212> TYPE: RNA
<213> ORGANISM: Artificial Sequence
<220> FEATURE:
<223> OTHER INFORMATION: Synthetic

<400> SEQUENCE: 259
gugaguggac cuggcugga                                                        19

<210> SEQ ID NO 260
<211> LENGTH: 19
<212> TYPE: RNA
<213> ORGANISM: Artificial Sequence
<220> FEATURE:
<223> OTHER INFORMATION: Synthetic

<400> SEQUENCE: 260
aaucuucgga gagcgacug                                                        19

<210> SEQ ID NO 261
<211> LENGTH: 19
<212> TYPE: RNA
<213> ORGANISM: Artificial Sequence
<220> FEATURE:
<223> OTHER INFORMATION: Synthetic

<400> SEQUENCE: 261
gagguguuca aaucgaauc                                                        19

<210> SEQ ID NO 262
<211> LENGTH: 19
<212> TYPE: RNA
<213> ORGANISM: Artificial Sequence
<220> FEATURE:
<223> OTHER INFORMATION: Synthetic

<400> SEQUENCE: 262
cucccaggag gcuuccuuc                                                        19

<210> SEQ ID NO 263
<211> LENGTH: 19
<212> TYPE: RNA
<213> ORGANISM: Artificial Sequence
<220> FEATURE:
<223> OTHER INFORMATION: Synthetic

<400> SEQUENCE: 263
ccagcccccu auucuggua                                                        19
```

```
<210> SEQ ID NO 264
<211> LENGTH: 19
<212> TYPE: RNA
<213> ORGANISM: Artificial Sequence
<220> FEATURE:
<223> OTHER INFORMATION: Synthetic

<400> SEQUENCE: 264
aacuaccagg aggcuuccu                                                    19

<210> SEQ ID NO 265
<211> LENGTH: 19
<212> TYPE: RNA
<213> ORGANISM: Artificial Sequence
<220> FEATURE:
<223> OTHER INFORMATION: Synthetic

<400> SEQUENCE: 265
uuccagcccc cuauucugg                                                    19

<210> SEQ ID NO 266
<211> LENGTH: 19
<212> TYPE: RNA
<213> ORGANISM: Artificial Sequence
<220> FEATURE:
<223> OTHER INFORMATION: Synthetic

<400> SEQUENCE: 266
guaacuacca aaaucccuc                                                    19

<210> SEQ ID NO 267
<211> LENGTH: 19
<212> TYPE: RNA
<213> ORGANISM: Artificial Sequence
<220> FEATURE:
<223> OTHER INFORMATION: Synthetic

<400> SEQUENCE: 267
cgggugcaag uguaggggu                                                    19

<210> SEQ ID NO 268
<211> LENGTH: 19
<212> TYPE: RNA
<213> ORGANISM: Artificial Sequence
<220> FEATURE:
<223> OTHER INFORMATION: Synthetic

<400> SEQUENCE: 268
uagagaugga aggaugaga                                                    19

<210> SEQ ID NO 269
<211> LENGTH: 19
<212> TYPE: RNA
<213> ORGANISM: Artificial Sequence
<220> FEATURE:
<223> OTHER INFORMATION: Synthetic

<400> SEQUENCE: 269
aggugaaauu gaccuuuug                                                    19

<210> SEQ ID NO 270
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 270
gaaagcaaag cucuggcuc                                                19

<210> SEQ ID NO 271
<211> LENGTH: 19
<212> TYPE: RNA
<213> ORGANISM: Artificial Sequence
<220> FEATURE:
<223> OTHER INFORMATION: Synthetic

<400> SEQUENCE: 271
cacaggcccc aaacuacca                                                19

<210> SEQ ID NO 272
<211> LENGTH: 19
<212> TYPE: RNA
<213> ORGANISM: Artificial Sequence
<220> FEATURE:
<223> OTHER INFORMATION: Synthetic

<400> SEQUENCE: 272
agccguaucu agcauaucc                                                19

<210> SEQ ID NO 273
<211> LENGTH: 19
<212> TYPE: RNA
<213> ORGANISM: Artificial Sequence
<220> FEATURE:
<223> OTHER INFORMATION: Synthetic

<400> SEQUENCE: 273
cccacccucc acccacuac                                                19

<210> SEQ ID NO 274
<211> LENGTH: 19
<212> TYPE: RNA
<213> ORGANISM: Artificial Sequence
<220> FEATURE:
<223> OTHER INFORMATION: Synthetic

<400> SEQUENCE: 274
ccuccuccaa caaaggagu                                                19

<210> SEQ ID NO 275
<211> LENGTH: 19
<212> TYPE: RNA
<213> ORGANISM: Artificial Sequence
<220> FEATURE:
<223> OTHER INFORMATION: Synthetic

<400> SEQUENCE: 275
ucaacucagu ugaaaaaac                                                19

<210> SEQ ID NO 276
<211> LENGTH: 19
<212> TYPE: RNA
<213> ORGANISM: Artificial Sequence
<220> FEATURE:
<223> OTHER INFORMATION: Synthetic

<400> SEQUENCE: 276
cugguccuuu ggccuaucc                                                19

<210> SEQ ID NO 277
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 277
caugggucaa aguccaccu                                                    19

<210> SEQ ID NO 278
<211> LENGTH: 19
<212> TYPE: RNA
<213> ORGANISM: Artificial Sequence
<220> FEATURE:
<223> OTHER INFORMATION: Synthetic

<400> SEQUENCE: 278
ucuccugggg gccuggaga                                                    19

<210> SEQ ID NO 279
<211> LENGTH: 19
<212> TYPE: RNA
<213> ORGANISM: Artificial Sequence
<220> FEATURE:
<223> OTHER INFORMATION: Synthetic

<400> SEQUENCE: 279
aggacugagc cuacggaaa                                                    19

<210> SEQ ID NO 280
<211> LENGTH: 19
<212> TYPE: RNA
<213> ORGANISM: Artificial Sequence
<220> FEATURE:
<223> OTHER INFORMATION: Synthetic

<400> SEQUENCE: 280
aggggauacc uucccacuc                                                    19

<210> SEQ ID NO 281
<211> LENGTH: 19
<212> TYPE: RNA
<213> ORGANISM: Artificial Sequence
<220> FEATURE:
<223> OTHER INFORMATION: Synthetic

<400> SEQUENCE: 281
cagcacugcu ucacacagg                                                    19

<210> SEQ ID NO 282
<211> LENGTH: 19
<212> TYPE: RNA
<213> ORGANISM: Artificial Sequence
<220> FEATURE:
<223> OTHER INFORMATION: Synthetic

<400> SEQUENCE: 282
gcccccugcc uggggcucu                                                    19

<210> SEQ ID NO 283
<211> LENGTH: 19
<212> TYPE: RNA
<213> ORGANISM: Artificial Sequence
<220> FEATURE:
<223> OTHER INFORMATION: Synthetic

<400> SEQUENCE: 283
```
uccaaggagc cuucuucac                                                19

<210> SEQ ID NO 284
<211> LENGTH: 19
<212> TYPE: RNA
<213> ORGANISM: Artificial Sequence
<220> FEATURE:
<223> OTHER INFORMATION: Synthetic

<400> SEQUENCE: 284
cccacuucca gcuccacuu                                                19

<210> SEQ ID NO 285
<211> LENGTH: 19
<212> TYPE: RNA
<213> ORGANISM: Artificial Sequence
<220> FEATURE:
<223> OTHER INFORMATION: Synthetic

<400> SEQUENCE: 285
ucugcaaggu uaagucaag                                                19

<210> SEQ ID NO 286
<211> LENGTH: 19
<212> TYPE: RNA
<213> ORGANISM: Artificial Sequence
<220> FEATURE:
<223> OTHER INFORMATION: Synthetic

<400> SEQUENCE: 286
gugagaacga ugagaaaua                                                19

<210> SEQ ID NO 287
<211> LENGTH: 19
<212> TYPE: RNA
<213> ORGANISM: Artificial Sequence
<220> FEATURE:
<223> OTHER INFORMATION: Synthetic

<400> SEQUENCE: 287
agggagaugg ugucuccuu                                                19

<210> SEQ ID NO 288
<211> LENGTH: 19
<212> TYPE: RNA
<213> ORGANISM: Artificial Sequence
<220> FEATURE:
<223> OTHER INFORMATION: Synthetic

<400> SEQUENCE: 288 uaagccuug aucugccug                                                 19

<210> SEQ ID NO 289
<211> LENGTH: 19
<212> TYPE: RNA
<213> ORGANISM: Artificial Sequence
<220> FEATURE:
<223> OTHER INFORMATION: Synthetic

<400> SEQUENCE: 289
gucuguggaa ugggagguu                                                19

<210> SEQ ID NO 290
<211> LENGTH: 19
<212> TYPE: RNA

```
<213> ORGANISM: Artificial Sequence
<220> FEATURE:
<223> OTHER INFORMATION: Synthetic

<400> SEQUENCE: 290
uggauuagcu gcgcugagg                                                    19

<210> SEQ ID NO 291
<211> LENGTH: 19
<212> TYPE: RNA
<213> ORGANISM: Artificial Sequence
<220> FEATURE:
<223> OTHER INFORMATION: Synthetic

<400> SEQUENCE: 291
gucccaucca cagcuggug                                                    19

<210> SEQ ID NO 292
<211> LENGTH: 19
<212> TYPE: RNA
<213> ORGANISM: Artificial Sequence
<220> FEATURE:
<223> OTHER INFORMATION: Synthetic

<400> SEQUENCE: 292
gcucagcugc uugaagggg                                                    19

<210> SEQ ID NO 293
<211> LENGTH: 19
<212> TYPE: RNA
<213> ORGANISM: Artificial Sequence
<220> FEATURE:
<223> OTHER INFORMATION: Synthetic

<400> SEQUENCE: 293
gagacucccu ccucuguaa                                                    19

<210> SEQ ID NO 294
<211> LENGTH: 19
<212> TYPE: RNA
<213> ORGANISM: Artificial Sequence
<220> FEATURE:
<223> OTHER INFORMATION: Synthetic

<400> SEQUENCE: 294
acuucuuucu gggggauug                                                    19

<210> SEQ ID NO 295
<211> LENGTH: 19
<212> TYPE: RNA
<213> ORGANISM: Artificial Sequence
<220> FEATURE:
<223> OTHER INFORMATION: Synthetic

<400> SEQUENCE: 295 gggguggca guaccuauc                                                     19

<210> SEQ ID NO 296
<211> LENGTH: 19
<212> TYPE: RNA
<213> ORGANISM: Artificial Sequence
<220> FEATURE:
<223> OTHER INFORMATION: Synthetic

<400> SEQUENCE: 296
ccccaguccc cuccuagcu                                                    19
```

```
<210> SEQ ID NO 297
<211> LENGTH: 19
<212> TYPE: RNA
<213> ORGANISM: Artificial Sequence
<220> FEATURE:
<223> OTHER INFORMATION: Synthetic

<400> SEQUENCE: 297
uugacuuuag ugguuucca                                                19

<210> SEQ ID NO 298
<211> LENGTH: 19
<212> TYPE: RNA
<213> ORGANISM: Artificial Sequence
<220> FEATURE:
<223> OTHER INFORMATION: Synthetic

<400> SEQUENCE: 298
aauguagaag uuaacaaag                                                19

<210> SEQ ID NO 299
<211> LENGTH: 19
<212> TYPE: RNA
<213> ORGANISM: Artificial Sequence
<220> FEATURE:
<223> OTHER INFORMATION: Synthetic

<400> SEQUENCE: 299
guaugcccca uuccuguga                                                19

<210> SEQ ID NO 300
<211> LENGTH: 19
<212> TYPE: RNA
<213> ORGANISM: Artificial Sequence
<220> FEATURE:
<223> OTHER INFORMATION: Synthetic

<400> SEQUENCE: 300
acaaaagcac aaccauucu                                                19

<210> SEQ ID NO 301
<211> LENGTH: 19
<212> TYPE: RNA
<213> ORGANISM: Artificial Sequence
<220> FEATURE:
<223> OTHER INFORMATION: Synthetic

<400> SEQUENCE: 301
ugaaguuacu ggagcaugg                                                19

<210> SEQ ID NO 302
<211> LENGTH: 19
<212> TYPE: RNA
<213> ORGANISM: Artificial Sequence
<220> FEATURE:
<223> OTHER INFORMATION: Synthetic

<400> SEQUENCE: 302
ggcucagcuc auccucccu                                                19

<210> SEQ ID NO 303
<211> LENGTH: 19
<212> TYPE: RNA
<213> ORGANISM: Artificial Sequence
<220> FEATURE:
```

<223> OTHER INFORMATION: Synthetic

<400> SEQUENCE: 303 ucuggcccu ucucccaug                                                  19

<210> SEQ ID NO 304
<211> LENGTH: 19
<212> TYPE: RNA
<213> ORGANISM: Artificial Sequence
<220> FEATURE:
<223> OTHER INFORMATION: Synthetic

<400> SEQUENCE: 304
ggggacaucu cggcccagc                                                 19

<210> SEQ ID NO 305
<211> LENGTH: 19
<212> TYPE: RNA
<213> ORGANISM: Artificial Sequence
<220> FEATURE:
<223> OTHER INFORMATION: Synthetic

<400> SEQUENCE: 305
caccccuauc ccauuucca                                                 19

<210> SEQ ID NO 306
<211> LENGTH: 19
<212> TYPE: RNA
<213> ORGANISM: Artificial Sequence
<220> FEATURE:
<223> OTHER INFORMATION: Synthetic

<400> SEQUENCE: 306
agaguucuuc cuuccccau                                                 19

<210> SEQ ID NO 307
<211> LENGTH: 19
<212> TYPE: RNA
<213> ORGANISM: Artificial Sequence
<220> FEATURE:
<223> OTHER INFORMATION: Synthetic

<400> SEQUENCE: 307
ucugggccuu cauaaaaug                                                 19

<210> SEQ ID NO 308
<211> LENGTH: 19
<212> TYPE: RNA
<213> ORGANISM: Artificial Sequence
<220> FEATURE:
<223> OTHER INFORMATION: Synthetic

<400> SEQUENCE: 308 gcagggaag ccagacugg                                                  19

<210> SEQ ID NO 309
<211> LENGTH: 19
<212> TYPE: RNA
<213> ORGANISM: Artificial Sequence
<220> FEATURE:
<223> OTHER INFORMATION: Synthetic

<400> SEQUENCE: 309
gucucaggag cgcuaaagc                                                 19

```
<210> SEQ ID NO 310
<211> LENGTH: 19
<212> TYPE: RNA
<213> ORGANISM: Artificial Sequence
<220> FEATURE:
<223> OTHER INFORMATION: Synthetic

<400> SEQUENCE: 310
cccuuccgug ggggucgu                                                 19

<210> SEQ ID NO 311
<211> LENGTH: 19
<212> TYPE: RNA
<213> ORGANISM: Artificial Sequence
<220> FEATURE:
<223> OTHER INFORMATION: Synthetic

<400> SEQUENCE: 311
ucuuucuggg acuagcccu                                                19

<210> SEQ ID NO 312
<211> LENGTH: 19
<212> TYPE: RNA
<213> ORGANISM: Artificial Sequence
<220> FEATURE:
<223> OTHER INFORMATION: Synthetic

<400> SEQUENCE: 312
ugcuguuuag gaccuggga                                                19

<210> SEQ ID NO 313
<211> LENGTH: 19
<212> TYPE: RNA
<213> ORGANISM: Artificial Sequence
<220> FEATURE:
<223> OTHER INFORMATION: Synthetic

<400> SEQUENCE: 313
accacaaugg gguaccugc                                                19

<210> SEQ ID NO 314
<211> LENGTH: 19
<212> TYPE: RNA
<213> ORGANISM: Artificial Sequence
<220> FEATURE:
<223> OTHER INFORMATION: Synthetic

<400> SEQUENCE: 314 ccgaggggu ccccaagag                                                 19

<210> SEQ ID NO 315
<211> LENGTH: 19
<212> TYPE: RNA
<213> ORGANISM: Artificial Sequence
<220> FEATURE:
<223> OTHER INFORMATION: Synthetic

<400> SEQUENCE: 315
gauccaggcu gucauguga                                                19

<210> SEQ ID NO 316
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 316
auuuauggug gcauguguu                                              19

<210> SEQ ID NO 317
<211> LENGTH: 19
<212> TYPE: RNA
<213> ORGANISM: Artificial Sequence
<220> FEATURE:
<223> OTHER INFORMATION: Synthetic

<400> SEQUENCE: 317
uguguauuug uuggcuacu                                              19

<210> SEQ ID NO 318
<211> LENGTH: 19
<212> TYPE: RNA
<213> ORGANISM: Artificial Sequence
<220> FEATURE:
<223> OTHER INFORMATION: Synthetic

<400> SEQUENCE: 318
uugugucuug aaaucuaga                                              19

<210> SEQ ID NO 319
<211> LENGTH: 19
<212> TYPE: RNA
<213> ORGANISM: Artificial Sequence
<220> FEATURE:
<223> OTHER INFORMATION: Synthetic

<400> SEQUENCE: 319
aauuauuuca cgcagaauu                                              19

<210> SEQ ID NO 320
<211> LENGTH: 19
<212> TYPE: RNA
<213> ORGANISM: Artificial Sequence
<220> FEATURE:
<223> OTHER INFORMATION: Synthetic

<400> SEQUENCE: 320
ugucacuguu ugucaggaa                                              19

<210> SEQ ID NO 321
<211> LENGTH: 19
<212> TYPE: RNA
<213> ORGANISM: Artificial Sequence
<220> FEATURE:
<223> OTHER INFORMATION: Synthetic

<400> SEQUENCE: 321
agagaaaaug ggcuagugg                                              19

<210> SEQ ID NO 322
<211> LENGTH: 19
<212> TYPE: RNA
<213> ORGANISM: Artificial Sequence
<220> FEATURE:
<223> OTHER INFORMATION: Synthetic

<400> SEQUENCE: 322
gaagcccagu cuugaguuc                                              19

<210> SEQ ID NO 323
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 323
cuugucuugu uaccauuua                                                    19

<210> SEQ ID NO 324
<211> LENGTH: 19
<212> TYPE: RNA
<213> ORGANISM: Artificial Sequence
<220> FEATURE:
<223> OTHER INFORMATION: Synthetic

<400> SEQUENCE: 324
aaaauugaca uuuaauuuu                                                    19

<210> SEQ ID NO 325
<211> LENGTH: 19
<212> TYPE: RNA
<213> ORGANISM: Artificial Sequence
<220> FEATURE:
<223> OTHER INFORMATION: Synthetic

<400> SEQUENCE: 325 ucaaucacu guuggugcc                                                     19

<210> SEQ ID NO 326
<211> LENGTH: 19
<212> TYPE: RNA
<213> ORGANISM: Artificial Sequence
<220> FEATURE:
<223> OTHER INFORMATION: Synthetic

<400> SEQUENCE: 326
cuaaucacuu aaguuauua                                                    19

<210> SEQ ID NO 327
<211> LENGTH: 19
<212> TYPE: RNA
<213> ORGANISM: Artificial Sequence
<220> FEATURE:
<223> OTHER INFORMATION: Synthetic

<400> SEQUENCE: 327 aauuauucu guuguauuc                                                     19

<210> SEQ ID NO 328
<211> LENGTH: 19
<212> TYPE: RNA
<213> ORGANISM: Artificial Sequence
<220> FEATURE:
<223> OTHER INFORMATION: Synthetic

<400> SEQUENCE: 328 cuuuuuuua aauuguaac                                                     19

<210> SEQ ID NO 329
<211> LENGTH: 19
<212> TYPE: RNA
<213> ORGANISM: Artificial Sequence
<220> FEATURE:
<223> OTHER INFORMATION: Synthetic

<400> SEQUENCE: 329
```

-continued

| | |
|---|---|
| cauauuuauc cggugggug | 19 |

<210> SEQ ID NO 330
<211> LENGTH: 19
<212> TYPE: RNA
<213> ORGANISM: Artificial Sequence
<220> FEATURE:
<223> OTHER INFORMATION: Synthetic

<400> SEQUENCE: 330

| | |
|---|---|
| gggacaggag uguguucaa | 19 |

<210> SEQ ID NO 331
<211> LENGTH: 19
<212> TYPE: RNA
<213> ORGANISM: Artificial Sequence
<220> FEATURE:
<223> OTHER INFORMATION: Synthetic

<400> SEQUENCE: 331

| | |
|---|---|
| agugggucau guuuuugcu | 19 |

<210> SEQ ID NO 332
<211> LENGTH: 19
<212> TYPE: RNA
<213> ORGANISM: Artificial Sequence
<220> FEATURE:
<223> OTHER INFORMATION: Synthetic

<400> SEQUENCE: 332

| | |
|---|---|
| uguggugaca caugguaca | 19 |

<210> SEQ ID NO 333
<211> LENGTH: 19
<212> TYPE: RNA
<213> ORGANISM: Artificial Sequence
<220> FEATURE:
<223> OTHER INFORMATION: Synthetic

<400> SEQUENCE: 333

| | |
|---|---|
| aggcuuggag cuugcaggu | 19 |

<210> SEQ ID NO 334
<211> LENGTH: 19
<212> TYPE: RNA
<213> ORGANISM: Artificial Sequence
<220> FEATURE:
<223> OTHER INFORMATION: Synthetic

<400> SEQUENCE: 334

| | |
|---|---|
| ucccuuucua cugugugu | 19 |

<210> SEQ ID NO 335
<211> LENGTH: 19
<212> TYPE: RNA
<213> ORGANISM: Artificial Sequence
<220> FEATURE:
<223> OTHER INFORMATION: Synthetic

<400> SEQUENCE: 335

| | |
|---|---|
| uuggagcagg acaauaaag | 19 |

<210> SEQ ID NO 336
<211> LENGTH: 19
<212> TYPE: RNA
<213> ORGANISM: Artificial Sequence

```
<220> FEATURE:
<223> OTHER INFORMATION: Synthetic

<400> SEQUENCE: 336
guccacuaga aaugcaccc                                                    19

<210> SEQ ID NO 337
<211> LENGTH: 19
<212> TYPE: RNA
<213> ORGANISM: Artificial Sequence
<220> FEATURE:
<223> OTHER INFORMATION: Synthetic

<400> SEQUENCE: 337
cccaccacuu cucaaaauu                                                    19

<210> SEQ ID NO 338
<211> LENGTH: 19
<212> TYPE: RNA
<213> ORGANISM: Artificial Sequence
<220> FEATURE:
<223> OTHER INFORMATION: Synthetic

<400> SEQUENCE: 338
uucagggauc uucuucauc                                                    19

<210> SEQ ID NO 339
<211> LENGTH: 19
<212> TYPE: RNA
<213> ORGANISM: Artificial Sequence
<220> FEATURE:
<223> OTHER INFORMATION: Synthetic

<400> SEQUENCE: 339
gucucaguua cuccucucu                                                    19

<210> SEQ ID NO 340
<211> LENGTH: 19
<212> TYPE: RNA
<213> ORGANISM: Artificial Sequence
<220> FEATURE:
<223> OTHER INFORMATION: Synthetic

<400> SEQUENCE: 340
auugcuagcc ucgccuuug                                                    19

<210> SEQ ID NO 341
<211> LENGTH: 19
<212> TYPE: RNA
<213> ORGANISM: Artificial Sequence
<220> FEATURE:
<223> OTHER INFORMATION: Synthetic

<400> SEQUENCE: 341
ucccucacuu gucucucua                                                    19

<210> SEQ ID NO 342
<211> LENGTH: 19
<212> TYPE: RNA
<213> ORGANISM: Artificial Sequence
<220> FEATURE:
<223> OTHER INFORMATION: Synthetic

<400> SEQUENCE: 342
ugauaccaaa ggucuaauu                                                    19
```

-continued

```
<210> SEQ ID NO 343
<211> LENGTH: 19
<212> TYPE: RNA
<213> ORGANISM: Artificial Sequence
<220> FEATURE:
<223> OTHER INFORMATION: Synthetic

<400> SEQUENCE: 343
uuccaggccu uuucaugau                                                  19

<210> SEQ ID NO 344
<211> LENGTH: 19
<212> TYPE: RNA
<213> ORGANISM: Artificial Sequence
<220> FEATURE:
<223> OTHER INFORMATION: Synthetic

<400> SEQUENCE: 344
aggauaaacc agcguuucu                                                  19

<210> SEQ ID NO 345
<211> LENGTH: 19
<212> TYPE: RNA
<213> ORGANISM: Artificial Sequence
<220> FEATURE:
<223> OTHER INFORMATION: Synthetic

<400> SEQUENCE: 345
cucauccggc cacuccgca                                                  19

<210> SEQ ID NO 346
<211> LENGTH: 19
<212> TYPE: RNA
<213> ORGANISM: Artificial Sequence
<220> FEATURE:
<223> OTHER INFORMATION: Synthetic

<400> SEQUENCE: 346
agaacaucug ggucaccgc                                                  19

<210> SEQ ID NO 347
<211> LENGTH: 19
<212> TYPE: RNA
<213> ORGANISM: Artificial Sequence
<220> FEATURE:
<223> OTHER INFORMATION: Synthetic

<400> SEQUENCE: 347
ucguucuugu aguauucca                                                  19

<210> SEQ ID NO 348
<211> LENGTH: 19
<212> TYPE: RNA
<213> ORGANISM: Artificial Sequence
<220> FEATURE:
<223> OTHER INFORMATION: Synthetic

<400> SEQUENCE: 348
agaggcuucu uggagugau                                                  19

<210> SEQ ID NO 349
<211> LENGTH: 19
<212> TYPE: RNA
<213> ORGANISM: Artificial Sequence
<220> FEATURE:
<223> OTHER INFORMATION: Synthetic
```

-continued

<400> SEQUENCE: 349
uucagguuga ugauccgca                                              19

<210> SEQ ID NO 350
<211> LENGTH: 19
<212> TYPE: RNA
<213> ORGANISM: Artificial Sequence
<220> FEATURE:
<223> OTHER INFORMATION: Synthetic

<400> SEQUENCE: 350
ucuaccugcu cacagaagu                                              19

<210> SEQ ID NO 351
<211> LENGTH: 19
<212> TYPE: RNA
<213> ORGANISM: Artificial Sequence
<220> FEATURE:
<223> OTHER INFORMATION: Synthetic

<400> SEQUENCE: 351
uuaaagguca ggccugcau                                              19

<210> SEQ ID NO 352
<211> LENGTH: 19
<212> TYPE: RNA
<213> ORGANISM: Artificial Sequence
<220> FEATURE:
<223> OTHER INFORMATION: Synthetic

<400> SEQUENCE: 352
uccugcagcu ccuucuugu                                              19

<210> SEQ ID NO 353
<211> LENGTH: 19
<212> TYPE: RNA
<213> ORGANISM: Artificial Sequence
<220> FEATURE:
<223> OTHER INFORMATION: Synthetic

<400> SEQUENCE: 353
augucaaaca caaaacuau                                              19

<210> SEQ ID NO 354
<211> LENGTH: 19
<212> TYPE: RNA
<213> ORGANISM: Artificial Sequence
<220> FEATURE:
<223> OTHER INFORMATION: Synthetic

<400> SEQUENCE: 354
gugcguucac uggucuuga                                              19

<210> SEQ ID NO 355
<211> LENGTH: 19
<212> TYPE: RNA
<213> ORGANISM: Artificial Sequence
<220> FEATURE:
<223> OTHER INFORMATION: Synthetic

<400> SEQUENCE: 355
ucagccacca gguaaaagg                                              19

<210> SEQ ID NO 356

```
<211> LENGTH: 19
<212> TYPE: RNA
<213> ORGANISM: Artificial Sequence
<220> FEATURE:
<223> OTHER INFORMATION: Synthetic

<400> SEQUENCE: 356
uucauguccu cuucugucu                                                  19

<210> SEQ ID NO 357
<211> LENGTH: 19
<212> TYPE: RNA
<213> ORGANISM: Artificial Sequence
<220> FEATURE:
<223> OTHER INFORMATION: Synthetic

<400> SEQUENCE: 357
augcucugga cccacuuau                                                  19

<210> SEQ ID NO 358
<211> LENGTH: 19
<212> TYPE: RNA
<213> ORGANISM: Artificial Sequence
<220> FEATURE:
<223> OTHER INFORMATION: Synthetic

<400> SEQUENCE: 358
aagccacaga ucuggcaga                                                  19

<210> SEQ ID NO 359
<211> LENGTH: 19
<212> TYPE: RNA
<213> ORGANISM: Artificial Sequence
<220> FEATURE:
<223> OTHER INFORMATION: Synthetic

<400> SEQUENCE: 359
cucuccucag ccugauuga                                                  19

<210> SEQ ID NO 360
<211> LENGTH: 19
<212> TYPE: RNA
<213> ORGANISM: Artificial Sequence
<220> FEATURE:
<223> OTHER INFORMATION: Synthetic

<400> SEQUENCE: 360
uuucucaggg agucugugc                                                  19

<210> SEQ ID NO 361
<211> LENGTH: 19
<212> TYPE: RNA
<213> ORGANISM: Artificial Sequence
<220> FEATURE:
<223> OTHER INFORMATION: Synthetic

<400> SEQUENCE: 361
ugaccggcug aggaaacau                                                  19

<210> SEQ ID NO 362
<211> LENGTH: 19
<212> TYPE: RNA
<213> ORGANISM: Artificial Sequence
<220> FEATURE:
<223> OTHER INFORMATION: Synthetic

<400> SEQUENCE: 362
```
ggagaagagc gggggccau                                              19

<210> SEQ ID NO 363
<211> LENGTH: 19
<212> TYPE: RNA
<213> ORGANISM: Artificial Sequence
<220> FEATURE:
<223> OTHER INFORMATION: Synthetic

<400> SEQUENCE: 363
gagcugcuga gcucagcug                                              19

<210> SEQ ID NO 364
<211> LENGTH: 19
<212> TYPE: RNA
<213> ORGANISM: Artificial Sequence
<220> FEATURE:
<223> OTHER INFORMATION: Synthetic

<400> SEQUENCE: 364
cggagaaggu gcuggcuag                                              19

<210> SEQ ID NO 365
<211> LENGTH: 19
<212> TYPE: RNA
<213> ORGANISM: Artificial Sequence
<220> FEATURE:
<223> OTHER INFORMATION: Synthetic

<400> SEQUENCE: 365
gcugaggacu ugcgcucuc                                              19

<210> SEQ ID NO 366
<211> LENGTH: 19
<212> TYPE: RNA
<213> ORGANISM: Artificial Sequence
<220> FEATURE:
<223> OTHER INFORMATION: Synthetic

<400> SEQUENCE: 366
uggcuggagu gugaugggg                                              19

<210> SEQ ID NO 367
<211> LENGTH: 19
<212> TYPE: RNA
<213> ORGANISM: Artificial Sequence
<220> FEATURE:
<223> OTHER INFORMATION: Synthetic

<400> SEQUENCE: 367
aacgugaaca gaguuggcu                                              19

<210> SEQ ID NO 368
<211> LENGTH: 19
<212> TYPE: RNA
<213> ORGANISM: Artificial Sequence
<220> FEATURE:
<223> OTHER INFORMATION: Synthetic

<400> SEQUENCE: 368
uuugacacag gggguucaa                                              19

<210> SEQ ID NO 369
<211> LENGTH: 19
<212> TYPE: RNA

-continued

```
<213> ORGANISM: Artificial Sequence
<220> FEATURE:
<223> OTHER INFORMATION: Synthetic

<400> SEQUENCE: 369 aagguggggcu gcauguggu                                              19

<210> SEQ ID NO 370
<211> LENGTH: 19
<212> TYPE: RNA
<213> ORGANISM: Artificial Sequence
<220> FEATURE:
<223> OTHER INFORMATION: Synthetic

<400> SEQUENCE: 370
ugaggugcgc ugguggaca                                               19

<210> SEQ ID NO 371
<211> LENGTH: 19
<212> TYPE: RNA
<213> ORGANISM: Artificial Sequence
<220> FEATURE:
<223> OTHER INFORMATION: Synthetic

<400> SEQUENCE: 371
ugcaaguaga gauacuccu                                               19

<210> SEQ ID NO 372
<211> LENGTH: 19
<212> TYPE: RNA
<213> ORGANISM: Artificial Sequence
<220> FEATURE:
<223> OTHER INFORMATION: Synthetic

<400> SEQUENCE: 372
cuucggcuua ugcacuggu                                               19

<210> SEQ ID NO 373
<211> LENGTH: 19
<212> TYPE: RNA
<213> ORGANISM: Artificial Sequence
<220> FEATURE:
<223> OTHER INFORMATION: Synthetic

<400> SEQUENCE: 373
cuccuugcau uuucugcuc                                               19

<210> SEQ ID NO 374
<211> LENGTH: 19
<212> TYPE: RNA
<213> ORGANISM: Artificial Sequence
<220> FEATURE:
<223> OTHER INFORMATION: Synthetic

<400> SEQUENCE: 374
cccugagaga agcuggcac                                               19

<210> SEQ ID NO 375
<211> LENGTH: 19
<212> TYPE: RNA
<213> ORGANISM: Artificial Sequence
<220> FEATURE:
<223> OTHER INFORMATION: Synthetic

<400> SEQUENCE: 375
agaaaagagg cucuggugc                                               19
```

-continued

```
<210> SEQ ID NO 376
<211> LENGTH: 19
<212> TYPE: RNA
<213> ORGANISM: Artificial Sequence
<220> FEATURE:
<223> OTHER INFORMATION: Synthetic

<400> SEQUENCE: 376
gcugugucac uccucauga                                                   19

<210> SEQ ID NO 377
<211> LENGTH: 19
<212> TYPE: RNA
<213> ORGANISM: Artificial Sequence
<220> FEATURE:
<223> OTHER INFORMATION: Synthetic

<400> SEQUENCE: 377
ugggcaaguu uuuguacag                                                   19

<210> SEQ ID NO 378
<211> LENGTH: 19
<212> TYPE: RNA
<213> ORGANISM: Artificial Sequence
<220> FEATURE:
<223> OTHER INFORMATION: Synthetic

<400> SEQUENCE: 378
acacaguguc cauugcccu                                                   19

<210> SEQ ID NO 379
<211> LENGTH: 19
<212> TYPE: RNA
<213> ORGANISM: Artificial Sequence
<220> FEATURE:
<223> OTHER INFORMATION: Synthetic

<400> SEQUENCE: 379
ugaccacuga ucccguuga                                                   19

<210> SEQ ID NO 380
<211> LENGTH: 19
<212> TYPE: RNA
<213> ORGANISM: Artificial Sequence
<220> FEATURE:
<223> OTHER INFORMATION: Synthetic

<400> SEQUENCE: 380
cuauagaagc cauggacuu                                                   19

<210> SEQ ID NO 381
<211> LENGTH: 19
<212> TYPE: RNA
<213> ORGANISM: Artificial Sequence
<220> FEATURE:
<223> OTHER INFORMATION: Synthetic

<400> SEQUENCE: 381
cggcucggcu ugggaaggc                                                   19

<210> SEQ ID NO 382
<211> LENGTH: 19
<212> TYPE: RNA
<213> ORGANISM: Artificial Sequence
<220> FEATURE:
```

<223> OTHER INFORMATION: Synthetic

<400> SEQUENCE: 382
cugaauucug uauugugcc                                              19

<210> SEQ ID NO 383
<211> LENGTH: 19
<212> TYPE: RNA
<213> ORGANISM: Artificial Sequence
<220> FEATURE:
<223> OTHER INFORMATION: Synthetic

<400> SEQUENCE: 383
aggucguagg uacugucuc                                              19

<210> SEQ ID NO 384
<211> LENGTH: 19
<212> TYPE: RNA
<213> ORGANISM: Artificial Sequence
<220> FEATURE:
<223> OTHER INFORMATION: Synthetic

<400> SEQUENCE: 384
gaggccaggc ugcggggga                                              19

<210> SEQ ID NO 385
<211> LENGTH: 19
<212> TYPE: RNA
<213> ORGANISM: Artificial Sequence
<220> FEATURE:
<223> OTHER INFORMATION: Synthetic

<400> SEQUENCE: 385
cccuuggugu ggccauggg                                              19

<210> SEQ ID NO 386
<211> LENGTH: 19
<212> TYPE: RNA
<213> ORGANISM: Artificial Sequence
<220> FEATURE:
<223> OTHER INFORMATION: Synthetic

<400> SEQUENCE: 386
ucggagccug ugaggcugc                                              19

<210> SEQ ID NO 387
<211> LENGTH: 19
<212> TYPE: RNA
<213> ORGANISM: Artificial Sequence
<220> FEATURE:
<223> OTHER INFORMATION: Synthetic

<400> SEQUENCE: 387
acauccucau uaucugucu                                              19

<210> SEQ ID NO 388
<211> LENGTH: 19
<212> TYPE: RNA
<213> ORGANISM: Artificial Sequence
<220> FEATURE:
<223> OTHER INFORMATION: Synthetic

<400> SEQUENCE: 388
ggcgucuuga agguguaca                                              19

```
<210> SEQ ID NO 389
<211> LENGTH: 19
<212> TYPE: RNA
<213> ORGANISM: Artificial Sequence
<220> FEATURE:
<223> OTHER INFORMATION: Synthetic

<400> SEQUENCE: 389
cugcacaggg uguugcugg                                                      19

<210> SEQ ID NO 390
<211> LENGTH: 19
<212> TYPE: RNA
<213> ORGANISM: Artificial Sequence
<220> FEATURE:
<223> OTHER INFORMATION: Synthetic

<400> SEQUENCE: 390
aggagguccc cgaacuccc                                                      19

<210> SEQ ID NO 391
<211> LENGTH: 19
<212> TYPE: RNA
<213> ORGANISM: Artificial Sequence
<220> FEATURE:
<223> OTHER INFORMATION: Synthetic

<400> SEQUENCE: 391
acauccauau ugucuacca                                                      19

<210> SEQ ID NO 392
<211> LENGTH: 19
<212> TYPE: RNA
<213> ORGANISM: Artificial Sequence
<220> FEATURE:
<223> OTHER INFORMATION: Synthetic

<400> SEQUENCE: 392 gagaguggggg uggccggaa                                                     19

<210> SEQ ID NO 393
<211> LENGTH: 19
<212> TYPE: RNA
<213> ORGANISM: Artificial Sequence
<220> FEATURE:
<223> OTHER INFORMATION: Synthetic

<400> SEQUENCE: 393
cuagggaucu gguaggcug                                                      19

<210> SEQ ID NO 394
<211> LENGTH: 19
<212> TYPE: RNA
<213> ORGANISM: Artificial Sequence
<220> FEATURE:
<223> OTHER INFORMATION: Synthetic

<400> SEQUENCE: 394
uuguccagag ugaaugucc                                                      19

<210> SEQ ID NO 395
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 395
gucauggcau ugugguuuu                                              19

<210> SEQ ID NO 396
<211> LENGTH: 19
<212> TYPE: RNA
<213> ORGANISM: Artificial Sequence
<220> FEATURE:
<223> OTHER INFORMATION: Synthetic

<400> SEQUENCE: 396
uccccaggag uggccacug                                              19

<210> SEQ ID NO 397
<211> LENGTH: 19
<212> TYPE: RNA
<213> ORGANISM: Artificial Sequence
<220> FEATURE:
<223> OTHER INFORMATION: Synthetic

<400> SEQUENCE: 397
gggggagcua uggcugagu                                              19

<210> SEQ ID NO 398
<211> LENGTH: 19
<212> TYPE: RNA
<213> ORGANISM: Artificial Sequence
<220> FEATURE:
<223> OTHER INFORMATION: Synthetic

<400> SEQUENCE: 398
ggcuuggggg ggcggggug                                              19

<210> SEQ ID NO 399
<211> LENGTH: 19
<212> TYPE: RNA
<213> ORGANISM: Artificial Sequence
<220> FEATURE:
<223> OTHER INFORMATION: Synthetic

<400> SEQUENCE: 399
gguguuucug ccugacuug                                              19

<210> SEQ ID NO 400
<211> LENGTH: 19
<212> TYPE: RNA
<213> ORGANISM: Artificial Sequence
<220> FEATURE:
<223> OTHER INFORMATION: Synthetic

<400> SEQUENCE: 400
ugaggacugc cccaucgag                                              19

<210> SEQ ID NO 401
<211> LENGTH: 19
<212> TYPE: RNA
<213> ORGANISM: Artificial Sequence
<220> FEATURE:
<223> OTHER INFORMATION: Synthetic

<400> SEQUENCE: 401
cugauuggcg gucucugcu                                              19

<210> SEQ ID NO 402
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 402
acagaucugc uauuucac                                                   19

<210> SEQ ID NO 403
<211> LENGTH: 19
<212> TYPE: RNA
<213> ORGANISM: Artificial Sequence
<220> FEATURE:
<223> OTHER INFORMATION: Synthetic

<400> SEQUENCE: 403 cugggaugg uggcagcga                                                   19

<210> SEQ ID NO 404
<211> LENGTH: 19
<212> TYPE: RNA
<213> ORGANISM: Artificial Sequence
<220> FEATURE:
<223> OTHER INFORMATION: Synthetic

<400> SEQUENCE: 404
gcagggaggg uguugcguc                                                  19

<210> SEQ ID NO 405
<211> LENGTH: 19
<212> TYPE: RNA
<213> ORGANISM: Artificial Sequence
<220> FEATURE:
<223> OTHER INFORMATION: Synthetic

<400> SEQUENCE: 405
agucggcugu uguccauug                                                  19

<210> SEQ ID NO 406
<211> LENGTH: 19
<212> TYPE: RNA
<213> ORGANISM: Artificial Sequence
<220> FEATURE:
<223> OTHER INFORMATION: Synthetic

<400> SEQUENCE: 406
caggaagaag cucggugaa                                                  19

<210> SEQ ID NO 407
<211> LENGTH: 19
<212> TYPE: RNA
<213> ORGANISM: Artificial Sequence
<220> FEATURE:
<223> OTHER INFORMATION: Synthetic

<400> SEQUENCE: 407
ggguacucgu aggucucac                                                  19

<210> SEQ ID NO 408
<211> LENGTH: 19
<212> TYPE: RNA
<213> ORGANISM: Artificial Sequence
<220> FEATURE:
<223> OTHER INFORMATION: Synthetic

<400> SEQUENCE: 408
```
cucucuccac cacgcugug                                                    19

<210> SEQ ID NO 409
<211> LENGTH: 19
<212> TYPE: RNA
<213> ORGANISM: Artificial Sequence
<220> FEATURE:
<223> OTHER INFORMATION: Synthetic

<400> SEQUENCE: 409
ucagcagacc ggccugcac                                                    19

<210> SEQ ID NO 410
<211> LENGTH: 19
<212> TYPE: RNA
<213> ORGANISM: Artificial Sequence
<220> FEATURE:
<223> OTHER INFORMATION: Synthetic

<400> SEQUENCE: 410
acuccaucac ucauggauu                                                    19

<210> SEQ ID NO 411
<211> LENGTH: 19
<212> TYPE: RNA
<213> ORGANISM: Artificial Sequence
<220> FEATURE:
<223> OTHER INFORMATION: Synthetic

<400> SEQUENCE: 411
ccuggcagga aagagccaa                                                    19

<210> SEQ ID NO 412
<211> LENGTH: 19
<212> TYPE: RNA
<213> ORGANISM: Artificial Sequence
<220> FEATURE:
<223> OTHER INFORMATION: Synthetic

<400> SEQUENCE: 412
cggcccacaa ucauuuucc                                                    19

<210> SEQ ID NO 413
<211> LENGTH: 19
<212> TYPE: RNA
<213> ORGANISM: Artificial Sequence
<220> FEATURE:
<223> OTHER INFORMATION: Synthetic

<400> SEQUENCE: 413
gaauuggugc uguccgauc                                                    19

<210> SEQ ID NO 414
<211> LENGTH: 19
<212> TYPE: RNA
<213> ORGANISM: Artificial Sequence
<220> FEATURE:
<223> OTHER INFORMATION: Synthetic

<400> SEQUENCE: 414
ggcacauagu ugucuucag                                                    19

<210> SEQ ID NO 415
<211> LENGTH: 19
<212> TYPE: RNA
<213> ORGANISM: Artificial Sequence

```
<220> FEATURE:
<223> OTHER INFORMATION: Synthetic

<400> SEQUENCE: 415
gaagaaccug gauucaugg                                                   19

<210> SEQ ID NO 416
<211> LENGTH: 19
<212> TYPE: RNA
<213> ORGANISM: Artificial Sequence
<220> FEATURE:
<223> OTHER INFORMATION: Synthetic

<400> SEQUENCE: 416
uccauggcca acagggugg                                                   19

<210> SEQ ID NO 417
<211> LENGTH: 19
<212> TYPE: RNA
<213> ORGANISM: Artificial Sequence
<220> FEATURE:
<223> OTHER INFORMATION: Synthetic

<400> SEQUENCE: 417
gaauuaucac cugcucguu                                                   19

<210> SEQ ID NO 418
<211> LENGTH: 19
<212> TYPE: RNA
<213> ORGANISM: Artificial Sequence
<220> FEATURE:
<223> OTHER INFORMATION: Synthetic

<400> SEQUENCE: 418
gggauguaga cgcucuggg                                                   19

<210> SEQ ID NO 419
<211> LENGTH: 19
<212> TYPE: RNA
<213> ORGANISM: Artificial Sequence
<220> FEATURE:
<223> OTHER INFORMATION: Synthetic

<400> SEQUENCE: 419
ugggccccug ggcucauug                                                   19

<210> SEQ ID NO 420
<211> LENGTH: 19
<212> TYPE: RNA
<213> ORGANISM: Artificial Sequence
<220> FEATURE:
<223> OTHER INFORMATION: Synthetic

<400> SEQUENCE: 420
ccaagugagu caaagugau                                                   19

<210> SEQ ID NO 421
<211> LENGTH: 19
<212> TYPE: RNA
<213> ORGANISM: Artificial Sequence
<220> FEATURE:
<223> OTHER INFORMATION: Synthetic

<400> SEQUENCE: 421
aggguuguug auggguagc                                                   19
```

<210> SEQ ID NO 422
<211> LENGTH: 19
<212> TYPE: RNA
<213> ORGANISM: Artificial Sequence
<220> FEATURE:
<223> OTHER INFORMATION: Synthetic

<400> SEQUENCE: 422
gggccucggu gcacaggaa                                                19

<210> SEQ ID NO 423
<211> LENGTH: 19
<212> TYPE: RNA
<213> ORGANISM: Artificial Sequence
<220> FEATURE:
<223> OTHER INFORMATION: Synthetic

<400> SEQUENCE: 423
aucucacuuc cucugcugg                                                19

<210> SEQ ID NO 424
<211> LENGTH: 19
<212> TYPE: RNA
<213> ORGANISM: Artificial Sequence
<220> FEATURE:
<223> OTHER INFORMATION: Synthetic

<400> SEQUENCE: 424
uugacagggg guggcugaa                                                19

<210> SEQ ID NO 425
<211> LENGTH: 19
<212> TYPE: RNA
<213> ORGANISM: Artificial Sequence
<220> FEATURE:
<223> OTHER INFORMATION: Synthetic

<400> SEQUENCE: 425
ucagguuuga gguugcggu                                                19

<210> SEQ ID NO 426
<211> LENGTH: 19
<212> TYPE: RNA
<213> ORGANISM: Artificial Sequence
<220> FEATURE:
<223> OTHER INFORMATION: Synthetic

<400> SEQUENCE: 426
guuggcuuug cuuuccgau                                                19

<210> SEQ ID NO 427
<211> LENGTH: 19
<212> TYPE: RNA
<213> ORGANISM: Artificial Sequence
<220> FEATURE:
<223> OTHER INFORMATION: Synthetic

<400> SEQUENCE: 427 uucccucaggu caagugguq                                               19

<210> SEQ ID NO 428
<211> LENGTH: 19
<212> TYPE: RNA
<213> ORGANISM: Artificial Sequence
<220> FEATURE:
<223> OTHER INFORMATION: Synthetic

```
<400> SEQUENCE: 428
ucaucgauga cgguguugu                                              19

<210> SEQ ID NO 429
<211> LENGTH: 19
<212> TYPE: RNA
<213> ORGANISM: Artificial Sequence
<220> FEATURE:
<223> OTHER INFORMATION: Synthetic

<400> SEQUENCE: 429
ggugacuuga agggaguu                                               19

<210> SEQ ID NO 430
<211> LENGTH: 19
<212> TYPE: RNA
<213> ORGANISM: Artificial Sequence
<220> FEATURE:
<223> OTHER INFORMATION: Synthetic

<400> SEQUENCE: 430
gaccaagacu uggugauag                                              19

<210> SEQ ID NO 431
<211> LENGTH: 19
<212> TYPE: RNA
<213> ORGANISM: Artificial Sequence
<220> FEATURE:
<223> OTHER INFORMATION: Synthetic

<400> SEQUENCE: 431
aagguguggu uggcccuag                                              19

<210> SEQ ID NO 432
<211> LENGTH: 19
<212> TYPE: RNA
<213> ORGANISM: Artificial Sequence
<220> FEATURE:
<223> OTHER INFORMATION: Synthetic

<400> SEQUENCE: 432
ugggaggagc uggaguuga                                              19

<210> SEQ ID NO 433
<211> LENGTH: 19
<212> TYPE: RNA
<213> ORGANISM: Artificial Sequence
<220> FEATURE:
<223> OTHER INFORMATION: Synthetic

<400> SEQUENCE: 433
gagauggggc ggcaguacu                                              19

<210> SEQ ID NO 434
<211> LENGTH: 19
<212> TYPE: RNA
<213> ORGANISM: Artificial Sequence
<220> FEATURE:
<223> OTHER INFORMATION: Synthetic

<400> SEQUENCE: 434
cuggugaugc ucugggugg                                              19

<210> SEQ ID NO 435
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 435
cugucuccug agucugugc                                                  19

<210> SEQ ID NO 436
<211> LENGTH: 19
<212> TYPE: RNA
<213> ORGANISM: Artificial Sequence
<220> FEATURE:
<223> OTHER INFORMATION: Synthetic

<400> SEQUENCE: 436
gggacauagu ucucuucgc                                                  19

<210> SEQ ID NO 437
<211> LENGTH: 19
<212> TYPE: RNA
<213> ORGANISM: Artificial Sequence
<220> FEATURE:
<223> OTHER INFORMATION: Synthetic

<400> SEQUENCE: 437
gacacugggu uuugcauag                                                  19

<210> SEQ ID NO 438
<211> LENGTH: 19
<212> TYPE: RNA
<213> ORGANISM: Artificial Sequence
<220> FEATURE:
<223> OTHER INFORMATION: Synthetic

<400> SEQUENCE: 438
cugggaacgg gagaugcag                                                  19

<210> SEQ ID NO 439
<211> LENGTH: 19
<212> TYPE: RNA
<213> ORGANISM: Artificial Sequence
<220> FEATURE:
<223> OTHER INFORMATION: Synthetic

<400> SEQUENCE: 439
gcaggacugu ucgugccac                                                  19

<210> SEQ ID NO 440
<211> LENGTH: 19
<212> TYPE: RNA
<213> ORGANISM: Artificial Sequence
<220> FEATURE:
<223> OTHER INFORMATION: Synthetic

<400> SEQUENCE: 440
ccggugcucu ucuuagggg                                                  19

<210> SEQ ID NO 441
<211> LENGTH: 19
<212> TYPE: RNA
<213> ORGANISM: Artificial Sequence
<220> FEATURE:
<223> OTHER INFORMATION: Synthetic

<400> SEQUENCE: 441
```

```
gccagauaau caacgcugc                                               19

<210> SEQ ID NO 442
<211> LENGTH: 19
<212> TYPE: RNA
<213> ORGANISM: Artificial Sequence
<220> FEATURE:
<223> OTHER INFORMATION: Synthetic

<400> SEQUENCE: 442
cucggcugga aguccaggg                                               19

<210> SEQ ID NO 443
<211> LENGTH: 19
<212> TYPE: RNA
<213> ORGANISM: Artificial Sequence
<220> FEATURE:
<223> OTHER INFORMATION: Synthetic

<400> SEQUENCE: 443 cgguggggc uugggagc                                                 19

<210> SEQ ID NO 444
<211> LENGTH: 19
<212> TYPE: RNA
<213> ORGANISM: Artificial Sequence
<220> FEATURE:
<223> OTHER INFORMATION: Synthetic

<400> SEQUENCE: 444
gaugaaguag auggcuugc                                               19

<210> SEQ ID NO 445
<211> LENGTH: 19
<212> TYPE: RNA
<213> ORGANISM: Artificial Sequence
<220> FEATURE:
<223> OTHER INFORMATION: Synthetic

<400> SEQUENCE: 445
uucucaucag aggugacgg                                               19

<210> SEQ ID NO 446
<211> LENGTH: 19
<212> TYPE: RNA
<213> ORGANISM: Artificial Sequence
<220> FEATURE:
<223> OTHER INFORMATION: Synthetic

<400> SEQUENCE: 446
accugaacgu aguccaccu                                               19

<210> SEQ ID NO 447
<211> LENGTH: 19
<212> TYPE: RNA
<213> ORGANISM: Artificial Sequence
<220> FEATURE:
<223> OTHER INFORMATION: Synthetic

<400> SEQUENCE: 447
ugggucuucu ccuugucca                                               19

<210> SEQ ID NO 448
<211> LENGTH: 19
<212> TYPE: RNA
```

```
<213> ORGANISM: Artificial Sequence
<220> FEATURE:
<223> OTHER INFORMATION: Synthetic

<400> SEQUENCE: 448
augguguucu gcagggccu                                                 19

<210> SEQ ID NO 449
<211> LENGTH: 19
<212> TYPE: RNA
<213> ORGANISM: Artificial Sequence
<220> FEATURE:
<223> OTHER INFORMATION: Synthetic

<400> SEQUENCE: 449
acgucugucc acuccugca                                                 19

<210> SEQ ID NO 450
<211> LENGTH: 19
<212> TYPE: RNA
<213> ORGANISM: Artificial Sequence
<220> FEATURE:
<223> OTHER INFORMATION: Synthetic

<400> SEQUENCE: 450
ggcucugagg acugccgca                                                 19

<210> SEQ ID NO 451
<211> LENGTH: 19
<212> TYPE: RNA
<213> ORGANISM: Artificial Sequence
<220> FEATURE:
<223> OTHER INFORMATION: Synthetic

<400> SEQUENCE: 451
agcuuggcac ccuuggaag                                                 19

<210> SEQ ID NO 452
<211> LENGTH: 19
<212> TYPE: RNA
<213> ORGANISM: Artificial Sequence
<220> FEATURE:
<223> OTHER INFORMATION: Synthetic

<400> SEQUENCE: 452
cgguggcccu cucaucaca                                                 19

<210> SEQ ID NO 453
<211> LENGTH: 19
<212> TYPE: RNA
<213> ORGANISM: Artificial Sequence
<220> FEATURE:
<223> OTHER INFORMATION: Synthetic

<400> SEQUENCE: 453
gcugccuccu gggcucugc                                                 19

<210> SEQ ID NO 454
<211> LENGTH: 19
<212> TYPE: RNA
<213> ORGANISM: Artificial Sequence
<220> FEATURE:
<223> OTHER INFORMATION: Synthetic

<400> SEQUENCE: 454
agggccagcu cuggagaug                                                 19
```

-continued

```
<210> SEQ ID NO 455
<211> LENGTH: 19
<212> TYPE: RNA
<213> ORGANISM: Artificial Sequence
<220> FEATURE:
<223> OTHER INFORMATION: Synthetic

<400> SEQUENCE: 455
gggagagggg agaugggaa                                                  19

<210> SEQ ID NO 456
<211> LENGTH: 19
<212> TYPE: RNA
<213> ORGANISM: Artificial Sequence
<220> FEATURE:
<223> OTHER INFORMATION: Synthetic

<400> SEQUENCE: 456
ggaggaagaa cgggagagg                                                  19

<210> SEQ ID NO 457
<211> LENGTH: 19
<212> TYPE: RNA
<213> ORGANISM: Artificial Sequence
<220> FEATURE:
<223> OTHER INFORMATION: Synthetic

<400> SEQUENCE: 457
guagagagga gguggaugg                                                  19

<210> SEQ ID NO 458
<211> LENGTH: 19
<212> TYPE: RNA
<213> ORGANISM: Artificial Sequence
<220> FEATURE:
<223> OTHER INFORMATION: Synthetic

<400> SEQUENCE: 458
aaggcugaga cuggcagag                                                  19

<210> SEQ ID NO 459
<211> LENGTH: 19
<212> TYPE: RNA
<213> ORGANISM: Artificial Sequence
<220> FEATURE:
<223> OTHER INFORMATION: Synthetic

<400> SEQUENCE: 459
cugaugucaa gugcuuuga                                                  19

<210> SEQ ID NO 460
<211> LENGTH: 19
<212> TYPE: RNA
<213> ORGANISM: Artificial Sequence
<220> FEATURE:
<223> OTHER INFORMATION: Synthetic

<400> SEQUENCE: 460
gggaaggguu caggguccc                                                  19

<210> SEQ ID NO 461
<211> LENGTH: 19
<212> TYPE: RNA
<213> ORGANISM: Artificial Sequence
<220> FEATURE:
```

-continued

<223> OTHER INFORMATION: Synthetic

<400> SEQUENCE: 461
caggcccuca ccucccagg 19

<210> SEQ ID NO 462
<211> LENGTH: 19
<212> TYPE: RNA
<213> ORGANISM: Artificial Sequence
<220> FEATURE:
<223> OTHER INFORMATION: Synthetic

<400> SEQUENCE: 462
cagaggaggu gccuugauc 19

<210> SEQ ID NO 463
<211> LENGTH: 19
<212> TYPE: RNA
<213> ORGANISM: Artificial Sequence
<220> FEATURE:
<223> OTHER INFORMATION: Synthetic

<400> SEQUENCE: 463
agcugggccc cgagugggc 19

<210> SEQ ID NO 464
<211> LENGTH: 19
<212> TYPE: RNA
<213> ORGANISM: Artificial Sequence
<220> FEATURE:
<223> OTHER INFORMATION: Synthetic

<400> SEQUENCE: 464
auuacugaua aaaaucaca 19

<210> SEQ ID NO 465
<211> LENGTH: 19
<212> TYPE: RNA
<213> ORGANISM: Artificial Sequence
<220> FEATURE:
<223> OTHER INFORMATION: Synthetic

<400> SEQUENCE: 465 gugggug gag gcauggcca 19

<210> SEQ ID NO 466
<211> LENGTH: 19
<212> TYPE: RNA
<213> ORGANISM: Artificial Sequence
<220> FEATURE:
<223> OTHER INFORMATION: Synthetic

<400> SEQUENCE: 466
aaguagcucc uaacuaagg 19

<210> SEQ ID NO 467
<211> LENGTH: 19
<212> TYPE: RNA
<213> ORGANISM: Artificial Sequence
<220> FEATURE:
<223> OTHER INFORMATION: Synthetic

<400> SEQUENCE: 467
cugaaggaug cuuuuugga 19

<210> SEQ ID NO 468
<211> LENGTH: 19
<212> TYPE: RNA
<213> ORGANISM: Artificial Sequence
<220> FEATURE:
<223> OTHER INFORMATION: Synthetic

<400> SEQUENCE: 468
cuaaaggaca ggaagaggc                                            19

<210> SEQ ID NO 469
<211> LENGTH: 19
<212> TYPE: RNA
<213> ORGANISM: Artificial Sequence
<220> FEATURE:
<223> OTHER INFORMATION: Synthetic

<400> SEQUENCE: 469
ucugguagag agucagguc                                            19

<210> SEQ ID NO 470
<211> LENGTH: 19
<212> TYPE: RNA
<213> ORGANISM: Artificial Sequence
<220> FEATURE:
<223> OTHER INFORMATION: Synthetic

<400> SEQUENCE: 470
agcccuuccc uccaaacau                                            19

<210> SEQ ID NO 471
<211> LENGTH: 19
<212> TYPE: RNA
<213> ORGANISM: Artificial Sequence
<220> FEATURE:
<223> OTHER INFORMATION: Synthetic

<400> SEQUENCE: 471
aaucuggcuc agagcccca                                            19

<210> SEQ ID NO 472
<211> LENGTH: 19
<212> TYPE: RNA
<213> ORGANISM: Artificial Sequence
<220> FEATURE:
<223> OTHER INFORMATION: Synthetic

<400> SEQUENCE: 472
acugaacgug aggugugga                                            19

<210> SEQ ID NO 473
<211> LENGTH: 19
<212> TYPE: RNA
<213> ORGANISM: Artificial Sequence
<220> FEATURE:
<223> OTHER INFORMATION: Synthetic

<400> SEQUENCE: 473
agauagcuga gggcuguga                                            19

<210> SEQ ID NO 474
<211> LENGTH: 19
<212> TYPE: RNA
<213> ORGANISM: Artificial Sequence
<220> FEATURE:
<223> OTHER INFORMATION: Synthetic

```
<400> SEQUENCE: 474
gcccaguggc cggagggaa                                              19

<210> SEQ ID NO 475
<211> LENGTH: 19
<212> TYPE: RNA
<213> ORGANISM: Artificial Sequence
<220> FEATURE:
<223> OTHER INFORMATION: Synthetic

<400> SEQUENCE: 475
gggacugaag gagagguag                                              19

<210> SEQ ID NO 476
<211> LENGTH: 19
<212> TYPE: RNA
<213> ORGANISM: Artificial Sequence
<220> FEATURE:
<223> OTHER INFORMATION: Synthetic

<400> SEQUENCE: 476
uggugagacu ugucuucug                                              19

<210> SEQ ID NO 477
<211> LENGTH: 19
<212> TYPE: RNA
<213> ORGANISM: Artificial Sequence
<220> FEATURE:
<223> OTHER INFORMATION: Synthetic

<400> SEQUENCE: 477
guccuugacu cccuggguu                                              19

<210> SEQ ID NO 478
<211> LENGTH: 19
<212> TYPE: RNA
<213> ORGANISM: Artificial Sequence
<220> FEATURE:
<223> OTHER INFORMATION: Synthetic

<400> SEQUENCE: 478
auccacuuug guuugcugg                                              19

<210> SEQ ID NO 479
<211> LENGTH: 19
<212> TYPE: RNA
<213> ORGANISM: Artificial Sequence
<220> FEATURE:
<223> OTHER INFORMATION: Synthetic

<400> SEQUENCE: 479
ggaaugaaaa aguccauua                                              19

<210> SEQ ID NO 480
<211> LENGTH: 19
<212> TYPE: RNA
<213> ORGANISM: Artificial Sequence
<220> FEATURE:
<223> OTHER INFORMATION: Synthetic

<400> SEQUENCE: 480
cuccugccaa gaaaaacag                                              19

<210> SEQ ID NO 481
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 481
uuuaguggcc uugcuucuc                                                        19

<210> SEQ ID NO 482
<211> LENGTH: 19
<212> TYPE: RNA
<213> ORGANISM: Artificial Sequence
<220> FEATURE:
<223> OTHER INFORMATION: Synthetic

<400> SEQUENCE: 482
gucuccacca ucuccucuu                                                        19

<210> SEQ ID NO 483
<211> LENGTH: 19
<212> TYPE: RNA
<213> ORGANISM: Artificial Sequence
<220> FEATURE:
<223> OTHER INFORMATION: Synthetic

<400> SEQUENCE: 483
gaccacugcu gagccuccg                                                        19

<210> SEQ ID NO 484
<211> LENGTH: 19
<212> TYPE: RNA
<213> ORGANISM: Artificial Sequence
<220> FEATURE:
<223> OTHER INFORMATION: Synthetic

<400> SEQUENCE: 484
aaguccuuua ccccucaag                                                        19

<210> SEQ ID NO 485
<211> LENGTH: 19
<212> TYPE: RNA
<213> ORGANISM: Artificial Sequence
<220> FEATURE:
<223> OTHER INFORMATION: Synthetic

<400> SEQUENCE: 485
cucuucaucu gggcaucua                                                        19

<210> SEQ ID NO 486
<211> LENGTH: 19
<212> TYPE: RNA
<213> ORGANISM: Artificial Sequence
<220> FEATURE:
<223> OTHER INFORMATION: Synthetic

<400> SEQUENCE: 486
ugcagauguc agcuuuccc                                                        19

<210> SEQ ID NO 487
<211> LENGTH: 19
<212> TYPE: RNA
<213> ORGANISM: Artificial Sequence
<220> FEATURE:
<223> OTHER INFORMATION: Synthetic

<400> SEQUENCE: 487
```
gccucaaagu ggguucccu            19

<210> SEQ ID NO 488
<211> LENGTH: 19
<212> TYPE: RNA
<213> ORGANISM: Artificial Sequence
<220> FEATURE:
<223> OTHER INFORMATION: Synthetic

<400> SEQUENCE: 488
uguccugcca uggccucag            19

<210> SEQ ID NO 489
<211> LENGTH: 19
<212> TYPE: RNA
<213> ORGANISM: Artificial Sequence
<220> FEATURE:
<223> OTHER INFORMATION: Synthetic

<400> SEQUENCE: 489
ucugcacccc acagcagcu            19

<210> SEQ ID NO 490
<211> LENGTH: 19
<212> TYPE: RNA
<213> ORGANISM: Artificial Sequence
<220> FEATURE:
<223> OTHER INFORMATION: Synthetic

<400> SEQUENCE: 490
uguccuucau cuucugccu            19

<210> SEQ ID NO 491
<211> LENGTH: 19
<212> TYPE: RNA
<213> ORGANISM: Artificial Sequence
<220> FEATURE:
<223> OTHER INFORMATION: Synthetic

<400> SEQUENCE: 491
ucaguuuucc cuuccuuuu            19

<210> SEQ ID NO 492
<211> LENGTH: 19
<212> TYPE: RNA
<213> ORGANISM: Artificial Sequence
<220> FEATURE:
<223> OTHER INFORMATION: Synthetic

<400> SEQUENCE: 492
gcugcucuag guuggccau            19

<210> SEQ ID NO 493
<211> LENGTH: 19
<212> TYPE: RNA
<213> ORGANISM: Artificial Sequence
<220> FEATURE:
<223> OTHER INFORMATION: Synthetic

<400> SEQUENCE: 493
cuccaagccc ugucccuug            19

<210> SEQ ID NO 494
<211> LENGTH: 19
<212> TYPE: RNA
<213> ORGANISM: Artificial Sequence

```
<220> FEATURE:
<223> OTHER INFORMATION: Synthetic

<400> SEQUENCE: 494
ucaucuccac cacccgagc                                                19

<210> SEQ ID NO 495
<211> LENGTH: 19
<212> TYPE: RNA
<213> ORGANISM: Artificial Sequence
<220> FEATURE:
<223> OTHER INFORMATION: Synthetic

<400> SEQUENCE: 495
gaccccacag uguccuugu                                                19

<210> SEQ ID NO 496
<211> LENGTH: 19
<212> TYPE: RNA
<213> ORGANISM: Artificial Sequence
<220> FEATURE:
<223> OTHER INFORMATION: Synthetic

<400> SEQUENCE: 496
cagaguucug gggacccag                                                19

<210> SEQ ID NO 497
<211> LENGTH: 19
<212> TYPE: RNA
<213> ORGANISM: Artificial Sequence
<220> FEATURE:
<223> OTHER INFORMATION: Synthetic

<400> SEQUENCE: 497
uagaguggcc uguagcucc                                                19

<210> SEQ ID NO 498
<211> LENGTH: 19
<212> TYPE: RNA
<213> ORGANISM: Artificial Sequence
<220> FEATURE:
<223> OTHER INFORMATION: Synthetic

<400> SEQUENCE: 498
aggacuagcc cuugggccu                                                19

<210> SEQ ID NO 499
<211> LENGTH: 19
<212> TYPE: RNA
<213> ORGANISM: Artificial Sequence
<220> FEATURE:
<223> OTHER INFORMATION: Synthetic

<400> SEQUENCE: 499
cugaggggac uggggaaga                                                19

<210> SEQ ID NO 500
<211> LENGTH: 19
<212> TYPE: RNA
<213> ORGANISM: Artificial Sequence
<220> FEATURE:
<223> OTHER INFORMATION: Synthetic

<400> SEQUENCE: 500
uggggcuggc ggggggccuc                                               19
```

```
<210> SEQ ID NO 501
<211> LENGTH: 19
<212> TYPE: RNA
<213> ORGANISM: Artificial Sequence
<220> FEATURE:
<223> OTHER INFORMATION: Synthetic

<400> SEQUENCE: 501
uguaugcugc uuucaaggu                                                  19

<210> SEQ ID NO 502
<211> LENGTH: 19
<212> TYPE: RNA
<213> ORGANISM: Artificial Sequence
<220> FEATURE:
<223> OTHER INFORMATION: Synthetic

<400> SEQUENCE: 502
uugguccaag ccuuccccu                                                  19

<210> SEQ ID NO 503
<211> LENGTH: 19
<212> TYPE: RNA
<213> ORGANISM: Artificial Sequence
<220> FEATURE:
<223> OTHER INFORMATION: Synthetic

<400> SEQUENCE: 503
ugugcuuggu cgcccagcu                                                  19

<210> SEQ ID NO 504
<211> LENGTH: 19
<212> TYPE: RNA
<213> ORGANISM: Artificial Sequence
<220> FEATURE:
<223> OTHER INFORMATION: Synthetic

<400> SEQUENCE: 504
ccauguguuc cugccccau                                                  19

<210> SEQ ID NO 505
<211> LENGTH: 19
<212> TYPE: RNA
<213> ORGANISM: Artificial Sequence
<220> FEATURE:
<223> OTHER INFORMATION: Synthetic

<400> SEQUENCE: 505
auauucccca ccccuuuac                                                  19

<210> SEQ ID NO 506
<211> LENGTH: 19
<212> TYPE: RNA
<213> ORGANISM: Artificial Sequence
<220> FEATURE:
<223> OTHER INFORMATION: Synthetic

<400> SEQUENCE: 506
cacaccacac ucccuccca                                                  19

<210> SEQ ID NO 507
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 507
cccugcauca cccccaucc                                               19

<210> SEQ ID NO 508
<211> LENGTH: 19
<212> TYPE: RNA
<213> ORGANISM: Artificial Sequence
<220> FEATURE:
<223> OTHER INFORMATION: Synthetic

<400> SEQUENCE: 508
cccaggguuc cccucaguc                                               19

<210> SEQ ID NO 509
<211> LENGTH: 19
<212> TYPE: RNA
<213> ORGANISM: Artificial Sequence
<220> FEATURE:
<223> OTHER INFORMATION: Synthetic

<400> SEQUENCE: 509
ugcccagccu gugccuguc                                               19

<210> SEQ ID NO 510
<211> LENGTH: 19
<212> TYPE: RNA
<213> ORGANISM: Artificial Sequence
<220> FEATURE:
<223> OTHER INFORMATION: Synthetic

<400> SEQUENCE: 510
ugcacugccc ugugccucu                                               19

<210> SEQ ID NO 511
<211> LENGTH: 19
<212> TYPE: RNA
<213> ORGANISM: Artificial Sequence
<220> FEATURE:
<223> OTHER INFORMATION: Synthetic

<400> SEQUENCE: 511
ccccacugca gagucsccu                                               19

<210> SEQ ID NO 512
<211> LENGTH: 19
<212> TYPE: RNA
<213> ORGANISM: Artificial Sequence
<220> FEATURE:
<223> OTHER INFORMATION: Synthetic

<400> SEQUENCE: 512
aagaaacuca cuucccgac                                               19

<210> SEQ ID NO 513
<211> LENGTH: 19
<212> TYPE: RNA
<213> ORGANISM: Artificial Sequence
<220> FEATURE:
<223> OTHER INFORMATION: Synthetic

<400> SEQUENCE: 513
acugcacugc ucacugcaa                                               19

<210> SEQ ID NO 514
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 514
ccucugugcc cgacuucca                                                   19

<210> SEQ ID NO 515
<211> LENGTH: 19
<212> TYPE: RNA
<213> ORGANISM: Artificial Sequence
<220> FEATURE:
<223> OTHER INFORMATION: Synthetic

<400> SEQUENCE: 515
cuucacaucu gucugcuac                                                   19

<210> SEQ ID NO 516
<211> LENGTH: 19
<212> TYPE: RNA
<213> ORGANISM: Artificial Sequence
<220> FEATURE:
<223> OTHER INFORMATION: Synthetic

<400> SEQUENCE: 516
acauggccuu caccacugc                                                   19

<210> SEQ ID NO 517
<211> LENGTH: 19
<212> TYPE: RNA
<213> ORGANISM: Artificial Sequence
<220> FEATURE:
<223> OTHER INFORMATION: Synthetic

<400> SEQUENCE: 517
uguauuuccc cacuugcua                                                   19

<210> SEQ ID NO 518
<211> LENGTH: 19
<212> TYPE: RNA
<213> ORGANISM: Artificial Sequence
<220> FEATURE:
<223> OTHER INFORMATION: Synthetic

<400> SEQUENCE: 518
acucccaggc ccuuuggau                                                   19

<210> SEQ ID NO 519
<211> LENGTH: 19
<212> TYPE: RNA
<213> ORGANISM: Artificial Sequence
<220> FEATURE:
<223> OTHER INFORMATION: Synthetic

<400> SEQUENCE: 519
ugcguugggc acccccccaa                                                  19

<210> SEQ ID NO 520
<211> LENGTH: 19
<212> TYPE: RNA
<213> ORGANISM: Artificial Sequence
<220> FEATURE:
<223> OTHER INFORMATION: Synthetic

<400> SEQUENCE: 520
```
cccugcaccc ccaaggauu                                                19

<210> SEQ ID NO 521
<211> LENGTH: 19
<212> TYPE: RNA
<213> ORGANISM: Artificial Sequence
<220> FEATURE:
<223> OTHER INFORMATION: Synthetic

<400> SEQUENCE: 521
ccuucacuuu cugcuccac                                                19

<210> SEQ ID NO 522
<211> LENGTH: 19
<212> TYPE: RNA
<213> ORGANISM: Artificial Sequence
<220> FEATURE:
<223> OTHER INFORMATION: Synthetic

<400> SEQUENCE: 522
acucuugcac gugucccuc                                                19

<210> SEQ ID NO 523
<211> LENGTH: 19
<212> TYPE: RNA
<213> ORGANISM: Artificial Sequence
<220> FEATURE:
<223> OTHER INFORMATION: Synthetic

<400> SEQUENCE: 523
cacaccacca ugcacacca                                                19

<210> SEQ ID NO 524
<211> LENGTH: 19
<212> TYPE: RNA
<213> ORGANISM: Artificial Sequence
<220> FEATURE:
<223> OTHER INFORMATION: Synthetic

<400> SEQUENCE: 524
uaggaacggu ccucauguc                                                19

<210> SEQ ID NO 525
<211> LENGTH: 19
<212> TYPE: RNA
<213> ORGANISM: Artificial Sequence
<220> FEATURE:
<223> OTHER INFORMATION: Synthetic

<400> SEQUENCE: 525
ugacccacug ucccauccu                                                19

<210> SEQ ID NO 526
<211> LENGTH: 19
<212> TYPE: RNA
<213> ORGANISM: Artificial Sequence
<220> FEATURE:
<223> OTHER INFORMATION: Synthetic

<400> SEQUENCE: 526
cuuucuccuu guccugccu                                                19

<210> SEQ ID NO 527
<211> LENGTH: 19
<212> TYPE: RNA

-continued

<213> ORGANISM: Artificial Sequence
<220> FEATURE:
<223> OTHER INFORMATION: Synthetic

<400> SEQUENCE: 527
aggcaucauu cugcccugc                                                      19

<210> SEQ ID NO 528
<211> LENGTH: 19
<212> TYPE: RNA
<213> ORGANISM: Artificial Sequence
<220> FEATURE:
<223> OTHER INFORMATION: Synthetic

<400> SEQUENCE: 528
ugccugaugu gguccucua                                                      19

<210> SEQ ID NO 529
<211> LENGTH: 19
<212> TYPE: RNA
<213> ORGANISM: Artificial Sequence
<220> FEATURE:
<223> OTHER INFORMATION: Synthetic

<400> SEQUENCE: 529
ggcacaagcu gucagccau                                                      19

<210> SEQ ID NO 530
<211> LENGTH: 19
<212> TYPE: RNA
<213> ORGANISM: Artificial Sequence
<220> FEATURE:
<223> OTHER INFORMATION: Synthetic

<400> SEQUENCE: 530
cauacgccac agcccaugg                                                      19

<210> SEQ ID NO 531
<211> LENGTH: 19
<212> TYPE: RNA
<213> ORGANISM: Artificial Sequence
<220> FEATURE:
<223> OTHER INFORMATION: Synthetic

<400> SEQUENCE: 531
uccuacccug cgaucugac                                                      19

<210> SEQ ID NO 532
<211> LENGTH: 19
<212> TYPE: RNA
<213> ORGANISM: Artificial Sequence
<220> FEATURE:
<223> OTHER INFORMATION: Synthetic

<400> SEQUENCE: 532
gcaccaggcc agacucguu                                                      19

<210> SEQ ID NO 533
<211> LENGTH: 19
<212> TYPE: RNA
<213> ORGANISM: Artificial Sequence
<220> FEATURE:
<223> OTHER INFORMATION: Synthetic

<400> SEQUENCE: 533
ugaggaaaca cugggccgg                                                      19

```
<210> SEQ ID NO 534
<211> LENGTH: 19
<212> TYPE: RNA
<213> ORGANISM: Artificial Sequence
<220> FEATURE:
<223> OTHER INFORMATION: Synthetic

<400> SEQUENCE: 534
aacagagggc ggaugagcu                                                  19

<210> SEQ ID NO 535
<211> LENGTH: 19
<212> TYPE: RNA
<213> ORGANISM: Artificial Sequence
<220> FEATURE:
<223> OTHER INFORMATION: Synthetic

<400> SEQUENCE: 535
ccuggaaugc uagggagca                                                  19

<210> SEQ ID NO 536
<211> LENGTH: 19
<212> TYPE: RNA
<213> ORGANISM: Artificial Sequence
<220> FEATURE:
<223> OTHER INFORMATION: Synthetic

<400> SEQUENCE: 536
ggagagucca agauggcuc                                                  19

<210> SEQ ID NO 537
<211> LENGTH: 19
<212> TYPE: RNA
<213> ORGANISM: Artificial Sequence
<220> FEATURE:
<223> OTHER INFORMATION: Synthetic

<400> SEQUENCE: 537
gccuuucaaa ccuggggag                                                  19

<210> SEQ ID NO 538
<211> LENGTH: 19
<212> TYPE: RNA
<213> ORGANISM: Artificial Sequence
<220> FEATURE:
<223> OTHER INFORMATION: Synthetic

<400> SEQUENCE: 538
gucccugcua aucugaugg                                                  19

<210> SEQ ID NO 539
<211> LENGTH: 19
<212> TYPE: RNA
<213> ORGANISM: Artificial Sequence
<220> FEATURE:
<223> OTHER INFORMATION: Synthetic

<400> SEQUENCE: 539
ggugaugccc uacaccccg                                                  19

<210> SEQ ID NO 540
<211> LENGTH: 19
<212> TYPE: RNA
<213> ORGANISM: Artificial Sequence
<220> FEATURE:
```

-continued

<223> OTHER INFORMATION: Synthetic

<400> SEQUENCE: 540
uuaagagaag gaaccuugg 19

<210> SEQ ID NO 541
<211> LENGTH: 19
<212> TYPE: RNA
<213> ORGANISM: Artificial Sequence
<220> FEATURE:
<223> OTHER INFORMATION: Synthetic

<400> SEQUENCE: 541 agaucccca cccuuaguu 19

<210> SEQ ID NO 542
<211> LENGTH: 19
<212> TYPE: RNA
<213> ORGANISM: Artificial Sequence
<220> FEATURE:
<223> OTHER INFORMATION: Synthetic

<400> SEQUENCE: 542
gucaacauaa aaacauuca 19

<210> SEQ ID NO 543
<211> LENGTH: 19
<212> TYPE: RNA
<213> ORGANISM: Artificial Sequence
<220> FEATURE:
<223> OTHER INFORMATION: Synthetic

<400> SEQUENCE: 543
aaaauuuagu caagaacag 19

<210> SEQ ID NO 544
<211> LENGTH: 19
<212> TYPE: RNA
<213> ORGANISM: Artificial Sequence
<220> FEATURE:
<223> OTHER INFORMATION: Synthetic

<400> SEQUENCE: 544
uugcuucuga aacucuuga 19

<210> SEQ ID NO 545
<211> LENGTH: 19
<212> TYPE: RNA
<213> ORGANISM: Artificial Sequence
<220> FEATURE:
<223> OTHER INFORMATION: Synthetic

<400> SEQUENCE: 545
aacgucuggu cuguccugu 19

<210> SEQ ID NO 546
<211> LENGTH: 19
<212> TYPE: RNA
<213> ORGANISM: Artificial Sequence
<220> FEATURE:
<223> OTHER INFORMATION: Synthetic

<400> SEQUENCE: 546
cgccccaggg uagaaugaa 19

```
<210> SEQ ID NO 547
<211> LENGTH: 19
<212> TYPE: RNA
<213> ORGANISM: Artificial Sequence
<220> FEATURE:
<223> OTHER INFORMATION: Synthetic

<400> SEQUENCE: 547
ggaggaagaa guucuguuc                                            19

<210> SEQ ID NO 548
<211> LENGTH: 19
<212> TYPE: RNA
<213> ORGANISM: Artificial Sequence
<220> FEATURE:
<223> OTHER INFORMATION: Synthetic

<400> SEQUENCE: 548
gcaggaaguc auuguuugg                                            19

<210> SEQ ID NO 549
<211> LENGTH: 19
<212> TYPE: RNA
<213> ORGANISM: Artificial Sequence
<220> FEATURE:
<223> OTHER INFORMATION: Synthetic

<400> SEQUENCE: 549
cuguccccau caaacaugg                                            19

<210> SEQ ID NO 550
<211> LENGTH: 19
<212> TYPE: RNA
<213> ORGANISM: Artificial Sequence
<220> FEATURE:
<223> OTHER INFORMATION: Synthetic

<400> SEQUENCE: 550
ggcagaggac agugguagc                                            19

<210> SEQ ID NO 551
<211> LENGTH: 19
<212> TYPE: RNA
<213> ORGANISM: Artificial Sequence
<220> FEATURE:
<223> OTHER INFORMATION: Synthetic

<400> SEQUENCE: 551
agcugaaagg ggaaugggg                                            19

<210> SEQ ID NO 552
<211> LENGTH: 19
<212> TYPE: RNA
<213> ORGANISM: Artificial Sequence
<220> FEATURE:
<223> OTHER INFORMATION: Synthetic

<400> SEQUENCE: 552
acuaugcaug cucauggga                                            19

<210> SEQ ID NO 553
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 553
aggccauugg ucuggugaa                                        19

<210> SEQ ID NO 554
<211> LENGTH: 19
<212> TYPE: RNA
<213> ORGANISM: Artificial Sequence
<220> FEATURE:
<223> OTHER INFORMATION: Synthetic

<400> SEQUENCE: 554
gggacuuaga gaauggcua                                        19

<210> SEQ ID NO 555
<211> LENGTH: 19
<212> TYPE: RNA
<213> ORGANISM: Artificial Sequence
<220> FEATURE:
<223> OTHER INFORMATION: Synthetic

<400> SEQUENCE: 555
aauaacuucu uccaggaug                                        19

<210> SEQ ID NO 556
<211> LENGTH: 19
<212> TYPE: RNA
<213> ORGANISM: Artificial Sequence
<220> FEATURE:
<223> OTHER INFORMATION: Synthetic

<400> SEQUENCE: 556
aggugcagcu cuugaagaa                                        19

<210> SEQ ID NO 557
<211> LENGTH: 19
<212> TYPE: RNA
<213> ORGANISM: Artificial Sequence
<220> FEATURE:
<223> OTHER INFORMATION: Synthetic

<400> SEQUENCE: 557
aacuaaugcu aggaggaga                                        19

<210> SEQ ID NO 558
<211> LENGTH: 19
<212> TYPE: RNA
<213> ORGANISM: Artificial Sequence
<220> FEATURE:
<223> OTHER INFORMATION: Synthetic

<400> SEQUENCE: 558
acuccuugag uugaucuaa                                        19

<210> SEQ ID NO 559
<211> LENGTH: 19
<212> TYPE: RNA
<213> ORGANISM: Artificial Sequence
<220> FEATURE:
<223> OTHER INFORMATION: Synthetic

<400> SEQUENCE: 559
cagcagccau uaauaaaua                                        19

<210> SEQ ID NO 560
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 560
aaccccagaa acuggagac                                               19

<210> SEQ ID NO 561
<211> LENGTH: 19
<212> TYPE: RNA
<213> ORGANISM: Artificial Sequence
<220> FEATURE:
<223> OTHER INFORMATION: Synthetic

<400> SEQUENCE: 561
cuuguguccu uagugcuua                                               19

<210> SEQ ID NO 562
<211> LENGTH: 19
<212> TYPE: RNA
<213> ORGANISM: Artificial Sequence
<220> FEATURE:
<223> OTHER INFORMATION: Synthetic

<400> SEQUENCE: 562
gagaaggucu gauugauuc                                               19

<210> SEQ ID NO 563
<211> LENGTH: 19
<212> TYPE: RNA
<213> ORGANISM: Artificial Sequence
<220> FEATURE:
<223> OTHER INFORMATION: Synthetic

<400> SEQUENCE: 563
ggcuaucuua aguucaggg                                               19

<210> SEQ ID NO 564
<211> LENGTH: 19
<212> TYPE: RNA
<213> ORGANISM: Artificial Sequence
<220> FEATURE:
<223> OTHER INFORMATION: Synthetic

<400> SEQUENCE: 564
uguccuuuuu cugauugug                                               19

<210> SEQ ID NO 565
<211> LENGTH: 19
<212> TYPE: RNA
<213> ORGANISM: Artificial Sequence
<220> FEATURE:
<223> OTHER INFORMATION: Synthetic

<400> SEQUENCE: 565
accacugucu cauguccuu                                               19

<210> SEQ ID NO 566
<211> LENGTH: 19
<212> TYPE: RNA
<213> ORGANISM: Artificial Sequence
<220> FEATURE:
<223> OTHER INFORMATION: Synthetic

<400> SEQUENCE: 566
```
cucugucuga uggccauca                                                    19

<210> SEQ ID NO 567
<211> LENGTH: 19
<212> TYPE: RNA
<213> ORGANISM: Artificial Sequence
<220> FEATURE:
<223> OTHER INFORMATION: Synthetic

<400> SEQUENCE: 567
uccaucagca uuugaaguc                                                    19

<210> SEQ ID NO 568
<211> LENGTH: 19
<212> TYPE: RNA
<213> ORGANISM: Artificial Sequence
<220> FEATURE:
<223> OTHER INFORMATION: Synthetic

<400> SEQUENCE: 568
uaaguacuuc cucugcccu                                                    19

<210> SEQ ID NO 569
<211> LENGTH: 19
<212> TYPE: RNA
<213> ORGANISM: Artificial Sequence
<220> FEATURE:
<223> OTHER INFORMATION: Synthetic

<400> SEQUENCE: 569
cucugacacc aaccucccu                                                    19

<210> SEQ ID NO 570
<211> LENGTH: 19
<212> TYPE: RNA
<213> ORGANISM: Artificial Sequence
<220> FEATURE:
<223> OTHER INFORMATION: Synthetic

<400> SEQUENCE: 570
cugauccccc acuccugcc                                                    19

<210> SEQ ID NO 571
<211> LENGTH: 19
<212> TYPE: RNA
<213> ORGANISM: Artificial Sequence
<220> FEATURE:
<223> OTHER INFORMATION: Synthetic

<400> SEQUENCE: 571
uccuagaauc caccuuccc                                                    19

<210> SEQ ID NO 572
<211> LENGTH: 19
<212> TYPE: RNA
<213> ORGANISM: Artificial Sequence
<220> FEATURE:
<223> OTHER INFORMATION: Synthetic

<400> SEQUENCE: 572
accucaggca cucccuuuu                                                    19

<210> SEQ ID NO 573
<211> LENGTH: 19
<212> TYPE: RNA
<213> ORGANISM: Artificial Sequence

```
<220> FEATURE:
<223> OTHER INFORMATION: Synthetic

<400> SEQUENCE: 573 caucccuuc uaaggccua                                              19

<210> SEQ ID NO 574
<211> LENGTH: 19
<212> TYPE: RNA
<213> ORGANISM: Artificial Sequence
<220> FEATURE:
<223> OTHER INFORMATION: Synthetic

<400> SEQUENCE: 574
cucuguaaaa aucugacuc                                             19

<210> SEQ ID NO 575
<211> LENGTH: 19
<212> TYPE: RNA
<213> ORGANISM: Artificial Sequence
<220> FEATURE:
<223> OTHER INFORMATION: Synthetic

<400> SEQUENCE: 575
ccaagcccug cccuccucc                                             19

<210> SEQ ID NO 576
<211> LENGTH: 19
<212> TYPE: RNA
<213> ORGANISM: Artificial Sequence
<220> FEATURE:
<223> OTHER INFORMATION: Synthetic

<400> SEQUENCE: 576
cuucuuccuc cacuggacc                                             19

<210> SEQ ID NO 577
<211> LENGTH: 19
<212> TYPE: RNA
<213> ORGANISM: Artificial Sequence
<220> FEATURE:
<223> OTHER INFORMATION: Synthetic

<400> SEQUENCE: 577
uuuccaagcc ucuccuucc                                             19

<210> SEQ ID NO 578
<211> LENGTH: 19
<212> TYPE: RNA
<213> ORGANISM: Artificial Sequence
<220> FEATURE:
<223> OTHER INFORMATION: Synthetic

<400> SEQUENCE: 578
uuucccaaga cacaaggcu                                             19

<210> SEQ ID NO 579
<211> LENGTH: 19
<212> TYPE: RNA
<213> ORGANISM: Artificial Sequence
<220> FEATURE:
<223> OTHER INFORMATION: Synthetic

<400> SEQUENCE: 579
uaugcucaaa ggccuuuuu                                             19
```

```
<210> SEQ ID NO 580
<211> LENGTH: 19
<212> TYPE: RNA
<213> ORGANISM: Artificial Sequence
<220> FEATURE:
<223> OTHER INFORMATION: Synthetic

<400> SEQUENCE: 580 ucgaguggc uggacccau                                                        19

<210> SEQ ID NO 581
<211> LENGTH: 19
<212> TYPE: RNA
<213> ORGANISM: Artificial Sequence
<220> FEATURE:
<223> OTHER INFORMATION: Synthetic

<400> SEQUENCE: 581
aggcauggcc ccugcacuu                                                       19

<210> SEQ ID NO 582
<211> LENGTH: 19
<212> TYPE: RNA
<213> ORGANISM: Artificial Sequence
<220> FEATURE:
<223> OTHER INFORMATION: Synthetic

<400> SEQUENCE: 582
ucacuuauug gaacaccaa                                                       19

<210> SEQ ID NO 583
<211> LENGTH: 19
<212> TYPE: RNA
<213> ORGANISM: Artificial Sequence
<220> FEATURE:
<223> OTHER INFORMATION: Synthetic

<400> SEQUENCE: 583
uaccaccacu gcuuccauu                                                       19

<210> SEQ ID NO 584
<211> LENGTH: 19
<212> TYPE: RNA
<213> ORGANISM: Artificial Sequence
<220> FEATURE:
<223> OTHER INFORMATION: Synthetic

<400> SEQUENCE: 584
aacucugccc aguguagcu                                                       19

<210> SEQ ID NO 585
<211> LENGTH: 19
<212> TYPE: RNA
<213> ORGANISM: Artificial Sequence
<220> FEATURE:
<223> OTHER INFORMATION: Synthetic

<400> SEQUENCE: 585
gugaaccagc acccugcca                                                       19

<210> SEQ ID NO 586
<211> LENGTH: 19
<212> TYPE: RNA
<213> ORGANISM: Artificial Sequence
<220> FEATURE:
<223> OTHER INFORMATION: Synthetic
```

<400> SEQUENCE: 586
cauucagggc ugggcagag                                                        19

<210> SEQ ID NO 587
<211> LENGTH: 19
<212> TYPE: RNA
<213> ORGANISM: Artificial Sequence
<220> FEATURE:
<223> OTHER INFORMATION: Synthetic

<400> SEQUENCE: 587
gggggccuuu aaggcacac                                                        19

<210> SEQ ID NO 588
<211> LENGTH: 19
<212> TYPE: RNA
<213> ORGANISM: Artificial Sequence
<220> FEATURE:
<223> OTHER INFORMATION: Synthetic

<400> SEQUENCE: 588
cguauggggc cccuuguag                                                        19

<210> SEQ ID NO 589
<211> LENGTH: 19
<212> TYPE: RNA
<213> ORGANISM: Artificial Sequence
<220> FEATURE:
<223> OTHER INFORMATION: Synthetic

<400> SEQUENCE: 589
accaguuaaa agcucuguc                                                        19

<210> SEQ ID NO 590
<211> LENGTH: 19
<212> TYPE: RNA
<213> ORGANISM: Artificial Sequence
<220> FEATURE:
<223> OTHER INFORMATION: Synthetic

<400> SEQUENCE: 590 ugcgggguaca gggaaggca                                                       19

<210> SEQ ID NO 591
<211> LENGTH: 19
<212> TYPE: RNA
<213> ORGANISM: Artificial Sequence
<220> FEATURE:
<223> OTHER INFORMATION: Synthetic

<400> SEQUENCE: 591
gggcccacuu guggcugcu                                                        19

<210> SEQ ID NO 592
<211> LENGTH: 19
<212> TYPE: RNA
<213> ORGANISM: Artificial Sequence
<220> FEATURE:
<223> OTHER INFORMATION: Synthetic

<400> SEQUENCE: 592
gggaggcugc aauagucug                                                        19

<210> SEQ ID NO 593

```
<211> LENGTH: 19
<212> TYPE: RNA
<213> ORGANISM: Artificial Sequence
<220> FEATURE:
<223> OTHER INFORMATION: Synthetic

<400> SEQUENCE: 593
acaugcucac auguuuaug                                               19

<210> SEQ ID NO 594
<211> LENGTH: 19
<212> TYPE: RNA
<213> ORGANISM: Artificial Sequence
<220> FEATURE:
<223> OTHER INFORMATION: Synthetic

<400> SEQUENCE: 594
caucauggca cacucagaa                                               19

<210> SEQ ID NO 595
<211> LENGTH: 19
<212> TYPE: RNA
<213> ORGANISM: Artificial Sequence
<220> FEATURE:
<223> OTHER INFORMATION: Synthetic

<400> SEQUENCE: 595
uccagccagg uccacucac                                               19

<210> SEQ ID NO 596
<211> LENGTH: 19
<212> TYPE: RNA
<213> ORGANISM: Artificial Sequence
<220> FEATURE:
<223> OTHER INFORMATION: Synthetic

<400> SEQUENCE: 596
cagucgcucu ccgaagauu                                               19

<210> SEQ ID NO 597
<211> LENGTH: 19
<212> TYPE: RNA
<213> ORGANISM: Artificial Sequence
<220> FEATURE:
<223> OTHER INFORMATION: Synthetic

<400> SEQUENCE: 597
gauucgauuu gaacaccuc                                               19

<210> SEQ ID NO 598
<211> LENGTH: 19
<212> TYPE: RNA
<213> ORGANISM: Artificial Sequence
<220> FEATURE:
<223> OTHER INFORMATION: Synthetic

<400> SEQUENCE: 598
gaaggaagcc uccugggag                                               19

<210> SEQ ID NO 599
<211> LENGTH: 19
<212> TYPE: RNA
<213> ORGANISM: Artificial Sequence
<220> FEATURE:
<223> OTHER INFORMATION: Synthetic

<400> SEQUENCE: 599
```

```
uaccagaaua gggggcugg                                              19

<210> SEQ ID NO 600
<211> LENGTH: 19
<212> TYPE: RNA
<213> ORGANISM: Artificial Sequence
<220> FEATURE:
<223> OTHER INFORMATION: Synthetic

<400> SEQUENCE: 600
aggaagccuc cugguaguu                                              19

<210> SEQ ID NO 601
<211> LENGTH: 19
<212> TYPE: RNA
<213> ORGANISM: Artificial Sequence
<220> FEATURE:
<223> OTHER INFORMATION: Synthetic

<400> SEQUENCE: 601
ccagaauagg gggcuggaa                                              19

<210> SEQ ID NO 602
<211> LENGTH: 19
<212> TYPE: RNA
<213> ORGANISM: Artificial Sequence
<220> FEATURE:
<223> OTHER INFORMATION: Synthetic

<400> SEQUENCE: 602
gagggauuuu gguaguuac                                              19

<210> SEQ ID NO 603
<211> LENGTH: 19
<212> TYPE: RNA
<213> ORGANISM: Artificial Sequence
<220> FEATURE:
<223> OTHER INFORMATION: Synthetic

<400> SEQUENCE: 603
accccuacac uugcacccg                                              19

<210> SEQ ID NO 604
<211> LENGTH: 19
<212> TYPE: RNA
<213> ORGANISM: Artificial Sequence
<220> FEATURE:
<223> OTHER INFORMATION: Synthetic

<400> SEQUENCE: 604
ucucauccuu ccaucucua                                              19

<210> SEQ ID NO 605
<211> LENGTH: 19
<212> TYPE: RNA
<213> ORGANISM: Artificial Sequence
<220> FEATURE:
<223> OTHER INFORMATION: Synthetic

<400> SEQUENCE: 605
caaaagguca auuucaccu                                              19

<210> SEQ ID NO 606
<211> LENGTH: 19
<212> TYPE: RNA
```

```
<213> ORGANISM: Artificial Sequence
<220> FEATURE:
<223> OTHER INFORMATION: Synthetic

<400> SEQUENCE: 606
gagccagagc uuugcuuuc                                              19

<210> SEQ ID NO 607
<211> LENGTH: 19
<212> TYPE: RNA
<213> ORGANISM: Artificial Sequence
<220> FEATURE:
<223> OTHER INFORMATION: Synthetic

<400> SEQUENCE: 607
ugguaguuug gggccugug                                              19

<210> SEQ ID NO 608
<211> LENGTH: 19
<212> TYPE: RNA
<213> ORGANISM: Artificial Sequence
<220> FEATURE:
<223> OTHER INFORMATION: Synthetic

<400> SEQUENCE: 608
ggauaugcua gauacggcu                                              19

<210> SEQ ID NO 609
<211> LENGTH: 19
<212> TYPE: RNA
<213> ORGANISM: Artificial Sequence
<220> FEATURE:
<223> OTHER INFORMATION: Synthetic

<400> SEQUENCE: 609
guagugggug gaggguggg                                              19

<210> SEQ ID NO 610
<211> LENGTH: 19
<212> TYPE: RNA
<213> ORGANISM: Artificial Sequence
<220> FEATURE:
<223> OTHER INFORMATION: Synthetic

<400> SEQUENCE: 610
acuccuuugu uggaggagg                                              19

<210> SEQ ID NO 611
<211> LENGTH: 19
<212> TYPE: RNA
<213> ORGANISM: Artificial Sequence
<220> FEATURE:
<223> OTHER INFORMATION: Synthetic

<400> SEQUENCE: 611
guuuuuucaa cugaguuga                                              19

<210> SEQ ID NO 612
<211> LENGTH: 19
<212> TYPE: RNA
<213> ORGANISM: Artificial Sequence
<220> FEATURE:
<223> OTHER INFORMATION: Synthetic

<400> SEQUENCE: 612
ggauaggcca aaggaccag                                              19
```

```
<210> SEQ ID NO 613
<211> LENGTH: 19
<212> TYPE: RNA
<213> ORGANISM: Artificial Sequence
<220> FEATURE:
<223> OTHER INFORMATION: Synthetic

<400> SEQUENCE: 613
agguggacuu ugacccaug                                                  19

<210> SEQ ID NO 614
<211> LENGTH: 19
<212> TYPE: RNA
<213> ORGANISM: Artificial Sequence
<220> FEATURE:
<223> OTHER INFORMATION: Synthetic

<400> SEQUENCE: 614
ucuccaggcc cccaggaga                                                  19

<210> SEQ ID NO 615
<211> LENGTH: 19
<212> TYPE: RNA
<213> ORGANISM: Artificial Sequence
<220> FEATURE:
<223> OTHER INFORMATION: Synthetic

<400> SEQUENCE: 615
uuuccguagg cucaguccu                                                  19

<210> SEQ ID NO 616
<211> LENGTH: 19
<212> TYPE: RNA
<213> ORGANISM: Artificial Sequence
<220> FEATURE:
<223> OTHER INFORMATION: Synthetic

<400> SEQUENCE: 616
gagugggaag guauccccu                                                  19

<210> SEQ ID NO 617
<211> LENGTH: 19
<212> TYPE: RNA
<213> ORGANISM: Artificial Sequence
<220> FEATURE:
<223> OTHER INFORMATION: Synthetic

<400> SEQUENCE: 617
ccugugugaa gcagugcug                                                  19

<210> SEQ ID NO 618
<211> LENGTH: 19
<212> TYPE: RNA
<213> ORGANISM: Artificial Sequence
<220> FEATURE:
<223> OTHER INFORMATION: Synthetic

<400> SEQUENCE: 618
agagccccag gcaggggggc                                                 19

<210> SEQ ID NO 619
<211> LENGTH: 19
<212> TYPE: RNA
<213> ORGANISM: Artificial Sequence
<220> FEATURE:
```

<223> OTHER INFORMATION: Synthetic

<400> SEQUENCE: 619
gugaagaagg cuccuugga                                                    19

<210> SEQ ID NO 620
<211> LENGTH: 19
<212> TYPE: RNA
<213> ORGANISM: Artificial Sequence
<220> FEATURE:
<223> OTHER INFORMATION: Synthetic

<400> SEQUENCE: 620
aaguggagcu ggaaguggg                                                    19

<210> SEQ ID NO 621
<211> LENGTH: 19
<212> TYPE: RNA
<213> ORGANISM: Artificial Sequence
<220> FEATURE:
<223> OTHER INFORMATION: Synthetic

<400> SEQUENCE: 621
cuugacuuaa ccuugcaga                                                    19

<210> SEQ ID NO 622
<211> LENGTH: 19
<212> TYPE: RNA
<213> ORGANISM: Artificial Sequence
<220> FEATURE:
<223> OTHER INFORMATION: Synthetic

<400> SEQUENCE: 622
uauuucucau cguucucac                                                    19

<210> SEQ ID NO 623
<211> LENGTH: 19
<212> TYPE: RNA
<213> ORGANISM: Artificial Sequence
<220> FEATURE:
<223> OTHER INFORMATION: Synthetic

<400> SEQUENCE: 623
aaggagacac caucuccccu                                                   19

<210> SEQ ID NO 624
<211> LENGTH: 19
<212> TYPE: RNA
<213> ORGANISM: Artificial Sequence
<220> FEATURE:
<223> OTHER INFORMATION: Synthetic

<400> SEQUENCE: 624
caggcagauc aaggacuua                                                    19

<210> SEQ ID NO 625
<211> LENGTH: 19
<212> TYPE: RNA
<213> ORGANISM: Artificial Sequence
<220> FEATURE:
<223> OTHER INFORMATION: Synthetic

<400> SEQUENCE: 625
aaccucccau uccacagac                                                    19

```
<210> SEQ ID NO 626
<211> LENGTH: 19
<212> TYPE: RNA
<213> ORGANISM: Artificial Sequence
<220> FEATURE:
<223> OTHER INFORMATION: Synthetic

<400> SEQUENCE: 626
ccucagcgca gcuaaucca                                                19

<210> SEQ ID NO 627
<211> LENGTH: 19
<212> TYPE: RNA
<213> ORGANISM: Artificial Sequence
<220> FEATURE:
<223> OTHER INFORMATION: Synthetic

<400> SEQUENCE: 627
caccagcugu ggaugggac                                                19

<210> SEQ ID NO 628
<211> LENGTH: 19
<212> TYPE: RNA
<213> ORGANISM: Artificial Sequence
<220> FEATURE:
<223> OTHER INFORMATION: Synthetic

<400> SEQUENCE: 628
ccccuucaag cagcugagc                                                19

<210> SEQ ID NO 629
<211> LENGTH: 19
<212> TYPE: RNA
<213> ORGANISM: Artificial Sequence
<220> FEATURE:
<223> OTHER INFORMATION: Synthetic

<400> SEQUENCE: 629
uuacagagga gggagucuc                                                19

<210> SEQ ID NO 630
<211> LENGTH: 19
<212> TYPE: RNA
<213> ORGANISM: Artificial Sequence
<220> FEATURE:
<223> OTHER INFORMATION: Synthetic

<400> SEQUENCE: 630
caauccccca gaaagaagu                                                19

<210> SEQ ID NO 631
<211> LENGTH: 19
<212> TYPE: RNA
<213> ORGANISM: Artificial Sequence
<220> FEATURE:
<223> OTHER INFORMATION: Synthetic

<400> SEQUENCE: 631
gauagguacu gcccacccc                                                19

<210> SEQ ID NO 632
<211> LENGTH: 19
<212> TYPE: RNA
<213> ORGANISM: Artificial Sequence
<220> FEATURE:
<223> OTHER INFORMATION: Synthetic
```

<400> SEQUENCE: 632
agcuaggagg ggacugggg                                                    19

<210> SEQ ID NO 633
<211> LENGTH: 19
<212> TYPE: RNA
<213> ORGANISM: Artificial Sequence
<220> FEATURE:
<223> OTHER INFORMATION: Synthetic

<400> SEQUENCE: 633
uggaaaccac uaaagucaa                                                    19

<210> SEQ ID NO 634
<211> LENGTH: 19
<212> TYPE: RNA
<213> ORGANISM: Artificial Sequence
<220> FEATURE:
<223> OTHER INFORMATION: Synthetic

<400> SEQUENCE: 634
cuuuguuaac uucuacauu                                                    19

<210> SEQ ID NO 635
<211> LENGTH: 19
<212> TYPE: RNA
<213> ORGANISM: Artificial Sequence
<220> FEATURE:
<223> OTHER INFORMATION: Synthetic

<400> SEQUENCE: 635
ucacaggaau ggggcauac                                                    19

<210> SEQ ID NO 636
<211> LENGTH: 19
<212> TYPE: RNA
<213> ORGANISM: Artificial Sequence
<220> FEATURE:
<223> OTHER INFORMATION: Synthetic

<400> SEQUENCE: 636
agaaugguug ugcuuuugu                                                    19

<210> SEQ ID NO 637
<211> LENGTH: 19
<212> TYPE: RNA
<213> ORGANISM: Artificial Sequence
<220> FEATURE:
<223> OTHER INFORMATION: Synthetic

<400> SEQUENCE: 637
ccaugcucca guaacuuca                                                    19

<210> SEQ ID NO 638
<211> LENGTH: 19
<212> TYPE: RNA
<213> ORGANISM: Artificial Sequence
<220> FEATURE:
<223> OTHER INFORMATION: Synthetic

<400> SEQUENCE: 638
agggaggaug agcugagcc                                                    19

<210> SEQ ID NO 639
<211> LENGTH: 19

```
<212> TYPE: RNA
<213> ORGANISM: Artificial Sequence
<220> FEATURE:
<223> OTHER INFORMATION: Synthetic

<400> SEQUENCE: 639
caugggagaa ggggccaga                                                   19

<210> SEQ ID NO 640
<211> LENGTH: 19
<212> TYPE: RNA
<213> ORGANISM: Artificial Sequence
<220> FEATURE:
<223> OTHER INFORMATION: Synthetic

<400> SEQUENCE: 640
gcugggccga gaugucccc                                                   19

<210> SEQ ID NO 641
<211> LENGTH: 19
<212> TYPE: RNA
<213> ORGANISM: Artificial Sequence
<220> FEATURE:
<223> OTHER INFORMATION: Synthetic

<400> SEQUENCE: 641
uggaaauggg auaggggug                                                   19

<210> SEQ ID NO 642
<211> LENGTH: 19
<212> TYPE: RNA
<213> ORGANISM: Artificial Sequence
<220> FEATURE:
<223> OTHER INFORMATION: Synthetic

<400> SEQUENCE: 642
auggggaagg aagaacucu                                                   19

<210> SEQ ID NO 643
<211> LENGTH: 19
<212> TYPE: RNA
<213> ORGANISM: Artificial Sequence
<220> FEATURE:
<223> OTHER INFORMATION: Synthetic

<400> SEQUENCE: 643
cauuuuauga aggcccaga                                                   19

<210> SEQ ID NO 644
<211> LENGTH: 19
<212> TYPE: RNA
<213> ORGANISM: Artificial Sequence
<220> FEATURE:
<223> OTHER INFORMATION: Synthetic

<400> SEQUENCE: 644
ccagucuggc uuccccugc                                                   19

<210> SEQ ID NO 645
<211> LENGTH: 19
<212> TYPE: RNA
<213> ORGANISM: Artificial Sequence
<220> FEATURE:
<223> OTHER INFORMATION: Synthetic

<400> SEQUENCE: 645
```
gcuuuagcgc uccugagac                                           19

<210> SEQ ID NO 646
<211> LENGTH: 19
<212> TYPE: RNA
<213> ORGANISM: Artificial Sequence
<220> FEATURE:
<223> OTHER INFORMATION: Synthetic

<400> SEQUENCE: 646
acgacccccc acggaaggg                                           19

<210> SEQ ID NO 647
<211> LENGTH: 19
<212> TYPE: RNA
<213> ORGANISM: Artificial Sequence
<220> FEATURE:
<223> OTHER INFORMATION: Synthetic

<400> SEQUENCE: 647
agggcuaguc ccagaaaga                                           19

<210> SEQ ID NO 648
<211> LENGTH: 19
<212> TYPE: RNA
<213> ORGANISM: Artificial Sequence
<220> FEATURE:
<223> OTHER INFORMATION: Synthetic

<400> SEQUENCE: 648
ucccaggucc uaaacagca                                           19

<210> SEQ ID NO 649
<211> LENGTH: 19
<212> TYPE: RNA
<213> ORGANISM: Artificial Sequence
<220> FEATURE:
<223> OTHER INFORMATION: Synthetic

<400> SEQUENCE: 649
gcagguaccc cauuguggu                                           19

<210> SEQ ID NO 650
<211> LENGTH: 19
<212> TYPE: RNA
<213> ORGANISM: Artificial Sequence
<220> FEATURE:
<223> OTHER INFORMATION: Synthetic

<400> SEQUENCE: 650
cucuugggga cccccucgg                                           19

<210> SEQ ID NO 651
<211> LENGTH: 19
<212> TYPE: RNA
<213> ORGANISM: Artificial Sequence
<220> FEATURE:
<223> OTHER INFORMATION: Synthetic

<400> SEQUENCE: 651
ucacaugaca gccuggauc                                           19

<210> SEQ ID NO 652
<211> LENGTH: 19
<212> TYPE: RNA
<213> ORGANISM: Artificial Sequence

```
<220> FEATURE:
<223> OTHER INFORMATION: Synthetic

<400> SEQUENCE: 652
aacacaugcc accauaaau                                                    19

<210> SEQ ID NO 653
<211> LENGTH: 19
<212> TYPE: RNA
<213> ORGANISM: Artificial Sequence
<220> FEATURE:
<223> OTHER INFORMATION: Synthetic

<400> SEQUENCE: 653
aguagccaac aaaucaca                                                     19

<210> SEQ ID NO 654
<211> LENGTH: 19
<212> TYPE: RNA
<213> ORGANISM: Artificial Sequence
<220> FEATURE:
<223> OTHER INFORMATION: Synthetic

<400> SEQUENCE: 654
ucuagauuuc aagacacaa                                                    19

<210> SEQ ID NO 655
<211> LENGTH: 19
<212> TYPE: RNA
<213> ORGANISM: Artificial Sequence
<220> FEATURE:
<223> OTHER INFORMATION: Synthetic

<400> SEQUENCE: 655
aauucugcgu gaaauaauu                                                    19

<210> SEQ ID NO 656
<211> LENGTH: 19
<212> TYPE: RNA
<213> ORGANISM: Artificial Sequence
<220> FEATURE:
<223> OTHER INFORMATION: Synthetic

<400> SEQUENCE: 656
uuccugacaa acagugaca                                                    19

<210> SEQ ID NO 657
<211> LENGTH: 19
<212> TYPE: RNA
<213> ORGANISM: Artificial Sequence
<220> FEATURE:
<223> OTHER INFORMATION: Synthetic

<400> SEQUENCE: 657
ccacuagccc auuuucucu                                                    19

<210> SEQ ID NO 658
<211> LENGTH: 19
<212> TYPE: RNA
<213> ORGANISM: Artificial Sequence
<220> FEATURE:
<223> OTHER INFORMATION: Synthetic

<400> SEQUENCE: 658
gaacucaaga cugggcuuc                                                    19
```

<210> SEQ ID NO 659
<211> LENGTH: 19
<212> TYPE: RNA
<213> ORGANISM: Artificial Sequence
<220> FEATURE:
<223> OTHER INFORMATION: Synthetic

<400> SEQUENCE: 659
uaaaugguaa caagacaag                                               19

<210> SEQ ID NO 660
<211> LENGTH: 19
<212> TYPE: RNA
<213> ORGANISM: Artificial Sequence
<220> FEATURE:
<223> OTHER INFORMATION: Synthetic

<400> SEQUENCE: 660
aaaauuaaau gucaauuuu                                               19

<210> SEQ ID NO 661
<211> LENGTH: 19
<212> TYPE: RNA
<213> ORGANISM: Artificial Sequence
<220> FEATURE:
<223> OTHER INFORMATION: Synthetic

<400> SEQUENCE: 661
ggcaccaaca gugauuuga                                               19

<210> SEQ ID NO 662
<211> LENGTH: 19
<212> TYPE: RNA
<213> ORGANISM: Artificial Sequence
<220> FEATURE:
<223> OTHER INFORMATION: Synthetic

<400> SEQUENCE: 662
uaauaacuua agugauuag                                               19

<210> SEQ ID NO 663
<211> LENGTH: 19
<212> TYPE: RNA
<213> ORGANISM: Artificial Sequence
<220> FEATURE:
<223> OTHER INFORMATION: Synthetic

<400> SEQUENCE: 663
gaauacaaca gaauaaauu                                               19

<210> SEQ ID NO 664
<211> LENGTH: 19
<212> TYPE: RNA
<213> ORGANISM: Artificial Sequence
<220> FEATURE:
<223> OTHER INFORMATION: Synthetic

<400> SEQUENCE: 664
guuacaauuu aaaaaaaag                                               19

<210> SEQ ID NO 665
<211> LENGTH: 19
<212> TYPE: RNA
<213> ORGANISM: Artificial Sequence
<220> FEATURE:
<223> OTHER INFORMATION: Synthetic

<400> SEQUENCE: 665
cacccaccgg auaaauaug                                                    19

<210> SEQ ID NO 666
<211> LENGTH: 19
<212> TYPE: RNA
<213> ORGANISM: Artificial Sequence
<220> FEATURE:
<223> OTHER INFORMATION: Synthetic

<400> SEQUENCE: 666
uugaacacac uccugucccc                                                   19

<210> SEQ ID NO 667
<211> LENGTH: 19
<212> TYPE: RNA
<213> ORGANISM: Artificial Sequence
<220> FEATURE:
<223> OTHER INFORMATION: Synthetic

<400> SEQUENCE: 667
agcaaaaaca ugacccacu                                                    19

<210> SEQ ID NO 668
<211> LENGTH: 19
<212> TYPE: RNA
<213> ORGANISM: Artificial Sequence
<220> FEATURE:
<223> OTHER INFORMATION: Synthetic

<400> SEQUENCE: 668
uguaccaugu gucaccaca                                                    19

<210> SEQ ID NO 669
<211> LENGTH: 19
<212> TYPE: RNA
<213> ORGANISM: Artificial Sequence
<220> FEATURE:
<223> OTHER INFORMATION: Synthetic

<400> SEQUENCE: 669
accugcaagc uccaagccu                                                    19

<210> SEQ ID NO 670
<211> LENGTH: 19
<212> TYPE: RNA
<213> ORGANISM: Artificial Sequence
<220> FEATURE:
<223> OTHER INFORMATION: Synthetic

<400> SEQUENCE: 670
acaccacagu agaaaggga                                                    19

<210> SEQ ID NO 671
<211> LENGTH: 19
<212> TYPE: RNA
<213> ORGANISM: Artificial Sequence
<220> FEATURE:
<223> OTHER INFORMATION: Synthetic

<400> SEQUENCE: 671
cuuuauuguc cugcuccaa                                                    19

<210> SEQ ID NO 672

```
<211> LENGTH: 19
<212> TYPE: RNA
<213> ORGANISM: Artificial Sequence
<220> FEATURE:
<223> OTHER INFORMATION: Synthetic

<400> SEQUENCE: 672
gggugcauuu cuaguggac                                                    19

<210> SEQ ID NO 673
<211> LENGTH: 23
<212> TYPE: RNA
<213> ORGANISM: Artificial Sequence
<220> FEATURE:
<223> OTHER INFORMATION: Synthetic

<400> SEQUENCE: 673
ugaagaggga aagcugacau cug                                               23

<210> SEQ ID NO 674
<211> LENGTH: 23
<212> TYPE: RNA
<213> ORGANISM: Artificial Sequence
<220> FEATURE:
<223> OTHER INFORMATION: Synthetic

<400> SEQUENCE: 674
caucacccaa gguuccuucu cuu                                               23

<210> SEQ ID NO 675
<211> LENGTH: 23
<212> TYPE: RNA
<213> ORGANISM: Artificial Sequence
<220> FEATURE:
<223> OTHER INFORMATION: Synthetic

<400> SEQUENCE: 675
uaguucacca gaccaauggc cua                                               23

<210> SEQ ID NO 676
<211> LENGTH: 23
<212> TYPE: RNA
<213> ORGANISM: Artificial Sequence
<220> FEATURE:
<223> OTHER INFORMATION: Synthetic

<400> SEQUENCE: 676
cuuuuaacug gugccuuccc ugu                                               23

<210> SEQ ID NO 677
<211> LENGTH: 23
<212> TYPE: RNA
<213> ORGANISM: Artificial Sequence
<220> FEATURE:
<223> OTHER INFORMATION: Synthetic

<400> SEQUENCE: 677
gagaggacug agccuacgga aag                                               23

<210> SEQ ID NO 678
<211> LENGTH: 23
<212> TYPE: RNA
<213> ORGANISM: Artificial Sequence
<220> FEATURE:
<223> OTHER INFORMATION: Synthetic

<400> SEQUENCE: 678
```
aguccuugau cugccugucu gug                                        23

<210> SEQ ID NO 679
<211> LENGTH: 23
<212> TYPE: RNA
<213> ORGANISM: Artificial Sequence
<220> FEATURE:
<223> OTHER INFORMATION: Synthetic

<400> SEQUENCE: 679
uucaaguggg ucauguuuuu gcu                                        23

<210> SEQ ID NO 680
<211> LENGTH: 23
<212> TYPE: RNA
<213> ORGANISM: Artificial Sequence
<220> FEATURE:
<223> OTHER INFORMATION: Synthetic

<400> SEQUENCE: 680
uuugcugugg ugacacaugg uac                                        23

<210> SEQ ID NO 681
<211> LENGTH: 23
<212> TYPE: RNA
<213> ORGANISM: Artificial Sequence
<220> FEATURE:
<223> OTHER INFORMATION: Synthetic

<400> SEQUENCE: 681
gaggaagaag gaaggagagg cuu                                        23

<210> SEQ ID NO 682
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 682
aagagggaaa gcugacauct t                                          21

<210> SEQ ID NO 683
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 683
ucacccaagg uuccuucuct t                                          21

<210> SEQ ID NO 684
<211> LENGTH: 21
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (1)..(19)
<223> OTHER INFORMATION: ribonucleotide modified as described

<400> SEQUENCE: 684
guucaccaga ccaauggcct t                                              21

<210> SEQ ID NO 685
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 685
uuuaacuggu gccuucccut t                                              21

<210> SEQ ID NO 686
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 686
gaggacugag ccuacggaat t                                              21

<210> SEQ ID NO 687
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 687
uccuugaucu gccugucugt t                                              21

<210> SEQ ID NO 688
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 688
caaguggguc auguuuuugt t                                              21

<210> SEQ ID NO 689
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(19)
<223> OTHER INFORMATION: ribonucleotide modified as described

<400> SEQUENCE: 689
ugcuguggug acacauggut t                                              21

<210> SEQ ID NO 690
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 690
gaugucagcu uucccucuut t                                              21

<210> SEQ ID NO 691
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 691
gagaaggaac cuugggugat t                                              21

<210> SEQ ID NO 692
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 692
ggccauuggu cuggugaact t                                              21

<210> SEQ ID NO 693
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 693
agggaaggca ccaguuaaat t                                              21

<210> SEQ ID NO 694
<211> LENGTH: 21
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 694
uuccguaggc ucaguccuct t                                              21

<210> SEQ ID NO 695
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 695
cagacaggca gaucaaggat t                                              21

<210> SEQ ID NO 696
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 696
caaaaacaug acccacuugt t                                              21

<210> SEQ ID NO 697
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 697
accauguguc accacagcat t                                              21

<210> SEQ ID NO 698
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
```

```
<222> LOCATION: (18)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 698
aagagggaaa gcugacauct t                                              21

<210> SEQ ID NO 699
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(6)
<223> OTHER INFORMATION: 2'-deoxy-2'-fluoro
<220> FEATURE:
<221> NAME/KEY: misc_feature
<222> LOCATION: (11)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 699
ucacccaagg uuccuucuct t                                              21

<210> SEQ ID NO 700
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
```

```
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 700
guucaccaga ccaauggcct t                                        21

<210> SEQ ID NO 701
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(3)
<223> OTHER INFORMATION: 2'-deoxy-2'-fluoro cytidine
<220> FEATURE:
<221> NAME/KEY: misc_feature
<222> LOCATION: (6)..(7)
<223> OTHER INFORMATION: 2'-deoxy-2'-fluoro cytidine
<220> FEATURE:
<221> NAME/KEY: misc_feature
<222> LOCATION: (10)..(10)
<223> OTHER INFORMATION: 2'-deoxy-2'-fluoro cytidine
<220> FEATURE:
<221> NAME/KEY: misc_feature
<222> LOCATION: (12)..(19)
<223> OTHER INFORMATION: 2'-deoxy-2'-fluoro cytidine
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 701
uuuaacuggu gccuucccut t                                        21

<210> SEQ ID NO 702
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
```

```
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 702
gaggacugag ccuacggaat t                                              21

<210> SEQ ID NO 703
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(5)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-deoxy-2'-fluoro
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 703
uccuugaucu gccugucugt t                                              21

<210> SEQ ID NO 704
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (12)..(12)
```

-continued

```
<223> OTHER INFORMATION: 2'-deoxy-2'-fluoro
<220> FEATURE:
<221> NAME/KEY: misc_feature
<222> LOCATION: (14)..(18)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 704
caaguggguc auguuuuugt t                                              21

<210> SEQ ID NO 705
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 705
ugcuguggug acacauggut t                                              21

<210> SEQ ID NO 706
<211> LENGTH: 21
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (9)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 706
gaugucagcu uucccucuut t                                              21

<210> SEQ ID NO 707
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(13)
<223> OTHER INFORMATION: Phosphorothioate 3'-Internucleotide Linkage
<220> FEATURE:
<221> NAME/KEY: misc_feature
<222> LOCATION: (17)..(17)
<223> OTHER INFORMATION: Phosphorothioate 3'-Internucleotide Linkage
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 707
gagaaggaac cuugggugat t                                              21

<210> SEQ ID NO 708
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
```

```
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 708
ggccauuggu cuggugaact t                                               21

<210> SEQ ID NO 709
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 709
agggaaggca ccaguuaaat t                                               21

<210> SEQ ID NO 710
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (15)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
```

```
<220> FEATURE:
<221> NAME/KEY: misc_feature
<222> LOCATION: (1)..(19)
<223> OTHER INFORMATION: ribonucleotide modified as described

<400> SEQUENCE: 710
uuccguaggc ucaguccuct t                                              21

<210> SEQ ID NO 711
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 711
cagacaggca gaucaaggat t                                              21

<210> SEQ ID NO 712
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
```

<223> OTHER INFORMATION: ribonucleotide modified as described

<400> SEQUENCE: 712
caaaaacaug acccacuugt t                                              21

<210> SEQ ID NO 713
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 713
accauguguc accacagcat t                                              21

<210> SEQ ID NO 714
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(11)
<223> OTHER INFORMATION: 2'-deoxy
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-deoxy
<220> FEATURE:
<221> NAME/KEY: misc_feature

```
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 714
aagagggaaa gcugacauct t                                              21

<210> SEQ ID NO 715
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy
<220> FEATURE:
<221> NAME/KEY: misc_feature
<222> LOCATION: (4)..(6)
<223> OTHER INFORMATION: 2'-deoxy-2'-fluoro
<220> FEATURE:
<221> NAME/KEY: misc_feature
<222> LOCATION: (7)..(10)
<223> OTHER INFORMATION: 2'-deoxy
<220> FEATURE:
<221> NAME/KEY: misc_feature
<222> LOCATION: (11)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 715
ucacccaagg uuccuucuct t                                              21

<210> SEQ ID NO 716
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
```

```
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-deoxy
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 716
guucaccaga ccaauggcct t                                      21

<210> SEQ ID NO 717
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(5)
<223> OTHER INFORMATION: 2'-deoxy
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-deoxy
```

```
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 717
uuuaacuggu gccuucccut t                                            21

<210> SEQ ID NO 718
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(5)
<223> OTHER INFORMATION: 2'-deoxy
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-deoxy
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(19)
<223> OTHER INFORMATION: 2'-deoxy
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 718
gaggacugag ccuacggaat t                                            21

<210> SEQ ID NO 719
```

```
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 719
uccuugaucu gccugucugt t                                              21

<210> SEQ ID NO 720
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
```

```
<222> LOCATION: (6)..(8)
<223> OTHER INFORMATION: 2'-deoxy
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 720
caaguggguc auguuuuugt t                                            21

<210> SEQ ID NO 721
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-deoxy
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
```

```
<221> NAME/KEY: misc_feature
<222> LOCATION: (10)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 721
ugcuguggug acacauggut t                                          21

<210> SEQ ID NO 722
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2'-deoxy
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy
<220> FEATURE:
<221> NAME/KEY: misc_feature
<222> LOCATION: (9)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
```

```
<220> FEATURE:
<221> NAME/KEY: misc_feature
<222> LOCATION: (1)..(19)
<223> OTHER INFORMATION: ribonucleotide modified as described

<400> SEQUENCE: 722
gaugucagcu uucccucuut t                                              21

<210> SEQ ID NO 723
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: 2'-deoxy
<220> FEATURE:
<221> NAME/KEY: misc_feature
<222> LOCATION: (10)..(13)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 723
gagaaggaac cuugggugat t                                              21

<210> SEQ ID NO 724
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2'-deoxy
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-deoxy
<220> FEATURE:
<221> NAME/KEY: misc_feature
<222> LOCATION: (10)..(12)
```

```
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 724
ggccauuggu cuggugaact t                                              21

<210> SEQ ID NO 725
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-deoxy
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 725
agggaaggca ccaguuaaat t                                              21
```

```
<210> SEQ ID NO 726
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(9)
<223> OTHER INFORMATION: 2'-deoxy
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-deoxy
<220> FEATURE:
<221> NAME/KEY: misc_feature
<222> LOCATION: (15)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 726
uuccguaggc ucaguccuct t                                              21

<210> SEQ ID NO 727
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(12)
<223> OTHER INFORMATION: 2'-deoxy
<220> FEATURE:
```

```
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(19)
<223> OTHER INFORMATION: 2'-deoxy
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 727
cagacaggca gaucaaggat t                                              21

<210> SEQ ID NO 728
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-deoxy
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 728
caaaaacaug acccacuugt t                                              21
```

```
<210> SEQ ID NO 729
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-deoxy
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 729
```

```
accauguguc accacagcat t                                              21

<210> SEQ ID NO 730
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(11)
<223> OTHER INFORMATION: 2'-O-methyl
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 730
aagagggaaa gcugacauct t                                              21

<210> SEQ ID NO 731
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(6)
<223> OTHER INFORMATION: 2'-deoxy-2'-fluoro
<220> FEATURE:
<221> NAME/KEY: misc_feature
<222> LOCATION: (7)..(10)
<223> OTHER INFORMATION: 2'-O-methyl
<220> FEATURE:
<221> NAME/KEY: misc_feature
```

```
<222> LOCATION: (11)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 731
ucacccaagg uuccuucuct t                                              21

<210> SEQ ID NO 732
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 732
guucaccaga ccaauggcct t                                              21
```

```
<210> SEQ ID NO 733
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(3)
<223> OTHER INFORMATION: 2'-deoxy-2'-Fluoro
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-Fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-Fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(19)
<223> OTHER INFORMATION: 2'-deoxy-2'-Fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 733
uuuaacuggu gccuucccut t                                              21

<210> SEQ ID NO 734
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-Fluoro
<220> FEATURE:
<221> NAME/KEY: misc_feature
<222> LOCATION: (8)..(10)
<223> OTHER INFORMATION: 2'-O-methyl
<220> FEATURE:
<221> NAME/KEY: misc_feature
<222> LOCATION: (11)..(13)
<223> OTHER INFORMATION: 2'-deoxy-2'-Fluoro
```

```
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-Fluoro
<220> FEATURE:
<221> NAME/KEY: misc_feature
<222> LOCATION: (16)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 734
gaggacugag ccuacggaat t                                              21

<210> SEQ ID NO 735
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(5)
<223> OTHER INFORMATION: 2'-deoxy-2'-Fluoro
<220> FEATURE:
<221> NAME/KEY: misc_feature
<222> LOCATION: (6)..(7)
<223> OTHER INFORMATION: 2'-O-methyl
<220> FEATURE:
<221> NAME/KEY: misc_feature
<222> LOCATION: (8)..(10)
<223> OTHER INFORMATION: 2'-deoxy-2'-Fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(14)
<223> OTHER INFORMATION: 2'-deoxy-2'-Fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 735
```
uccuugaucu gccugucugt t                                               21

<210> SEQ ID NO 736
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-deoxy-2'-Fluoro
<220> FEATURE:
<221> NAME/KEY: misc_feature
<222> LOCATION: (2)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-Fluoro
<220> FEATURE:
<221> NAME/KEY: misc_feature
<222> LOCATION: (6)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-Fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-Fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 736
caaguggguc auguuuugt t                                                21

<210> SEQ ID NO 737
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature

```
<222> LOCATION: (1)..(1)
<223> OTHER INFORMATION: 2'-deoxy-2'-Fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-Fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-Fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-Fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-Fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-Fluoro
<220> FEATURE:
<221> NAME/KEY: misc_feature
<222> LOCATION: (17)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-Fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 737
ugcuguggug acacauggut t                                         21

<210> SEQ ID NO 738
<211> LENGTH: 21
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-Fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-Fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(19)
<223> OTHER INFORMATION: 2'-deoxy-2'-Fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 738
gaugucagcu uucccucuut t                                              21

<210> SEQ ID NO 739
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: 2'-O-methyl
<220> FEATURE:
<221> NAME/KEY: misc_feature
<222> LOCATION: (10)..(13)
<223> OTHER INFORMATION: 2'-deoxy-2'-Fluoro
<220> FEATURE:
<221> NAME/KEY: misc_feature
<222> LOCATION: (14)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-Fluoro
<220> FEATURE:
<221> NAME/KEY: misc_feature
<222> LOCATION: (18)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 739
gagaaggaac cuugggugat t                                              21

<210> SEQ ID NO 740
<211> LENGTH: 21
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-Fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-Fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(12)
<223> OTHER INFORMATION: 2'-deoxy-2'-Fluoro
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-Fluoro
<220> FEATURE:
<221> NAME/KEY: misc_feature
<222> LOCATION: (16)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-Fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 740
ggccauuggu cuggugaact t                                        21

<210> SEQ ID NO 741
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(12)
```

<223> OTHER INFORMATION: 2'-deoxy-2'-Fluoro
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(16)
<223> OTHER INFORMATION: 2'-deoxy-2'-Fluoro
<220> FEATURE:
<221> NAME/KEY: misc_feature
<222> LOCATION: (17)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 741
agggaaggca ccaguuaaat t                                              21

<210> SEQ ID NO 742
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-Fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-Fluoro
<220> FEATURE:
<221> NAME/KEY: misc_feature
<222> LOCATION: (7)..(9)
<223> OTHER INFORMATION: 2'-O-methyl
<220> FEATURE:
<221> NAME/KEY: misc_feature
<222> LOCATION: (10)..(12)
<223> OTHER INFORMATION: 2'-deoxy-2'-Fluoro
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(19)
<223> OTHER INFORMATION: 2'-deoxy-2'-Fluoro
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 742
uuccguaggc ucaguccuct t                                              21

<210> SEQ ID NO 743
<211> LENGTH: 21
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-Fluoro
<220> FEATURE:
<221> NAME/KEY: misc_feature
<222> LOCATION: (2)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-Fluoro
<220> FEATURE:
<221> NAME/KEY: misc_feature
<222> LOCATION: (6)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-Fluoro
<220> FEATURE:
<221> NAME/KEY: misc_feature
<222> LOCATION: (15)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 743
cagacaggca gaucaaggat t                                              21

<210> SEQ ID NO 744
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-Fluoro
<220> FEATURE:
<221> NAME/KEY: misc_feature
<222> LOCATION: (2)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-Fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(11)
<223> OTHER INFORMATION: 2'-O-methyl
<220> FEATURE:
```

```
<221> NAME/KEY: misc_feature
<222> LOCATION: (12)..(14)
<223> OTHER INFORMATION: 2'-deoxy-2'-Fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 744
caaaaacaug acccacuugt t                                              21

<210> SEQ ID NO 745
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(3)
<223> OTHER INFORMATION: 2'-deoxy-2'-Fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-Fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-Fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-Fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(13)
<223> OTHER INFORMATION: 2'-deoxy-2'-Fluoro
<220> FEATURE:
<221> NAME/KEY: misc_feature
<222> LOCATION: (14)..(14)
<223> OTHER INFORMATION: 2'-O-methyl
```

```
<220> FEATURE:
<221> NAME/KEY: misc_feature
<222> LOCATION: (15)..(15)
<223> OTHER INFORMATION: 2'-deoxy-2'-Fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 745
accauguguc accacagcat t                                              21

<210> SEQ ID NO 746
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 746
aagagggaaa gcugacauct t                                              21

<210> SEQ ID NO 747
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 747
ucacccaagg uuccuucuct t                                              21

<210> SEQ ID NO 748
```

```
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 748
guucaccaga ccaauggcct t                                        21

<210> SEQ ID NO 749
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 749
uuuaacuggu gccuucccut t                                        21

<210> SEQ ID NO 750
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 750
gaggacugag ccuacggaat t                                        21

<210> SEQ ID NO 751
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 751
uccuugaucu gccugucugt t                                              21

<210> SEQ ID NO 752
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 5'-3 attached terminal deoxyabasic moiety

<400> SEQUENCE: 752 caagugdgguc auguuuuugt t                                             21

<210> SEQ ID NO 753
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 753
ugcuguggug acacauggut t                                              21

<210> SEQ ID NO 754
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described
```

-continued

```
<400> SEQUENCE: 754
gaugucagcu uucccucuut t                                              21

<210> SEQ ID NO 755
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 755
gagaaggaac cuugggugat t                                              21

<210> SEQ ID NO 756
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 756
ggccauuggu cuggugaact t                                              21

<210> SEQ ID NO 757
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 757
agggaaggca ccaguuaaat t                                              21

<210> SEQ ID NO 758
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described
```

-continued

```
<400> SEQUENCE: 758
uuccguaggc ucaguccuct t                                              21

<210> SEQ ID NO 759
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 759
cagacaggca gaucaaggat t                                              21

<210> SEQ ID NO 760
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 760
caaaaacaug acccacuugt t                                              21

<210> SEQ ID NO 761
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 761
accauguguc accacagcat t                                              21

<210> SEQ ID NO 762
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
```

```
<223> OTHER INFORMATION: 2'-deoxy-2'-Fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-Fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(19)
<223> OTHER INFORMATION: 2'-deoxy-2'-Fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 762
gaugucagcu uucccucuut t                                              21

<210> SEQ ID NO 763
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: 2'-O-methyl
<220> FEATURE:
<221> NAME/KEY: misc_feature
<222> LOCATION: (10)..(13)
<223> OTHER INFORMATION: 2'-deoxy-2'-Fluoro
<220> FEATURE:
<221> NAME/KEY: misc_feature
<222> LOCATION: (14)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-Fluoro
<220> FEATURE:
<221> NAME/KEY: misc_feature
<222> LOCATION: (18)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 763
gagaaggaac cuugggugat t                                              21

<210> SEQ ID NO 764
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-Fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-Fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(12)
<223> OTHER INFORMATION: 2'-deoxy-2'-Fluoro
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-Fluoro
<220> FEATURE:
<221> NAME/KEY: misc_feature
<222> LOCATION: (16)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-Fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 764
ggccauuggu cuggugaact t                                            21

<210> SEQ ID NO 765
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-Fluoro
<220> FEATURE:
<221> NAME/KEY: misc_feature
<222> LOCATION: (13)..(14)
<223> OTHER INFORMATION: 2'-O-methyl
<220> FEATURE:
```

```
<221> NAME/KEY: misc_feature
<222> LOCATION: (15)..(16)
<223> OTHER INFORMATION: 2'-deoxy-2'-Fluoro
<220> FEATURE:
<221> NAME/KEY: misc_feature
<222> LOCATION: (17)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 765
agggaaggca ccaguuaaat t                                              21

<210> SEQ ID NO 766
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-Fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-Fluoro
<220> FEATURE:
<221> NAME/KEY: misc_feature
<222> LOCATION: (7)..(9)
<223> OTHER INFORMATION: 2'-O-methyl
<220> FEATURE:
<221> NAME/KEY: misc_feature
<222> LOCATION: (10)..(12)
<223> OTHER INFORMATION: 2'-deoxy-2'-Fluoro
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(19)
<223> OTHER INFORMATION: 2'-deoxy-2'-Fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 766
uuccguaggc ucaguccuct t                                              21

<210> SEQ ID NO 767
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-Fluoro
```

```
<220> FEATURE:
<221> NAME/KEY: misc_feature
<222> LOCATION: (2)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-Fluoro
<220> FEATURE:
<221> NAME/KEY: misc_feature
<222> LOCATION: (6)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-Fluoro
<220> FEATURE:
<221> NAME/KEY: misc_feature
<222> LOCATION: (15)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 767
cagacaggca gaucaaggat t                                           21

<210> SEQ ID NO 768
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-Fluoro
<220> FEATURE:
<221> NAME/KEY: misc_feature
<222> LOCATION: (2)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-Fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-Fluoro
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (12)..(14)
<223> OTHER INFORMATION: 2'-deoxy-2'-Fluoro
<220> FEATURE:
<221> NAME/KEY: misc_feature
<222> LOCATION: (15)..(15)
```

```
<223> OTHER INFORMATION: 2'-O-methyl
<220> FEATURE:
<221> NAME/KEY: misc_feature
<222> LOCATION: (16)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 768
caaaaacaug acccacuugt t                                               21

<210> SEQ ID NO 769
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(3)
<223> OTHER INFORMATION: 2'-deoxy-2'-Fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-Fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-Fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-Fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(13)
<223> OTHER INFORMATION: 2'-deoxy-2'-Fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-Fluoro
<220> FEATURE:
<221> NAME/KEY: misc_feature
```

```
<222> LOCATION: (16)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 769
accauguguc accacagcat t                                              21

<210> SEQ ID NO 770
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 770
gaugucagcu uucccucuut t                                              21

<210> SEQ ID NO 771
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 771
gagaaggaac cuugggugat t                                              21

<210> SEQ ID NO 772
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety
```

<400> SEQUENCE: 772
ggccauuggu cuggugaact t                                              21

<210> SEQ ID NO 773
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 773
agggaaggca ccaguuaaat t                                              21

<210> SEQ ID NO 774
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 774
uuccguaggc ucaguccuct t                                              21

<210> SEQ ID NO 775
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 775
cagacaggca gaucaaggat t                                              21

<210> SEQ ID NO 776
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety -continued

```
<400> SEQUENCE: 776
caaaaacaug acccacuugt t                                              21

<210> SEQ ID NO 777
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 777
accauguguc accacagcat t                                              21

<210> SEQ ID NO 778
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 778
ggaagaagga aggagaggct t                                              21

<210> SEQ ID NO 779
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified as described

<400> SEQUENCE: 779
gccucuccuu ccuucuucct t                                              21

<210> SEQ ID NO 780
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety
<220> FEATURE:
<221> NAME/KEY: misc_feature
<222> LOCATION: (1)..(1)
<223> OTHER INFORMATION: 2'-deoxy-2'-Fluoro
<220> FEATURE:
<221> NAME/KEY: misc_feature
<222> LOCATION: (2)..(3)
<223> OTHER INFORMATION: 2'-deoxy
<220> FEATURE:
<221> NAME/KEY: misc_feature
<222> LOCATION: (4)..(4)
```

```
<223> OTHER INFORMATION: 2'-deoxy-2'-Fluoro
<220> FEATURE:
<221> NAME/KEY: misc_feature
<222> LOCATION: (5)..(5)
<223> OTHER INFORMATION: 2'-deoxy
<220> FEATURE:
<221> NAME/KEY: misc_feature
<222> LOCATION: (6)..(6)
<223> OTHER INFORMATION: 2'-deoxy-2'-Fluoro
<220> FEATURE:
<221> NAME/KEY: misc_feature
<222> LOCATION: (7)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-Fluoro
<220> FEATURE:
<221> NAME/KEY: misc_feature
<222> LOCATION: (9)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-Fluoro
<220> FEATURE:
<221> NAME/KEY: misc_feature
<222> LOCATION: (12)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-Fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(17)
<223> OTHER INFORMATION: 2'-deoxy-2'-Fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-Fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moiety

<400> SEQUENCE: 780
ugguacacag uggugucgut t                                        21

<210> SEQ ID NO 781
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-Fluoro
<220> FEATURE:
<221> NAME/KEY: misc_feature
```

<222> LOCATION: (3)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-Fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(8)
<223> OTHER INFORMATION: 2'-deoxy-2'-Fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-Fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-Fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-Fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(18)
<223> OTHER INFORMATION: 2'-deoxy-2'-Fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 781
acgacaccac uguguaccat t                                              21

<210> SEQ ID NO 782
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap
 that is optionally present
<220> FEATURE:
<221> NAME/KEY: misc_feature
<222> LOCATION: (21)..(21)

<223> OTHER INFORMATION: 3'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (1)..(19)
<223> OTHER INFORMATION: n stands for any ribonucleotide modified as
      described
<220> FEATURE:
<221> NAME/KEY: misc_feature
<222> LOCATION: (20)..(21)
<223> OTHER INFORMATION: n is any nucleotide

<400> SEQUENCE: 782
nnnnnnnnnn nnnnnnnnn           21

<210> SEQ ID NO 783
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally absent)
<220> FEATURE:
<221> NAME/KEY: misc_feature
<222> LOCATION: (1)..(19)
<223> OTHER INFORMATION: n stands for any ribonucleotide modified as
      described
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)
<220> FEATURE:
<221> NAME/KEY: misc_feature
<222> LOCATION: (20)..(21)
<223> OTHER INFORMATION: n is any nucleotide

<400> SEQUENCE: 783
nnnnnnnnnn nnnnnnnnn           21

<210> SEQ ID NO 784
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n stands for any ribonucleotide wherein any
      pyrimidine is 2'- Fluoro and any purine is 2' -o- methyl
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally absent)
<220> FEATURE:
<221> NAME/KEY: misc_feature
<222> LOCATION: (20)..(21)
<223> OTHER INFORMATION: n is any nucleotide

<400> SEQUENCE: 784
nnnnnnnnnn nnnnnnnnn           21

<210> SEQ ID NO 785
<211> LENGTH: 21
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n stands for any ribonucleotide wherein any
      pyrimidine is 2'-Fluoro and any purine is 2'-O-methyl
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally absent)
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)
<220> FEATURE:
<221> NAME/KEY: misc_feature
<222> LOCATION: (20)..(21)
<223> OTHER INFORMATION: n is any nucleotide

<400> SEQUENCE: 785
nnnnnnnnnn nnnnnnnnnn n                                                  21

<210> SEQ ID NO 786
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n stands for any ribonucleotide wherein any
      pyrimidine is 2'-O-methyl or 2'-Fluoro
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (20)..(21)
<223> OTHER INFORMATION: n is any nucleotide

<400> SEQUENCE: 786
nnnnnnnnnn nnnnnnnnnn n                                                  21

<210> SEQ ID NO 787
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n stands for any ribonucleotide wherein any
      pyrimidine is 2'-Fluoro
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally absent)
<220> FEATURE:
<221> NAME/KEY: misc_feature
<222> LOCATION: (21)..(21)
```

```
<223> OTHER INFORMATION: 3'-3 attached terminal glyceryl moiety or
      inverted deoxyabasic (optionally present)
<220> FEATURE:
<221> NAME/KEY: misc_feature
<222> LOCATION: (20)..(21)
<223> OTHER INFORMATION: n is any nucleotide

<400> SEQUENCE: 787 nnnnnnnnn nnnnnnnnn                                               21

<210> SEQ ID NO 788
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n stands for any ribonucleotide wherein any
      pyrimidine is 2'-Fluoro and any purine is 2'-Deoxy
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap that is
      optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic, inverted nucleotide or other terminal cap that is
      optionally present
<220> FEATURE:
<221> NAME/KEY: misc_feature
<222> LOCATION: (20)..(21)
<223> OTHER INFORMATION: n is any nucleotide

<400> SEQUENCE: 788 nnnnnnnnn nnnnnnnnn                                               21

<210> SEQ ID NO 789
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n stands for any ribonucleotide wherein any
      pyrimidine is 2'-Fluoro
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap that is
      optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic,
      inverted nucleotide or other terminal cap that is optionally
      present
<220> FEATURE:
<221> NAME/KEY: misc_feature
<222> LOCATION: (20)..(21)
<223> OTHER INFORMATION: n is any nucleotide

<400> SEQUENCE: 789 nnnnnnnnn nnnnnnnnn                                               21
```

```
<210> SEQ ID NO 790
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any ribonucleotide wherein any pyrimidine
      is 2'-Fluoro and any purine is 2'-Deoxy
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally absent)
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)
<220> FEATURE:
<221> NAME/KEY: misc_feature
<222> LOCATION: (20)..(21)
<223> OTHER INFORMATION: n is any nucleotide

<400> SEQUENCE: 790
nnnnnnnnnn nnnnnnnnnn n                                              21

<210> SEQ ID NO 791
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap that is
      optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic, inverted nucleotide or other terminal cap that is
      optionally present
<220> FEATURE:
<221> NAME/KEY: misc_feature
<222> LOCATION: (1)..(19)
<223> OTHER INFORMATION: ribonucleotide modified as described

<400> SEQUENCE: 791
cauaaacaug ugagcaugut                                                21

<210> SEQ ID NO 792
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally present)
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)
```

<400> SEQUENCE: 792
acaugcucac auguuuaugt                                                  21

<210> SEQ ID NO 793
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-Methyl
<220> FEATURE:
<221> NAME/KEY: misc_feature
<222> LOCATION: (4)..(6)
<223> OTHER INFORMATION: 2'-O-Methyl
<220> FEATURE:
<221> NAME/KEY: misc_feature
<222> LOCATION: (8)..(8)
<223> OTHER INFORMATION: 2'-O-Methyl
<220> FEATURE:
<221> NAME/KEY: misc_feature
<222> LOCATION: (10)..(10)
<223> OTHER INFORMATION: 2'-O-Methyl
<220> FEATURE:
<221> NAME/KEY: misc_feature
<222> LOCATION: (12)..(14)
<223> OTHER INFORMATION: 2'-O-Methyl
<220> FEATURE:
<221> NAME/KEY: misc_feature
<222> LOCATION: (16)..(16)
<223> OTHER INFORMATION: 2'-O-Methyl
<220> FEATURE:
<221> NAME/KEY: misc_feature
<222> LOCATION: (18)..(18)
<223> OTHER INFORMATION: 2'-O-Methyl
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally present)
<220> FEATURE:
<221> NAME/KEY: misc_feature

```
<222> LOCATION: (1)..(19)
<223> OTHER INFORMATION: ribonucleotide modified as described

<400> SEQUENCE: 793
cauaaacaug ugagcaugut                                              21

<210> SEQ ID NO 794
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (1)..(1)
<223> OTHER INFORMATION: 2'-O-Methyl
<220> FEATURE:
<221> NAME/KEY: misc_feature
<222> LOCATION: (3)..(3)
<223> OTHER INFORMATION: 2'-O-Methyl
<220> FEATURE:
<221> NAME/KEY: misc_feature
<222> LOCATION: (5)..(5)
<223> OTHER INFORMATION: 2'-O-Methyl
<220> FEATURE:
<221> NAME/KEY: misc_feature
<222> LOCATION: (9)..(9)
<223> OTHER INFORMATION: 2'-O-Methyl
<220> FEATURE:
<221> NAME/KEY: misc_feature
<222> LOCATION: (11)..(11)
<223> OTHER INFORMATION: 2'-O-Methyl
<220> FEATURE:
<221> NAME/KEY: misc_feature
<222> LOCATION: (13)..(13)
<223> OTHER INFORMATION: 2'-O-Methyl
<220> FEATURE:
<221> NAME/KEY: misc_feature
<222> LOCATION: (17)..(17)
<223> OTHER INFORMATION: 2'-O-Methyl
<220> FEATURE:
<221> NAME/KEY: misc_feature
<222> LOCATION: (19)..(19)
<223> OTHER INFORMATION: 2'-O-Methyl
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally present)
```

```
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)

<400> SEQUENCE: 794
acaugcucac auguuuaugt                                                    21

<210> SEQ ID NO 795
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-Methyl or 2'-deoxy-2'-fluoro
<220> FEATURE:
<221> NAME/KEY: misc_feature
<222> LOCATION: (3)..(3)
<223> OTHER INFORMATION: 2'-O-Methyl or 2'-deoxy-2'-fluoro
<220> FEATURE:
<221> NAME/KEY: misc_feature
<222> LOCATION: (7)..(7)
<223> OTHER INFORMATION: 2'-O-Methyl or 2'-deoxy-2'-fluoro
<220> FEATURE:
<221> NAME/KEY: misc_feature
<222> LOCATION: (9)..(9)
<223> OTHER INFORMATION: 2'-O-Methyl or 2'-deoxy-2'-fluoro
<220> FEATURE:
<221> NAME/KEY: misc_feature
<222> LOCATION: (11)..(11)
<223> OTHER INFORMATION: 2'-O-Methyl or 2'-deoxy-2'-fluoro
<220> FEATURE:
<221> NAME/KEY: misc_feature
<222> LOCATION: (15)..(15)
<223> OTHER INFORMATION: 2'-O-Methyl or 2'-deoxy-2'-fluoro
<220> FEATURE:
<221> NAME/KEY: misc_feature
<222> LOCATION: (17)..(17)
<223> OTHER INFORMATION: 2'-O-Methyl or 2'-deoxy-2'-fluoro
<220> FEATURE:
<221> NAME/KEY: misc_feature
<222> LOCATION: (19)..(19)
<223> OTHER INFORMATION: 2'-O-Methyl or 2'-deoxy-2'-fluoro
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap that
      is optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic, inverted nucleotide or other terminal cap that
      is optionally present
<220> FEATURE:
<221> NAME/KEY: misc_feature
<222> LOCATION: (1)..(19)
<223> OTHER INFORMATION: ribonucleotide modified as described

<400> SEQUENCE: 795
cauaaacaug ugagcaugut                                                    21

<210> SEQ ID NO 796
<211> LENGTH: 21
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally present)
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)

<400> SEQUENCE: 796
acaugcucac auguuuaugt                                                    21

<210> SEQ ID NO 797
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy
<220> FEATURE:
<221> NAME/KEY: misc_feature
<222> LOCATION: (4)..(6)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (12)..(14)
<223> OTHER INFORMATION: 2'-deoxy
<220> FEATURE:
<221> NAME/KEY: misc_feature
<222> LOCATION: (16)..(16)
```

```
<223> OTHER INFORMATION: 2'-deoxy
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (1)..(19)
<223> OTHER INFORMATION: ribonucleotide modified as described

<400> SEQUENCE: 797
cauaaacaug ugagcaugut                                              21

<210> SEQ ID NO 798
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
```

```
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (1)..(1)
<223> OTHER INFORMATION: 5'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (21)..(21)
<223> OTHER INFORMATION: 3'-3 attached terminal deoxyabasic moiety,
      inverted abasic, inverted nucleotide or other terminal cap
      that is optionally present
<220> FEATURE:
<221> NAME/KEY: misc_feature
<222> LOCATION: (1)..(19)
<223> OTHER INFORMATION: ribonucleotide modified as described

<400> SEQUENCE: 798
cauaaacaug ugagcaugut                                          21

<210> SEQ ID NO 799
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (3)..(3)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy
<220> FEATURE:
```

```
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: Phosphorothioate or Phosphorodithioate
      3'-Internucleotide Linkage (optionally present)
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal glyceryl moiety or
      inverted deoxyabasic (optionally present)

<400> SEQUENCE: 799
acaugcucac auguuuaugt                                              21

<210> SEQ ID NO 800
<211> LENGTH: 14
<212> TYPE: RNA
<213> ORGANISM: Artificial Sequence
<220> FEATURE:
<223> OTHER INFORMATION: Synthetic

<400> SEQUENCE: 800
auauaucuau uucg                                                    14

<210> SEQ ID NO 801
<211> LENGTH: 14
<212> TYPE: RNA
<213> ORGANISM: Artificial Sequence
<220> FEATURE:
<223> OTHER INFORMATION: Synthetic

<400> SEQUENCE: 801
cgaaauagau auau                                                    14

<210> SEQ ID NO 802
<211> LENGTH: 23
<212> TYPE: RNA
<213> ORGANISM: Artificial Sequence
<220> FEATURE:
<223> OTHER INFORMATION: Synthetic

<400> SEQUENCE: 802
```

```
cgaaaauaga uauaucuauu ucg                                          23

<210> SEQ ID NO 803
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: ribonucleotide modified as described

<400> SEQUENCE: 803
cgaaauagau auaucuauuu cgtt                                         24

<210> SEQ ID NO 804
<211> LENGTH: 6053
<212> TYPE: RNA
<213> ORGANISM: Homo sapiens

<400> SEQUENCE: 804
gaaauuuuga aaguggugg gaugaagaag aucccugaag agaggaguaa cugagacaaa     60
ggcgaggcua gcaauagaga gacaagugag ggaauuagac cuuugguauc aucaugaaaa   120
ggccuggaag aaacgcuggu uuauccgcg gaguggccgg augagcggug acccagaugu    180
ucuggaauac uacaagaacg aucacuccaa gaagccucug cggaucauca accugaacuu   240
cugugagcag guagaugcag gccugaccuu uaacaagaag gagcugcagg auaguuuugu   300
guuugacauc aagaccagug aacgcaccuu uuaccuggug gcugagacag aagaggacau   360
gaauaagugg guccagagca ucugccagau cuggugcuuc aaucaggcug aggagagcac   420
agacucccug agaaauguuu ccucagccgg ucauggcccc cgcucuucuc agcugagcu   480 cagcagcucu agccagcacc uucuccgaga gcgcaaguccu ucagcccau cacacuccag   540 ccagccaacu cuguucacgu uugaaccccc ugugucaaac cacaugcagc ccaccuuguc   600
caccagcgca ccucaggagu aucucuacuu gcaccagugc auaagccgaa gagcagaaaa   660
ugcaaggagu gccagcuucu cucagggcac cagagccucu uuucucauga ggagugacac   720
agcuguacaa aaacuugccc agggcaaugg acacugugu aacggauca guggucaagu    780 ccauggcuuc uauagccuuc ccaagccgag ccggcacaau acagaauuca gagacaguac   840
cuacgaccuc ccccgcagcc uggccucca uggccacacc aagggcagcc ucacaggcuc   900
cgagacagau aauggaggau guacaccuu caagacgccc agcaacaccc ugugcaggga   960
guucggggac cuccuggua caauauggga uguuccggcc accccacucu cagccuacca  1020
gaucccuagg acauucacuc uggacaaaaa ccacaaugcc augacaguggccacuccugg  1080 ggacucagcc auagcucccc cacccgccc ccccaagcca agucaggcag aaacaccucg   1140
auggggcagu ccucagcaga gaccgccaau cagugaaaau agcagaucug ucgcugccac  1200 caucccccaga cgcaacaccc ucccugcaau ggacaacagc cgacuucacc gagcuucuuc  1260
cugugagacc uacgaguacc cacagcgugg uggagagagu gcaggccggu cugcugaauc  1320
caugagugau ggaguuggcu cuuuccugcc agggaaaaug auugugggcc gaucggacag  1380
caccaauucu gaagacaacu augugcccau gaauccaggu ucuucacccc uguuggccau  1440
ggaacgagca ggugauaauu cccagagcgu cuacaucccca augagcccag ggcccauca   1500
```

-continued

```
cuuugacuca cuuggcuacc caucaacaac ccuuccugug caccgaggcc ccagcagagg    1560
aagugagauu cagccacccc cugucaaccg caaccucaaa ccugaucgga aagcaaagcc    1620
aacaccacuu gaccugagga acaacaccgu caucgaugaa cuccccuuca agucaccuau    1680
caccaagucu uggucuaggg ccaaccacac cuucaacucc agccucuccc aguacugccg    1740
ccccaucucc acccagagca ucaccagcac agacucagga cacagcgaag agaacuaugu    1800
cccuaugcaa aacccagugu cugcaucucc cguucccagu ggcacgaaca guccugcccc    1860
uaagaagagc accggcagcg uugauuaucu ggcccuggac uuccagccga gcuccccaag    1920 ccccccaccgc aagccaucua cuucauccgu caccucugau gagaaggugg acuacguuca    1980
ggugacaaag gagaagaccc aggcccugca gaacaccaug caggagugga cagacgugcg    2040
gcaguccuca gagccuucca agggugccaa gcugugauga gagggccacc gcagagccca    2100
ggaggcagca ucccagagc uggcccuucc caucuccccu ucccccucuc ccguucuucc    2160
ucccauccac cuccucucua cucugccagu ucagccuuc aaagcacuug acaucaggga    2220
cccugaaccc uuccccuggg aggugagggc cugaucaagg caccuccucu gcccacucgg    2280
ggcccagcug ugauuuuuau caguaauggc caugccucca cccaccuuag uuaggagcua    2340
cuuccaaaaa gcauccuuca gccucuuccu guccuuuaga ccugacucuc uaccagaugu    2400
uuggagggaa gggcuggggc ucugagcag auuccacacc ucacguucag ucacagcccu    2460
cagcuaucuu cccuccggcc acugggcuac cucuccuuca gucccagaag acaagucuca    2520
ccaacccagg gagucaagga ccagcaaacc aaaguggaua auggacuuuu cauuccugu    2580 uuuucuuggc aggagagaag caaggccacu aaaagaggag augguggaga cggaggcuca    2640
gcaguggucu ugaggguaa aggacuuaga ugcccagaug aagagggaaa gcugacaucu    2700
gcagggaacc cacuuugagg cugaggccau ggcaggacag cugcugug ggugcagaggc    2760 agaagaugaa ggacaaaagg aagggaaaac ugauggccaa ccuagagcag caaggagcag    2820
ggcuuggagc ucggguggug gagaugacaa ggacacugug gggucugggu ccccagaacu    2880
cuggagcuac aggccacucu aggcccaagg gcuaguccuc uucccaguc cccucagagg    2940 cccccgccag ccccaccuug aaagcagcau acaggggaag gcuuggacca agcugggcga    3000
ccaagcacau ggggcaggaa cauggucauaa aggggugggg aauaugggag ggagugugou    3060 guggaugggg gugaugcagg gacugagggg aacccuggga caggcacagg cugggcagag    3120
gcacagggca gugcagggga cucugcagug gggucgggaa gugaguuucu uugcagugag    3180
cagugcagug gaaucgggc acagagguag cagacagaug ugaagcagug gugaaggcca    3240
uguagcaagu ggggaaauac auccaaaggg ccugggaguu ggggggugcc caacgcaauc    3300
cuuggggggu caggguggag cagaaaguga aggaggaca cgucaagag ugguguacau    3360 ggugguguga caugaggacc guuccuagga ugggacagug ggucaggcag acaaggagaa    3420
aagcagggca gaaugaugcc uagaggacca caucaggcau ggcugacagc uugugcccau    3480
gggcuguggc guaugucaga ucgcagggua ggaacgaguc uggccuggug ccggcccagu    3540 guuccucag cucauccgcc cucuguugcu cccuagcauu ccaggagcca ucuuggacuc    3600
uccucccagg guuugaaagg ccaucagauu agcagggacg ggguguaggg caucacccaa    3660
gguuccuucu cuuaaacuaa ggguggggga ucgaaguguu uuauguuga cuguucuuga    3720 cuaaauuuuc aagaguuuca gaagcaacag gacagaccag acguuucauu cuacccuggg    3780
```

-continued

```
gcgaacagaa cuucuuccuc ccaaacaaug acuuccugcc auguuugaug gggacagcua    3840
ccacuguccu cugccccau uccccuuuca gcucccauga gcaugcauag uuaccagac      3900 caauggccua gccauucucu aagucccauc cuggaagaag uuauuccuuc aagagcugca    3960
ccucuccucc uagcauuagu uuagaucaac ucaaggagua uuuauuaaug gcugcugucu    4020
ccaguuucug ggguuaagca cuaaggacac aagaaucaau cagaccuucu cccugaacuu   4080
aagauagcca caaucagaaa aaggacaagg acaugagaca guggugaugg ccaucagaca   4140
gagacuucaa augcugaugg agggcagagg aaguacuuag ggagguuggu gucagaggca    4200 ggagugggg aucagggaag guggauucua ggaaaaggga gugccugagg uaggccuuag     4260
aaggggauga gucagauuuu uacagaggag gagggcaggg cuugggucca guggaggaag   4320
aaggaaggag aggcuuggaa agccuugugu cuugggaaaa aaaggccuuu gagcauaugg   4380
guccagccac ucagaagugc agggccaug ccuggguguu ccaauaagug aauggaagca    4440
guggugguag cuacacuggg cagaguuggc agggugcugg uucacucugc ccagcccuga    4500
augugugccu uaaaggcccc cuacaagggg ccccauacga cagagcuuuu aacuggugcc   4560
uucccuguac ccgcagcagc cacaagsggg cccagacuau ugcagccucc cauaaacaug   4620
ugagcauguu cugagugugc caugauguga guggaccugg cuggaaucuu cggagagcga   4680
cugagguguu caaaucgaau cucccaggag gcuuccuucc agccccucuau ucgguaacu    4740 accaggaggc uuccuuccag cccccuauuc ugguaacuac caaaauccccu cggggugcaag   4800 uguaggggua gagauggaag gaugagaggu gaaauugacc uuuugaaagc aaagcucugg    4860
cucacaggcc ccaaacuacc agccguaucu agcauauccc cacccuccac ccacuaccuc    4920
cuccaacaaa ggagucaacu caguugaaaa aacugguccu uuggccuauc caugggucaa   4980
aguccaccuc uccuggggc cuggagagga cugagccuac ggaaagggga uaccuuccca     5040
cucagcacug cuucacacag gcccccugcc uggggcucuc caaggagccu ucuucaccca   5100
cuuccagcuc cacuucugca agguuaaguc aagugagaac gaugagaaau agggagaugg   5160
ugucuccuua aguccuugau cugccugucu guggaauggg agguuggauu agcugcgcug    5220
aggucccauc cacagcuggu gcucagcugc uugaagggga gacucccucc ucuguaacuu   5280
cuuucugggg gauggggug gcaguaccu aucccagc cccuccuagc uugacuuuag       5340
ugguuuccaa uagaaaguu aacaaaguau gccccauucc ugucaaaa gcacaaccau      5400 ucugaaguua cuggagcaug ggcucagcuc auccuccccu uggccccuuc ucccauggggg    5460 acaucucggc ccagcacccc uauucccauuu ccagaguucu ccuucccca ucugggccuu    5520 cauaaaaugc agggaaagcc agacuggucu caggagcgcu aaagccccuuc cgugggggu   5580 cgucuuucug ggacuagccc ugcuguuuag gaccuggac acaauggggg uaccugccga    5640
gggggucccc aagagaucca ggcugucaug ugauuuaugg uggcaugugu uguguauuug    5700
uuggcuacuu gugucuugaa aucuagaauu auuucacgca gaauugucac uguuugcag    5760 gaagagaaaa ugggcuagug gaagcccagu cuugaguucu ugucuuguua ccauuaaaa    5820 uugacauuua auuuucaaau cacguuuggu gccuaaucac uuaaguuauu aauuauucu    5880 guuguauucu uuuuuuaaa uguaacaua uuuauccggu ggguggaca ggagugugu      5940 caagugggauc auguuuugc guggugaca cauggguaaag gcuggagcu ugcagguccc    6000 uuucuacugu ggguguggag caggacaaua aaguccacua gaaaugcacc cca          6053
```

RNA INTERFERENCE MEDIATED INHIBITION OF GRB2 ASSOCIATED BINDING PROTEIN (GAB2) GENE EXPRESSION USING SHORT INTERFERING NUCLEIC ACID (SINA)

This application is a continuation of U.S. patent application Ser. No. 10/923,380, filed Aug. 20, 2004, which is a continuation-in-part of International Patent Application No. PCT/US03/04909, filed Feb. 18, 2003, and parent U.S. patent application Ser. No. 10/923,380 is also a continuation-in-part of International Patent Application No. PCT/US04/16390, filed May 24, 2004, which is a continuation-in-part of U.S. patent application Ser. No. 10/826,966, filed Apr. 16, 2004, which is continuation-in-part of U.S. patent application Ser. No. 10/757,803, filed Jan. 14, 2004, which is a continuation-in-part of U.S. patent application Ser. No. 10/720,448, filed Nov. 24, 2003, which is a continuation-in-part of U.S. patent application Ser. No. 10/693,059, filed Oct. 23, 2003, which is a continuation-in-part of U.S. patent application Ser. No. 10/444,853, filed May 23, 2003, which is a continuation-in-part of International Patent Application No. PCT/US03/05346, filed Feb. 20, 2003, and a continuation-in-part of International Patent Application No. PCT/US03/05028, filed Feb. 20, 2003, both of which claim the benefit of U.S. Provisional Application No. 60/358,580 filed Feb. 20, 2002, U.S. Provisional Application No. 60/363,124 filed Mar. 11, 2002, U.S. Provisional Application No. 60/386,782 filed Jun. 6, 2002, U.S. Provisional Application No. 60/406,784 filed Aug. 29, 2002, U.S. Provisional Application No. 60/408,378 filed Sep. 5, 2002, U.S. Provisional Application No. 60/409,293 filed Sep. 9, 2002, and U.S. Provisional Application No. 60/440,129 filed Jan. 15, 2003. The instant application claims the benefit of all the listed applications, which are hereby incorporated by reference herein in their entireties, including the drawings.

SEQUENCE LISTING

The sequence listing submitted via EFS, in compliance with 37 CFR §1.52(e)(5), is incorporated herein by reference. The sequence listing text file submitted via EFS contains the file "SequenceListing19USCNT", created on Sep. 2, 2008, which is 189,671 bytes in size.

FIELD OF THE INVENTION

The present invention relates to compounds, compositions, and methods for the study, diagnosis, and treatment of traits, diseases and conditions that respond to the modulation of GRB2 associated binding protein (GAB2) gene expression and/or activity. The present invention is also directed to compounds, compositions, and methods relating to traits, diseases and conditions that respond to the modulation of expression and/or activity of genes involved in GAB2 gene expression pathways or other cellular processes that mediate the maintenance or development of such traits, diseases and conditions. Specifically, the invention relates to small nucleic acid molecules, such as short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against GAB2 gene expression. Such small nucleic acid molecules are useful, for example, in providing compositions for treatment of traits, diseases and conditions that can respond to modulation of GAB2 expression in a subject, such as cancer, including malignant blood diseases (leukemia); inflammatory diseases or conditions; allergic diseases or conditions; and/or proliferative diseases or conditions as described herein or otherwise known in the art.

BACKGROUND OF THE INVENTION

The following is a discussion of relevant art pertaining to RNAi. The discussion is provided only for understanding of the invention that follows. The summary is not an admission that any of the work described below is prior art to the claimed invention.

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double-stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898, 031; Clemens et al., 1997, J. Interferon & Cytokine Res., 17, 503-524; Adah et al., 2001, Curr. Med. Chem., 8, 1189).

The presence of long dsRNAs in cells stimulates the activity of a ribonuclease III enzyme referred to as dicer (Bass, 2000, Cell, 101, 235; Zamore et al., 2000, Cell, 101, 25-33; Hammond et al., 2000, Nature, 404, 293). Dicer is involved in the processing of the dsRNA into short pieces of dsRNA known as short interfering RNAs (siRNAs) (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and comprise about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in C.

*elegans*. Bahramian and ZarbI, 1999, *Molecular and Cellular Biology,* 19, 274-283 and Wianny and Goetz, 1999, *Nature Cell Biol.,* 2, 70, describe RNAi mediated by dsRNA in mammalian systems. Hammond et al., 2000, *Nature,* 404, 293, describe RNAi in *Drosophila* cells transfected with dsRNA. Elbashir et al., 2001, *Nature,* 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, *EMBO J.,* 20, 6877 and Tuschl et al., International PCT Publication No. WO 01/75164) has revealed certain requirements for siRNA length, structure, chemical composition, and sequence that are essential to mediate efficient RNAi activity. These studies have shown that 21-nucleotide siRNA duplexes are most active when containing 3'-terminal dinucleotide overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with 2'-deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence (Elbashir et al., 2001, *EMBO J.,* 20, 6877). Other studies have indicated that a 5'-phosphate on the target-complementary strand of an siRNA duplex is required for siRNA activity and that ATP is utilized to maintain the 5'-phosphate moiety on the siRNA (Nykanen et al., 2001, *Cell,* 107, 309).

Studies have shown that replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been reported to be well tolerated, whereas complete substitution with deoxyribonucleotides results in no RNAi activity (Elbashir et al., 2001, *EMBO J.,* 20, 6877 and Tuschl et al., International PCT Publication No. WO 01/75164). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 preliminarily suggest that siRNA may include modifications to either the phosphate-sugar backbone or the nucleoside to include at least one of a nitrogen or sulfur heteroatom, however, neither application postulates to what extent such modifications would be tolerated in siRNA molecules, nor provides any further guidance or examples of such modified siRNA. Kreutzer et al., Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. However, Kreutzer et al. similarly fails to provide examples or guidance as to what extent these modifications would be tolerated in dsRNA molecules.

Parrish et al., 2000, *Molecular Cell,* 6, 1077-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl)uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

The use of longer dsRNA has been described. For example, Beach et al., International PCT Publication No. WO 01/68836, describes specific methods for attenuating gene expression using endogenously-derived dsRNA. Tuschl et al., International PCT Publication No. WO 01/75164, describe a *Drosophila* in vitro RNAi system and the use of specific siRNA molecules for certain functional genomic and certain therapeutic applications; although Tuschl, 2001, *Chem. Biochem.,* 2, 239-245, doubts that RNAi can be used to cure genetic diseases or viral infection due to the danger of activating interferon response. Li et al., International PCT Publication No. WO 00/44914, describe the use of specific long (141 bp-488 bp) enzymatically synthesized or vector expressed dsRNAs for attenuating the expression of certain target genes. Zernicka-Goetz et al., International PCT Publication No. WO 01/36646, describe certain methods for inhibiting the expression of particular genes in mammalian cells using certain long (550 bp-714 bp), enzymatically synthesized or vector expressed dsRNA molecules. Fire et al., International PCT Publication No. WO 99/32619, describe particular methods for introducing certain long dsRNA molecules into cells for use in inhibiting gene expression in nematodes. Plaetinck et al., International PCT Publication No. WO 00/01846, describe certain methods for identifying specific genes responsible for conferring a particular phenotype in a cell using specific long dsRNA molecules. Mello et al., International PCT Publication No. WO 01/29058, describe the identification of specific genes involved in dsRNA-mediated RNAi. Pachuck et al., International PCT Publication No. WO 00/63364, describe certain long (at least 200 nucleotide) dsRNA constructs. Deschamps Depaillette et al., International PCT Publication No. WO 99/07409, describe specific compositions consisting of particular dsRNA molecules combined with certain anti-viral agents. Waterhouse et al., International PCT Publication No. 99/53050 and 1998, *PNAS,* 95, 13959-13964, describe certain methods for decreasing the phenotypic expression of a nucleic acid in plant cells using certain dsRNAs. Driscoll et al., International PCT Publication No. WO 01/49844, describe specific DNA expression constructs for use in facilitating gene silencing in targeted organisms.

Others have reported on various RNAi and gene-silencing systems. For example, Parrish et al., 2000, *Molecular Cell,* 6, 1077-1087, describe specific chemically modified dsRNA constructs targeting the unc-22 gene of *C. elegans*. Grossniklaus, International PCT Publication No. WO 01/38551, describes certain methods for regulating polycomb gene expression in plants using certain dsRNAs. Churikov et al., International PCT Publication No. WO 01/42443, describe certain methods for modifying genetic characteristics of an organism using certain dsRNAs. Cogoni et al., International PCT Publication No. WO 01/53475, describe certain methods for isolating a *Neurospora* silencing gene and uses thereof. Reed et al., International PCT Publication No. WO 01/68836, describe certain methods for gene silencing in plants. Honer et al., International PCT Publication No. WO 01/70944, describe certain methods of drug screening using transgenic nematodes as Parkinson's Disease models using certain dsRNAs. Deak et al., International PCT Publication No. WO 01/72774, describe certain *Drosophila*-derived gene products that may be related to RNAi in *Drosophila*. Arndt et al., International PCT Publication No. WO 01/92513 describe certain methods for mediating gene suppression by using factors that enhance RNAi. Tuschl et al., International PCT Publication No. WO 02/44321, describe certain synthetic siRNA constructs. Pachuk et al., International PCT Publication No. WO 00/63364, and Satishchandran et al., International PCT Publication No. WO 01/04313, describe certain methods and compositions for inhibiting the function of certain polynucleotide sequences using certain long (over 250 bp), vector expressed dsRNAs. Echeverri et al., International PCT Publication No. WO 02/38805, describe certain *C. elegans* genes identified via RNAi. Kreutzer et al., International PCT Publications Nos. WO 02/055692, WO 02/055693, and EP 1144623 B1 describes certain methods for inhibiting gene expression using dsRNA. Graham et al., International PCT Publications Nos. WO 99/49029 and WO 01/70949, and AU 4037501 describe certain vector expressed siRNA molecules. Fire et al., U.S. Pat. No. 6,506,559, describe certain methods for inhibiting gene expression in vitro using certain long dsRNA (299 bp-1033 bp) constructs that mediate RNAi. Martinez et al., 2002, *Cell*, 110, 563-574, describe certain single-stranded siRNA constructs, including certain 5'-phosphorylated single-stranded siRNAs that mediate RNA interference in HeLa cells. Harborth et al., 2003, Antisense & Nucleic Acid Drug Development, 13, 83-105, describe certain chemically and structurally modified siRNA molecules. Chiu and Rana, 2003, RNA, 9, 1034-1048, describe certain chemically and structurally modified siRNA molecules. Woolf et al., International PCT Publication Nos. WO 03/064626 and WO 03/064625 describe certain chemically modified dsRNA constructs.

SUMMARY OF THE INVENTION

This invention relates to compounds, compositions, and methods useful for modulating GRB2 associated binding protein (GAB2) gene expression using short interfering nucleic acid (siNA) molecules. This invention also relates to compounds, compositions, and methods useful for modulating the expression and activity of other genes involved in pathways of GAB2 gene expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of GAB2 genes.

An siNA of the invention can be unmodified or chemically modified. An siNA of the instant invention can be chemically synthesized, expressed from a vector or enzymatically synthesized. The instant invention also features various chemically modified synthetic short interfering nucleic acid (siNA) molecules capable of modulating GAB2 gene expression or activity in cells by RNA interference (RNAi). The use of chemically modified siNA improves various properties of native siNA molecules through increased resistance to nuclease degradation in vivo and/or through improved cellular uptake. Further, contrary to earlier published studies, siNA having multiple chemical modifications retains its RNAi activity. The siNA molecules of the instant invention provide useful reagents and methods for a variety of therapeutic, veterinary, diagnostic, target validation, genomic discovery, genetic engineering, and pharmacogenomic applications.

In one embodiment, the invention features one or more siNA molecules and methods that independently or in combination modulate the expression of GAB2 genes encoding proteins, such as proteins comprising GAB2 proteins associated with the maintenance and/or development of cancer, including malignant blood disease (leukemia); inflammatory diseases or conditions; allergic diseases or conditions; or proliferative diseases or conditions, such as genes encoding sequences comprising those sequences referred to by GenBank Accession Nos. shown in Table I, referred to herein generally as GAB2. The description below of the various aspects and embodiments of the invention is provided with reference to exemplary GRB2 associated binding protein (GAB2) gene, referred to herein as GAB2, but otherwise known as GRB2 associated binding protein. However, the various aspects and embodiments are also directed to other GAB2 genes, such as GAB2 homolog genes and transcript variants including other genes involved in GAB2 regulatory pathways and polymorphisms (e.g., single nucleotide polymorphism, (SNPs)) associated with certain GAB2 genes. As such, the various aspects and embodiments are also directed to other genes that are involved in GAB2 mediated pathways of signal transduction or gene expression that are involved, for example, in the maintenance and/or development of cancer. These additional genes can be analyzed for target sites using the methods described for GAB2 genes herein. Thus, the modulation of other genes and the effects of such modulation of the other genes can be performed, determined, and measured as described herein.

In one embodiment, the invention features a double-stranded short interfering nucleic acid (siNA) molecule that down-regulates expression of a GAB2 gene, wherein said siNA molecule comprises about 15 to about 28 base pairs.

In one embodiment, the invention features a double-stranded short interfering nucleic acid (siNA) molecule that directs cleavage of a GAB2 RNA via RNA interference (RNAi), wherein the double-stranded siNA molecule comprises a first and a second strand, each strand of the siNA molecule is about 18 to about 28 nucleotides in length, the first strand of the siNA molecule comprises nucleotide sequence having sufficient complementarity to the GAB2 RNA for the siNA molecule to direct cleavage of the GAB2 RNA via RNA interference, and the second strand of said siNA molecule comprises nucleotide sequence that is complementary to the first strand.

In one embodiment, the invention features a double-stranded short interfering nucleic acid (siNA) molecule that directs cleavage of a GAB2 RNA via RNA interference (RNAi), wherein the double-stranded siNA molecule comprises a first and a second strand, each strand of the siNA molecule is about 18 to about 23 nucleotides in length, the first strand of the siNA molecule comprises nucleotide sequence having sufficient complementarity to the GAB2 RNA for the siNA molecule to direct cleavage of the GAB2 RNA via RNA interference, and the second strand of said siNA molecule comprises nucleotide sequence that is complementary to the first strand.

In one embodiment, the invention features a chemically synthesized double-stranded short interfering nucleic acid (siNA) molecule that directs cleavage of a GAB2 RNA via RNA interference (RNAi), wherein each strand of the siNA molecule is about 18 to about 28 nucleotides in length; and one strand of the siNA molecule comprises nucleotide sequence having sufficient complementarity to the GAB2 RNA for the siNA molecule to direct cleavage of the GAB2 RNA via RNA interference.

In one embodiment, the invention features a chemically synthesized double-stranded short interfering nucleic acid (siNA) molecule that directs cleavage of a GAB2 RNA via RNA interference (RNAi), wherein each strand of the siNA molecule is about 18 to about 23 nucleotides in length; and one strand of the siNA molecule comprises nucleotide sequence having sufficient complementarity to the GAB2 RNA for the siNA molecule to direct cleavage of the GAB2 RNA via RNA interference.

In one embodiment, the invention features an siNA molecule that down-regulates expression of a GAB2 gene, for example, wherein the GAB2 gene comprises GAB2 encoding sequence. In one embodiment, the invention features an siNA molecule that down-regulates expression of a GAB2 gene, for example, wherein the GAB2 gene comprises GAB2 non-coding sequence or regulatory elements involved in GAB2 gene expression.

In one embodiment, an siNA of the invention is used to inhibit the expression of GAB2 genes or a GAB2 gene family, wherein the genes or gene family sequences share sequence homology. Such homologous sequences can be identified as is known in the art, for example using sequence alignments. siNA molecules can be designed to target such homologous sequences, for example using perfectly complementary sequences or by incorporating non-canonical base pairs, for example mismatches and/or wobble base pairs that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing GAB2 targets that share sequence homology. As such, one advantage of using siNAs of the invention is that a single siNA can be designed to include nucleic acid sequence that is complementary to the nucleotide sequence that is conserved between the homologous genes. In this approach, a single siNA can be used to inhibit expression of more than one gene instead of using more than one siNA molecule to target the different genes.

In one embodiment, the invention features an siNA molecule having RNAi activity against GAB2 RNA, wherein the siNA molecule comprises a sequence complementary to any RNA having GAB2 encoding sequence, such as those sequences having GenBank Accession Nos. shown in Table I. In another embodiment, the invention features an siNA molecule having RNAi activity against GAB2 RNA, wherein the siNA molecule comprises a sequence complementary to an RNA having variant GAB2 encoding sequence, for example other mutant GAB2 genes not shown in Table I but known in the art to be associated with the maintenance and/or development of cancer, malignant blood disease (leukemia), inflammatory diseases or conditions, allergic diseases or conditions, or proliferative diseases or conditions described herein or otherwise known in the art. Chemical modifications as shown in Tables III and IV or otherwise described herein can be applied to any siNA construct of the invention. In another embodiment, an siNA molecule of the invention includes a nucleotide sequence that can interact with nucleotide sequence of a GAB2 gene and thereby mediate silencing of GAB2 gene expression, for example, wherein the siNA mediates regulation of GAB2 gene expression by cellular processes that modulate the chromatin structure or methylation patterns of the GAB2 gene and prevent transcription of the GAB2 gene.

In one embodiment, siNA molecules of the invention are used to down regulate or inhibit the expression of GAB2 proteins arising from GAB2 haplotype polymorphisms that are associated with a disease or condition, (e.g., cancer, malignant blood disease (leukemia), inflammatory diseases or conditions, allergic diseases or conditions, and proliferative diseases or conditions). Analysis of GAB2 genes, or GAB2 protein or RNA levels can be used to identify subjects with such polymorphisms or those subjects who are at risk of developing traits, conditions, or diseases described herein. These subjects are amenable to treatment, for example, treatment with siNA molecules of the invention and any other composition useful in treating diseases related to GAB2 gene expression. As such, analysis of GAB2 protein or RNA levels can be used to determine treatment type and the course of therapy in treating a subject. Monitoring of GAB2 protein or RNA levels can be used to predict treatment outcome and to determine the efficacy of compounds and compositions that modulate the level and/or activity of certain GAB2 proteins associated with a trait, condition, or disease.

In one embodiment of the invention an siNA molecule comprises an antisense strand comprising a nucleotide sequence that is complementary to a nucleotide sequence or a portion thereof encoding a GAB2 protein. The siNA further comprises a sense strand, wherein said sense strand comprises a nucleotide sequence of a GAB2 gene or a portion thereof.

In another embodiment, an siNA molecule comprises an antisense region comprising a nucleotide sequence that is complementary to a nucleotide sequence encoding a GAB2 protein or a portion thereof. The siNA molecule further comprises a sense region, wherein said sense region comprises a nucleotide sequence of a GAB2 gene or a portion thereof.

In another embodiment, the invention features an siNA molecule comprising a nucleotide sequence in the antisense region of the siNA molecule that is complementary to a nucleotide sequence or portion of sequence of a GAB2 gene. In another embodiment, the invention features an siNA molecule comprising a region, for example, the antisense region of the siNA construct, complementary to a sequence comprising a GAB2 gene sequence or a portion thereof.

In one embodiment, the antisense region of GAB2 siNA constructs comprises a sequence complementary to sequence having any of SEQ ID NOs. 1-336 or 673-681. In one embodiment, the antisense region of GAB2 constructs comprises sequence having any of SEQ ID NOs. 337-672, 690-697, 706-713, 722-729, 738-745, 754-777, 779-781, 783, 785, 787, 790, 792, 794, 796, or 799. In another embodiment, the sense region of GAB2 constructs comprises sequence having any of SEQ ID NOs. 1-336, 673-689, 698-705, 714-721, 730-737, 746-753, 778, 780, 782, 784, 786, 788, 789, 791, 793, 795, 797, or 798.

In one embodiment, an siNA molecule of the invention comprises any of SEQ ID NOs. 1-799. The sequences shown in SEQ ID NOs: 1-799 are not limiting. An siNA molecule of the invention can comprise any contiguous GAB2 sequence (e.g., about 15 to about 25 or more, or about 15, 16, 17, 18, 19, 20, 21, 22, 23, 24, or 25 or more contiguous GAB2 nucleotides). In yet another embodiment, the invention features an siNA molecule comprising a sequence, for example, the antisense sequence of the siNA construct, complementary to a sequence or portion of sequence comprising sequence represented by GenBank Accession Nos. shown in Table I. Chemical modifications in Tables III and IV and described herein can be applied to any siNA construct of the invention.

In one embodiment of the invention an siNA molecule comprises an antisense strand having about 15 to about 30 (e.g., about 15, 16, 17, 18, 19, 20, 21, 22, 23, 24, 25, 26, 27, 28, 29, or 30) nucleotides, wherein the antisense strand is complementary to a RNA sequence or a portion thereof encoding a GAB2 protein, and wherein said siNA further comprises a sense strand having about 15 to about 30 (e.g., about 15, 16, 17, 18, 19, 20, 21, 22, 23, 24, 25, 26, 27, 28, 29, or 30) nucleotides, and wherein said sense strand and said antisense strand are distinct nucleotide sequences where at least about 15 nucleotides in each strand are complementary to the other strand.

In another embodiment of the invention an siNA molecule of the invention comprises an antisense region having about 15 to about 30 (e.g., about 15, 16, 17, 18, 19, 20, 21, 22, 23, 24, 25, 26, 27, 28, 29, or 30) nucleotides, wherein the antisense region is complementary to a RNA sequence encoding a GAB2 protein, and wherein said siNA further comprises a sense region having about 15 to about 30 (e.g., about 15, 16, 17, 18, 19, 20, 21, 22, 23, 24, 25, 26, 27, 28, 29, or 30) nucleotides, wherein said sense region and said antisense region are comprised in a linear molecule where the sense region comprises at least about 15 nucleotides that are complementary to the antisense region.

In one embodiment, an siNA molecule of the invention has RNAi activity that modulates expression of RNA encoded by a GAB2 gene. Because GAB2 genes can share some degree of sequence homology with each other, siNA molecules can be designed to target a class of GAB2 genes or alternately specific GAB2 genes (e.g., polymorphic variants) by selecting sequences that are either shared amongst different GAB2 targets or alternatively that are unique for a specific GAB2 target. Therefore, in one embodiment, the siNA molecule can be designed to target conserved regions of GAB2 RNA sequences having homology among several GAB2 gene variants so as to target a class of GAB2 genes with one siNA molecule. Accordingly, in one embodiment, the siNA molecule of the invention modulates the expression of one or both GAB2 alleles in a subject. In another embodiment, the siNA molecule can be designed to target a sequence that is unique to a specific GAB2 RNA sequence (e.g., a single GAB2 allele or GAB2 single nucleotide polymorphism (SNP)) due to the high degree of specificity that the siNA molecule requires to mediate RNAi activity.

In one embodiment, nucleic acid molecules of the invention that act as mediators of the RNA interference gene silencing response are double-stranded nucleic acid molecules. In another embodiment, the siNA molecules of the invention consist of duplex nucleic acid molecules containing about 15 to about 30 base pairs between oligonucleotides comprising about 15 to about 30 (e.g., about 15, 16, 17, 18, 19, 20, 21, 22, 23, 24, 25, 26, 27, 28, 29, or 30) nucleotides. In yet another embodiment, siNA molecules of the invention comprise duplex nucleic acid molecules with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs. In yet another embodiment, siNA molecules of the invention comprise duplex nucleic acid molecules with blunt ends, where both ends are blunt, or alternatively, where one of the ends is blunt.

In one embodiment, the invention features one or more chemically modified siNA constructs having specificity for GAB2 expressing nucleic acid molecules, such as RNA encoding a GAB2 protein. In one embodiment, the invention features a RNA based siNA molecule (e.g., an siNA comprising 2'-OH nucleotides) having specificity for GAB2 expressing nucleic acid molecules that includes one or more chemical modifications described herein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, (e.g., RNA based siNA constructs), are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, an siNA molecule of the invention comprises modified nucleotides while maintaining the ability to mediate RNAi. The modified nucleotides can be used to improve in vitro or in vivo characteristics such as stability, activity, and/or bioavailability. For example, an siNA molecule of the invention can comprise modified nucleotides as a percentage of the total number of nucleotides present in the siNA molecule. As such, an siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single-stranded, the percent modification can be based upon the total number of nucleotides present in the single-stranded siNA molecules. Likewise, if the siNA molecule is double-stranded, the percent modification can be based upon the total number of nucleotides present in the sense strand, antisense strand, or both the sense and antisense strands.

One aspect of the invention features a double-stranded short interfering nucleic acid (siNA) molecule that downregulates expression of a GAB2 gene. In one embodiment, the double-stranded siNA molecule comprises one or more chemical modifications and each strand of the double-stranded siNA is about 21 nucleotides long. In one embodiment, the double-stranded siNA molecule does not contain any ribonucleotides. In another embodiment, the double-stranded siNA molecule comprises one or more ribonucleotides. In one embodiment, each strand of the double-stranded siNA molecule independently comprises about 15 to about 30 (e.g., about 15, 16, 17, 18, 19, 20, 21, 22, 23, 24, 25, 26, 27, 28, 29, or 30) nucleotides, wherein each strand comprises about 15 to about 30 (e.g., about 15, 16, 17, 18, 19, 20, 21, 22, 23, 24, 25, 26, 27, 28, 29, or 30) nucleotides that are complementary to the nucleotides of the other strand. In one embodiment, one of the strands of the double-stranded siNA molecule comprises a nucleotide sequence that is complementary to a nucleotide sequence or a portion thereof of the GAB2 gene, and the second strand of the double-stranded siNA molecule comprises a nucleotide sequence substantially similar to the nucleotide sequence of the GAB2 gene or a portion thereof.

In another embodiment, the invention features a double-stranded short interfering nucleic acid (siNA) molecule that down-regulates expression of a GAB2 gene comprising an antisense region, wherein the antisense region comprises a nucleotide sequence that is complementary to a nucleotide sequence of the GAB2 gene or a portion thereof, and a sense region, wherein the sense region comprises a nucleotide sequence substantially similar to the nucleotide sequence of the GAB2 gene or a portion thereof. In one embodiment, the antisense region and the sense region independently comprise about 15 to about 30 (e.g. about 15, 16, 17, 18, 19, 20, 21, 22, 23, 24, 25, 26, 27, 28, 29, or 30) nucleotides, wherein the antisense region comprises about 15 to about 30 (e.g. about 15, 16, 17, 18, 19, 20, 21, 22, 23, 24, 25, 26, 27, 28, 29, or 30) nucleotides that are complementary to nucleotides of the sense region.

In another embodiment, the invention features a double-stranded short interfering nucleic acid (siNA) molecule that down-regulates expression of a GAB2 gene comprising a sense region and an antisense region, wherein the antisense region comprises a nucleotide sequence that is complementary to a nucleotide sequence of RNA encoded by the GAB2 gene or a portion thereof and the sense region comprises a nucleotide sequence that is complementary to the antisense region.

In one embodiment, an siNA molecule of the invention comprises blunt ends, i.e., ends that do not include any overhanging nucleotides. For example, an siNA molecule comprising modifications described herein (e.g., comprising nucleotides having Formulae I-VII or siNA constructs comprising "Stab 00"-"Stab 32" (Table IV) or any combination thereof (see Table IV)) and/or any length described herein can comprise blunt ends or ends with no overhanging nucleotides.

In one embodiment, any siNA molecule of the invention can comprise one or more blunt ends, i.e. where a blunt end does not have any overhanging nucleotides. In one embodiment, the blunt ended siNA molecule has a number of base pairs equal to the number of nucleotides present in each strand of the siNA molecule. In another embodiment, the siNA molecule comprises one blunt end, for example wherein the 5'-end of the antisense strand and the 3'-end of the sense strand do not have any overhanging nucleotides. In another example, the siNA molecule comprises one blunt end, for example wherein the 3'-end of the antisense strand and the 5'-end of the sense strand do not have any overhanging nucleotides. In another example, an siNA molecule comprises two blunt ends, for example wherein the 3'-end of the antisense strand and the 5'-end of the sense strand as well as the 5'-end of the antisense strand and 3'-end of the sense strand do not have any overhanging nucleotides. A blunt ended siNA molecule can comprise, for example, from about 15 to about 30 nucleotides (e.g., about 15, 16, 17, 18, 19, 20, 21, 22, 23, 24, 25, 26, 27, 28, 29, or 30 nucleotides). Other nucleotides present in a blunt ended siNA molecule can comprise, for example, mismatches, bulges, loops, or wobble base pairs to modulate the activity of the siNA molecule to mediate RNA interference.

By "blunt ends" is meant symmetric termini or termini of a double-stranded siNA molecule having no overhanging nucleotides. The two strands of a double-stranded siNA molecule align with each other without over-hanging nucleotides at the termini. For example, a blunt ended siNA construct comprises terminal nucleotides that are complementary between the sense and antisense regions of the siNA molecule.

In one embodiment, the invention features a double-stranded short interfering nucleic acid (siNA) molecule that down-regulates expression of a GAB2 gene, wherein the siNA molecule is assembled from two separate oligonucleotide fragments wherein one fragment comprises the sense region and the second fragment comprises the antisense region of the siNA molecule. The sense region can be connected to the antisense region via a linker molecule, such as a polynucleotide linker or a non-nucleotide linker.

In one embodiment, the invention features double-stranded short interfering nucleic acid (siNA) molecule that down-regulates expression of a GAB2 gene, wherein the siNA molecule comprises about 15 to about 30 (e.g. about 15, 16, 17, 18, 19, 20, 21, 22, 23, 24, 25, 26, 27, 28, 29, or 30) base pairs, and wherein each strand of the siNA molecule comprises one or more chemical modifications. In another embodiment, one of the strands of the double-stranded siNA molecule comprises a nucleotide sequence that is complementary to a nucleotide sequence of a GAB2 gene or a portion thereof, and the second strand of the double-stranded siNA molecule comprises a nucleotide sequence substantially similar to the nucleotide sequence or a portion thereof of the GAB2 gene. In another embodiment, one of the strands of the double-stranded siNA molecule comprises a nucleotide sequence that is complementary to a nucleotide sequence of a GAB2 gene or portion thereof, and the second strand of the double-stranded siNA molecule comprises a nucleotide sequence substantially similar to the nucleotide sequence or portion thereof of the GAB2 gene. In another embodiment, each strand of the siNA molecule comprises about 15 to about 30 (e.g. about 15, 16, 17, 18, 19, 20, 21, 22, 23, 24, 25, 26, 27, 28, 29, or 30) nucleotides, and each strand comprises at least about 15 to about 30 (e.g. about 15, 16, 17, 18, 19, 20, 21, 22, 23, 24, 25, 26, 27, 28, 29, or 30) nucleotides that are complementary to the nucleotides of the other strand. The GAB2 gene can comprise, for example, sequences referred to in Table I.

In one embodiment, an siNA molecule of the invention comprises no ribonucleotides. In another embodiment, an siNA molecule of the invention comprises ribonucleotides.

In one embodiment, an siNA molecule of the invention comprises an antisense region comprising a nucleotide sequence that is complementary to a nucleotide sequence of a GAB2 gene or a portion thereof, and the siNA further comprises a sense region comprising a nucleotide sequence substantially similar to the nucleotide sequence of the GAB2 gene or a portion thereof. In another embodiment, the antisense region and the sense region each comprise about 15 to about 30 (e.g. about 15, 16, 17, 18, 19, 20, 21, 22, 23, 24, 25, 26, 27, 28, 29, or 30) nucleotides and the antisense region comprises at least about 15 to about 30 (e.g. about 15, 16, 17, 18, 19, 20, 21, 22, 23, 24, 25, 26, 27, 28, 29, or 30) nucleotides that are complementary to nucleotides of the sense region. The GAB2 gene can comprise, for example, sequences referred to in Table I. In another embodiment, the siNA is a double-stranded nucleic acid molecule, where each of the two strands of the siNA molecule independently comprise about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) nucleotides, and where one of the strands of the siNA molecule comprises at least about 15 (e.g. about 15, 16, 17, 18, 19, 20, 21, 22, 23, 24 or 25 or more) nucleotides that are complementary to the nucleic acid sequence of the GAB2 gene or a portion thereof.

In one embodiment, an siNA molecule of the invention comprises a sense region and an antisense region, wherein the antisense region comprises a nucleotide sequence that is complementary to a nucleotide sequence of RNA encoded by a GAB2 gene, or a portion thereof, and the sense region comprises a nucleotide sequence that is complementary to the antisense region. In one embodiment, the siNA molecule is assembled from two separate oligonucleotide fragments, wherein one fragment comprises the sense region and the second fragment comprises the antisense region of the siNA molecule. In another embodiment, the sense region is connected to the antisense region via a linker molecule. In another embodiment, the sense region is connected to the antisense region via a linker molecule, such as a nucleotide or non-nucleotide linker. The GAB2 gene can comprise, for example, sequences referred in to Table I.

In one embodiment, the invention features a double-stranded short interfering nucleic acid (siNA) molecule that down-regulates expression of a GAB2 gene comprising a sense region and an antisense region, wherein the antisense region comprises a nucleotide sequence that is complementary to a nucleotide sequence of RNA encoded by the GAB2 gene or a portion thereof and the sense region comprises a nucleotide sequence that is complementary to the antisense region, and wherein the siNA molecule has one or more modified pyrimidine and/or purine nucleotides. In one embodiment, the pyrimidine nucleotides in the sense region are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides. In another embodiment of any of the above-described siNA molecules, any nucleotides present in a non-complementary region of the sense strand (e.g. overhang region) are 2'-deoxy nucleotides.

In one embodiment, the invention features a double-stranded short interfering nucleic acid (siNA) molecule that down-regulates expression of a GAB2 gene, wherein the siNA molecule is assembled from two separate oligonucleotide fragments wherein one fragment comprises the sense region and the second fragment comprises the antisense region of the siNA molecule, and wherein the fragment comprising the sense region includes a terminal cap moiety at the 5'-end, the 3'-end, or both of the 5' and 3' ends of the fragment. In one embodiment, the terminal cap moiety is an inverted deoxy abasic moiety or glyceryl moiety. In one embodiment, each of the two fragments of the siNA molecule independently comprise about 15 to about 30 (e.g. about 15, 16, 17, 18, 19, 20, 21, 22, 23, 24, 25, 26, 27, 28, 29, or 30) nucleotides. In another embodiment, each of the two fragments of the siNA molecule independently comprise about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) nucleotides. In a non-limiting example, each of the two fragments of the siNA molecule comprise about 21 nucleotides.

In one embodiment, the invention features an siNA molecule comprising at least one modified nucleotide, wherein the modified nucleotide is a 2'-deoxy-2'-fluoro nucleotide.

The siNA can be, for example, about 15 to about 40 nucleotides in length. In one embodiment, all pyrimidine nucleotides present in the siNA are 2'-deoxy-2'-fluoro pyrimidine nucleotides. In one embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-deoxy-2'-fluoro cytidine and at least one 2'-deoxy-2'-fluoro uridine nucleotides. In one embodiment, all uridine nucleotides present in the siNA are 2'-deoxy-2'-fluoro uridine nucleotides. In one embodiment, all cytidine nucleotides present in the siNA are 2'-deoxy-2'-fluoro cytidine nucleotides. In one embodiment, all adenosine nucleotides present in the siNA are 2'-deoxy-2'-fluoro adenosine nucleotides. In one embodiment, all guanosine nucleotides present in the siNA are 2'-deoxy-2'-fluoro guanosine nucleotides. The siNA can further comprise at least one modified internucleotidic linkage, such as phosphorothioate linkage. In one embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a method of increasing the stability of an siNA molecule against cleavage by ribonucleases comprising introducing at least one modified nucleotide into the siNA molecule, wherein the modified nucleotide is a 2'-deoxy-2'-fluoro nucleotide. In one embodiment, all pyrimidine nucleotides present in the siNA are 2'-deoxy-2'-fluoro pyrimidine nucleotides. In one embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-deoxy-2'-fluoro cytidine and at least one 2'-deoxy-2'-fluoro uridine nucleotides. In one embodiment, all uridine nucleotides present in the siNA are 2'-deoxy-2'-fluoro uridine nucleotides. In one embodiment, all cytidine nucleotides present in the siNA are 2'-deoxy-2'-fluoro cytidine nucleotides. In one embodiment, all adenosine nucleotides present in the siNA are 2'-deoxy-2'-fluoro adenosine nucleotides. In one embodiment, all guanosine nucleotides present in the siNA are 2'-deoxy-2'-fluoro guanosine nucleotides. The siNA can further comprise at least one modified internucleotidic linkage, such as phosphorothioate linkage. In one embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a double-stranded short interfering nucleic acid (siNA) molecule that down-regulates expression of a GAB2 gene comprising a sense region and an antisense region, wherein the antisense region comprises a nucleotide sequence that is complementary to a nucleotide sequence of RNA encoded by the GAB2 gene or a portion thereof and the sense region comprises a nucleotide sequence that is complementary to the antisense region, and wherein the purine nucleotides present in the antisense region comprise 2'-deoxy-purine nucleotides. In an alternative embodiment, the purine nucleotides present in the antisense region comprise 2'-O-methyl purine nucleotides. In either of the above embodiments, the antisense region can comprise a phosphorothioate internucleotide linkage at the 3' end of the antisense region. Alternatively, in either of the above embodiments, the antisense region can comprise a glyceryl modification at the 3' end of the antisense region. In another embodiment of any of the above-described siNA molecules, any nucleotides present in a non-complementary region of the antisense strand (e.g. overhang region) are 2'-deoxy nucleotides.

In one embodiment, the antisense region of an siNA molecule of the invention comprises sequence complementary to a portion of a GAB2 transcript having sequence unique to a particular GAB2 disease related allele, such as sequence comprising a single nucleotide polymorphism (SNP) associated with the disease specific allele. As such, the antisense region of an siNA molecule of the invention can comprise sequence complementary to sequences that are unique to a particular allele to provide specificity in mediating selective RNAi against the disease, condition, or trait related allele.

In one embodiment, the invention features a double-stranded short interfering nucleic acid (siNA) molecule that down-regulates expression of a GAB2 gene, wherein the siNA molecule is assembled from two separate oligonucleotide fragments wherein one fragment comprises the sense region and the second fragment comprises the antisense region of the siNA molecule. In another embodiment, the siNA molecule is a double-stranded nucleic acid molecule, where each strand is about 21 nucleotides long and where about 19 nucleotides of each fragment of the siNA molecule are base-paired to the complementary nucleotides of the other fragment of the siNA molecule, wherein at least two 3' terminal nucleotides of each fragment of the siNA molecule are not base-paired to the nucleotides of the other fragment of the siNA molecule. In another embodiment, the siNA molecule is a double-stranded nucleic acid molecule, where each strand is about 19 nucleotide long and where the nucleotides of each fragment of the siNA molecule are base-paired to the complementary nucleotides of the other fragment of the siNA molecule to form at least about 15 (e.g., 15, 16, 17, 18, or 19) base pairs, wherein one or both ends of the siNA molecule are blunt ends. In one embodiment, each of the two 3' terminal nucleotides of each fragment of the siNA molecule is a 2'-deoxy-pyrimidine nucleotide, such as a 2'-deoxy-thymidine. In another embodiment, all nucleotides of each fragment of the siNA molecule are base-paired to the complementary nucleotides of the other fragment of the siNA molecule. In another embodiment, the siNA molecule is a double-stranded nucleic acid molecule of about 19 to about 25 base pairs having a sense region and an antisense region, where about 19 nucleotides of the antisense region are base-paired to the nucleotide sequence or a portion thereof of the RNA encoded by the GAB2 gene. In another embodiment, about 21 nucleotides of the antisense region are base-paired to the nucleotide sequence or a portion thereof of the RNA encoded by the GAB2 gene. In any of the above embodiments, the 5'-end of the fragment comprising said antisense region can optionally include a phosphate group.

In one embodiment, the invention features a double-stranded short interfering nucleic acid (siNA) molecule that inhibits the expression of a GAB2 RNA sequence (e.g., wherein said target RNA sequence is encoded by a GAB2 gene involved in the GAB2 pathway), wherein the siNA molecule does not contain any ribonucleotides and wherein each strand of the double-stranded siNA molecule is about 15 to about 30 nucleotides. In one embodiment, the siNA molecule is 21 nucleotides in length. Examples of non-ribonucleotide containing siNA constructs are combinations of stabilization chemistries shown in Table IV in any combination of Sense/Antisense chemistries, such as Stab 7/8, Stab 7/11, Stab 8/8, Stab 18/8, Stab 18/11, Stab 12/13, Stab 7/13, Stab 18/13, Stab 7/19, Stab 8/19, Stab 18/19, Stab 7/20, Stab 8/20, Stab 18/20, Stab 7/32, Stab 8/32, or Stab 18/32 (e.g., any siNA having Stab 7, 8, 11, 12, 13, 14, 15, 17, 18, 19, 20, or 32 sense or antisense strands or any combination thereof).

In one embodiment, the invention features a chemically synthesized double-stranded RNA molecule that directs cleavage of a GAB2 RNA via RNA interference, wherein each strand of said RNA molecule is about 15 to about 30 nucleotides in length; one strand of the RNA molecule comprises nucleotide sequence having sufficient complementarity to the GAB2 RNA for the RNA molecule to direct cleavage of the GAB2 RNA via RNA interference; and wherein at least one strand of the RNA molecule optionally comprises one or more chemically modified nucleotides described herein, such as without limitation deoxynucleotides, 2'-O-methyl nucleotides, 2'-deoxy-2'-fluoro nucleotides, 2'-O-methoxyethyl nucleotides etc.

In one embodiment, the invention features a medicament comprising an siNA molecule of the invention.

In one embodiment, the invention features an active ingredient comprising an siNA molecule of the invention.

In one embodiment, the invention features the use of a double-stranded short interfering nucleic acid (siNA) molecule to inhibit, down-regulate, or reduce expression of a GAB2 gene, wherein the siNA molecule comprises one or more chemical modifications and each strand of the double-stranded siNA is independently about 15 to about 30 or more (e.g., about 15, 16, 17, 18, 19, 20, 21, 22, 23, 24, 25, 26, 27, 28, 29 or 30 or more) nucleotides long. In one embodiment, the siNA molecule of the invention is a double-stranded nucleic acid molecule comprising one or more chemical modifications, where each of the two fragments of the siNA molecule independently comprise about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) nucleotides and where one of the strands comprises at least 15 nucleotides that are complementary to nucleotide sequence of GAB2 encoding RNA or a portion thereof. In a non-limiting example, each of the two fragments of the siNA molecule comprise about 21 nucleotides. In another embodiment, the siNA molecule is a double-stranded nucleic acid molecule comprising one or more chemical modifications, where each strand is about 21 nucleotide long and where about 19 nucleotides of each fragment of the siNA molecule are base-paired to the complementary nucleotides of the other fragment of the siNA molecule, wherein at least two 3' terminal nucleotides of each fragment of the siNA molecule are not base-paired to the nucleotides of the other fragment of the siNA molecule. In another embodiment, the siNA molecule is a double-stranded nucleic acid molecule comprising one or more chemical modifications, where each strand is about 19 nucleotide long and where the nucleotides of each fragment of the siNA molecule are base-paired to the complementary nucleotides of the other fragment of the siNA molecule to form at least about 15 (e.g., 15, 16, 17, 18, or 19) base pairs, wherein one or both ends of the siNA molecule are blunt ends. In one embodiment, each of the two 3' terminal nucleotides of each fragment of the siNA molecule is a 2'-deoxy-pyrimidine nucleotide, such as a 2'-deoxy-thymidine. In another embodiment, all nucleotides of each fragment of the siNA molecule are base-paired to the complementary nucleotides of the other fragment of the siNA molecule. In another embodiment, the siNA molecule is a double-stranded nucleic acid molecule of about 19 to about 25 base pairs having a sense region and an antisense region and comprising one or more chemical modifications, where about 19 nucleotides of the antisense region are base-paired to the nucleotide sequence or a portion thereof of the RNA encoded by the GAB2 gene. In another embodiment, about 21 nucleotides of the antisense region are base-paired to the nucleotide sequence or a portion thereof of the RNA encoded by the GAB2 gene. In any of the above embodiments, the 5'-end of the fragment comprising said antisense region can optionally include a phosphate group.

In one embodiment, the invention features the use of a double-stranded short interfering nucleic acid (siNA) molecule that inhibits, down-regulates, or reduces expression of a GAB2 gene, wherein one of the strands of the double-stranded siNA molecule is an antisense strand which comprises nucleotide sequence that is complementary to nucleotide sequence of GAB2 RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification.

In one embodiment, the invention features a double-stranded short interfering nucleic acid (siNA) molecule that inhibits, down-regulates, or reduces expression of a GAB2 gene, wherein one of the strands of the double-stranded siNA molecule is an antisense strand which comprises nucleotide sequence that is complementary to nucleotide sequence of GAB2 RNA or a portion thereof, wherein the other strand is a sense strand which comprises nucleotide sequence that is complementary to a nucleotide sequence of the antisense strand and wherein a majority of the pyrimidine nucleotides present in the double-stranded siNA molecule comprises a sugar modification.

In one embodiment, the invention features a double-stranded short interfering nucleic acid (siNA) molecule that inhibits, down-regulates, or reduces expression of a GAB2 gene, wherein one of the strands of the double-stranded siNA molecule is an antisense strand which comprises nucleotide sequence that is complementary to nucleotide sequence of GAB2 RNA that encodes a protein or portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, each strand of the siNA molecule comprises about 15 to about 30 or more (e.g., about 15, 16, 17, 18, 19, 20, 21, 22, 23, 24, 25, 26, 27, 28, 29, or 30 or more) nucleotides, wherein each strand comprises at least about 15 nucleotides that are complementary to the nucleotides of the other strand. In one embodiment, the siNA molecule is assembled from two oligonucleotide fragments, wherein one fragment comprises the nucleotide sequence of the antisense strand of the siNA molecule and a second fragment comprises nucleotide sequence of the sense region of the siNA molecule. In one embodiment, the sense strand is connected to the antisense strand via a linker molecule, such as a polynucleotide linker or a non-nucleotide linker. In a further embodiment, the pyrimidine nucleotides present in the sense strand are 2'-deoxy-2'fluoro pyrimidine nucleotides and the purine nucleotides present in the sense region are 2'-deoxy purine nucleotides. In another embodiment, the pyrimidine nucleotides present in the sense strand are 2'-deoxy-2'fluoro pyrimidine nucleotides and the purine nucleotides present in the sense region are 2'-O-methyl purine nucleotides. In still another embodiment, the pyrimidine nucleotides present in the antisense strand are 2'-deoxy-2'-fluoro pyrimidine nucleotides and any purine nucleotides present in the antisense strand are 2'-deoxy purine nucleotides. In another embodiment, the antisense strand comprises one or more 2'-deoxy-2'-fluoro pyrimidine nucleotides and one or more 2'-O-methyl purine nucleotides. In another embodiment, the pyrimidine nucleotides present in the antisense strand are 2'-deoxy-2'-fluoro pyrimidine nucleotides and any purine nucleotides present in the antisense strand are 2'-O-methyl purine nucleotides. In a further embodiment, the sense strand comprises a 3'-end and a 5'-end, wherein a terminal cap moiety (e.g., an inverted deoxy abasic moiety or inverted deoxy nucleotide moiety such as inverted thymidine) is present at the 5'-end, the 3'-end, or both of the 5' and 3' ends of the sense strand. In another embodiment, the antisense strand comprises a phosphorothioate internucleotide linkage at the 3' end of the antisense strand. In another embodiment, the antisense strand comprises a glyceryl modification at the 3' end. In another embodiment, the 5'-end of the antisense strand optionally includes a phosphate group.

In any of the above-described embodiments of a double-stranded short interfering nucleic acid (siNA) molecule that inhibits expression of a GAB2 gene, wherein a majority of the pyrimidine nucleotides present in the double-stranded siNA molecule comprises a sugar modification, each of the two strands of the siNA molecule can comprise about 15 to about 30 or more (e.g., about 15, 16, 17, 18, 19, 20, 21, 22, 23, 24, 25, 26, 27, 28, 29, or 30 or more) nucleotides. In one embodiment, about 15 to about 30 or more (e.g., about 15, 16, 17, 18, 19, 20, 21, 22, 23, 24, 25, 26, 27, 28, 29, or 30 or more) nucleotides of each strand of the siNA molecule are base-paired to the complementary nucleotides of the other strand of the siNA molecule. In another embodiment, about 15 to about 30 or more (e.g., about 15, 16, 17, 18, 19, 20, 21, 22, 23, 24, 25, 26, 27, 28, 29, or 30 or more) nucleotides of each strand of the siNA molecule are base-paired to the complementary nucleotides of the other strand of the siNA molecule, wherein at least two 3' terminal nucleotides of each strand of the siNA molecule are not base-paired to the nucleotides of the other strand of the siNA molecule. In another embodiment, each of the two 3' terminal nucleotides of each fragment of the siNA molecule is a 2'-deoxy-pyrimidine, such as 2'-deoxy-thymidine. In one embodiment, each strand of the siNA molecule is base-paired to the complementary nucleotides of the other strand of the siNA molecule. In one embodiment, about 15 to about 30 (e.g., about 15, 16, 17, 18, 19, 20, 21, 22, 23, 24, 25, 26, 27, 28, 29, or 30) nucleotides of the antisense strand are base-paired to the nucleotide sequence of the GAB2 RNA or a portion thereof. In one embodiment, about 18 to about 25 (e.g., about 18, 19, 20, 21, 22, 23, 24, or 25) nucleotides of the antisense strand are base-paired to the nucleotide sequence of the GAB2 RNA or a portion thereof.

In one embodiment, the invention features a double-stranded short interfering nucleic acid (siNA) molecule that inhibits expression of a GAB2 gene, wherein one of the strands of the double-stranded siNA molecule is an antisense strand which comprises nucleotide sequence that is complementary to nucleotide sequence of GAB2 RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the 5'-end of the antisense strand optionally includes a phosphate group.

In one embodiment, the invention features a double-stranded short interfering nucleic acid (siNA) molecule that inhibits expression of a GAB2 gene, wherein one of the strands of the double-stranded siNA molecule is an antisense strand which comprises nucleotide sequence that is complementary to nucleotide sequence of GAB2 RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the nucleotide sequence or a portion thereof of the antisense strand is complementary to a nucleotide sequence of the untranslated region or a portion thereof of the GAB2 RNA.

In one embodiment, the invention features a double-stranded short interfering nucleic acid (siNA) molecule that inhibits expression of a GAB2 gene, wherein one of the strands of the double-stranded siNA molecule is an antisense strand which comprises nucleotide sequence that is complementary to nucleotide sequence of GAB2 RNA or a portion thereof, wherein the other strand is a sense strand which comprises nucleotide sequence that is complementary to a nucleotide sequence of the antisense strand, wherein a majority of the pyrimidine nucleotides present in the double-stranded siNA molecule comprises a sugar modification, and wherein the nucleotide sequence of the antisense strand is complementary to a nucleotide sequence of the GAB2 RNA or a portion thereof that is present in the GAB2 RNA.

In one embodiment, the invention features a composition comprising an siNA molecule of the invention in a pharmaceutically acceptable carrier or diluent.

In a non-limiting example, the introduction of chemically modified nucleotides into nucleic acid molecules provides a powerful tool in overcoming potential limitations of in vivo stability and bioavailability inherent to native RNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically modified siNA can also minimize the possibility of activating interferon activity in humans.

In any of the embodiments of siNA molecules described herein, the antisense region of an siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of an siNA molecule of the invention can comprise ribonucleotides or deoxyribonucleotides that are chemically modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

One embodiment of the invention provides an expression vector comprising a nucleic acid sequence encoding at least one siNA molecule of the invention in a manner that allows expression of the nucleic acid molecule. Another embodiment of the invention provides a mammalian cell comprising such an expression vector. The mammalian cell can be a human cell. The siNA molecule of the expression vector can comprise a sense region and an antisense region. The antisense region can comprise sequence complementary to a RNA or DNA sequence encoding GAB2 and the sense region can comprise sequence complementary to the antisense region. The siNA molecule can comprise two distinct strands having complementary sense and antisense regions. The siNA molecule can comprise a single strand having complementary sense and antisense regions.

In one embodiment, the invention features a chemically modified short interfering nucleic acid (siNA) molecule capable of mediating RNA interference (RNAi) against GAB2 inside a cell or reconstituted in vitro system, wherein the chemical modification comprises one or more (e.g., about 1, 2, 3, 4, 5, 6, 7, 8, 9, 10, or more) nucleotides comprising a backbone modified internucleotide linkage having Formula I:

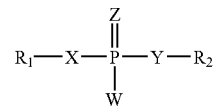

wherein each R1 and R2 is independently any nucleotide, non-nucleotide, or polynucleotide which can be naturally-occurring or chemically modified, each X and Y is independently O, S, N, alkyl, or substituted alkyl, each Z and W is independently O, S, N, alkyl, substituted alkyl, O-alkyl, S-alkyl, alkaryl, aralkyl, or acetyl and wherein W, X, Y, and Z are optionally not all O. In another embodiment, a backbone modification of the invention comprises a phosphonoacetate and/or thiophosphonoacetate internucleotide linkage (see for example Sheehan et al., 2003, Nucleic Acids Research, 31, 4109-4118).

The chemically modified internucleotide linkages having Formula I, for example, wherein any Z, W, X, and/or Y independently comprises a sulphur atom, can be present in one or both oligonucleotide strands of the siNA duplex, for example, in the sense strand, the antisense strand, or both strands. The siNA molecules of the invention can comprise one or more (e.g., about 1, 2, 3, 4, 5, 6, 7, 8, 9, 10, or more) chemically modified internucleotide linkages having Formula I at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically modified internucleotide linkages having Formula I at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine nucleotides with chemically modified internucleotide linkages having Formula I in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine nucleotides with chemically modified internucleotide linkages having Formula I in the sense strand, the antisense strand, or both strands. In another embodiment, an siNA molecule of the invention having internucleotide linkage(s) of Formula I also comprises a chemically modified nucleotide or non-nucleotide having any of Formulae I-VII.

In one embodiment, the invention features a chemically modified short interfering nucleic acid (siNA) molecule capable of mediating RNA interference (RNAi) against GAB2 inside a cell or reconstituted in vitro system, wherein the chemical modification comprises one or more (e.g., about 1, 2, 3, 4, 5, 6, 7, 8, 9, 10, or more) nucleotides or non-nucleotides having Formula II:

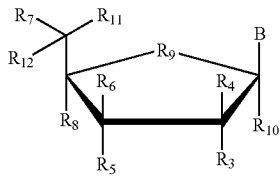

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalkylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically modified nucleotide or non-nucleotide of Formula II can be present in one or both oligonucleotide strands of the siNA duplex, for example in the sense strand, the antisense strand, or both strands. The siNA molecules of the invention can comprise one or more chemically modified nucleotide or non-nucleotide of Formula II at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically modified nucleotides or non-nucleotides of Formula II at the 5'-end of the sense strand, the antisense strand, or both strands. In another non-limiting example, an exemplary siNA molecule of the invention can comprise about 1 to about 5 or more (e.g., about 1, 2, 3, 4, 5, or more) chemically modified nucleotides or non-nucleotides of Formula II at the 3'-end of the sense strand, the antisense strand, or both strands.

In one embodiment, the invention features a chemically modified short interfering nucleic acid (siNA) molecule capable of mediating RNA interference (RNAi) against GAB2 inside a cell or reconstituted in vitro system, wherein the chemical modification comprises one or more (e.g., about 1, 2, 3, 4, 5, 6, 7, 8, 9, 10, or more) nucleotides or non-nucleotides having Formula III:

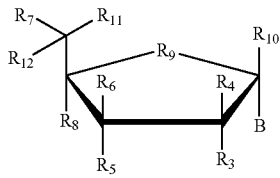

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalkylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be employed to be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically modified nucleotide or non-nucleotide of Formula III can be present in one or both oligonucleotide strands of the siNA duplex, for example, in the sense strand, the antisense strand, or both strands. The siNA molecules of the invention can comprise one or more chemically modified nucleotide or non-nucleotide of Formula III at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically modified nucleotide(s) or non-nucleotide(s) of Formula III at the 5'-end of the sense strand, the antisense strand, or both strands. In another non-limiting example, an exemplary siNA molecule of the invention can comprise about 1 to about 5 or more (e.g., about 1, 2, 3, 4, 5, or more) chemically modified nucleotide or non-nucleotide of Formula III at the 3'-end of the sense strand, the antisense strand, or both strands.

In another embodiment, an siNA molecule of the invention comprises a nucleotide having Formula II or III, wherein the nucleotide having Formula II or III is in an inverted configuration. For example, the nucleotide having Formula II or III is connected to the siNA construct in a 3'-3',3'-2',2'-3', or 5'-5' configuration, such as at the 3'-end, the 5'-end, or both of the 3' and 5'-ends of one or both siNA strands.

In one embodiment, the invention features a chemically modified short interfering nucleic acid (siNA) molecule capable of mediating RNA interference (RNAi) against GAB2 inside a cell or reconstituted in vitro system, wherein the chemical modification comprises a 5'-terminal phosphate group having Formula IV:

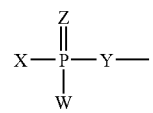

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, alkylhalo, or acetyl; and wherein W, X, Y and Z are not all O.

In one embodiment, the invention features an siNA molecule having a 5'-terminal phosphate group having Formula IV on the target-complementary strand, for example, a strand complementary to a target RNA, wherein the siNA molecule comprises an all RNA siNA molecule. In another embodiment, the invention features an siNA molecule having a 5'-terminal phosphate group having Formula IV on the target-complementary strand wherein the siNA molecule also comprises about 1 to about 3 (e.g., about 1, 2, or 3) nucleotide 3'-terminal nucleotide overhangs having about 1 to about 4 (e.g., about 1, 2, 3, or 4) deoxyribonucleotides on the 3'-end of one or both strands. In another embodiment, a 5'-terminal phosphate group having Formula IV is present on the target-complementary strand of an siNA molecule of the invention, for example an siNA molecule having chemical modifications having any of Formulae I-VII.

In one embodiment, the invention features a chemically modified short interfering nucleic acid (siNA) molecule capable of mediating RNA interference (RNAi) against GAB2 inside a cell or reconstituted in vitro system, wherein the chemical modification comprises one or more phosphorothioate internucleotide linkages. For example, in a non-limiting example, the invention features a chemically modified short interfering nucleic acid (siNA) having about 1, 2, 3, 4, 5, 6, 7, 8 or more phosphorothioate internucleotide linkages in one siNA strand. In yet another embodiment, the invention features a chemically modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phospliorothioate internucleotide linkages at the 3'-end, the 5'-end, or both of the 3'- and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

In one embodiment, the invention features an siNA molecule, wherein the sense strand comprises one or more, for example, about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In another embodiment, the invention features an siNA molecule, wherein the sense strand comprises about 1 to about 5, specifically about 1, 2, 3, 4, or 5 phosphorothioate internucleotide linkages, and/or one or more (e.g., about 1, 2, 3, 4, 5, or more) 2'-deoxy, 2'-O-methyl, 2'-deoxy-2'-fluoro, and/or one or more (e.g., about 1, 2, 3, 4, 5, or more) universal base modified nucleotides, and optionally a terminal cap molecule at the 3-end, the 5'-end, or both of the 3'- and 5'-ends of the sense strand; and wherein the antisense strand comprises about 1 to about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically modified with 2'-deoxy, 2'-O-methyl and/or 2'-deoxy-2'-fluoro nucleotides, with or without about 1 to about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

In one embodiment, the invention features an siNA molecule, wherein the antisense strand comprises one or more, for example, about 1, 2, 3, 4, 5, 6, 7, 8, 9, 10, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In another embodiment, the invention features an siNA molecule, wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In one embodiment, the invention features a chemically modified short interfering nucleic acid (siNA) molecule having about 1 to about 5 or more (specifically about 1, 2, 3, 4, 5 or more) phosphorothioate internucleotide linkages in each strand of the siNA molecule.

In another embodiment, the invention features an siNA molecule comprising 2'-5' internucleotide linkages. The 2'-5' internucleotide linkage(s) can be at the 3'-end, the 5'-end, or both of the 3'- and 5'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In another embodiment, a chemically modified siNA molecule of the invention comprises a duplex having two strands, one or both of which can be chemically modified, wherein each strand is independently about 15 to about 30 (e.g., about 15, 16, 17, 18, 19, 20, 21, 22, 23, 24, 25, 26, 27, 28, 29, or 30) nucleotides in length, wherein the duplex has about 15 to about 30 (e.g., about 15, 16, 17, 18, 19, 20, 21, 22, 23, 24, 25, 26, 27, 28, 29, or 30) base pairs, and wherein the chemical modification comprises a structure having any of Formulae I-VII. For example, an exemplary chemically modified siNA molecule of the invention comprises a duplex having two strands, one or both of which can be chemically modified with a chemical modification having any of Formulae I-VII or any combination thereof, wherein each strand consists of about 21 nucleotides, each having a 2-nucleotide 3'-terminal nucleotide overhang, and wherein the duplex has about 19 base pairs. In another embodiment, an siNA molecule of the invention comprises a single-stranded hairpin structure, wherein the siNA is about 36 to about 70 (e.g., about 36, 40, 45, 50, 55, 60, 65, or 70) nucleotides in length having about 15 to about 30 (e.g., about 15, 16, 17, 18, 19, 20, 21, 22, 23, 24, 25, 26, 27, 28, 29, or 30) base pairs, and wherein the siNA can include a chemical modification comprising a structure having any of Formulae I-VII or any combination thereof. For example, an exemplary chemically modified siNA molecule of the invention comprises a linear oligonucleotide having about 42 to about 50 (e.g., about 42, 43, 44, 45, 46, 47, 48, 49, or 50) nucleotides that is chemically modified with a chemical modification having any of Formulae I-VII or any combination thereof, wherein the linear oligonucleotide forms a hairpin structure having about 19 to about 21 (e.g., 19, 20, or 21) base pairs and a 2-nucleotide 3'-terminal nucleotide overhang. In another embodiment, a linear hairpin siNA molecule of the invention contains a stem loop motif, wherein the loop portion of the siNA molecule is biodegradable. For example, a linear hairpin siNA molecule of the invention is designed such that degradation of the loop portion of the siNA molecule in vivo can generate a double-stranded siNA molecule with 3'-terminal overhangs, such as 3'-terminal nucleotide overhangs comprising about 2 nucleotides.

In another embodiment, an siNA molecule of the invention comprises a hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs, and wherein the siNA can include one or more chemical modifications comprising a structure having any of Formulae I-VII or any combination thereof. For example, an exemplary chemically modified siNA molecule of the invention comprises a linear oligonucleotide having about 25 to about 35 (e.g., about 25, 26, 27, 28, 29, 30, 31, 32, 33, 34, or 35) nucleotides that is chemically modified with one or more chemical modifications having any of Formulae I-VII or any combination thereof, wherein the linear oligonucleotide forms a hairpin structure having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs and a 5'-terminal phosphate group that can be chemically modified as described herein (for example a 5'-terminal phosphate group having Formula IV). In another embodiment, a linear hairpin siNA molecule of the invention contains a stem loop motif, wherein the loop portion of the siNA molecule is biodegradable. In one embodiment, a linear hairpin siNA molecule of the invention comprises a loop portion comprising a non-nucleotide linker.

In another embodiment, an siNA molecule of the invention comprises an asymmetric hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs, and wherein the siNA can include one or more chemical modifications comprising a structure having any of Formulae I-VII or any combination thereof. For example, an exemplary chemically modified siNA molecule of the invention comprises a linear oligonucleotide having about 25 to about 35 (e.g., about 25, 26, 27, 28, 29, 30, 31, 32, 33, 34, or 35) nucleotides that is chemically modified with one or more chemical modifications having any of Formulae I-VII or any combination thereof, wherein the linear oligonucleotide forms an asymmetric hairpin structure having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs and a 5'-terminal phosphate group that can be chemically modified as described herein (for example a 5'-terminal phosphate group having Formula IV). In one embodiment, an asymmetric hairpin siNA molecule of the invention contains a stem loop motif, wherein the loop portion of the siNA molecule is biodegradable. In another embodiment, an asymmetric hairpin siNA molecule of the invention comprises a loop portion comprising a non-nucleotide linker.

In another embodiment, an siNA molecule of the invention comprises an asymmetric double-stranded structure having separate polynucleotide strands comprising sense and antisense regions, wherein the antisense region is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length, wherein the sense region and the antisense region have at least 3 complementary nucleotides, and wherein the siNA can include one or more chemical modifications comprising a structure having any of Formulae I-VII or any combination thereof. For example, an exemplary chemically modified siNA molecule of the invention comprises an asymmetric double-stranded structure having separate polynucleotide strands comprising sense and antisense regions, wherein the antisense region is about 18 to about 23 (e.g., about 18, 19, 20, 21, 22, or 23) nucleotides in length and wherein the sense region is about 3 to about 15 (e.g., about 3, 4, 5, 6, 7, 8, 9, 10, 11, 12, 13, 14, or 15) nucleotides in length, wherein the sense region the antisense region have at least 3 complementary nucleotides, and wherein the siNA can include one or more chemical modifications comprising a structure having any of Formulae I-VII or any combination thereof. In another embodiment, the asymmetric double-stranded siNA molecule can also have a 5'-terminal phosphate group that can be chemically modified as described herein (for example a 5'-terminal phosphate group having Formula IV).

In another embodiment, an siNA molecule of the invention comprises a circular nucleic acid molecule, wherein the siNA is about 38 to about 70 (e.g., about 38, 40, 45, 50, 55, 60, 65, or 70) nucleotides in length having about 15 to about 30 (e.g., about 15, 16, 17, 18, 19, 20, 21, 22, 23, 24, 25, 26, 27, 28, 29, or 30) base pairs, and wherein the siNA can include a chemical modification, which comprises a structure having any of Formulae I-VII or any combination thereof. For example, an exemplary chemically modified siNA molecule of the invention comprises a circular oligonucleotide having about 42 to about 50 (e.g., about 42, 43, 44, 45, 46, 47, 48, 49, or 50) nucleotides that is chemically modified with a chemical modification having any of Formulae I-VII or any combination thereof, wherein the circular oligonucleotide forms a dumbbell shaped structure having about 19 base pairs and 2 loops.

In another embodiment, a circular siNA molecule of the invention contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In one embodiment, an siNA molecule of the invention comprises at least one (e.g., about 1, 2, 3, 4, 5, 6, 7, 8, 9, 10, or more) abasic moiety, for example a compound having Formula V:

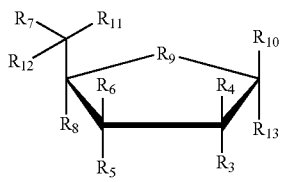

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalkylamino, substituted silyl, or group having Formula I or II; R9 is O, S, CH2, S=O, CHF, or CF2.

In one embodiment, an siNA molecule of the invention comprises at least one (e.g., about 1, 2, 3, 4, 5, 6, 7, 8, 9, 10, or more) inverted abasic moiety, for example a compound having Formula VI:

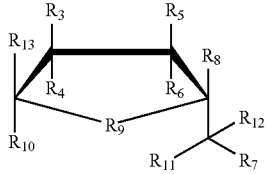

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalkylamino, substituted silyl, or group having Formula I or II; R9 is O, S, CH2, S=O, CHF, or CF2, and either R5, R3, R8 or R13 serves as a point of attachment to the siNA molecule of the invention.

In another embodiment, an siNA molecule of the invention comprises at least one (e.g., about 1, 2, 3, 4, 5, 6, 7, 8, 9, 10, or more) substituted polyalkyl moieties, for example a compound having Formula VII:

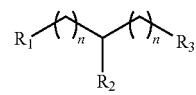

wherein each n is independently an integer from 1 to 12, each R1, R2 and R3 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalkylamino, substituted silyl, or a group having Formula I, and R1, R2 or R3 serves as points of attachment to the siNA molecule of the invention.

In another embodiment, the invention features a compound having Formula VII, wherein R1 and R2 are hydroxyl (OH) groups, n=1, and R3 comprises O and is the point of attachment to the 3'-end, the 5'-end, or both of the 3' and 5'-ends of one or both strands of a double-stranded siNA molecule of the invention or to a single-stranded siNA molecule of the invention. This modification is referred to herein as "glyceryl" (for example modification 6 in FIG. 10).

In another embodiment, a chemically modified nucleoside or non-nucleoside (e.g. a moiety having any of Formula V, VI or VII) of the invention is at the 3'-end, the 5'-end, or both of the 3' and 5'-ends of an siNA molecule of the invention. For example, chemically modified nucleoside or non-nucleoside (e.g., a moiety having Formula V, VI or VII) can be present at the 3'-end, the 5'-end, or both of the 3' and 5'-ends of the antisense strand, the sense strand, or both antisense and sense strands of the siNA molecule. In one embodiment, the chemically modified nucleoside or non-nucleoside (e.g., a moiety having Formula V, VI or VII) is present at the 5'-end and 3'-end of the sense strand and the 3'-end of the antisense strand of a double-stranded siNA molecule of the invention. In one embodiment, the chemically modified nucleoside or non-nucleoside (e.g., a moiety having Formula V, VI or VII) is present at the terminal position of the 5'-end and 3'-end of the sense strand and the 3'-end of the antisense strand of a double-stranded siNA molecule of the invention. In one embodiment, the chemically modified nucleoside or non-nucleoside (e.g., a moiety having Formula V, VI or VII) is present at the two terminal positions of the 5'-end and 3'-end of the sense strand and the 3'-end of the antisense strand of a double-stranded siNA molecule of the invention. In one embodiment, the chemically modified nucleoside or non-nucleoside (e.g., a moiety having Formula V, VI or VII) is present at the penultimate position of the 5'-end and 3'-end of the sense strand and the 3'-end of the antisense strand of a double-stranded siNA molecule of the invention. In addition, a moiety having Formula VII can be present at the 3'-end or the 5'-end of a hairpin siNA molecule as described herein.

In another embodiment, an siNA molecule of the invention comprises an abasic residue having Formula V or VI, wherein the abasic residue having Formula VI or VI is connected to the siNA construct in a 3'-3',3'-2',2'-3', or 5'-5' configuration, such as at the 3'-end, the 5'-end, or both of the 3' and 5'-ends of one or both siNA strands.

In one embodiment, an siNA molecule of the invention comprises one or more (e.g., about 1, 2, 3, 4, 5, 6, 7, 8, 9, 10, or more) locked nucleic acid (LNA) nucleotides, for example, at the 5'-end, the 3'-end, both of the 5' and 3'-ends, or any combination thereof, of the siNA molecule.

In another embodiment, an siNA molecule of the invention comprises one or more (e.g., about 1; 2, 3, 4, 5, 6, 7, 8, 9, 10, or more) acyclic nucleotides, for example, at the 5'-end, the 3'-end, both of the 5' and 3'-ends, or any combination thereof, of the siNA molecule.

In one embodiment, the invention features a chemically modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), wherein any nucleotides comprising a 3'-terminal nucleotide overhang that are present in said sense region are 2'-deoxy nucleotides.

In one embodiment, the invention features a chemically modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), wherein any (e.g., one or more or all) purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides), and wherein any nucleotides comprising a 3'-terminal nucleotide overhang that are present in said sense region are 2'-deoxy nucleotides.

In one embodiment, the invention features a chemically modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and wherein any nucleotides comprising a 3'-terminal nucleotide overhang that are present in said antisense region are 2'-deoxy nucleotides.

In one embodiment, the invention features a chemically modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically modified short interfering nucleic acid (siNA) molecule of the invention capable of mediating RNA interference (RNAi) against GAB2 inside a cell or reconstituted in vitro system comprising a sense region, wherein one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and an antisense region, wherein one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). The sense region and/or the antisense region can have a terminal cap modification, such as any modification described herein or shown in FIG. 10, that is optionally present at the 3'-end, the 5'-end, or both of the 3' and 5'-ends of the sense and/or antisense sequence. The sense and/or antisense region can optionally further comprise a 3'-terminal nucleotide overhang having about 1 to about 4 (e.g., about 1, 2, 3, or 4) 2'-deoxynucleotides. The overhang nucleotides can further comprise one or more (e.g., about 1, 2, 3, 4 or more) phosphorothioate, phosphonoacetate, and/or thiophosphonoacetate internucleotide linkages. Non-limiting examples of these chemically modified siNAs are shown in FIGS. 4 and 5 and Tables III and IV herein. In any of these described embodiments, the purine nucleotides present in the sense region are alternatively 2'-O-methyl purine nucleotides (e.g., wherein all purine nucleotides are 2'-O-methyl purine nucleotides or alternately a plurality of purine nucleotides are 2'-O-methyl purine nucleotides) and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). Also, in any of these embodiments, one or more purine nucleotides present in the sense region are alternatively purine ribonucleotides (e.g., wherein all purine nucleotides are purine ribonucleotides or alternately a plurality of purine nucleotides are purine ribonucleotides) and any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). Additionally, in any of these embodiments, one or more purine nucleotides present in the sense region and/or present in the antisense region are alternatively selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides).

In another embodiment, any modified nucleotides present in the siNA molecules of the invention, preferably in the antisense strand of the siNA molecules of the invention, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a Northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides.

In one embodiment, the sense strand of a double-stranded siNA molecule of the invention comprises a terminal cap moiety, (see for example FIG. 10) such as an inverted deoxyabasic moiety, at the 3'-end, 5'-end, or both 3' and 5'-ends of the sense strand.

In one embodiment, the invention features a chemically modified short interfering nucleic acid molecule (siNA) capable of mediating RNA interference (RNAi) against GAB2 inside a cell or reconstituted in vitro system, wherein the chemical modification comprises a conjugate covalently attached to the chemically modified siNA molecule. Non-limiting examples of conjugates contemplated by the invention include conjugates and ligands described in Vargeese et al., U.S. Ser. No. 10/427,160, filed Apr. 30, 2003, incorporated by reference herein in its entirety, including the drawings. In another embodiment, the conjugate is covalently attached to the chemically modified siNA molecule via a biodegradable linker. In one embodiment, the conjugate molecule is attached at the 3'-end of either the sense strand, the antisense strand, or both strands of the chemically modified siNA molecule. In another embodiment, the conjugate molecule is attached at the 5'-end of either the sense strand, the antisense strand, or both strands of the chemically modified siNA molecule. In yet another embodiment, the conjugate molecule is attached both the 3'-end and 5'-end of either the sense strand, the antisense strand, or both strands of the chemically modified siNA molecule, or any combination thereof. In one embodiment, a conjugate molecule of the invention comprises a molecule that facilitates delivery of a chemically modified siNA molecule into a biological system, such as a cell. In another embodiment, the conjugate molecule attached to the chemically modified siNA molecule is a polyethylene glycol, human serum albumin, or a ligand for a cellular receptor that can mediate cellular uptake. Examples of specific conjugate molecules contemplated by the instant invention that can be attached to chemically modified siNA molecules are described in Vargeese et al., U.S. Ser. No. 10/201,394, filed Jul. 22, 2002 incorporated by reference herein. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

In one embodiment, the invention features a short interfering nucleic acid (siNA) molecule of the invention, wherein the siNA further comprises a nucleotide, non-nucleotide, or mixed nucleotide/non-nucleotide linker that joins the sense region of the siNA to the antisense region of the siNA. In one embodiment, a nucleotide linker of the invention can be a linker of >2 nucleotides in length, for example about 3, 4, 5, 6, 7, 8, 9, or 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has a sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. (See, for example, Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628.)

In yet another embodiment, a non-nucleotide linker of the invention comprises abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In one embodiment, the invention features a short interfering nucleic acid (siNA) molecule capable of mediating RNA interference (RNAi) inside a cell or reconstituted in vitro system, wherein one or both strands of the siNA molecule that are assembled from two separate oligonucleotides do not comprise any ribonucleotides. For example, an siNA molecule can be assembled from a single oligonucleotide where the sense and antisense regions of the siNA comprise separate oligonucleotides that do not have any ribonucleotides (e.g., nucleotides having a 2'-OH group) present in the oligonucleotides. In another example, an siNA molecule can be assembled from a single oligonucleotide where the sense and antisense regions of the siNA are linked or circularized by a nucleotide or non-nucleotide linker as described herein, wherein the oligonucleotide does not have any ribonucleotides (e.g., nucleotides having a 2'-OH group) present in the oligonucleotide. Applicant has surprisingly found that the presence of ribonucleotides (e.g., nucleotides having a 2'-hydroxyl group) within the siNA molecule is not required or essential to support RNAi activity. As such, in one embodiment, all positions within the siNA can include chemically modified nucleotides and/or non-nucleotides such as nucleotides and or non-nucleotides having Formula I, II, III, IV, V, VI, or VII or any combination thereof to the extent that the ability of the siNA molecule to support RNAi activity in a cell is maintained.

In one embodiment, an siNA molecule of the invention is a single-stranded siNA molecule that mediates RNAi activity in a cell or reconstituted in vitro system comprising a single-stranded polynucleotide having complementarity to a target nucleic acid sequence. In another embodiment, the single-stranded siNA molecule of the invention comprises a 5'-terminal phosphate group. In another embodiment, the single-stranded siNA molecule of the invention comprises a 5'-terminal phosphate group and a 3'-terminal phosphate group (e.g., a 2',3'-cyclic phosphate). In another embodiment, the single-stranded siNA molecule of the invention comprises about 15 to about 30 (e.g., about 15, 16, 17, 18, 19, 20, 21, 22, 23, 24, 25, 26, 27, 28, 29, or 30) nucleotides. In yet another embodiment, the single-stranded siNA molecule of the invention comprises one or more chemically modified nucleotides or non-nucleotides described herein. For example, all the positions within the siNA molecule can include chemically modified nucleotides such as nucleotides having any of Formulae I-VII, or any combination thereof to the extent that the ability of the siNA molecule to support RNAi activity in a cell is maintained.

In one embodiment, an siNA molecule of the invention is a single-stranded siNA molecule that mediates RNAi activity in a cell or reconstituted in vitro system comprising a single-stranded polynucleotide having complementarity to a target nucleic acid sequence, wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 10, that is optionally present at the 3'-end and/or the 5'-end. The siNA optionally further comprises about 1 to about 4 or more (e.g., about 1, 2, 3, 4 or more) terminal 2'-deoxynucleotides at the 3'-end of the siNA molecule, wherein the terminal nucleotides can further comprise one or more (e.g., 1, 2, 3, 4 or more) phosphorothioate, phosphonoacetate, and/or thiophosphonoacetate internucleotide linkages, and wherein the siNA optionally further comprises a terminal phosphate group, such as a 5'-terminal phosphate group. In any of these embodiments, any purine nucleotides present in the antisense region are alternatively 2'-deoxy purine nucleotides (e.g., wherein all purine nucleotides are 2'-deoxy purine nucleotides or alternately a plurality of purine nucleotides are 2'-deoxy purine nucleotides). Also, in any of these embodiments, any purine nucleotides present in the siNA (i.e., purine nucleotides present in the sense and/or antisense region) can alternatively be locked nucleic acid (LNA) nucleotides (e.g., wherein all purine nucleotides are LNA nucleotides or alternately a plurality of purine nucleotides are LNA nucleotides). Also, in any of these embodiments, any purine nucleotides present in the siNA are alternatively 2'-methoxyethyl purine nucleotides (e.g., wherein all purine nucleotides are 2'-methoxyethyl purine nucleotides or alternately a plurality of purine nucleotides are 2'-methoxyethyl purine nucleotides). In another embodiment, any modified nucleotides present in the single-stranded siNA molecules of the invention comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the single-stranded siNA molecules of the invention are preferably resistant to nuclease degradation while at the same time maintaining the capacity to mediate RNAi.

In one embodiment, an siNA molecule of the invention comprises chemically modified nucleotides or non-nucleotides (e.g., having any of Formulae I-VII, such as 2'-deoxy, 2'-deoxy-2'-fluoro, or 2'-O-methyl nucleotides) at alternating positions within one or more strands or regions of the siNA molecule. For example, such chemical modifications can be introduced at every other position of a RNA based siNA molecule, starting at either the first or second nucleotide from the 3'-end or 5'-end of the siNA. In a non-limiting example, a double-stranded siNA molecule of the invention in which each strand of the siNA is 21 nucleotides in length is featured wherein positions 1, 3, 5, 7, 9, 11, 13, 15, 17, 19 and 21 of each strand are chemically modified (e.g., with compounds having any of Formulae I-VII, such as 2'-deoxy, 2'-deoxy-2'-fluoro, or 2'-O-methyl nucleotides). In another non-limiting example, a double-stranded siNA molecule of the invention in which each strand of the siNA is 21 nucleotides in length is featured wherein positions 2, 4, 6, 8, 10, 12, 14, 16, 18, and 20 of each strand are chemically modified (e.g., with compounds having any of Formulae I-VII, such as 2'-deoxy, 2'-deoxy-2'-fluoro, or 2'-O-methyl nucleotides). Such siNA molecules can further comprise terminal cap moieties and/or backbone modifications as described herein.

In one embodiment, the invention features a method for modulating the expression of a GAB2 gene within a cell comprising: (a) synthesizing an siNA molecule of the invention, which can be chemically modified, wherein one of the siNA strands comprises a sequence complementary to RNA of the GAB2 gene; and (b) introducing the siNA molecule into a cell under conditions suitable to modulate the expression of the GAB2 gene in the cell.

In one embodiment, the invention features a method for modulating the expression of a GAB2 gene within a cell comprising: (a) synthesizing an siNA molecule of the invention, which can be chemically modified, wherein one of the siNA strands comprises a sequence complementary to RNA of the GAB2 gene and wherein the sense strand sequence of the siNA comprises a sequence identical or substantially similar to the sequence of the target RNA; and (b) introducing the siNA molecule into a cell under conditions suitable to modulate the expression of the GAB2 gene in the cell.

In another embodiment, the invention features a method for modulating the expression of more than one GAB2 gene within a cell comprising: (a) synthesizing siNA molecules of the invention, which can be chemically modified, wherein one of the siNA strands comprises a sequence complementary to RNA of the GAB2 genes; and (b) introducing the siNA molecules into a cell under conditions suitable to modulate the expression of the GAB2 genes in the cell.

In another embodiment, the invention features a method for modulating the expression of two or more GAB2 genes within a cell comprising: (a) synthesizing one or more siNA molecules of the invention, which can be chemically modified, wherein the siNA strands comprise sequences complementary to RNA of the GAB2 genes and wherein the sense strand sequences of the siNAs comprise sequences identical or substantially similar to the sequences of the target RNAs; and (b) introducing the siNA molecules into a cell under conditions suitable to modulate the expression of the GAB2 genes in the cell.

In another embodiment, the invention features a method for modulating the expression of more than one GAB2 gene within a cell comprising: (a) synthesizing an siNA molecule of the invention, which can be chemically modified, wherein one of the siNA strands comprises a sequence complementary to RNA of the GAB2 gene and wherein the sense strand sequence of the siNA comprises a sequence identical or substantially similar to the sequences of the target RNAs; and (b) introducing the siNA molecule into a cell under conditions suitable to modulate the expression of the GAB2 genes in the cell.

In one embodiment, siNA molecules of the invention are used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with siNAs targeting a specific nucleotide sequence within the cells under conditions suitable for uptake of the siNAs by these cells (e.g. using delivery reagents such as cationic lipids, liposomes and the like or using techniques such as electroporation to facilitate the delivery of siNAs into cells). The cells are then reintroduced back into the same patient or other patients. In one embodiment, the invention features a method of modulating the expression of a GAB2 gene in a tissue explant comprising: (a) synthesizing an siNA molecule of the invention, which can be chemically modified, wherein one of the siNA strands comprises a sequence complementary to RNA of the GAB2 gene; and (b) introducing the siNA molecule into a cell of the tissue explant derived from a particular organism under conditions suitable to modulate the expression of the GAB2 gene in the tissue explant. In another embodiment, the method further comprises introducing the tissue explant back into the organism the tissue was derived from or into another organism under conditions suitable to modulate the expression of the GAB2 gene in that organism.

In one embodiment, the invention features a method of modulating the expression of a GAB2 gene in a tissue explant comprising: (a) synthesizing an siNA molecule of the invention, which can be chemically modified, wherein one of the siNA strands comprises a sequence complementary to RNA of the GAB2 gene and wherein the sense strand sequence of the siNA comprises a sequence identical or substantially similar to the sequence of the target RNA; and (b) introducing the siNA molecule into a cell of the tissue explant derived from a particular organism under conditions suitable to modulate the expression of the GAB2 gene in the tissue explant. In another embodiment, the method further comprises introducing the tissue explant back into the organism the tissue was derived from or into another organism under conditions suitable to modulate the expression of the GAB2 gene in that organism.

In another embodiment, the invention features a method of modulating the expression of more than one GAB2 gene in a tissue explant comprising: (a) synthesizing siNA molecules of the invention, which can be chemically modified, wherein one of the siNA strands comprises a sequence complementary to RNA of the GAB2 genes; and (b) introducing the siNA molecules into a cell of the tissue explant derived from a particular organism under conditions suitable to modulate the expression of the GAB2 genes in the tissue explant. In another embodiment, the method further comprises introducing the tissue explant back into the organism the tissue was derived from or into another organism under conditions suitable to modulate the expression of the GAB2 genes in that organism.

In one embodiment, the invention features a method of modulating the expression of a GAB2 gene in a subject or organism comprising: (a) synthesizing an siNA molecule of the invention, which can be chemically modified, wherein one of the siNA strands comprises a sequence complementary to RNA of the GAB2 gene; and (b) introducing the siNA molecule into the subject or organism under conditions suitable to modulate the expression of the GAB2 gene in the subject or organism. The level of GAB2 protein or RNA can be determined using various methods well-known in the art.

In another embodiment, the invention features a method of modulating the expression of more than one GAB2 gene in a subject or organism comprising: (a) synthesizing siNA molecules of the invention, which can be chemically modified, wherein one of the siNA strands comprises a sequence complementary to RNA of the GAB2 genes; and (b) introducing the siNA molecules into the subject or organism under conditions suitable to modulate the expression of the GAB2 genes in the subject or organism. The level of GAB2 protein or RNA can be determined as is known in the art.

In one embodiment, the invention features a method for modulating the expression of a GAB2 gene within a cell comprising: (a) synthesizing an siNA molecule of the invention, which can be chemically modified, wherein the siNA comprises a single-stranded sequence having complementarity to RNA of the GAB2 gene; and (b) introducing the siNA molecule into a cell under conditions suitable to modulate the expression of the GAB2 gene in the cell.

In another embodiment, the invention features a method for modulating the expression of more than one GAB2 gene within a cell comprising: (a) synthesizing siNA molecules of the invention, which can be chemically modified, wherein the siNA comprises a single-stranded sequence having complementarity to RNA of the GAB2 gene; and (b) contacting the cell in vitro or in vivo with the siNA molecule under conditions suitable to modulate the expression of the GAB2 genes in the cell.

In one embodiment, the invention features a method of modulating the expression of a GAB2 gene in a tissue explant comprising: (a) synthesizing an siNA molecule of the invention, which can be chemically modified, wherein the siNA comprises a single-stranded sequence having complementarity to RNA of the GAB2 gene; and (b) contacting a cell of the tissue explant derived from a particular subject or organism with the siNA molecule under conditions suitable to modulate the expression of the GAB2 gene in the tissue explant. In another embodiment, the method further comprises introducing the tissue explant back into the subject or organism the tissue was derived from or into another subject or organism under conditions suitable to modulate the expression of the GAB2 gene in that subject or organism.

In another embodiment, the invention features a method of modulating the expression of more than one GAB2 gene in a tissue explant comprising: (a) synthesizing siNA molecules of the invention, which can be chemically modified, wherein the siNA comprises a single-stranded sequence having complementarity to RNA of the GAB2 gene; and (b) introducing the siNA molecules into a cell of the tissue explant derived from a particular subject or organism under conditions suitable to modulate the expression of the GAB2 genes in the tissue explant. In another embodiment, the method further comprises introducing the tissue explant back into the subject or organism the tissue was derived from or into another subject or organism under conditions suitable to modulate the expression of the GAB2 genes in that subject or organism.

In one embodiment, the invention features a method of modulating the expression of a GAB2 gene in a subject or organism comprising: (a) synthesizing an siNA molecule of the invention, which can be chemically modified, wherein the siNA comprises a single-stranded sequence having complementarity to RNA of the GAB2 gene; and (b) introducing the siNA molecule into the subject or organism under conditions suitable to modulate the expression of the GAB2 gene in the subject or organism.

In another embodiment, the invention features a method of modulating the expression of more than one GAB2 gene in a subject or organism comprising: (a) synthesizing siNA molecules of the invention, which can be chemically modified, wherein the siNA comprises a single-stranded sequence having complementarity to RNA of the GAB2 gene; and (b) introducing the siNA molecules into the subject or organism under conditions suitable to modulate the expression of the GAB2 genes in the subject or organism.

In one embodiment, the invention features a method of modulating the expression of a GAB2 gene in a subject or organism comprising contacting the subject or organism with an siNA molecule of the invention under conditions suitable to modulate the expression of the GAB2 gene in the subject or organism.

In one embodiment, the invention features a method for treating or preventing cancer in a subject or organism comprising contacting the subject or organism with an siNA molecule of the invention under conditions suitable to modulate the expression of the GAB2 gene in the subject or organism.

In one embodiment, the invention features a method for treating or preventing a proliferative disease or condition in a subject or organism comprising contacting the subject or organism with an siNA molecule of the invention under conditions suitable to modulate the expression of the GAB2 gene in the subject or organism.

In one embodiment, the invention features a method for treating or preventing an inflammatory disease or condition in a subject or organism comprising contacting the subject or organism with an siNA molecule of the invention under conditions suitable to modulate the expression of the GAB2 gene in the subject or organism.

In one embodiment, the invention features a method for treating or preventing an allergic disease or condition in a subject or organism comprising contacting the subject or organism with an siNA molecule of the invention under conditions suitable to modulate the expression of the GAB2 gene in the subject or organism.

In one embodiment, the invention features a method for treating or preventing malignant blood disease (leukemia, such as chronic myeloid leukemia, CML; acute myeloid leukemias, AML; secondary leukemias, acute lymphoblastic leukemias, ALL; or chronic lymphoid leukemia; CLL) in a subject or organism comprising contacting the subject or organism with an siNA molecule of the invention under conditions suitable to modulate the expression of the GAB2 gene in the subject or organism.

In another embodiment, the invention features a method of modulating the expression of more than one GAB2 gene in a subject or organism comprising contacting the subject or organism with one or more siNA molecules of the invention under conditions suitable to modulate the expression of the GAB2 genes in the subject or organism.

The siNA molecules of the invention can be designed to down regulate or inhibit target (e.g., GAB2) gene expression through RNAi targeting of a variety of RNA molecules. In one embodiment, the siNA molecules of the invention are used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to inhibit gene expression through the appropriate exons to specifically inhibit or to distinguish among the functions of gene family members. For example, a protein that contains an alternatively spliced transmembrane domain can be expressed in both membrane bound and secreted forms. Use of the invention to target the exon containing the transmembrane domain can be used to determine the functional consequences of pharmaceutical targeting of membrane bound as opposed to the secreted form of the protein. Non-limiting examples of applications of the invention relating to targeting these RNA molecules include therapeutic pharmaceutical applications, pharmaceutical discovery applications, molecular diagnostic and gene function applications, and gene mapping, for example using single nucleotide polymorphism mapping with siNA molecules of the invention. Such applications can be implemented using known gene sequences or from partial sequences available from an expressed sequence tag (EST).

In another embodiment, the siNA molecules of the invention are used to target conserved sequences corresponding to a gene family or gene families such as GAB2 family genes. As such, siNA molecules targeting multiple GAB2 targets can provide increased therapeutic effect. In addition, siNA can be used to characterize pathways of gene function in a variety of applications. For example, the present invention can be used to inhibit the activity of target gene(s) in a pathway to determine the function of uncharacterized gene(s) in gene function analysis, mRNA function analysis, or translational analysis. The invention can be used to determine potential target gene pathways involved in various diseases and conditions toward pharmaceutical development. The invention can be used to understand pathways of gene expression involved in, for example, cancer, malignant blood disease (leukemia), inflammatory diseases or conditions, allergic diseases or conditions, or proliferative diseases or conditions.

In one embodiment, siNA molecule(s) and/or methods of the invention are used to down regulate the expression of gene(s) that encode RNA referred to by Genbank Accession Nos., for example, GAB2 genes encoding RNA sequence(s) referred to herein by Genbank Accession number, for example, Genbank Accession Nos. shown in Table I.

In one embodiment, the invention features a method comprising: (a) generating a library of siNA constructs having a predetermined complexity; and (b) assaying the siNA constructs of (a) above, under conditions suitable to determine RNAi target sites within the target RNA sequence. In one embodiment, the siNA molecules of (a) have strands of a fixed length, for example, about 23 nucleotides in length. In another embodiment, the siNA molecules of (a) are of differing length, for example having strands of about 15 to about 30 (e.g., about 15, 16, 17, 18, 19, 20, 21, 22, 23, 24, 25, 26, 27, 28, 29, or 30) nucleotides in length. In one embodiment, the assay can comprise a reconstituted in vitro siNA assay as described herein. In another embodiment, the assay can comprise a cell culture system in which target RNA is expressed. In another embodiment, fragments of target RNA are analyzed for detectable levels of cleavage, for example by gel electrophoresis, Northern blot analysis, or RNAse protection assays, to determine the most suitable target site(s) within the target RNA sequence. The target RNA sequence can be obtained as is known in the art, for example, by cloning and/or transcription for in vitro systems, and by cellular expression in in vivo systems.

In one embodiment, the invention features a method comprising: (a) generating a randomized library of siNA constructs having a predetermined complexity, such as of 4N, where N represents the number of base paired nucleotides in each of the siNA construct strands (e.g. for an siNA construct having 21 nucleotide sense and antisense strands with 19 base pairs, the complexity would be $4^{19}$); and (b) assaying the siNA constructs of (a) above, under conditions suitable to determine RNAi target sites within the target GAB2 RNA sequence. In another embodiment, the siNA molecules of (a) have strands of a fixed length, for example about 23 nucleotides in length. In yet another embodiment, the siNA molecules of (a) are of differing length, for example having strands of about 15 to about 30 (e.g., about 15, 16, 17, 18, 19, 20, 21, 22, 23, 24, 25, 26, 27, 28, 29, or 30) nucleotides in length. In one embodiment, the assay can comprise a reconstituted in vitro siNA assay as described in Example 6 herein. In another embodiment, the assay can comprise a cell culture system in which target RNA is expressed. In another embodiment, fragments of GAB2 RNA are analyzed for detectable levels of cleavage, for example, by gel electrophoresis, Northern blot analysis, or RNAse protection assays, to determine the most suitable target site(s) within the target GAB2 RNA sequence. The target GAB2 RNA sequence can be obtained as is known in the art, for example, by cloning and/or transcription for in vitro systems, and by cellular expression in in vivo systems.

In another embodiment, the invention features a method comprising: (a) analyzing the sequence of a RNA target encoded by a target gene; (b) synthesizing one or more sets of siNA molecules having sequence complementary to one or more regions of the RNA of (a); and (c) assaying the siNA molecules of (b) under conditions suitable to determine RNAi targets within the target RNA sequence. In one embodiment, the siNA molecules of (b) have strands of a fixed length, for example about 23 nucleotides in length. In another embodiment, the siNA molecules of (b) are of differing length, for example having strands of about 15 to about 30 (e.g., about 15, 16, 17, 18, 19, 20, 21, 22, 23, 24, 25, 26, 27, 28, 29, or 30) nucleotides in length. In one embodiment, the assay can comprise a reconstituted in vitro siNA assay as described herein. In another embodiment, the assay can comprise a cell culture system in which target RNA is expressed. Fragments of target RNA are analyzed for detectable levels of cleavage, for example by gel electrophoresis, Northern blot analysis, or RNAse protection assays, to determine the most suitable target site(s) within the target RNA sequence. The target RNA sequence can be obtained as is known in the art, for example, by cloning and/or transcription for in vitro systems, and by expression in in vivo systems.

By "target site" is meant a sequence within a target RNA that is "targeted" for cleavage mediated by an siNA construct which contains sequences within its antisense region that are complementary to the target sequence.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1-5% of the target RNA is sufficient to detect above the background for most methods of detection.

In one embodiment, the invention features a composition comprising an siNA molecule of the invention, which can be chemically modified, in a pharmaceutically acceptable carrier or diluent. In another embodiment, the invention features a pharmaceutical composition comprising siNA molecules of the invention, which can be chemically modified, targeting one or more genes in a pharmaceutically acceptable carrier or diluent. In another embodiment, the invention features a method for diagnosing a disease or condition in a subject comprising administering to the subject a composition of the invention under conditions suitable for the diagnosis of the disease or condition in the subject. In another embodiment, the invention features a method for treating or preventing a disease or condition in a subject, comprising administering to the subject a composition of the invention under conditions suitable for the treatment or prevention of the disease or condition in the subject, alone or in conjunction with one or more other therapeutic compounds. In yet another embodiment, the invention features a method for treating, maintaining or preventing cancer, malignant blood disease (leukemia), inflammatory diseases or conditions, allergic diseases or conditions, or proliferative diseases or conditions in a subject comprising administering to the subject a composition of the invention under conditions suitable for the treatment, maintenance, or prevention of cancer, malignant blood disease (leukemia), inflammatory disease or condition, allergic disease or condition, or proliferative disease or condition in the subject.

In another embodiment, the invention features a method for validating a GAB2 gene target, comprising: (a) synthesizing an siNA molecule of the invention, which can be chemically modified, wherein one of the siNA strands includes a sequence complementary to RNA of a GAB2 target gene; (b) introducing the siNA molecule into a cell, tissue, subject, or organism under conditions suitable for modulating expression of the GAB2 target gene in the cell, tissue, subject, or organism; and (c) determining the function of the gene by assaying for any phenotypic change in the cell, tissue, subject, or organism.

In another embodiment, the invention features a method for validating a GAB2 target comprising: (a) synthesizing an siNA molecule of the invention, which can be chemically modified, wherein one of the siNA strands includes a sequence complementary to RNA of a GAB2 target gene; (b) introducing the siNA molecule into a biological system under conditions suitable for modulating expression of the GAB2 target gene in the biological system; and (c) determining the function of the gene by assaying for any phenotypic change in the biological system.

By "biological system" is meant, material, in a purified or unpurified form, from biological sources, including but not limited to human or animal, wherein the system comprises the components required for RNAi activity. The term "biological system" includes, for example, a cell, tissue, subject, or organism, or extract thereof. The term biological system also includes reconstituted RNAi systems that can be used in an in vitro setting.

By "phenotypic change" is meant any detectable change to a cell that occurs in response to contact or treatment with a nucleic acid molecule of the invention (e.g., siNA). Such detectable changes include, but are not limited to, changes in shape, size, proliferation, motility, protein expression or RNA expression or other physical or chemical changes as can be assayed by methods known in the art. The detectable change can also include expression of reporter genes/molecules such as Green Florescent Protein (GFP) or various tags that are used to identify an expressed protein or any other cellular component that can be assayed.

In one embodiment, the invention features a kit containing an siNA molecule of the invention, which can be chemically modified, that can be used to modulate the expression of a GAB2 target gene in a biological system, including, for example, in a cell, tissue, subject, or organism. In another embodiment, the invention features a kit containing more than one siNA molecule of the invention, which can be chemically modified, that can be used to modulate the expression of more than one GAB2 target gene in a biological system, including, for example, in a cell, tissue, subject, or organism.

In one embodiment, the invention features a cell containing one or more siNA molecules of the invention, which can be chemically modified. In another embodiment, the cell containing an siNA molecule of the invention is a mammalian cell. In yet another embodiment, the cell containing an siNA molecule of the invention is a human cell.

In one embodiment, the synthesis of an siNA molecule of the invention, which can be chemically modified, comprises: (a) synthesis of two complementary strands of the siNA molecule; (b) annealing the two complementary strands together under conditions suitable to obtain a double-stranded siNA molecule. In another embodiment, synthesis of the two complementary strands of the siNA molecule is by solid phase oligonucleotide synthesis. In yet another embodiment, synthesis of the two complementary strands of the siNA molecule is by solid phase tandem oligonucleotide synthesis.

In one embodiment, the invention features a method for synthesizing an siNA duplex molecule comprising: (a) synthesizing a first oligonucleotide sequence strand of the siNA molecule, wherein the first oligonucleotide sequence strand comprises a cleavable linker molecule that can be used as a scaffold for the synthesis of the second oligonucleotide sequence strand of the siNA; (b) synthesizing the second oligonucleotide sequence strand of siNA on the scaffold of the first oligonucleotide sequence strand, wherein the second oligonucleotide sequence strand further comprises a chemical moiety than can be used to purify the siNA duplex; (c) cleaving the linker molecule of (a) under conditions suitable for the two siNA oligonucleotide strands to hybridize and form a stable duplex; and (d) purifying the siNA duplex utilizing the chemical moiety of the second oligonucleotide sequence strand. In one embodiment, cleavage of the linker molecule in (c) above takes place during deprotection of the oligonucleotide, for example, under hydrolysis conditions using an alkylamine base such as methylamine. In one embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity as the solid support derivatized linker, such that cleavage of the solid support derivatized linker and the cleavable linker of (a) takes place concomitantly. In another embodiment, the chemical moiety of (b) that can be used to isolate the attached oligonucleotide sequence comprises a trityl group, for example a dimethoxytrityl group, which can be employed in a trityl-on synthesis strategy as described herein. In yet another embodiment, the chemical moiety, such as a dimethoxytrityl group, is removed during purification, for example, using acidic conditions.

In a further embodiment, the method for siNA synthesis is a solution phase synthesis or hybrid phase synthesis wherein both strands of the siNA duplex are synthesized in tandem using a cleavable linker attached to the first sequence which acts a scaffold for synthesis of the second sequence. Cleavage of the linker under conditions suitable for hybridization of the separate siNA sequence strands results in formation of the double-stranded siNA molecule.

In another embodiment, the invention features a method for synthesizing an siNA duplex molecule comprising: (a) synthesizing one oligonucleotide sequence strand of the siNA molecule, wherein the sequence comprises a cleavable linker molecule that can be used as a scaffold for the synthesis of another oligonucleotide sequence; (b) synthesizing a second oligonucleotide sequence having complementarity to the first sequence strand on the scaffold of (a), wherein the second sequence comprises the other strand of the double-stranded siNA molecule and wherein the second sequence further comprises a chemical moiety than can be used to isolate the attached oligonucleotide sequence; (c) purifying the product of (b) utilizing the chemical moiety of the second oligonucleotide sequence strand under conditions suitable for isolating the full-length sequence comprising both siNA oligonucleotide strands connected by the cleavable linker and under conditions suitable for the two siNA oligonucleotide strands to hybridize and form a stable duplex. In one embodiment, cleavage of the linker molecule in (c) above takes place during deprotection of the oligonucleotide, for example, under hydrolysis conditions. In another embodiment, cleavage of the linker molecule in (c) above takes place after deprotection of the oligonucleotide. In another embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity or differing reactivity as the solid support derivatized linker, such that cleavage of the solid support derivatized linker and the cleavable linker of (a) takes place either concomitantly or sequentially. In one embodiment, the chemical moiety of (b) that can be used to isolate the attached oligonucleotide sequence comprises a trityl group, for example a dimethoxytrityl group.

In another embodiment, the invention features a method for making a double-stranded siNA molecule in a single synthetic process comprising: (a) synthesizing an oligonucleotide having a first and a second sequence, wherein the first sequence is complementary to the second sequence, and the first oligonucleotide sequence is linked to the second sequence via a cleavable linker, and wherein a terminal 5'-protecting group, for example, a 5'-O-dimethoxytrityl group (5'-O-DMT) remains on the oligonucleotide having the second sequence; (b) deprotecting the oligonucleotide whereby the deprotection results in the cleavage of the linker joining the two oligonucleotide sequences; and (c) purifying the product of (b) under conditions suitable for isolating the double-stranded siNA molecule, for example using a trityl-on synthesis strategy as described herein.

In another embodiment, the method of synthesis of siNA molecules of the invention comprises the teachings of Scaringe et al., U.S. Pat. Nos. 5,889,136; 6,008,400; and 6,111,086, incorporated by reference herein in their entirety.

In one embodiment, the invention features siNA constructs that mediate RNAi against GAB2, wherein the siNA construct comprises one or more chemical modifications, for example, one or more chemical modifications having any of Formulae I-VII or any combination thereof that increases the nuclease resistance of the siNA construct.

In another embodiment, the invention features a method for generating siNA molecules with increased nuclease resistance comprising (a) introducing nucleotides having any of Formula I-VII or any combination thereof into an siNA molecule, and (b) assaying the siNA molecule of step (a) under conditions suitable for isolating siNA molecules having increased nuclease resistance.

In another embodiment, the invention features a method for generating siNA molecules with improved toxicologic profiles (e.g., have attenuated or no immunostimulatory properties) comprising (a) introducing nucleotides having any of Formula I-VII (e.g., siNA motifs referred to in Table IV) or any combination thereof into an siNA molecule, and (b) assaying the siNA molecule of step (a) under conditions suitable for isolating siNA molecules having improved toxicologic profiles.

In another embodiment, the invention features a method for generating siNA molecules that do not stimulate an interferon response (e.g., no interferon response or attenuated interferon response) in a cell, subject, or organism, comprising (a) introducing nucleotides having any of Formula I-VII (e.g., siNA motifs referred to in Table IV) or any combination thereof into an siNA molecule, and (b) assaying the siNA molecule of step (a) under conditions suitable for isolating siNA molecules that do not stimulate an interferon response.

By "improved toxicologic profile", is meant that the chemically modified siNA construct exhibits decreased toxicity in a cell, subject, or organism compared to an unmodified siNA or siNA molecule having fewer modifications or modifications that are less effective in imparting improved toxicology. In a non-limiting example, siNA molecules with improved toxicologic profiles are associated with a decreased or attenuated immunostimulatory response in a cell, subject, or organism compared to an unmodified siNA or siNA molecule having fewer modifications or modifications that are less effective in imparting improved toxicology. In one embodiment, an siNA molecule with an improved toxicological profile comprises no ribonucleotides. In one embodiment, an siNA molecule with an improved toxicological profile comprises less than 5 ribonucleotides (e.g., 1, 2, 3, or 4 ribonucleotides). In one embodiment, an siNA molecule with an improved toxicological profile comprises Stab 7, Stab 8, Stab 11, Stab 12, Stab 13, Stab 16, Stab 17, Stab 18, Stab 19, Stab 20, Stab 23, Stab 24, Stab 25, Stab 26, Stab 27, Stab 28, Stab 29, Stab 30, Stab 31, Stab 32 or any combination thereof (see Table IV). In one embodiment, the level of immunostimulatory response associated with a given siNA molecule can be measured as is known in the art, for example by determining the level of PKR/interferon response, proliferation, B-cell activation, and/or cytokine production in assays to quantitate the immunostimulatory response of particular siNA molecules (see, for example, Leifer et al., 2003, J. Immunother. 26, 313-9; and U.S. Pat. No. 5,968,909, incorporated in its entirety by reference).

In one embodiment, the invention features siNA constructs that mediate RNAi against 5GAB2, wherein the siNA construct comprises one or more chemical modifications described herein that modulates the binding affinity between the sense and antisense strands of the siNA construct.

In another embodiment, the invention features a method for generating siNA molecules with increased binding affinity between the sense and antisense strands of the siNA molecule comprising (a) introducing nucleotides having any of Formula I-VII or any combination thereof into an siNA molecule, and (b) assaying the siNA molecule of step (a) under conditions suitable for isolating siNA molecules having increased binding affinity between the sense and antisense strands of the siNA molecule.

In one embodiment, the invention features siNA constructs that mediate RNAi against GAB2, wherein the siNA construct comprises one or more chemical modifications described herein that modulates the binding affinity between the antisense strand of the siNA construct and a complementary target RNA sequence within a cell.

In one embodiment, the invention features siNA constructs that mediate RNAi against GAB2, wherein the siNA construct comprises one or more chemical modifications described herein that modulates the binding affinity between the antisense strand of the siNA construct and a complementary target DNA sequence within a cell.

In another embodiment, the invention features a method for generating siNA molecules with increased binding affinity between the antisense strand of the siNA molecule and a complementary target RNA sequence comprising (a) introducing nucleotides having any of Formula I-VII or any combination thereof into an siNA molecule, and (b) assaying the siNA molecule of step (a) under conditions suitable for isolating siNA molecules having increased binding affinity between the antisense strand of the siNA molecule and a complementary target RNA sequence.

In another embodiment, the invention features a method for generating siNA molecules with increased binding affinity between the antisense strand of the siNA molecule and a complementary target DNA sequence comprising (a) introducing nucleotides having any of Formula I-VII or any combination thereof into an siNA molecule, and (b) assaying the siNA molecule of step (a) under conditions suitable for isolating siNA molecules having increased binding affinity between the antisense strand of the siNA molecule and a complementary target DNA sequence.

In one embodiment, the invention features siNA constructs that mediate RNAi against GAB2, wherein the siNA construct comprises one or more chemical modifications described herein that modulate the polymerase activity of a cellular polymerase capable of generating additional endogenous siNA molecules having sequence homology to the chemically modified siNA construct.

In another embodiment, the invention features a method for generating siNA molecules capable of mediating increased polymerase activity of a cellular polymerase capable of generating additional endogenous siNA molecules having sequence homology to a chemically modified siNA molecule comprising (a) introducing nucleotides having any of Formula I-VII or any combination thereof into an siNA molecule, and (b) assaying the siNA molecule of step (a) under conditions suitable for isolating siNA molecules capable of mediating increased polymerase activity of a cellular polymerase capable of generating additional endogenous siNA molecules having sequence homology to the chemically modified siNA molecule.

In one embodiment, the invention features chemically modified siNA constructs that mediate RNAi against GAB2 in a cell, wherein the chemical modifications do not significantly effect the interaction of siNA with a target RNA molecule, DNA molecule and/or proteins or other factors that are essential for RNAi in a manner that would decrease the efficacy of RNAi mediated by such siNA constructs.

In another embodiment, the invention features a method for generating siNA molecules with improved RNAi activity against GAB2 comprising (a) introducing nucleotides having any of Formula I-VII or any combination thereof into an siNA molecule, and (b) assaying the siNA molecule of step (a) under conditions suitable for isolating siNA molecules having improved RNAi activity.

In yet another embodiment, the invention features a method for generating siNA molecules with improved RNAi activity against GAB2 target RNA comprising (a) introducing nucleotides having any of Formula I-VII or any combination thereof into an siNA molecule, and (b) assaying the siNA molecule of step (a) under conditions suitable for isolating siNA molecules having improved RNAi activity against the target RNA.

In yet another embodiment, the invention features a method for generating siNA molecules with improved RNAi activity against GAB2 target DNA comprising (a) introducing nucleotides having any of Formula I-VII or any combination thereof into an siNA molecule, and (b) assaying the siNA molecule of step (a) under conditions suitable for isolating siNA molecules having improved RNAi activity against the target DNA.

In one embodiment, the invention features siNA constructs that mediate RNAi against GAB2, wherein the siNA construct comprises one or more chemical modifications described herein that modulates the cellular uptake of the siNA construct.

In another embodiment, the invention features a method for generating siNA molecules against GAB2 with improved cellular uptake comprising (a) introducing nucleotides having any of Formula I-VII or any combination thereof into an siNA molecule, and (b) assaying the siNA molecule of step (a) under conditions suitable for isolating siNA molecules having improved cellular uptake.

In one embodiment, the invention features siNA constructs that mediate RNAi against GAB2, wherein the siNA construct comprises one or more chemical modifications described herein that increases the bioavailability of the siNA construct, for example, by attaching polymeric conjugates such as polyethyleneglycol or equivalent conjugates that improve the pharmacokinetics of the siNA construct, or by attaching conjugates that target specific tissue types or cell types in vivo. Non-limiting examples of such conjugates are described in Vargeese et al., U.S. Ser. No. 10/201,394 incorporated by reference herein.

In one embodiment, the invention features a method for generating siNA molecules of the invention with improved bioavailability comprising (a) introducing a conjugate into the structure of an siNA molecule, and (b) assaying the siNA molecule of step (a) under conditions suitable for isolating siNA molecules having improved bioavailability. Such conjugates can include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; polyamines, such as spermine or spermidine; and others.

In one embodiment, the invention features a double-stranded short interfering nucleic acid (siNA) molecule that comprises a first nucleotide sequence complementary to a target RNA sequence or a portion thereof, and a second sequence having complementarity to said first sequence, wherein said second sequence is chemically modified in a manner that it can no longer act as a guide sequence for efficiently mediating RNA interference and/or be recognized by cellular proteins that facilitate RNAi.

In one embodiment, the invention features a double-stranded short interfering nucleic acid (siNA) molecule that comprises a first nucleotide sequence complementary to a target RNA sequence or a portion thereof, and a second sequence having complementarity to said first sequence, wherein the second sequence is designed or modified in a manner that prevents its entry into the RNAi pathway as a guide sequence or as a sequence that is complementary to a target nucleic acid (e.g., RNA) sequence. Such design or modifications are expected to enhance the activity of siNA and/or improve the specificity of siNA molecules of the invention. These modifications are also expected to minimize any off-target effects and/or associated toxicity.

In one embodiment, the invention features a double-stranded short interfering nucleic acid (siNA) molecule that comprises a first nucleotide sequence complementary to a target RNA sequence or a portion thereof, and a second sequence having complementarity to said first sequence, wherein said second sequence is incapable of acting as a guide sequence for mediating RNA interference.

In one embodiment, the invention features a double-stranded short interfering nucleic acid (siNA) molecule that comprises a first nucleotide sequence complementary to a target RNA sequence or a portion thereof, and a second sequence having complementarity to said first sequence, wherein said second sequence does not have a terminal 5'-hydroxyl (5'-OH) or 5'-phosphate group.

In one embodiment, the invention features a double-stranded short interfering nucleic acid (siNA) molecule that comprises a first nucleotide sequence complementary to a target RNA sequence or a portion thereof, and a second sequence having complementarity to said first sequence, wherein said second sequence comprises a terminal cap moiety at the 5'-end of said second sequence. In one embodiment, the terminal cap moiety comprises an inverted abasic, inverted deoxy abasic, inverted nucleotide moiety, a group shown in FIG. 10, an alkyl or cycloalkyl group, a heterocycle, or any other group that prevents RNAi activity in which the second sequence serves as a guide sequence or template for RNAi.

In one embodiment, the invention features a double-stranded short interfering nucleic acid (siNA) molecule that comprises a first nucleotide sequence complementary to a target RNA sequence or a portion thereof, and a second sequence having complementarity to said first sequence, wherein said second sequence comprises a terminal cap moiety at the 5'-end and 3'-end of said second sequence. In one embodiment, each terminal cap moiety individually comprises an inverted abasic, inverted deoxy abasic, inverted nucleotide moiety, a group shown in FIG. 10, an alkyl or cycloalkyl group, a heterocycle, or any other group that prevents RNAi activity in which the second sequence serves as a guide sequence or template for RNAi.

In one embodiment, the invention features a method for generating siNA molecules of the invention with improved specificity for down regulating or inhibiting the expression of a target nucleic acid (e.g., a DNA or RNA such as a gene or its corresponding RNA), comprising (a) introducing one or more chemical modifications into the structure of an siNA molecule, and (b) assaying the siNA molecule of step (a) under conditions suitable for isolating siNA molecules having improved specificity. In another embodiment, the chemical modification used to improve specificity comprises terminal cap modifications at the 5'-end, 3'-end, or both 5' and 3'-ends of the siNA molecule. The terminal cap modifications can comprise, for example, structures shown in FIG. 10 (e.g. inverted deoxyabasic moieties) or any other chemical modification that renders a portion of the siNA molecule (e.g. the sense strand) incapable of mediating RNA interference against an off target nucleic acid sequence. In a non-limiting example, an siNA molecule is designed such that only the antisense sequence of the siNA molecule can serve as a guide sequence for RISC mediated degradation of a corresponding target RNA sequence. This can be accomplished by rendering the sense sequence of the siNA inactive by introducing chemical modifications to the sense strand that preclude recognition of the sense strand as a guide sequence by RNAi machinery. In one embodiment, such chemical modifications comprise any chemical group at the 5'-end of the sense strand of the siNA, or any other group that serves to render the sense strand inactive as a guide sequence for mediating RNA interference. These modifications, for example, can result in a molecule where the 5'-end of the sense strand no longer has a free 5'-hydroxyl (5'-OH) or a free 5'-phosphate group (e.g., phosphate, diphosphate, triphosphate, cyclic phosphate etc.). Non-limiting examples of such siNA constructs are described herein, such as "Stab 9/10", "Stab 7/8", "Stab 7/19", "Stab 17/22", "Stab 23/24", "Stab 24/25", and "Stab 24/26" chemistries and variants thereof (see Table IV) wherein the 5'-end and 3'-end of the sense strand of the siNA do not comprise a hydroxyl group or phosphate group.

In one embodiment, the invention features a method for generating siNA molecules of the invention with improved specificity for down regulating or inhibiting the expression of a target nucleic acid (e.g., a DNA or RNA such as a gene or its corresponding RNA), comprising introducing one or more chemical modifications into the structure of an siNA molecule that prevent a strand or portion of the siNA molecule from acting as a template or guide sequence for RNAi activity. In one embodiment, the inactive strand or sense region of the siNA molecule is the sense strand or sense region of the siNA molecule, i.e. the strand or region of the siNA that does not have complementarity to the target nucleic acid sequence. In one embodiment, such chemical modifications comprise any chemical group at the 5'-end of the sense strand or region of the siNA that does not comprise a 5'-hydroxyl (5'-OH) or 5'-phosphate group, or any other group that serves to render the sense strand or sense region inactive as a guide sequence for mediating RNA interference. Non-limiting examples of such siNA constructs are described herein, such as "Stab 9/10", "Stab 7/8", "Stab 7/19", "Stab 17/22", "Stab 23/24", "Stab 24/25", and "Stab 24/26" chemistries and variants thereof (see Table IV) wherein the 5'-end and 3'-end of the sense strand of the siNA do not comprise a hydroxyl group or phosphate group.

In one embodiment, the invention features a method for screening siNA molecules that are active in mediating RNA interference against a target nucleic acid sequence comprising (a) generating a plurality of unmodified siNA molecules, (b) screening the siNA molecules of step (a) under conditions suitable for isolating siNA molecules that are active in mediating RNA interference against the target nucleic acid sequence, and (c) introducing chemical modifications (e.g. chemical modifications as described herein or as otherwise known in the art) into the active siNA molecules of (b). In one embodiment, the method further comprises re-screening the chemically modified siNA molecules of step (c) under conditions suitable for isolating chemically modified siNA molecules that are active in mediating RNA interference against the target nucleic acid sequence.

In one embodiment, the invention features a method for screening chemically modified siNA molecules that are active in mediating RNA interference against a target nucleic acid sequence comprising (a) generating a plurality of chemically modified siNA molecules (e.g. siNA molecules as described herein or as otherwise known in the art), and (b) screening the siNA molecules of step (a) under conditions suitable for isolating chemically modified siNA molecules that are active in mediating RNA interference against the target nucleic acid sequence.

The term "ligand" refers to any compound or molecule, such as a drug, peptide, hormone, or neurotransmitter that is capable of interacting with another compound, such as a receptor, either directly or indirectly. The receptor that interacts with a ligand can be present on the surface of a cell or can alternately be an intercellular receptor. Interaction of the ligand with the receptor can result in a biochemical reaction, or can simply be a physical interaction or association.

In another embodiment, the invention features a method for generating siNA molecules of the invention with improved bioavailability comprising (a) introducing an excipient formulation to an siNA molecule, and (b) assaying the siNA molecule of step (a) under conditions suitable for isolating siNA molecules having improved bioavailability. Such excipients include polymers such as cyclodextrins, lipids, cationic lipids, polyamines, phospholipids, nanoparticles, receptors, ligands, and others.

In another embodiment, the invention features a method for generating siNA molecules of the invention with improved bioavailability comprising (a) introducing nucleotides having any of Formulae I-VII or any combination thereof into an siNA molecule, and (b) assaying the siNA molecule of step (a) under conditions suitable for isolating siNA molecules having improved bioavailability.

In another embodiment, polyethylene glycol (PEG) can be covalently attached to siNA compounds of the present invention. The attached PEG can be any molecular weight, preferably from about 2,000 to about 50,000 daltons (Da).

The present invention can be used alone or as a component of a kit having at least one of the reagents necessary to carry out the in vitro or in vivo introduction of RNA to test samples and/or subjects. For example, preferred components of the kit include an siNA molecule of the invention and a vehicle that promotes introduction of the siNA into cells of interest as described herein (e.g., using lipids and other methods of transfection known in the art, see for example Beigelman et al, U.S. Pat. No. 6,395,713). The kit can be used for target validation, such as in determining gene function and/or activity, or in drug optimization, and in drug discovery (see for example Usman et al., U.S. Ser. No. 60/402,996). Such a kit can also include instructions to allow a user of the kit to practice the invention.

The term "short interfering nucleic acid", "siNA", "short interfering RNA", "siRNA", "short interfering nucleic acid molecule", "short interfering oligonucleotide molecule", or "chemically modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). Non limiting examples of siNA molecules of the invention are shown in FIGS. 4-6, and Tables II and III herein. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof). Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide pan be processed either in vivo or in vitro to generate an active siNA molecule capable of mediating RNAi. The siNA can also comprise a single-stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single-stranded polynucleotide can further comprise a terminal phosphate group, such as a 5'-phosphate (see for example Martinez et al., 2002, *Cell.*, 110, 563-574 and Schwarz et al., 2002, *Molecular Cell*, 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptg-sRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level and the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, *Science,* 303, 672-676; Pal-Bhadra et al., 2004, *Science,* 303, 669-672; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237).

In one embodiment, an siNA molecule of the invention is a duplex forming oligonucleotide "DFO", (see for example FIGS. 14-15 and Vaish et al., U.S. Ser. No. 10/727,780 filed Dec. 3, 2003 and International PCT Application No. US04/16390, filed May 24, 2004).

In one embodiment, an siNA molecule of the invention is a multifunctional siNA, (see for example FIGS. 16-21 and Jadhav et al., U.S. Ser. No. 60/543,480 filed Feb. 10, 2004 and International PCT Application No. US04/16390, filed May 24, 2004). The multifunctional siNA of the invention can comprise sequence targeting, for example, two regions of GAB2 RNA (see for example target sequences in Tables II and III).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant an siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence. In one embodiment, inhibition, down regulation, or reduction of gene expression is associated with post transcriptional silencing, such as RNAi mediated cleavage of a target nucleic acid molecule (e.g. RNA) or inhibition of translation. In one embodiment, inhibition, down regulation, or reduction of gene expression is associated with pretranscriptional silencing.

By "gene", or "target gene", is meant a nucleic acid that encodes an RNA, for example, nucleic acid sequences including, but not limited to, structural genes encoding a polypeptide. A gene or target gene can also encode a functional RNA (FRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of FRNA or ncRNA involved in functional or regulatory cellular processes. Aberrant FRNA or ncRNA activity leading to disease can therefore be modulated by siNA molecules of the invention. siNA molecules targeting FRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, *Science*, 300, 258-260.

By "non-canonical base pair" is meant any non-Watson Crick base pair, such as mismatches and/or wobble base pairs, including flipped mismatches, single hydrogen bond mismatches, trans-type mismatches, triple base interactions, and quadruple base interactions. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N-3-amino(H2), GA sheared, UC 4-carbonyl-amino, UU imino-carbonyl, AC reverse wobble, AU Hoogsteen, AU reverse Watson Crick, CG reverse Watson Crick, GC N3-amino-amino N3, AA N1-amino symmetric, AA N7-amino symmetric, GA N7-N1 amino-carbonyl, GA+ carbonyl-amino N7-N1, GG N1-carbonyl symmetric, GG N3-amino symmetric, CC carbonyl-amino symmetric, CC N3-amino symmetric, UU 2-carbonyl-imino symmetric, UU 4-carbonyl-imino symmetric, AA amino-N3, AA N1-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H-N3, GA carbonyl-C2-H, UU imino-4-carbonyl 2 carbonyl-C5-H, AC amino(A) N3(C)-carbonyl, GC imino amino-carbonyl, Gpsi imino-2-carbonyl amino-2-carbonyl, and GU imino amino-2-carbonyl base pairs.

By "GAB2" as used herein is meant, any GRB2 associated binding protein (GAB2) protein, peptide, or polypeptide having GAB2 or GAB2 family activity, such as encoded by GAB2 Genbank Accession Nos. shown in Table I or any other GAB2 transcript derived from a GAB2 gene and/or generated by GAB2 translocation. The term "GAB2" also refers to nucleic acid sequences encoding any GAB2 protein, peptide, or polypeptide having GAB2 activity. The term "GAB2" is also meant to include other GAB2 encoding sequence, such as GAB2 isoforms mutant GAB2 genes, splice variants of GAB2 genes, and GAB2 gene polymorphisms.

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.).

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of an siNA molecule having complementarity to an antisense region of the siNA molecule. In addition, the sense region of an siNA molecule can comprise a nucleic acid sequence having homology with a target nucleic acid sequence.

By "antisense region" is meant a nucleotide sequence of an siNA molecule having complementarity to a target nucleic acid sequence. In addition, the antisense region of an siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol. LII pp.* 123-133; Frier et al., 1986, *Proc. Nat. Acad. Sci. USA* 83:9373-9377; Turner et al., 1987, *J. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence. In one embodiment, an siNA molecule of the invention comprises about 15 to about 30 or more (e.g., about 15, 16, 17, 18, 19, 20, 21, 22, 23, 24, 25, 26, 27, 28, 29, or 30 or more) nucleotides that are complementary to one or more target nucleic acid molecules or a portion thereof.

In one embodiment, siNA molecules of the invention that down regulate or reduce GAB2 gene expression are used for preventing cancer, malignant blood disease (leukemia), inflammatory diseases or conditions, allergic diseases or conditions, or proliferative diseases or conditions in a subject or organism.

In one embodiment, the siNA molecules of the invention are used to treat cancer, malignant blood disease (leukemia), inflammatory diseases or conditions, allergic diseases or conditions, or proliferative diseases or conditions in a subject or organism.

By "cancer" or "proliferative disease" is meant, any disease, condition, trait, genotype or phenotype characterized by unregulated cell growth or replication as is known in the art; including leukemias such as chronic myeloid leukemia, CML; acute myeloid leukemias, AML; secondary leukemias, acute lymphoblastic leukemias, ALL; chronic lymphoid leukemia; CLL; AIDS related cancers such as Kaposi's sarcoma; blood vessel tumors (haemangioblastomas); tumors in the adrenal glands; clear-cell kidney cancers; von Hippel-Lindau (VHL) disease, breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and any other cancer or proliferative disease, condition, trait, genotype or phenotype that can respond to the modulation of disease related gene (e.g., GAB2) expression in a cell or tissue, alone or in combination with other therapies.

By "inflammatory disease" or "inflammatory condition" as used herein is meant any disease, condition, trait, genotype or phenotype characterized by an inflammatory or allergic process as is known in the art, such as inflammation, acute inflammation, chronic inflammation, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconiosis, and any other inflammatory disease, condition, trait, genotype or phenotype that can respond to the modulation of disease related gene expression in a cell or tissue, alone or in combination with other therapies.

By "autoimmune disease" or "autoimmune condition" as used herein is meant, any disease, condition, trait, genotype or phenotype characterized by autoimmunity as is known in the art, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and any other autoimmune disease, condition, trait, genotype or phenotype that can respond to the modulation of disease related gene expression in a cell or tissue, alone or in combination with other therapies.

By "infection" or "infectious disease" as used herein is meant any disease, condition, trait, genotype or phenotype associated with an infectious agent, such as a virus, bacteria, fungus, prion, or parasite. Non-limiting examples of various viral genes that can be targeted using siNA molecules of the invention include Hepatitis C Virus (HCV, for example Genbank Accession Nos: D11168, D50483.1, L38318 and S82227), Hepatitis B Virus (HBV, for example GenBank Accession No. AF100308.1), Human Immunodeficiency Virus type I (HIV-1, for example GenBank Accession No. U51188), Human Immunodeficiency Virus type 2 (HIV-2, for example GenBank Accession No. X60667), West Nile Virus (WNV for example GenBank accession No. NC_001563), cytomegalovirus (CMV for example GenBank Accession No. NC_001347), respiratory syncytial virus (RSV for example GenBank Accession No. NC_001781), influenza virus (for example GenBank Accession No. AF037412, rhinovirus (for example, GenBank accession numbers: D00239, X02316, X01087, L24917, M16248, K02121, X01087), papillomavirus (for example GenBank Accession No. NC_001353), Herpes Simplex Virus (HSV for example GenBank Accession No. NC_001345), and other viruses such as HTLV (for example GenBank Accession No. AJ430458). Due to the high sequence variability of many viral genomes, selection of siNA molecules for broad therapeutic applications would likely involve the conserved regions of the viral genome. Nonlimiting examples of conserved regions of the viral genomes include but are not limited to 5'-Non Coding Regions (NCR), 3'-Non Coding Regions (NCR) and/or internal ribosome entry sites (IRES). siRNA molecules designed against conserved regions of various viral genomes will enable efficient inhibition of viral replication in diverse patient populations and may ensure the effectiveness of the siRNA molecules against viral quasi species which evolve due to mutations in the non-conserved regions of the viral genome. Non-limiting examples of bacterial infections include Actinomycosis, Anthrax, Aspergillosis, Bacteremia, Bacterial Infections and Mycoses, *Bartonella* Infections, Botulism, Brucellosis, *Burkholderia* Infections, *Campylobacter* Infections, Candidiasis, Cat-Scratch Disease, *Chlamydia* Infections, Cholera, *Clostridium* Infections, Coccidioidomycosis, Cross Infection, Cryptococcosis, Dermatomycoses, Dermatomycoses, Diphtheria, Ehrlichiosis, *Escherichia coli* Infections, Fasciitis, Necrotizing, *Fusobacterium* Infections, Gas Gangrene, Gram-Negative Bacterial Infections, Gram-Positive Bacterial Infections, Histoplasmosis, Impetigo, *Klebsiella* Infections, Legionellosis, Leprosy, Leptospirosis, *Listeria* Infections, Lyme Disease, *Maduromycosis*, Melioidosis, *Mycobacterium* Infections, *Mycoplasma* Infections, Mycoses, *Nocardia* Infections, Onychomycosis, Ornithosis, Plague, Pneumococcal Infections, *Pseudomonas* Infections, Q Fever, Rat-Bite Fever, Relapsing Fever, Rheumatic Fever, *Rickettsia* Infections, Rocky Mountain Spotted Fever, *Salmonella* Infections, Scarlet Fever, Scrub Typhus, Sepsis, Sexually Transmitted Diseases—Bacterial, Bacterial Skin Diseases, Staphylococcal Infections, Streptococcal Infections, Tetanus, Tick-Borne Diseases, Tuberculosis, Tularemia, Typhoid Fever, Typhus, Epidemic Louse-Borne, *Vibrio* Infections, Yaws, *Yersinia* Infections, Zoonoses, and Zygomycosis. Non-limiting examples of fungal infections include Aspergillosis, Blastomycosis, Coccidioidomycosis, Cryptococcosis, Fungal Infections of Fingernails and Toenails, Fungal Sinusitis, Histoplasmosis, Histoplasmosis, Mucormycosis, Nail Fungal Infection, Paracoccidioidomycosis, Sporotrichosis, Valley Fever (Coccidioidomycosis), and Mold Allergy.

In one embodiment of the present invention, each sequence of an siNA molecule of the invention is independently about 15 to about 30 nucleotides in length, in specific embodiments about 15, 16, 17, 18, 19, 20, 21, 22, 23, 24, 25, 26, 27, 28, 29, or 30 nucleotides in length. In another embodiment, the siNA duplexes of the invention independently comprise about 15 to about 30 base pairs (e.g., about 15, 16, 17, 18, 19, 20, 21, 22, 23, 24, 25, 26, 27, 28, 29, or 30). In another embodiment, one or more strands of the siNA molecule of the invention independently comprises about 15 to about 30 nucleotides (e.g., about 15, 16, 17, 18, 19, 20, 21, 22, 23, 24, 25, 26, 27, 28, 29, or 30) that are complementary to a target nucleic acid molecule. In yet another embodiment, siNA molecules of the invention comprising hairpin or circular structures are about 35 to about 55 (e.g., about 35, 40, 45, 50 or 55) nucleotides in length, or about 38 to about 44 (e.g., about 38, 39, 40, 41, 42, 43, or 44) nucleotides in length and comprising about 15 to about 25 (e.g., about 15, 16, 17, 18, 19, 20, 21, 22, 23, 24, or 25) base pairs. Exemplary siNA molecules of the invention are shown in Table II. Exemplary synthetic siNA molecules of the invention are shown in Table III and/or FIGS. 4-5.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The siNA molecules of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. In particular embodiments, the nucleic acid molecules of the invention comprise sequences shown in Tables II-III and/or FIGS. 4-5. Examples of such nucleic acid molecules consist essentially of sequences defined in these tables and figures. Furthermore, the chemically modified constructs described in Table IV can be applied to any siNA sequence of the invention.

In another aspect, the invention provides mammalian cells containing one or more siNA molecules of this invention. The one or more siNA molecules can independently be targeted to the same or different sites.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The term "phosphorothioate" as used herein refers to an internucleotide linkage having Formula I, wherein Z and/or W comprise a sulfur atom. Hence, the term phosphorothioate refers to both phosphorothioate and phosphorodithioate internucleotide linkages.

The term "phosphonoacetate" as used herein refers to an internucleotide linkage having Formula I, wherein Z and/or W comprise an acetyl or protected acetyl group.

The term "thiophosphonoacetate" as used herein refers to an internucleotide linkage having Formula I, wherein Z comprises an acetyl or protected acetyl group and W comprises a sulfur atom or alternately W comprises an acetyl or protected acetyl group and Z comprises a sulfur atom.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

The term "acyclic nucleotide" as used herein refers to any nucleotide having an acyclic ribose sugar.

The nucleic acid molecules of the instant invention, individually, or in combination or in conjunction with other drugs, can be used to for preventing or treating cancer, malignant blood disease (leukemia), inflammatory diseases or conditions, allergic diseases or conditions, or proliferative diseases or conditions in a subject or organism as described herein or otherwise known in the art. For example, the siNA molecules can be administered to a subject or can be administered to other appropriate cells evident to those skilled in the art, individually or in combination with one or more drugs under conditions suitable for the treatment.

In a further embodiment, the siNA molecules can be used in combination with other known treatments to prevent or treat cancer, malignant blood disease (leukemia), inflammatory diseases or conditions, allergic diseases or conditions, or proliferative diseases or conditions, or any proliferative disease or condition in a subject or organism. For example, the described molecules could be used in combination with one or more known compounds, treatments, or procedures to prevent or treat cancer, malignant blood disease (leukemia), inflammatory diseases or conditions, allergic diseases or conditions, or proliferative diseases or conditions, or any proliferative disease or condition in a subject or organism as are known in the art.

In one embodiment, the invention features an expression vector comprising a nucleic acid sequence encoding at least one siNA molecule of the invention, in a manner which allows expression of the siNA molecule. For example, the vector can contain sequence(s) encoding both strands of an siNA molecule comprising a duplex. The vector can also contain sequence(s) encoding a single nucleic acid molecule that is self-complementary and thus forms an siNA molecule. Non-limiting examples of such expression vectors are described in Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al., 2002, *Nature Medicine*, advance online publication doi: 10.1038/nm725.

In another embodiment, the invention features a mammalian cell, for example, a human cell, including an expression vector of the invention.

In yet another embodiment, the expression vector of the invention comprises a sequence for an siNA molecule having complementarity to a RNA molecule referred to by a Genbank Accession numbers, for example Genbank Accession Nos. shown in Table I.

In one embodiment, an expression vector of the invention comprises a nucleic acid sequence encoding two or more siNA molecules, which can be the same or different.

In another aspect of the invention, siNA molecules that interact with target RNA molecules and down-regulate gene encoding target RNA molecules (for example target RNA molecules referred to by Genbank Accession numbers herein) are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules. Such vectors can be repeatedly administered as necessary. Once expressed, the siNA molecules bind and down-regulate gene function or expression via RNA interference (RNAi). Delivery of siNA expressing vectors can be systemic, such as by intravenous or intramuscular administration, by administration to target cells ex-planted from a subject followed by reintroduction into the subject, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

BRIEF DESCRIPTION OF THE DRAWINGS

FIG. 1 shows a non-limiting example of a scheme for the synthesis of siNA molecules. The complementary siNA sequence strands, strand 1 and strand 2, are synthesized in tandem and are connected by a cleavable linkage, such as a nucleotide succinate or abasic succinate, which can be the same or different from the cleavable linker used for solid phase synthesis on a solid support. The synthesis can be either solid phase or solution phase, in the example shown, the synthesis is a solid phase synthesis. The synthesis is performed such that a protecting group, such as a dimethoxytrityl group, remains intact on the terminal nucleotide of the tandem oligonucleotide. Upon cleavage and deprotection of the oligonucleotide, the two siNA strands spontaneously hybridize to form an siNA duplex, which allows the purification of the duplex by utilizing the properties of the terminal protecting group, for example by applying a trityl on purification method wherein only duplexes/oligonucleotides with the terminal protecting group are isolated.

FIG. 4A: The sense strand comprises 21 nucleotides wherein the two terminal 3'-nucleotides are optionally base paired and wherein all nucleotides present are ribonucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety wherein the two terminal 3'-nucleotides are optionally complementary to the target RNA sequence, and wherein all nucleotides present are ribonucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4B: The sense strand comprises 21 nucleotides wherein the two terminal 3'-nucleotides are optionally base paired and wherein all pyrimidine nucleotides that may be present are 2'deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the sense and antisense strand.

FIG. 4C: The sense strand comprises 21 nucleotides having 5'- and 3'-terminal cap moieties wherein the two terminal 3'-nucleotides are optionally base paired and wherein all pyrimidine nucleotides that may be present are 2'-O-methyl or 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4D: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that may be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4E: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4F: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that may be present are 2'-deoxy nucleotides. The antisense strand comprises 21 nucleotides, optionally having a 3'-terminal-glyceryl moiety and wherein the two terminal 3'-nucleotides are optionally complementary to the target RNA sequence, and having one 3'-terminal phosphorothioate internucleotide linkage and wherein all pyrimidine nucleotides that may be present are 2'-deoxy-2'-fluoro modified nucleotides and all purine nucleotides that may be present are 2'-deoxy nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 7A: A DNA oligomer is synthesized with a 5'-restriction site (R1) sequence followed by a region having sequence identical (sense region of siNA) to a predetermined GAB2 target sequence, wherein the sense region comprises, for example, about 19, 20, 21, or 22 nucleotides (N) in length, which is followed by a loop sequence of defined sequence (X), comprising, for example, about 3 to about 10 nucleotides.

FIG. 7B: The synthetic construct is then extended by DNA polymerase to generate a hairpin structure having self-complementary sequence that will result in an siNA transcript having specificity for a GAB2 target sequence and having self-complementary sense and antisense regions.

FIG. 7C: The construct is heated (for example to about 95° C.) to linearize the sequence, thus allowing extension of a complementary second DNA strand using a primer to the 3'-restriction sequence of the first strand. The double-stranded DNA is then inserted into an appropriate vector for expression in cells. The construct can be designed such that a 3'-terminal nucleotide overhang results from the transcription, for example, by engineering restriction sites and/or utilizing a poly-U termination region as described in Paul et al., 2002, *Nature Biotechnology*, 29, 505-508.

FIG. 8A: A DNA oligomer is synthesized with a 5'-restriction (R1) site sequence followed by a region having sequence identical (sense region of siNA) to a predetermined GAB2 target sequence, wherein the sense region comprises, for example, about 19, 20, 21, or 22 nucleotides (N) in length, and which is followed by a 3'-restriction site (R2) which is adjacent to a loop sequence of defined sequence (X).

FIG. 8B: The synthetic construct is then extended by DNA polymerase to generate a hairpin structure having self-complementary sequence.

FIG. 8C: The construct is processed by restriction enzymes specific to R1 and R2 to generate a double-stranded DNA which is then inserted into an appropriate vector for expression in cells. The transcription cassette is designed such that a U6 promoter region flanks each side of the dsDNA which generates the separate sense and antisense strands of the siNA. Poly T termination sequences can be added to the constructs to generate U overhangs in the resulting transcript.

FIG. 9A: A pool of siNA oligonucleotides are synthesized wherein the antisense region of the siNA constructs has complementarity to target sites across the target nucleic acid sequence, and wherein the sense region comprises sequence complementary to the antisense region of the siNA.

FIGS. 9B&C: (FIG. 9B) The sequences are pooled and are inserted into vectors such that (FIG. 9C) transfection of a vector into cells results in the expression of the siNA.

FIG. 9D: Cells are sorted based on phenotypic change that is associated with modulation of the target nucleic acid sequence.

FIG. 9E: The siNA is isolated from the sorted cells and is sequenced to identify efficacious target sites within the target nucleic acid sequence.

FIG. 11 shows a non-limiting example of a strategy used to identify chemically modified siNA constructs of the invention that are nuclease resistance while preserving the ability to mediate RNAi activity. Chemical modifications are introduced into the siNA construct based on educated design parameters (e.g. introducing 2'-modifications, base modifications, backbone modifications, terminal cap modifications etc). The modified construct in tested in an appropriate system (e.g. human serum for nuclease resistance, shown, or an animal model for PK/delivery parameters). In parallel, the siNA construct is tested for RNAi activity, for example in a cell culture system such as a luciferase reporter assay). Lead siNA constructs are then identified which possess a particular characteristic while maintaining RNAi activity, and can be further modified and assayed once again. This same approach can be used to identify siNA-conjugate molecules with improved pharmacokinetic profiles, delivery, and RNAi activity.

FIG. 12 shows non-limiting examples of phosphorylated siNA molecules of the invention, including linear and duplex constructs and asymmetric derivatives thereof.

FIG. 13 shows non-limiting examples of chemically modified terminal phosphate groups of the invention.

FIG. 14A shows a non-limiting example of methodology used to design self complementary DFO constructs utilizing palindrome and/or repeat nucleic acid sequences that are identified in a target nucleic acid sequence. (i) A palindrome or repeat sequence is identified in a nucleic acid target sequence. (ii) A sequence is designed that is complementary to the target nucleic acid sequence and the palindrome sequence. (iii) An inverse repeat sequence of the non-palindrome/repeat portion of the complementary sequence is appended to the 3'-end of the complementary sequence to generate a self complementary DFO molecule comprising sequence complementary to the nucleic acid target. (iv) The DFO molecule can self-assemble to form a double-stranded oligonucleotide. FIG. 14B shows a non-limiting representative example of a duplex forming oligonucleotide sequence. FIG. 14C shows a non-limiting example of the self assembly schematic of a representative duplex forming oligonucleotide sequence. FIG. 14D shows a non-limiting example of the self assembly schematic of a representative duplex forming oligonucleotide sequence followed by interaction with a target nucleic acid sequence resulting in modulation of gene expression.

FIG. 15 shows a non-limiting example of the design of self complementary DFO constructs utilizing palindrome and/or repeat nucleic acid sequences that are incorporated into the DFO constructs that have sequence complementary to any target nucleic acid sequence of interest. Incorporation of these palindrome/repeat sequences allow the design of DFO constructs that form duplexes in which each strand is capable of mediating modulation of target gene expression, for example by RNAi. First, the target sequence is identified. A complementary sequence is then generated in which nucleotide or non-nucleotide modifications (shown as X or Y) are introduced into the complementary sequence that generate an artificial palindrome (shown as XYXYXY in the Figure). An inverse repeat of the non-palindrome/repeat complementary sequence is appended to the 3'-end of the complementary sequence to generate a self complementary DFO comprising sequence complementary to the nucleic acid target. The DFO can self-assemble to form a double-stranded oligonucleotide.

FIG. 16 shows non-limiting examples of multifunctional siNA molecules of the invention comprising two separate polynucleotide sequences that are each capable of mediating RNAi directed cleavage of differing target nucleic acid sequences. FIG. 16A shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 3'-ends of each polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. FIG. 16B shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 5'-ends of each polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences.

FIG. 17 shows non-limiting examples of multifunctional siNA molecules of the invention comprising a single polynucleotide sequence comprising distinct regions that are each capable of mediating RNAi directed cleavage of differing target nucleic acid sequences. FIG. 17A shows a non-limiting example of a multifunctional siNA molecule having a first region that is complementary to a first target nucleic acid sequence (complementary region 1) and a second region that is complementary to a second target nucleic acid sequence (complementary region 2), wherein the second complementary region is situated at the 3'-end of the polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. FIG. 17B shows a non-limiting example of a multifunctional siNA molecule having a first region that is complementary to a first target nucleic acid sequence (complementary region 1) and a second region that is complementary to a second target nucleic acid sequence (complementary region 2), wherein the first complementary region is situated at the 5'-end of the polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. In one embodiment, these multifunctional siNA constructs are processed in vivo or in vitro to generate multifunctional siNA constructs as shown in FIG. 16.

FIG. 18 shows non-limiting examples of multifunctional siNA molecules of the invention comprising two separate polynucleotide sequences that are each capable of mediating RNAi directed cleavage of differing target nucleic acid sequences and wherein the multifunctional siNA construct further comprises a self complementary, palindrome, or repeat region, thus enabling shorter bifunctional siNA constructs that can mediate RNA interference against differing target nucleic acid sequences. FIG. 18A shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 3'-ends of each polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. FIG. 18B shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 5'-ends of each polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences.

FIG. 19 shows non-limiting examples of multifunctional siNA molecules of the invention comprising a single polynucleotide sequence comprising distinct regions that are each capable of mediating RNAi directed cleavage of differing target nucleic acid sequences and wherein the multifunctional siNA construct further comprises a self complementary, palindrome, or repeat region, thus enabling shorter bifunctional siNA constructs that can mediate RNA interference against differing target nucleic acid sequences. FIG. 19A shows a non-limiting example of a multifunctional siNA molecule having a first region that is complementary to a first target nucleic acid sequence (complementary region 1) and a second region that is complementary to a second target nucleic acid sequence (complementary region 2), wherein the second complementary region is situated at the 3'-end of the polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. FIG. 19B shows a non-limiting example of a multifunctional siNA molecule having a first region that is complementary to a first target nucleic acid sequence (complementary region 1) and a second region that is complementary to a second target nucleic acid sequence (complementary region 2), wherein the first complementary region is situated at the 5'-end of the polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. In one embodiment, these multifunctional siNA constructs are processed in vivo or in vitro to generate multifunctional siNA constructs as shown in FIG. 18.

FIG. 20 shows a non-limiting example of how multifunctional siNA molecules of the invention can target two separate target nucleic acid molecules, such as separate RNA molecules encoding differing proteins, for example, a cytokine and its corresponding receptor, differing viral strains, a virus and a cellular protein involved in viral infection or replication, or differing proteins involved in a common or divergent biologic pathway that is implicated in the maintenance of progression of disease. Each strand of the multifunctional siNA construct comprises a region having complementarity to separate target nucleic acid molecules. The multifunctional siNA molecule is designed such that each strand of the siNA can be utilized by the RISC complex to initiate RNA interference mediated cleavage of its corresponding target. These design parameters can include destabilization of each end of the siNA construct (see for example Schwarz et al., 2003, *Cell,* 115, 199-208). Such destabilization can be accomplished for example by using guanosine-cytidine base pairs, alternate base pairs (e.g., wobbles), or destabilizing chemically modified nucleotides at terminal nucleotide positions as is known in the art.

FIG. 21 shows a non-limiting example of how multifunctional siNA molecules of the invention can target two separate target nucleic acid sequences within the same target nucleic acid molecule, such as alternate coding regions of a RNA, coding and non-coding regions of a RNA, or alternate splice variant regions of a RNA. Each strand of the multifunctional siNA construct comprises a region having complementarity to the separate regions of the target nucleic acid molecule. The multifunctional siNA molecule is designed such that each strand of the siNA can be utilized by the RISC complex to initiate RNA interference mediated cleavage of its corresponding target region. These design parameters can include destabilization of each end of the siNA construct (see for example Schwarz et al., 2003, *Cell,* 115, 199-208). Such destabilization can be accomplished for example by using guanosine-cytidine base pairs, alternate base pairs (e.g., wobbles), or destabilizing chemically modified nucleotides at terminal nucleotide positions as is known in the art.

DETAILED DESCRIPTION OF THE INVENTION

Figure 2:
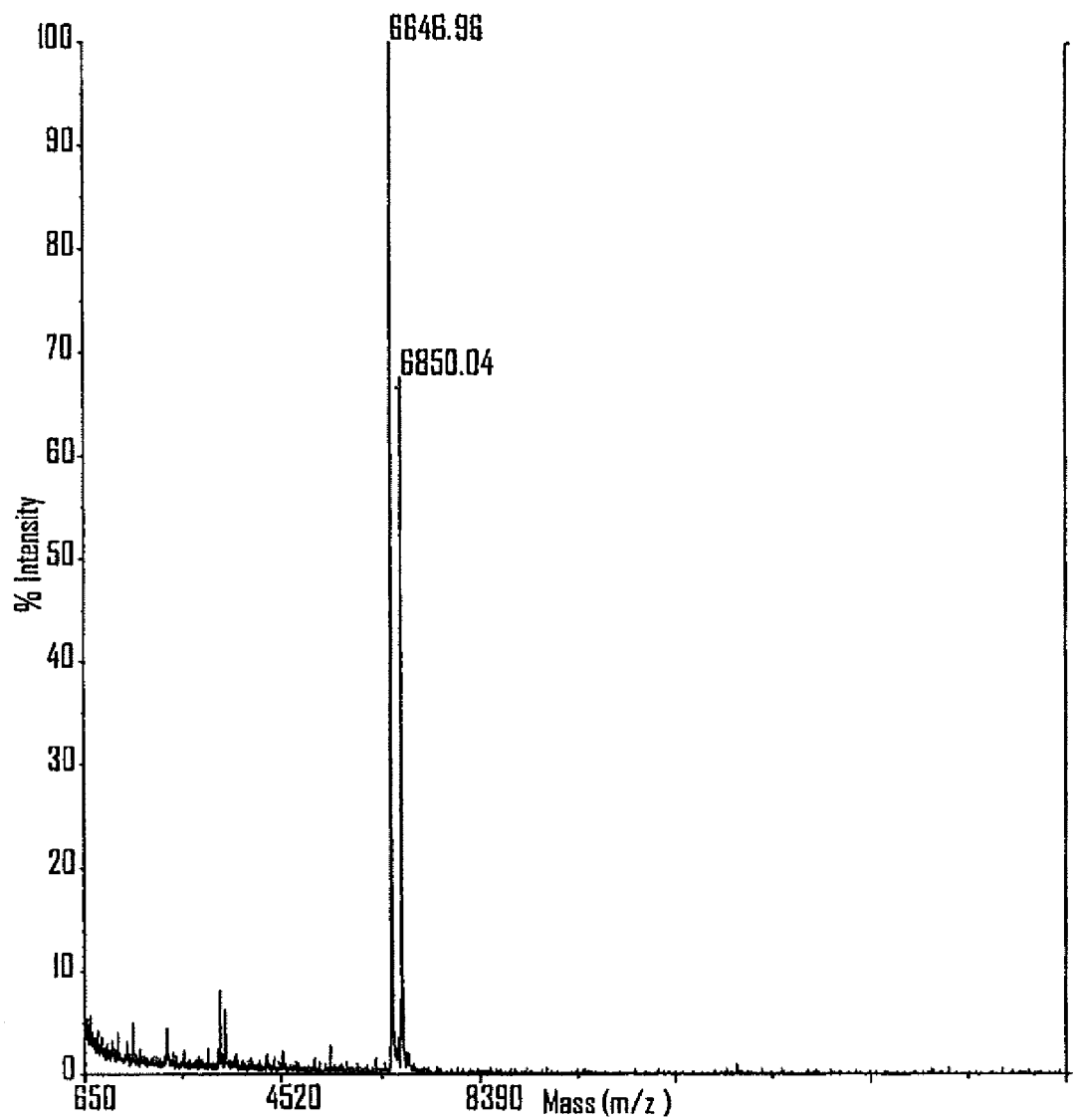
FIG. 2 shows a MALDI-TOF mass spectrum of a purified siNA duplex synthesized by a method of the invention. The two peaks shown correspond to the predicted mass of the separate siNA sequence strands. This result demonstrates that the siNA duplex generated from tandem synthesis can be purified as a single entity using a simple trityl-on purification methodology.
Figure 3:
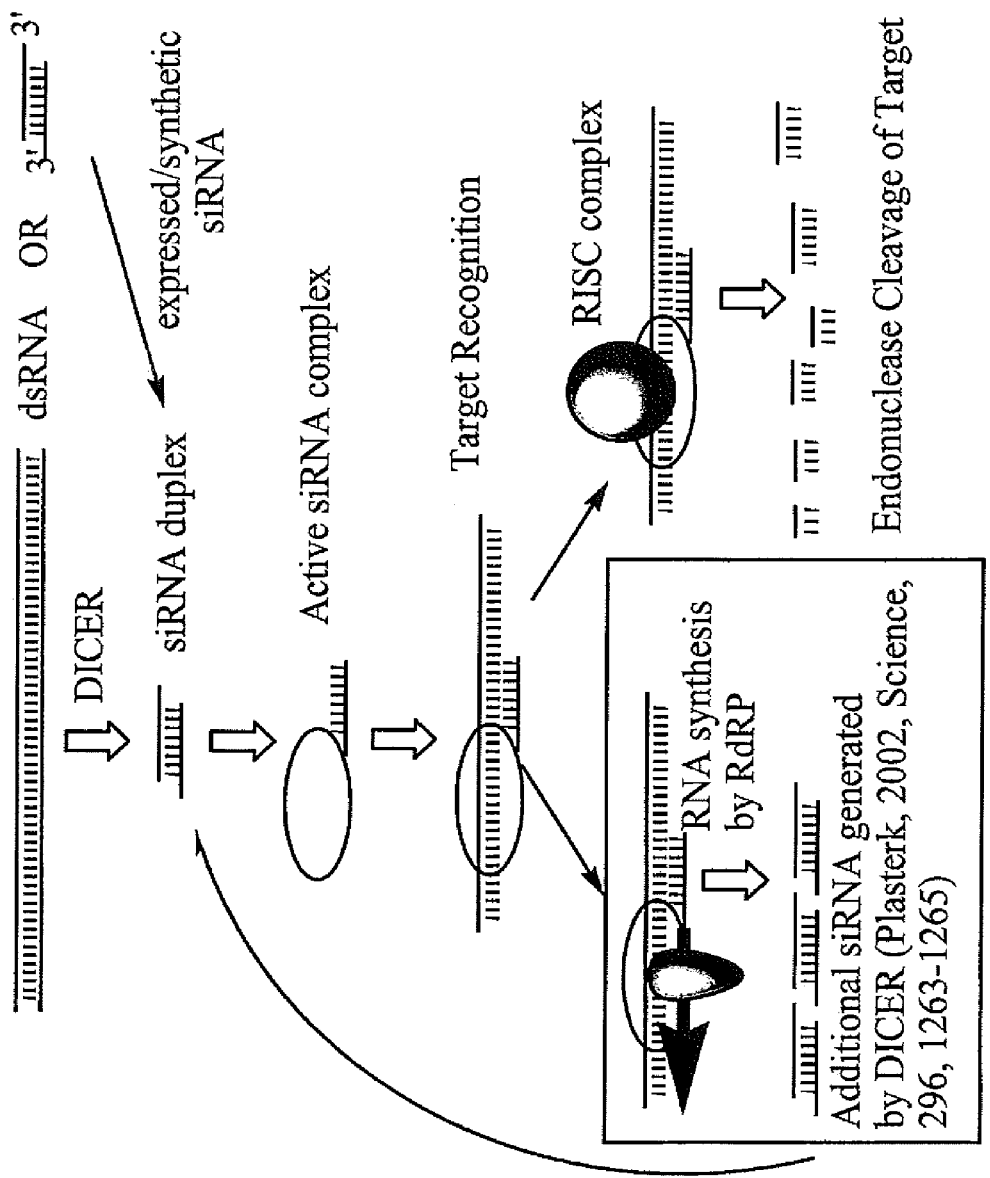
FIG. 3 shows a non-limiting proposed mechanistic representation of target RNA degradation involved in RNAi. Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex forms which recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.
Figure 4:
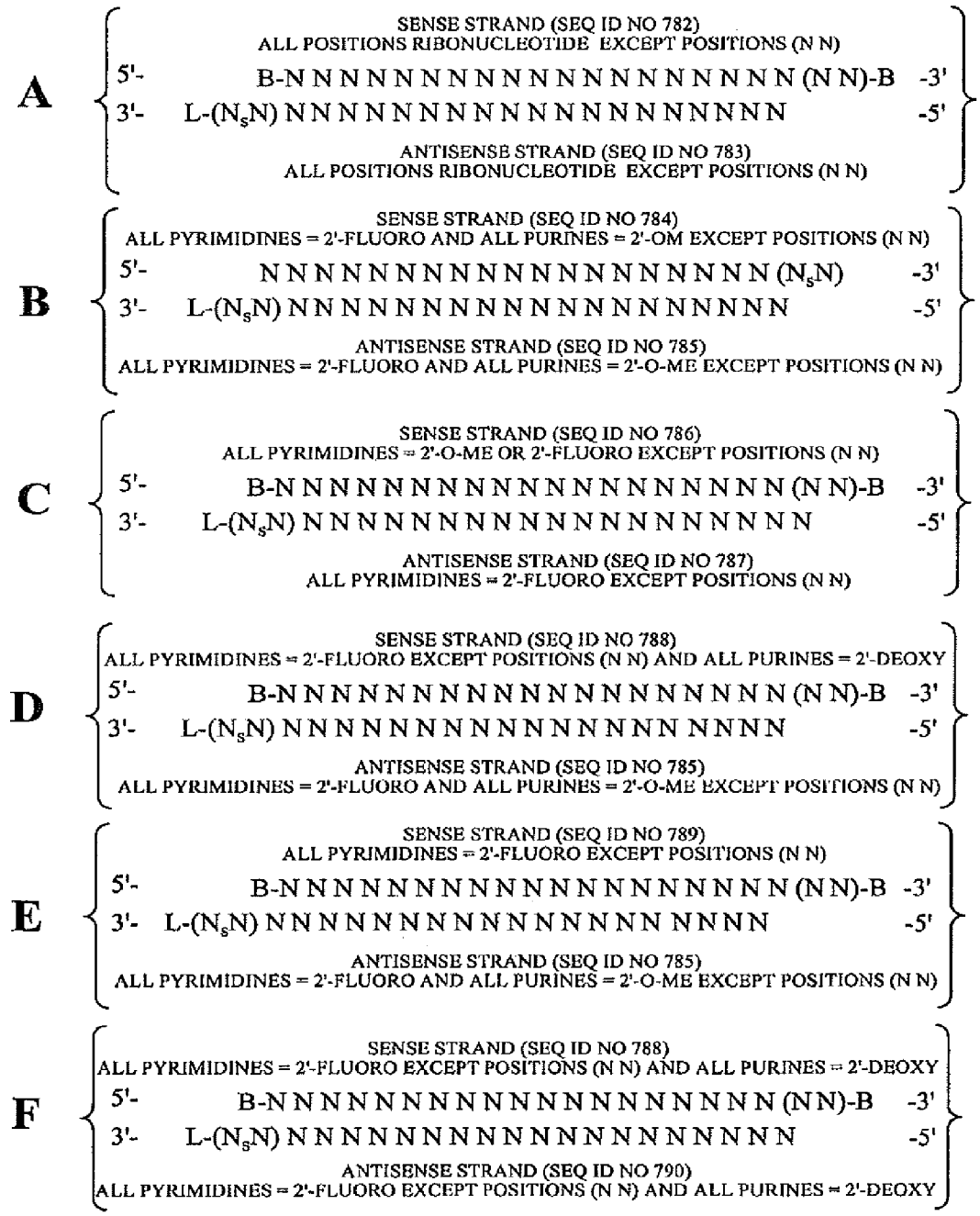
FIG. 4A-F shows non-limiting examples of chemically modified siNA constructs of the present invention. In the figure, N stands for any nucleotide (adenosine, guanosine, cytosine, uridine, or optionally thymidine, for example thymidine can be substituted in the overhanging regions designated by parenthesis (N N). Various modifications are shown for the sense and antisense strands of the siNA constructs. The antisense strand of constructs A-F comprise sequence complementary to any target nucleic acid sequence of the invention. Furthermore, when a glyceryl moiety (L) is present at the 3'-end of the antisense strand for any construct shown in FIG. 4 A-F, the modified internucleotide linkage is optional.
Figure 5:
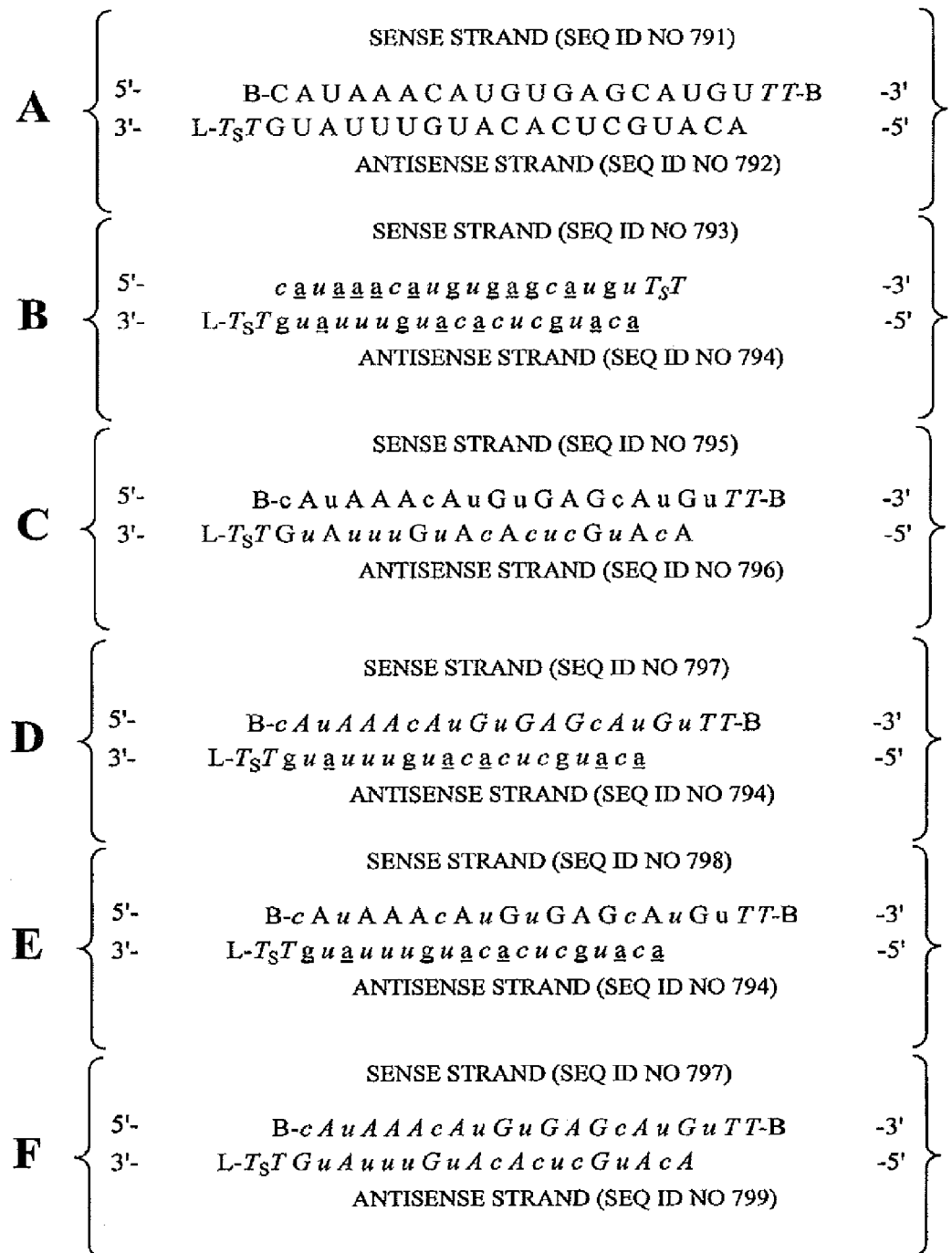
FIG. 5A-F shows non-limiting examples of specific chemically modified siNA sequences of the invention. A-F applies the chemical modifications described in FIG. 4A-F to a GAB2 siNA sequence. Such chemical modifications can be applied to any GAB2 sequence and/or GAB2 polymorphism sequence.
Figure 6:
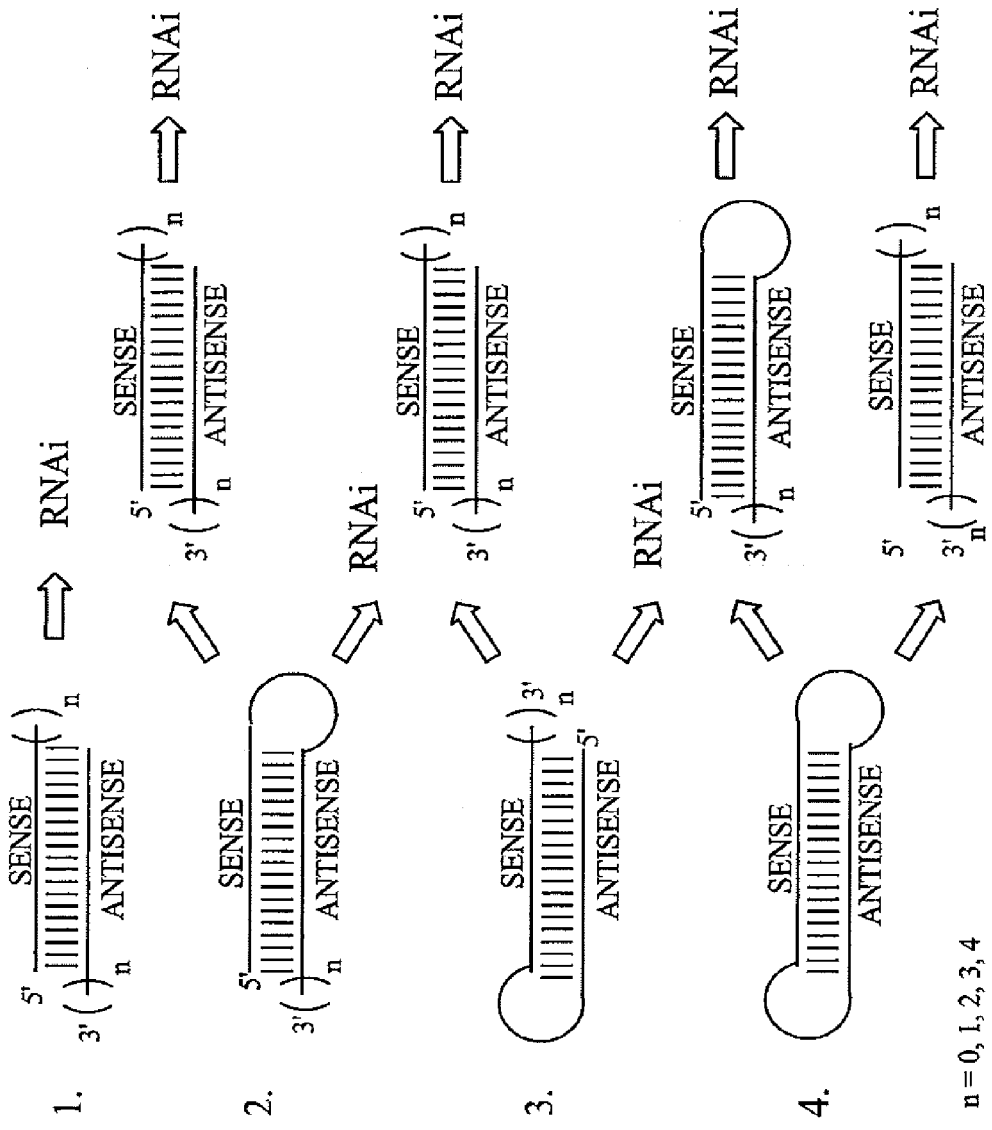
FIG. 6 shows non-limiting examples of different siNA constructs of the invention. The examples shown (constructs 1, 2, and 3) have 19 representative base pairs; however, different embodiments of the invention described herein include any number of base pairs described herein. Bracketed regions represent nucleotide overhangs, for example, comprising about 1, 2, 3, or 4 nucleotides in length, preferably about 2 nucleotides. Constructs 1 and 2 can be used independently for RNAi activity. Construct 2 can comprise a polynucleotide or non-nucleotide linker, which can optionally be designed as a biodegradable linker. In one embodiment, the loop structure shown in construct 2 can comprise a biodegradable linker that results in the formation of construct 1 in vivo and/or in vitro. In another example, construct 3 can be used to generate construct 2 under the same principle wherein a linker is used to generate the active siNA construct 2 in vivo and/or in vitro, which can optionally utilize another biodegradable linker to generate the active siNA construct 1 in vivo and/or in vitro. As such, the stability and/or activity of the siNA constructs can be modulated based on the design of the siNA construct for use in vivo or in vitro and/or in vitro.

Mechanism of Action of Nucleic Acid Molecules of the Invention

The discussion that follows discusses the proposed mechanism of RNA interference mediated by short interfering RNA as is presently known, and is not meant to be limiting and is not an admission of prior art. Applicant demonstrates herein that chemically modified short interfering nucleic acids possess similar or improved capacity to mediate RNAi as do siRNA molecules and are expected to possess improved stability and activity in vivo; therefore, this discussion is not meant to be limiting only to siRNA and can be applied to siNA as a whole. By "improved capacity to mediate RNAi" or "improved RNAi activity" is meant to include RNAi activity measured in vitro and/or in vivo where the RNAi activity is a reflection of both the ability of the siNA to mediate RNAi and the stability of the siNAs of the invention. In this invention, the product of these activities can be increased in vitro and/or in vivo compared to an all RNA siRNA or an siNA containing a plurality of ribonucleotides. In some cases, the activity or stability of the siNA molecule can be decreased (i.e., less than ten-fold), but the overall activity of the siNA molecule is enhanced in vitro and/or in vivo.

RNA interference refers to the process of sequence specific post-transcriptional gene silencing in animals mediated by short interfering RNAs (siRNAs) (Fire et al., 1998, *Nature,* 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes which is commonly shared by diverse flora and phyla (Fire et al., 1999, *Trends Genet.,* 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, *Nature,* 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al., 2001, *Science,* 293, 834). The RNAi response also features an endonuclease complex containing an siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, *Genes Dev.,* 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). As such, siNA molecules of the invention can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Fire et al., 1998, *Nature,* 391, 806, were the first to observe RNAi in *C. elegans.* Wianny and Goetz, 1999, *Nature Cell Biol.,* 2, 70, describe RNAi mediated by dsRNA in mouse embryos. Hammond et al., 2000, *Nature,* 404, 293, describe RNAi in *Drosophila* cells transfected with dsRNA. Elbashir et al., 2001, *Nature,* 411, 494, describe RNAi induced by introduction of duplexes of synthetic 21-nucleotide RNAs in cultured mammalian cells including human embryonic kidney and HeLa cells. Recent work in *Drosophila* embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, *EMBO J.,* 20, 6877). Other studies have indicated that a 5'-phosphate on the target-complementary strand of an siRNA duplex is required for siRNA activity and that ATP is utilized to maintain the 5'-phosphate moiety on the siRNA (Nykanen et al., 2001, *Cell,* 107, 309); however, siRNA molecules lacking a 5'-phosphate are active when introduced exogenously, suggesting that 5'-phosphorylation of siRNA constructs may occur in vivo.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small" refers to nucleic acid motifs no more than 100 nucleotides in length, preferably no more than 80 nucleotides in length, and most preferably no more than 50 nucleotides in length; e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.,* 74, 59, Brennan et al., 1998, *Biotechnol Bioeng.,* 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example; small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides. Table V outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, *J. Am. Chem. Soc.,* 109, 7845; Scaringe et al., 1990, *Nucleic Acids Res.,* 18, 5433; and Wincott et al., 1995, *Nucleic Acids Res.* 23, 2677-2684 Wincott et al., 1997, *Methods Mol. Bio.,* 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 min coupling step for alkylsilyl protected nucleotides and a 2.5 min coupling step for 2'-O-methylated nucleotides. Table V outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 µmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detrylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM 12, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 µL TEA and 1 mL TEA.3HF to provide a 1.4 M HF concentration) and heated to 65° C. After 1.5 h, the oligomer is quenched with 1.5 M NH$_4$HCO$_3$.

Alternatively, for the one-pot protocol, the polymer-bound trityl-on oligoribonucleotide is transferred to a 4 mL glass screw top vial and suspended in a solution of 33% ethanolic methylamine/DMSO:1/1 (0.8 mL) at 65° C. for 15 minutes. The vial is brought to room temperature TEA-3HF (0.1 mL) is added and the vial is heated at 65° C. for 15 minutes. The sample is cooled at −20° C. and then quenched with 1.5 M NH$_4$HCO$_3$.

For purification of the trityl-on oligomers, the quenched NH$_4$HCO$_3$ solution is loaded onto a C-18 containing cartridge that had been prewashed with acetonitrile followed by 50 mM TEAA. After washing the loaded cartridge with water, the RNA is detrylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 *Nucleic Acids Res.* 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides,* 16, 951; Bellon et al., 1997, *Bioconjugate Chem.* 8, 204), or by hybridization following synthesis and/or deprotection.

The siNA molecules of the invention can also be synthesized via a tandem synthesis methodology as described in Example 1 herein, wherein both siNA strands are synthesized as a single contiguous oligonucleotide fragment or strand separated by a cleavable linker which is subsequently cleaved to provide separate siNA fragments or strands that hybridize and permit purification of the siNA duplex. The linker can be a polynucleotide linker or a non-nucleotide linker. The tandem synthesis of siNA as described herein can be readily adapted to both multiwell/multiplate synthesis platforms such as 96 well or similarly larger multi-well platforms. The tandem synthesis of siNA as described herein can also be readily adapted to large scale synthesis platforms employing batch reactors, synthesis columns and the like.

An siNA molecule can also be assembled from two distinct nucleic acid strands or fragments wherein one fragment includes the sense region and the second fragment includes the antisense region of the RNA molecule.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, *TIBS* 17, 34; Usman et al., 1994, *Nucleic Acids Symp. Ser.* 31, 163). siNA constructs can be purified by gel electrophoresis using general methods or can be purified by high pressure liquid chromatography (HPLC; see Wincott et al., supra, the totality of which is hereby incorporated herein by reference) and re-suspended in water.

In another aspect of the invention, siNA molecules of the invention are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules.

Optimizing Activity of the Nucleic Acid Molecule of the Invention.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., International Publication PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic Acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi is cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

Short interfering nucleic acid (siNA) molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, *Nucleic Acids Res.* 23, 2677; Caruthers et al., 1992, *Methods in Enzymology* 211, 3-19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, *J. Am. Chem. Soc.*, 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C methylene bicyclo nucleotide (see for example Wengel et al., International PCT Publication No. WO 00/66604 and WO 99/14226).

In another embodiment, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of novel conjugates and complexes for the delivery of molecules, including, but not limited to, small molecules, lipids, cholesterol, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable linker" as used herein, refers to a nucleic acid or non-nucleic acid linker molecule that is designed as a biodegradable linker to connect one molecule to another molecule, for example, a biologically active molecule to an siNA molecule of the invention or the sense and antisense strands of an siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O- amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example, enzymatic degradation or chemical degradation.

The term "biologically active molecule" as used herein refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Therapeutic nucleic acid molecules (e.g., siNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In yet another embodiment, siNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

Use of the nucleic acid-based molecules of the invention will lead to better treatments by affording the possibility of combination therapies (e.g., multiple siNA molecules targeted to different genes; nucleic acid molecules coupled with known small molecule modulators; or intermittent treatment with combinations of molecules, including different motifs and/or other chemical or biological molecules). The treatment of subjects with siNA molecules can also include combinations of different types of nucleic acid molecules, such as enzymatic nucleic acid molecules (ribozymes), allozymes, antisense, 2,5-A oligoadenylate, decoys, and aptamers.

In another aspect an siNA molecule of the invention comprises one or more 5' and/or a 3'-cap structure, for example, on only the sense siNA strand, the antisense siNA strand, or both siNA strands.

Figure 10:
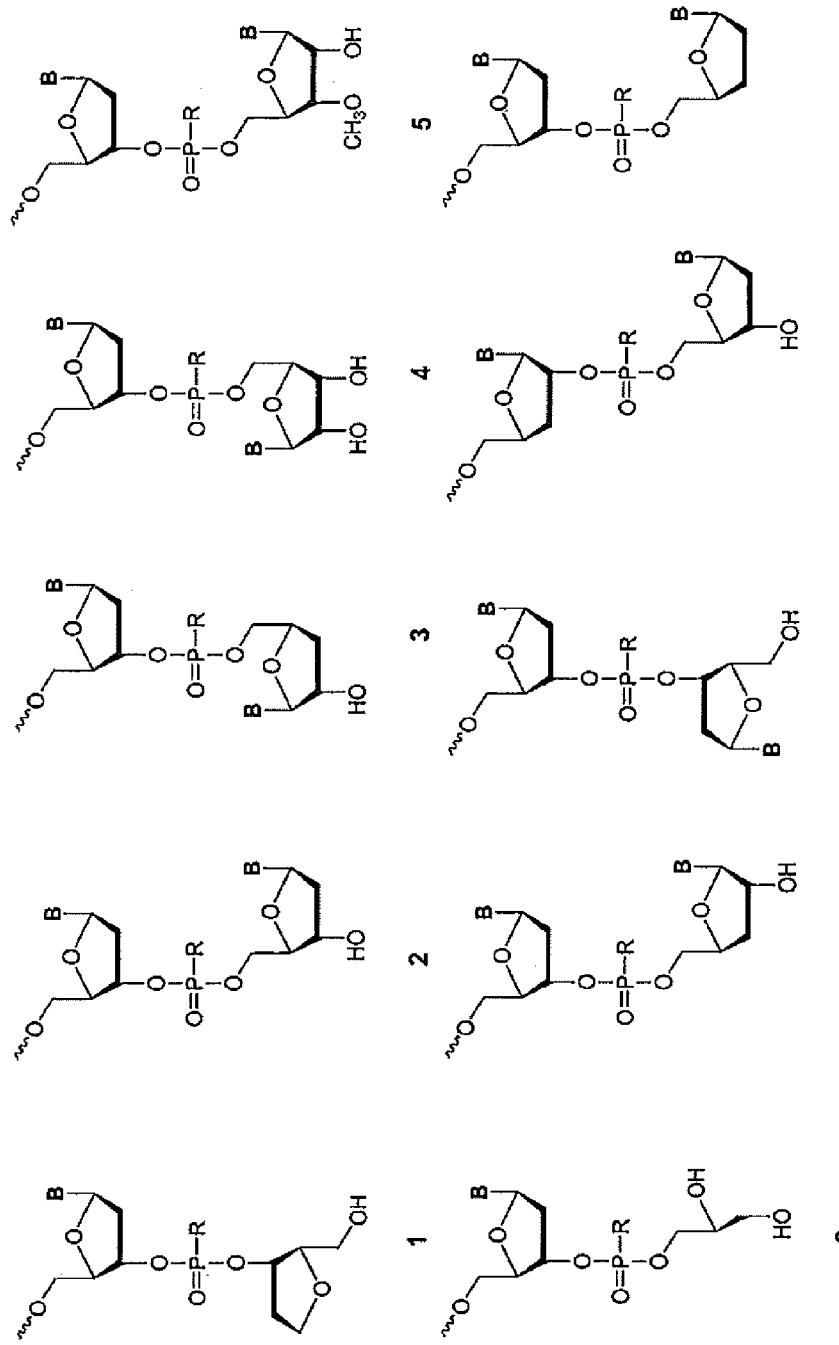
FIG. 10 shows non-limiting examples of different stabilization chemistries (1-10) that can be used, for example, to stabilize the 3'-end of siNA sequences of the invention, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to modified and unmodified backbone chemistries indicated in the figure, these chemistries can be combined with different backbone modifications as described herein, for example, backbone modifications having Formula I. In addition, the 2'-deoxy nucleotide shown 5' to the terminal modifications shown can be another modified or unmodified nucleotide or non-nucleotide described herein, for example modifications having any of Formulae I-VII or any combination thereof.

By "cap structure" is meant chemical modifications, which have been incorporated at either terminus of the oligonucleotide (see, for example, Adamic et al., U.S. Pat. No. 5,998, 203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Non-limiting examples of cap moieties are shown in FIG. 10.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups that are unsaturated hydrocarbon groups containing at least one carbon-carbon double bond, including straight-chain, branched-chain, and cyclic groups. Preferably, the alkenyl group has 1 to 12 carbons. More preferably, it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups that have an unsaturated hydrocarbon group containing at least one carbon-carbon triple bond, including straight-chain, branched-chain, and cyclic groups. Preferably, the alkynyl group has 1 to 12 carbons. More preferably, it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide and ester groups. An "aryl" group refers to an aromatic group that has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and suitable heterocylic groups include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

"Nucleotide" as used herein, and as recognized in the art, includes natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistry*, 35, 14090; Uhlman & Peyman, supra). By "modified bases" in this aspect is meant nucleotide bases other than adenine, guanine, cytosine and uracil at 1' position or their equivalents.

In one embodiment, the invention features modified siNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, *Nucleic Acid Analogues: Synthesis and Properties*, in *Modern Synthetic Methods*, VCH, 331-417, and Mesmaeker et al., 1994, *Novel Backbone Replacements for Oligonucleotides*, in *Carbohydrate Modifications in Antisense Research*, ACS, 24-39.

By "abasic" is meant sugar moieties lacking a base or having other chemical groups in place of a base at the 1' position, see for example Adamic et al., U.S. Pat. No. 5,998, 203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'—$NH_2$ or 2'-O—$NH_2$, which can be modified or unmodified. Such modified groups are described, for example, in Eckstein et al., U.S. Pat. No. 5,672,695 and Matulic-Adamic et al., U.S. Pat. No. 6,248,878, which are both incorporated by reference in their entireties.

Various modifications to nucleic acid siNA structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Administration of Nucleic Acid Molecules

An siNA molecule of the invention can be adapted for use to prevent or treat various diseases or conditions that can respond to the level of GAB2 in a cell or tissue, including allergic conditions, including allergy induced asthma; allergic rhinitis; allergic dermatitis; allergic conjuctivitis; cancer, including malignant blood diseases, such as lymphomas (e.g., non-Hodgkins and Hodgkins lymphomas); leukemias (e.g., chronic myeloid leukemia, CML; acute myeloid leukemias, AML; secondary leukemias, acute lymphoblastic leukemias, ALL; chronic lymphoid leukemia; CLL); polycytemia vera; idiopathic myelofibrosis; essential thrombocythemia; myelodysplastic syndromes; autoimmune disease (e.g., multiple sclerosis, lupus, rheumatoid arthritis, insulin dependent diabetes, encephalitis, Rasmussen's encephalitis, thyroiditis, Crohn's disease, fibromyalgia, Grave's disease, Guillain Barre syndrome, chronic fatigue syndrome, autoimmune hepatitis, Meniere's disease, Myasthenia Gravis, cardiomyopathy, polymyalgia, Psoriasis, ulcerative collitis, etc.); viral infection (e.g., HIV, HCV, HBV, RSV, CMV, HSV, influenza, rhinovirus etc.); or any other trait, disease or condition that is related to or will respond to the levels of GAB2 in a cell or tissue, alone or in combination with other therapies. For example, an siNA molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules of the invention are formulated as described in United States Patent Application Publication No. 20030077829, incorporated by reference herein in its entirety.

In one embodiment, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a subject.

In one embodiment, an siNA molecule of the invention is complexed with membrane disruptive agents such as those described in U.S. Patent Application Publication No. 20010007666, incorporated by reference herein in its entirety including the drawings. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety including the drawings.

In one embodiment, an siNA molecule of the invention is complexed with delivery systems as described in U.S. Patent Application Publication No. 2003077829 and International PCT Publication Nos. WO 00/03683 and WO 02/087541, all incorporated by reference herein in their entirety including the drawings.

In one embodiment, delivery systems of the invention include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid N,NI,NII,NIII-tetramethyl-N,NI,NII,NIII-tetrapalmity-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N[1-(2,3-dioleoyloxy)-N,N,N-tri-methyl-ammoniummethylsulfate) (Boehringer Manheim); and (4) Lipofectamine, 3:1 (M/M) liposome formulation of the polycationic lipid DOSPA and the neutral lipid DOPE (GIBCO BRL).

In one embodiment, delivery systems of the invention include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

In one embodiment, siNA molecules of the invention are formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; and Sagara, U.S. Pat. No. 6,586,524, incorporated by reference herein.

In one embodiment, an siNA molecule of the invention comprises a bioconjugate, for example a nucleic acid conjugate as described in Vargeese et al., U.S. Ser. No. 10/427,160, filed Apr. 30, 2003; U.S. Pat. Nos. 6,528,631; 6,335,434; 6,235,886; 6,153,737; 5,214,136; 5,138,045, all incorporated by reference herein.

Thus, the invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced to a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as creams, gels, sprays, oils and other suitable compositions for topical, dermal, or transdermal administration as is known in the art. The compositions of the present invention can also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic or local administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

In one embodiment, siNA molecules of the invention are administered to a subject by systemic administration in a pharmaceutically acceptable composition or formulation. By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells.

By "pharmaceutically acceptable formulation" or "pharmaceutically acceptable composition" is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as Pluronic P85),; biodegradable polymers, such as poly (DL-lactide-coglycolide) microspheres for sustained release delivery (Emerich, D F et al, 1999, *Cell Transplant*, 8, 47-58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.,* 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem.* *Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta*, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In one embodiment, the invention comprises compositions suitable for administering nucleic acid molecules of the invention to specific cell types. For example, the asialoglycoprotein receptor (ASGPr) (Wu and Wu, 1987, *J. Biol. Chem.* 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatennary or monoatennary chains (Baenziger and Fiete, 1980, *Cell,* 22, 611-620; Connolly et al., 1982, *J. Biol. Chem.;* 257, 939-945). Lee and Lee, 1987, *Glycoconjugate J.,* 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.,* 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavailability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 60/362,016, filed Mar. 6, 2002. Alternatively, certain siNA molecules of the instant invention can be expressed within cells from eukaryotic promoters (e.g., Izant and Weintraub, 1985, *Science,* 229, 345; McGarry and Lindquist, 1986, *Proc. Natl. Acad. Sci.,* USA 83, 399; Scanlon et al., 1991, *Proc. Natl. Acad. Sci. USA,* 88, 10591-5; Kashani-Sabet et al., 1992, *Antisense Res. Dev.,* 2, 3-15; propulic et al., 1992, *J. Virol.,* 66, 1432-41; Weerasinghe et al., 1991, *J. Virol.,* 65, 5531-4; Ojwang et al., 1992, *Proc. Natl. Acad. Sci. USA,* 89, 10802-6; Chen et al., 1992, *Nucleic Acids Res.,* 20, 4581-9; Sarver et al., 1990 *Science,* 247, 1222-1225; Thompson et al., 1995, *Nucleic Acids Res.,* 23, 2259; Good et al., 1997, *Gene Therapy,* 4, 45. Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, *Nucleic Acids Symp. Ser.,* 27, 15-6; Taira et al., 1991, *Nucleic Acids Res.,* 19, 5125-30; Ventura et al., 1993, *Nucleic Acids Res.,* 21, 3249-55; Chowrira et al., 1994, *J. Biol. Chem.,* 269, 25856.

In another aspect of the invention, RNA molecules of the present invention can be expressed from transcription units (see for example Couture et al., 1996, *TIG.,* 12, 510) inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pats. Nos. 5,902,880 and 6,146,886). The recombinant vectors capable of expressing the siNA molecules can be delivered as described above, and persist in target cells. Alternatively, viral vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell (for a review see Couture et al., 1996, *TIG.,* 12, 510).

In one aspect the invention features an expression vector comprising a nucleic acid sequence encoding at least one siNA molecule of the instant invention. The expression vector can encode one or both strands of an siNA duplex, or a single self-complementary strand that self hybridizes into an siNA duplex. The nucleic acid sequences encoding the siNA molecules of the instant invention can be operably linked in a manner that allows expression of the siNA molecule (see for example Paul et al., 2002, *Nature Biotechnology,* 19, 505; Miyagishi and Taira, 2002, *Nature Biotechnology,* 19, 497; Lee et al., 2002, *Nature Biotechnology,* 19, 500; and Novina et al., 2002, *Nature Medicine,* advance online publication doi: 10.1038/nm725).

In another aspect, the invention features an expression vector comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siNA molecules of the instant invention, wherein said sequence is operably linked to said initiation region and said termination region in a manner that allows expression and/or delivery of the siNA molecule. The vector can optionally include an open reading frame (ORF) for a protein operably linked on the 5' side or the 3'-side of the sequence encoding the siNA of the invention; and/or an intron (intervening sequences).

Transcription of the siNA molecule sequences can be driven from a promoter for eukaryotic RNA polymerase I (pol I), RNA polymerase II (pol I), or RNA polymerase III (pol III). Transcripts from pol 11 or pol III promoters are expressed at high levels in all cells; the levels of a given pol H promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA,* 87, 6743-7; Gao and Huang 1993, *Nucleic Acids Res.,* 21, 2867-72; Lieber et al., 1993, *Methods Enzymol.,* 217, 47-66; Zhou et al., 1990, *Mol. Cell. Biol.,* 10, 4529-37). Several investigators have demonstrated that nucleic acid molecules expressed from such promoters can function in mammalian cells (e.g. Kashani-Sabet et al., 1992, *Antisense Res. Dev.,* 2, 3-15; Ojwang et al., 1992, *Proc. Natl. Acad. Sci. USA,* 89, 10802-6; Chen et al., 1992, *Nucleic Acids Res.,* 20, 4581-9; Yu et al., 1993, *Proc. Natl. Acad. Sci. USA,* 90, 6340-4; L'Huillier et al., 1992, *EMBO J.,* 11, 4411-8; Lisziewicz et al., 1993, *Proc. Natl. Acad. Sci. U.S.A,* 90, 8000-4; Thompson et al., 1995, *Nucleic Acids Res.,* 23, 2259; Sullenger & Cech, 1993, *Science,* 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, *Nucleic Acid Res.,* 22, 2830; Noonberg et al., U.S. Pat. No. 5,624,803; Good et al., 1997, *Gene Ther.,* 4, 45; Beigelman et al., International PCT Publication No. WO 96/18736. The above siNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another aspect the invention features an expression vector comprising a nucleic acid sequence encoding at least one of the siNA molecules of the invention in a manner that allows expression of that siNA molecule. The expression vector comprises in one embodiment; a) a transcription initiation region; b) a transcription termination region; and c) a nucleic acid sequence encoding at least one strand of the siNA molecule, wherein the sequence is operably linked to the initiation region and the termination region in a manner that allows expression and/or delivery of the siNA molecule.

In another embodiment the expression vector comprises: a) a transcription initiation region; b) a transcription termination region; c) an open reading frame; and d) a nucleic acid sequence encoding at least one strand of an siNA molecule, wherein the sequence is operably linked to the 3'-end of the open reading frame and wherein the sequence is operably linked to the initiation region, the open reading frame and the termination region in a manner that allows expression and/or delivery of the siNA molecule. In yet another embodiment, the expression vector comprises: a) a transcription initiation region; b) a transcription termination region; c) an intron; and d) a nucleic acid sequence encoding at least one siNA molecule, wherein the sequence is operably linked to the initiation region, the intron and the termination region in a manner which allows expression and/or delivery of the nucleic acid molecule.

In another embodiment, the expression vector comprises: a) a transcription initiation region; b) a transcription termination region; c) an intron; d) an open reading frame; and e) a nucleic acid sequence encoding at least one strand of an siNA molecule, wherein the sequence is operably linked to the 3'-end of the open reading frame and wherein the sequence is operably linked to the initiation region, the intron, the open reading frame and the termination region in a manner which allows expression and/or delivery of the siNA molecule.

GAB2 Biology and Biochemistry IgE-dependent activation of mast cells is an essential feature of the allergic response. The engagement of IgE-occupied receptors initiates a series of molecular events that cause the release of preformed, and the de novo synthesis of, various allergic mediators. Recent investigations demonstrate a critical role for non-enzymatic proteins that facilitate the activation and coordination of biochemical signals required for mast cell activation. Among these LAT, SLP-76 and GAB2 are critically important as adapters that facilitate events initiated by IgE receptor-dependent activation of Src family protein tyrosine kinases, Lyn and Fyn. An evaluation of the role of these adapters points to complementary, but independent, steps in early signaling and the possibility that preference for one over another adaptor complex may result in selective mast cell responses (Rivera, 2002, *Curr Opin Immunol.*, 14, 688-693).

The recently cloned scaffolding molecule GAB2 can assemble multiple molecules involved in signaling pathways. Bone marrow-derived mast cells isolated from GAB2(−/−) mice have defective signaling, most likely due to the lack of the activation of phosphatidylinositol-3 kinase (PI3-kinase). The role of GAB2 has been investigated using rat basophilic leukemia 2H3 cell line mast cells (Xie et al., 2002, *J. Immunology*, 168, 4682-4691). Fc epsilon R1 aggregation was shown to induce tyrosine phosphorylation of GAB2 and translocation of a significant fraction of GAB2 from the cytosol to the plasma membrane. As in other cells, GAB2 was found to associate with several signaling molecules, including Src homology 2-containing protein tyrosine phosphatase 2, GRB2, Lyn, and phospholipase C gamma (PLC gamma). The association of GAB2 with Lyn and PLC gamma was shown to be enhanced after receptor aggregation. Overexpression of GAB2 in rat basophilic leukemia 2H3 cell line cells inhibited the Fc epsilon R1-induced tyrosine phosphorylation of the subunits of the receptor, and the phosphorylation and/or activation of Syk and mitogen-activated protein kinase. Downstream events, such as calcium mobilization, degranulation, and induction of TNF-alpha and IL-6 gene transcripts were decreased in GAB2 overexpressing cells, although Akt phosphorylation as a measure of PI3-kinase activation was otherwise unaffected. These results suggest that in addition to the positive effects mediated by PI3-kinase that are apparent in GAB2(−/−) mast cells, GAB2 may have negative regulatory effects on Fc epsilon R1-induced mast cell signaling and functions by interacting with Lyn and PLC gamma (Xie et al., 2002, *J. Immunology*, 168, 4682-4691).

GAB2 has been implicated in transformation mediated by the BCR/ABL oncogene. The BCR/ABL oncogene is known to cause chronic myelogenous leukemia (CML) in humans and a CML-like disease, as well as lymphoid leukemia, in mice. p210 BCR/ABL is an activated tyrosine kinase that phosphorylates itself and several cellular signaling proteins. The autophosphorylation site tyrosine 177 binds the adaptor GRB2 and helps determine the lineage and severity of BCR/ABL disease. Furthermore, the Tyr177 mutation (BCR/ABL-Y177F) dramatically impairs myeloid leukemogenesis, while diminishing lymphoid leukemogenesis. It has been shown that Tyr177 recruits the scaffolding adaptor GAB2 protein via a GRB2/GAB2 complex (Sattler et al., 2002, *Cancer Cell*, 1, 479-492). When compared with BCR/ABL-expressing Ba/F3 cells, BCR/ABL-Y177F cells exhibit markedly reduced GAB2 tyrosine phosphorylation and association of phosphatidylinositol-3 kinase (PI3K) and Shp2 with GAB2 and BCR/ABL, and decreased PI3K/Akt and Ras/Erk activation, cell proliferation, and spontaneous migration. Interestingly, bone marrow myeloid progenitors from Gab2 (−/−) mice are resistant to transformation by BCR/ABL, whereas lymphoid transformation is diminished as a consequence of markedly increased apoptosis. BCR/ABL-evoked PI3K/Akt and Ras/Erk activation also are impaired in GAB2 (−/−) primary myeloid and lymphoid cells. These results identify Gab2 and its associated proteins as key determinants of the lineage and severity of BCR/ABL transformation (Sattler et al., 2002, *Cancer Cell*, 1, 479-492).

Gab2 is also implicated in the development of breast cancer. Daly et al., 2002, *Oncogene*, 21, 5175-5181, report a marked overexpression of Gab2 in a subset of breast cancer cell lines compared to normal breast epithelial strains and a trend for increased Gab2 expression in estrogen receptor (ER)-positive cell lines. Overexpression of GAB2 relative to normal ductal epithelium was also observed in some primary breast cancers. In MCF-7 breast cancer cells, Gab2 was markedly tyrosine phosphorylated in response to heregulin administration and also following EGF, insulin or bFGF administration, thus indicating that a variety of RTKs implicated in breast cancer development or progression couple to the GAB2 docking protein. In hormone-responsive breast cancer cells, GAB2 mRNA and protein expression are induced by estradiol in a manner sensitive to the pure anti-estrogen ICI 182780, indicating that this regulation is mediated via the estrogen receptor. GAB2 therefore represents a novel link between steroid and growth factor signaling in breast cancer, and when overexpressed, may modulate the sensitivity of breast cancer cells to these important growth regulators.

Recently, Gu et al., 2002, *Nature,* 412, 186-190, have described an animal model of allergic response via GAB2. In this study, GAB2 (−/−) mice were used to elucidate the role of GAB2 in the allergic response. GAB2 (−/−) mice were viable and generally healthy; however, the response of GAB2 (−/−) mast cells to stimulation of the high affinity immunoglobulin-E (IgE) receptor FcER1 (e.g., degranulation and cytokine gene expression response) was found to be defective in GAB2 (−/−) mice. Accordingly, allergic reactions, such as passive cutaneous and systemic anaphylaxis, are markedly impaired in the GAB2 (−/−) mice. Biochemical analyses revealed that signalling pathways dependent on PI(3)K, a critical component of FcER1 signalling, are defective in GAB2 (−/−) mast cells. Furthermore, GAB2 was identified as the principal activator of PI(3)K in response to FcER1 activation, thereby providing genetic evidence that Dos/Gab family scaffolds regulate the PI(3)K pathway in vivo. As such, GAB2 and associated signalling molecules provide new targets for developing drugs to treat allergy.

Based upon the current understanding of GAB2, the modulation of GAB2 and related genes is instrumental in the development of new therapeutics for inflammatory diseases and conditions, autoimmune diseases and conditions, allergic diseases and conditions and/or cancer. As such, modulation of GAB2 using small interfering nucleic acid (siNA) mediated RNAi represents a novel approach to the treatment and diagnosis of diseases and conditions related GAB2 activity and/or gene expression, such as inflammatory diseases and conditions, autoimmune diseases and conditions, allergic diseases and conditions and/or cancer.

EXAMPLES

The following are non-limiting examples showing the selection, isolation, synthesis and activity of nucleic acids of the instant invention.

Example 1

Tandem Synthesis of siNA Constructs

Exemplary siNA molecules of the invention are synthesized in tandem using a cleavable linker, for example, a succinyl-based linker. Tandem synthesis as described herein is followed by a one-step purification process that provides RNAi molecules in high yield. This approach is highly amenable to siNA synthesis in support of high throughput RNAi screening, and can be readily adapted to multi-column or multi-well synthesis platforms.

After completing a tandem synthesis of an siNA oligo and its complement in which the 5'-terminal dimethoxytrityl (5'-O-DMT) group remains intact (trityl on synthesis), the oligonucleotides are deprotected as described above. Following deprotection, the siNA sequence strands are allowed to spontaneously hybridize. This hybridization yields a duplex in which one strand has retained the 5'-O-DMT group while the complementary strand comprises a terminal 5'-hydroxyl. The newly formed duplex behaves as a single molecule during routine solid-phase extraction purification (Trityl-On purification) even though only one molecule has a dimethoxytrityl group. Because the strands form a stable duplex, this dimethoxytrityl group (or an equivalent group, such as other trityl groups or other hydrophobic moieties) is all that is required to purify the pair of oligos, for example, by using a C18 cartridge.

Standard phosphoramidite synthesis chemistry is used up to the point of introducing a tandem linker, such as an inverted deoxy abasic succinate or glyceryl succinate linker (see FIG. 1) or an equivalent cleavable linker. A non-limiting example of linker coupling conditions that can be used includes a hindered base such as diisopropylethylamine (DIPA) and/or DMAP in the presence of an activator reagent such as Bromotripyrrolidinophosphoniumhexafluororophosphate (PyBrOP). After the linker is coupled, standard synthesis chemistry is utilized to complete synthesis of the second sequence leaving the terminal the 5'-O-DMT intact. Following synthesis, the resulting oligonucleotide is deprotected according to the procedures described herein and quenched with a suitable buffer, for example with 50 mM NaOAc or 1.5 M $NH_4H_2CO_3$.

Purification of the siNA duplex can be readily accomplished using solid phase extraction, for example, using a Waters C18 SepPak Ig cartridge conditioned with 1 column volume (CV) of acetonitrile, 2 CV H2O, and 2 CV 50 mM NaOAc. The sample is loaded and then washed with 1 CV H2O or 50 mM NaOAc. Failure sequences are eluted with 1 CV 14% ACN (Aqueous with 50 mM NaOAc and 50 mM NaCl). The column is then washed, for example with 1 CV H2O followed by on-column detritylation, for example by passing 1 CV of 1% aqueous trifluoroacetic acid (TFA) over the column, then adding a second CV of 1% aqueous TFA to the column and allowing to stand for approximately 10 minutes. The remaining TFA solution is removed and the column washed with H20 followed by 1 CV 1M NaCl and additional H2O. The siNA duplex product is then eluted, for example, using 1 CV 20% aqueous CAN.

FIG. 2 provides an example of MALDI-TOF mass spectrometry analysis of a purified siNA construct in which each peak corresponds to the calculated mass of an individual siNA strand of the siNA duplex. The same purified siNA provides three peaks when analyzed by capillary gel electrophoresis (CGE), one peak presumably corresponding to the duplex siNA, and two peaks presumably corresponding to the separate siNA sequence strands. Ion exchange HPLC analysis of the same siNA contract only shows a single peak. Testing of the purified siNA construct using a luciferase reporter assay described below demonstrated the same RNAi activity compared to siNA constructs generated from separately synthesized oligonucleotide sequence strands.

Example 2

Identification of Potential siNA Target Sites in any RNA Sequence

The sequence of an RNA target of interest, such as a viral or human mRNA transcript, is screened for target sites, for example by using a computer folding algorithm. In a non-limiting example, the sequence of a gene or RNA gene transcript derived from a database, such as Genbank, is used to generate siNA targets having complementarity to the target. Such sequences can be obtained from a database, or can be determined experimentally as known in the art. Target sites that are known, for example, those target sites determined to be effective target sites based on studies with other nucleic acid molecules, for example ribozymes or antisense, or those targets known to be associated with a disease or condition such as those sites containing mutations or deletions, can be used to design siNA molecules targeting those sites. Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siNA molecules for efficacy, for example by using in vitro RNA cleavage assays, cell culture, or animal models. In a non-limiting example, anywhere from 1 to 1000 target sites are chosen within the transcript based on the size of the siNA construct to be used. High throughput screening assays can be developed for screening siNA molecules using methods known in the art, such as with multi-well or multi-plate assays to determine efficient reduction in target gene expression.

Example 3

Selection of siNA Molecule Target Sites in a RNA

The following non-limiting steps can be used to carry out the selection of siNAs targeting a given gene sequence or transcript.

1. The target sequence is parsed in silico into a list of all fragments or subsequences of a particular length, for example 23 nucleotide fragments, contained within the target sequence. This step is typically carried out using a custom Perl script, but commercial sequence analysis programs such as Oligo, MacVector, or the GCG Wisconsin Package can be employed as well.

2. In some instances the siNAs correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence; the goal is to find subsequences that are present in most or all of the target sequences. Alternately, the ranking can identify subsequences that are unique to a target sequence, such as a mutant target sequence. Such an approach would enable the use of siNA to target specifically the mutant sequence and not effect the expression of the normal sequence.

3. In some instances the siNA subsequences are absent in one or more sequences while present in the desired target sequence; such would be the case if the siNA targets a gene with a paralogous family member that is to remain untargeted. As in case 2 above, a subsequence list of a particular length is generated for each of the targets, and then the lists are compared to find sequences that are present in the target gene but are absent in the untargeted paralog.

4. The ranked siNA subsequences can be further analyzed and ranked according to GC content. A preference can be given to sites containing 30-70% GC, with a further preference to sites containing 40-60% GC.

5. The ranked siNA subsequences can be further analyzed and ranked according to self-folding and internal hairpins. Weaker internal folds are preferred; strong hairpin structures are to be avoided.

6. The ranked siNA subsequences can be further analyzed and ranked according to whether they have runs of GGG or CCC in the sequence. GGG (or even more Gs) in either strand can make oligonucleotide synthesis problematic and can potentially interfere with RNAi activity, so it is avoided whenever better sequences are available. CCC is searched in the target strand because that will place GGG in the antisense strand.

7. The ranked siNA subsequences can be further analyzed and ranked according to whether they have the dinucleotide UU (uridine dinucleotide) on the 3'-end of the sequence, and/or AA on the 5'-end of the sequence (to yield 3' UU on the antisense sequence). These sequences allow one to design siNA molecules with terminal TT thymidine dinucleotides.

8. Four or five target sites are chosen from the ranked list of subsequences as described above. For example, in subsequences having 23 nucleotides, the right 21 nucleotides of each chosen 23-mer subsequence are then designed and synthesized for the upper (sense) strand of the siNA duplex, while the reverse complement of the left 21 nucleotides of each chosen 23-mer subsequence are then designed and synthesized for the lower (antisense) strand of the siNA duplex (see Tables II and III). If terminal TT residues are desired for the sequence (as described in paragraph 7), then the two 3' terminal nucleotides of both the sense and antisense strands are replaced by TT prior to synthesizing the oligos.

9. The siNA molecules are screened in an in vitro, cell culture or animal model system to identify the most active siNA molecule or the most preferred target site within the target RNA sequence.

10. Other design considerations can be used when selecting target nucleic acid sequences, see, for example, Reynolds et al., 2004, *Nature Biotechnology Advanced Online Publication*, 1 Feb. 2004, doi:10.1038/nbt936 and Ui-Tei et al., 2004, *Nucleic Acids Research*, 32, doi: 10.1093/nar/gkh247.

Figure 7:
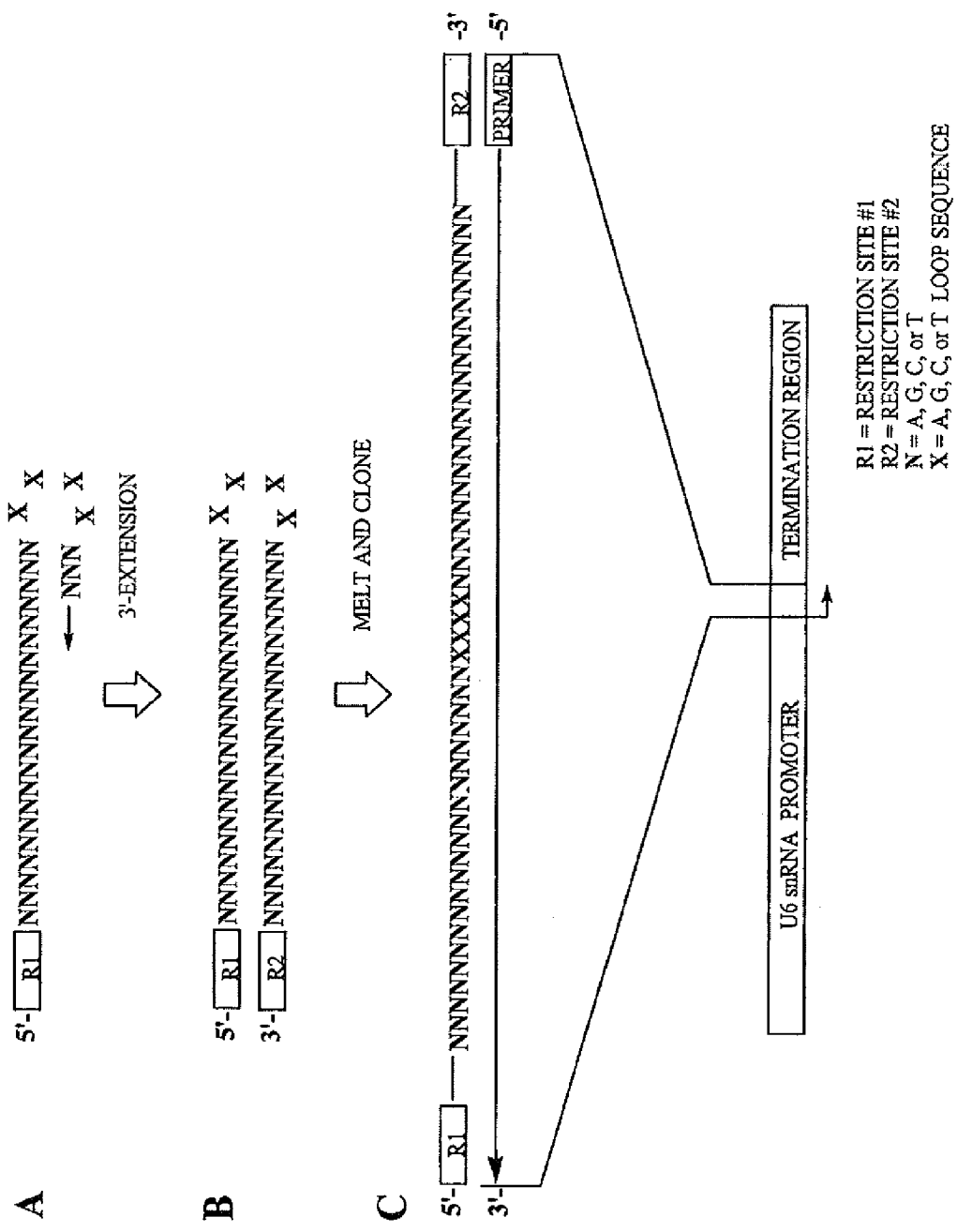
FIG. 7A-C is a diagrammatic representation of a scheme utilized in generating an expression cassette to generate siNA hairpin constructs.
Figure 8:
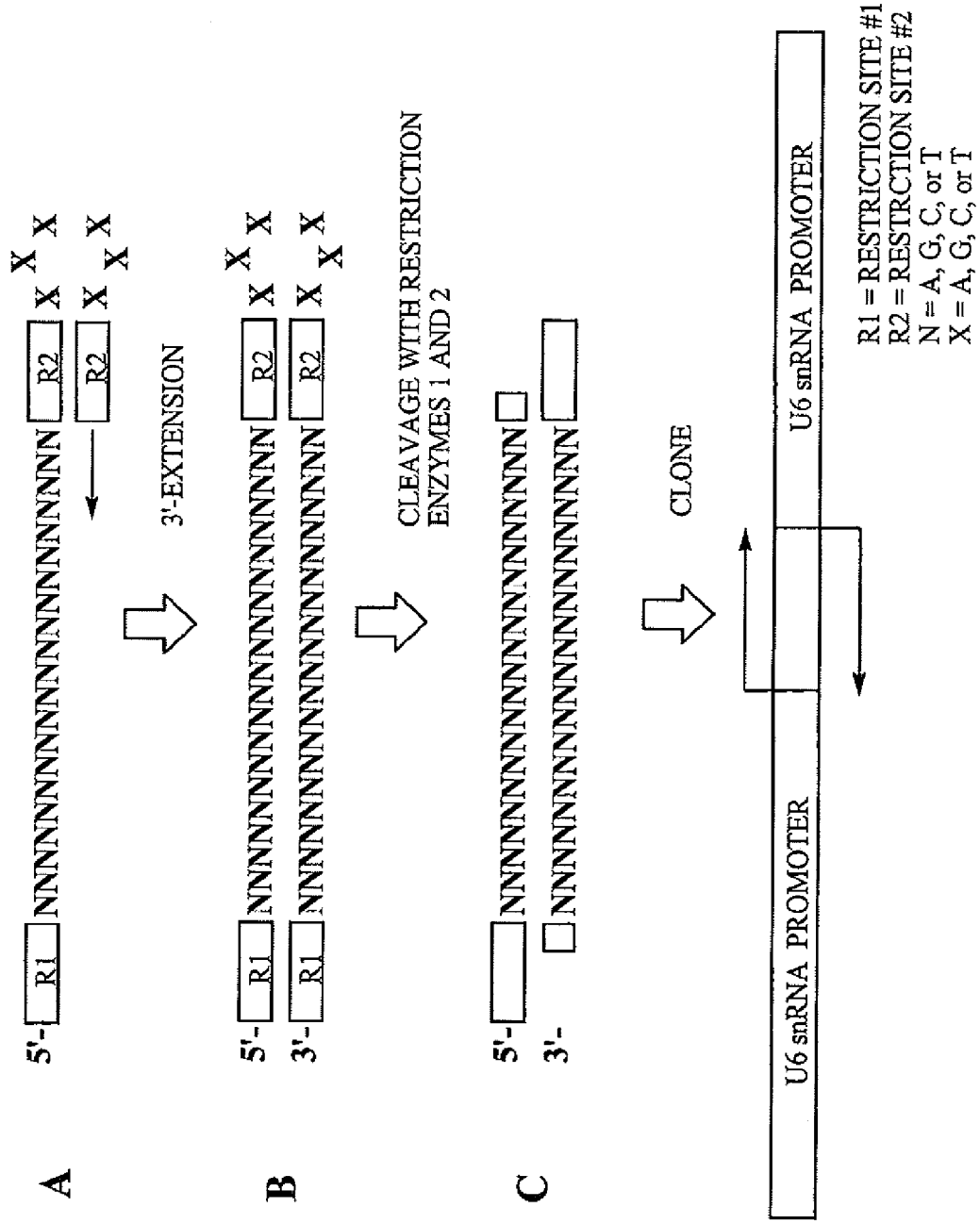
FIG. 8A-C is a diagrammatic representation of a scheme utilized in generating an expression cassette to generate double-stranded siNA constructs.
Figure 9:
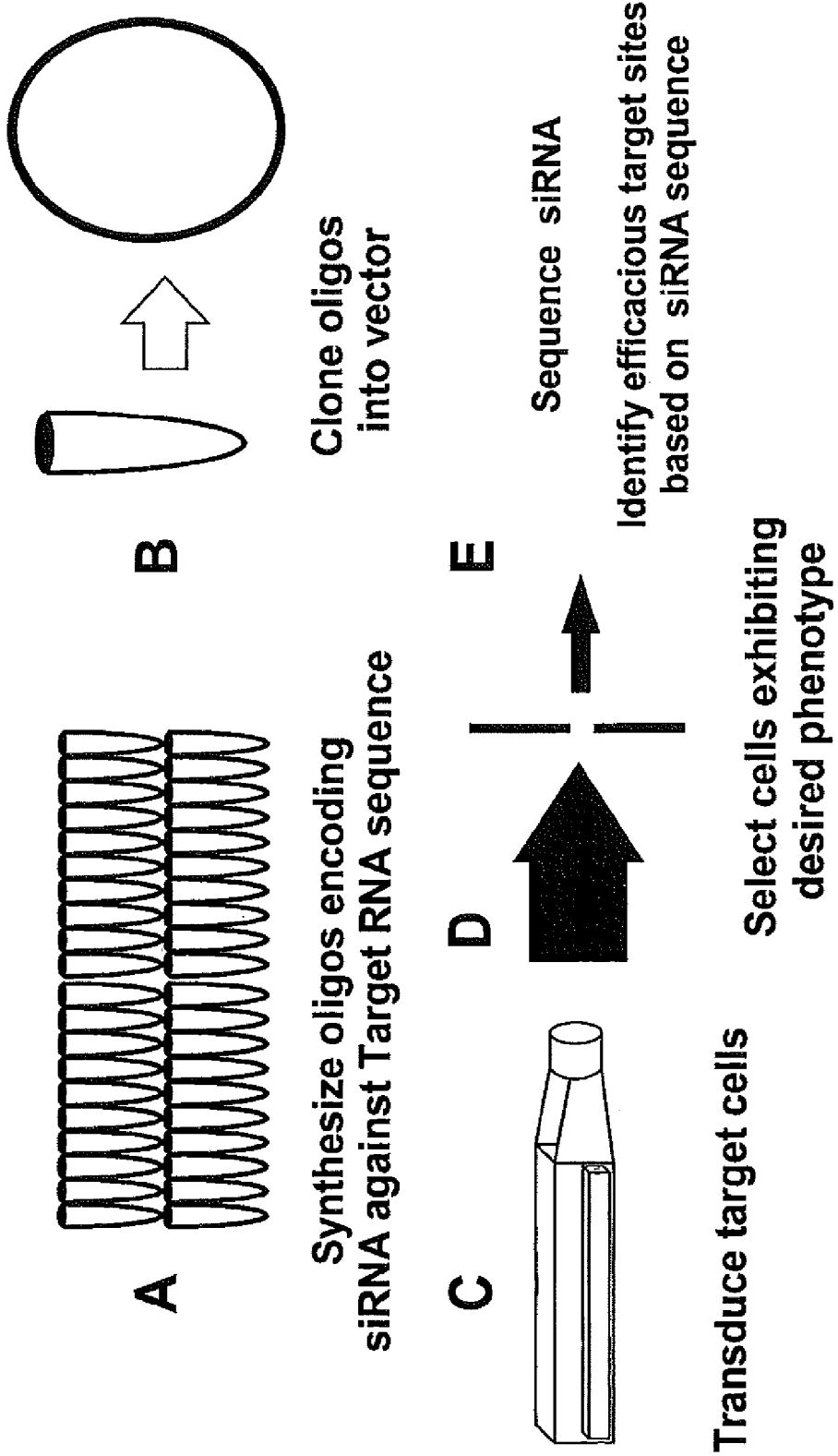
FIG. 9A-E is a diagrammatic representation of a method used to determine target sites for siNA mediated RNAi within a particular target nucleic acid sequence, such as messenger RNA.

In an alternate approach, a pool of siNA constructs specific to a GAB2 target sequence is used to screen for target sites in cells expressing GAB2 RNA, such as cultured human mast cells or 293T cells. The general strategy used in this approach is shown in FIG. 9. A non-limiting example of such is a pool comprising sequences having any of SEQ ID NOS 1-799. Cells expressing GAB2 (e.g., cultured human mast cells or 293T cells) are transfected with the pool of siNA constructs and cells that demonstrate a phenotype associated with GAB2 inhibition are sorted. The pool of siNA constructs can be expressed from transcription cassettes inserted into appropriate vectors (see for example FIG. 7 and FIG. 8). The siNA from cells demonstrating a positive phenotypic change (e.g., decreased proliferation, decreased GAB2 mRNA levels or decreased GAB2 protein expression), are sequenced to determine the most suitable target site(s) within the target GAB2 RNA sequence.

Example 4

GAB2 Targeted siNA Design siNA target sites were chosen by analyzing sequences of the GAB2 RNA target and optionally prioritizing the target sites on the basis of folding (structure of any given sequence analyzed to determine siNA accessibility to the target), by using a library of siNA molecules as described in Example 3, or alternately by using an in vitro siNA system as described in Example 6 herein. siNA molecules were designed that could bind each target and are optionally individually analyzed by computer folding to assess whether the siNA molecule can interact with the target sequence. Varying the length of the siNA molecules can be chosen to optimize activity. Generally, a sufficient number of complementary nucleotide bases are chosen to bind to, or otherwise interact with, the target RNA, but the degree of complementarity can be modulated to accommodate siNA duplexes or varying length or base composition. By using such methodologies, siNA molecules can be designed to target sites within any known RNA sequence, for example those RNA sequences corresponding to the any gene transcript.

Chemically modified siNA constructs are designed to provide nuclease stability for systemic administration in vivo and/or improved pharmacokinetic, localization, and delivery properties while preserving the ability to mediate RNAi activity. Chemical modifications as described herein are introduced synthetically using synthetic methods described herein and those generally known in the art. The synthetic siNA constructs are then assayed for nuclease stability in serum and/or cellular/tissue extracts (e.g. liver extracts). The synthetic siNA constructs are also tested in parallel for RNAi activity using an appropriate assay, such as a luciferase reporter assay as described herein or another suitable assay that can quantity RNAi activity. Synthetic siNA constructs that possess both nuclease stability and RNAi activity can be further modified and re-evaluated in stability and activity assays. The chemical modifications of the stabilized active siNA constructs can then be applied to any siNA sequence targeting any chosen RNA and used, for example, in target screening assays to pick lead siNA compounds for therapeutic development (see for example FIG. 11).

Example 5

Chemical Synthesis and Purification of siNA siNA molecules can be designed to interact with various sites in the RNA message, for example, target sequences within the RNA sequences described herein. The sequence of one strand of the siNA molecule(s) is complementary to the target site sequences described above. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086 all incorporated by reference herein in their entirety).

In a non-limiting example, RNA oligonucleotides are synthesized in a stepwise fashion using the phosphoramidite chemistry as is known in the art. Standard phosphoramidite chemistry involves the use of nucleosides comprising any of 5'-O-dimethoxytrityl, 2'-O-tert-butyldimethylsilyl, 3'-O-2-Cyanoethyl N,N-diisopropylphosphoroamidite groups, and exocyclic amine protecting groups (e.g. N6-benzoyl adenosine, N4 acetyl cytidine, and N2-isobutyryl guanosine). Alternately, 2'-O-Silyl Ethers can be used in conjunction with acid-labile 2'-O-orthoester protecting groups in the synthesis of RNA as described by Scaringe supra. Differing 2' chemistries can require different protecting groups, for example 2'-deoxy-2'-amino nucleosides can utilize N-phthaloyl protection as described by Usman et al., U.S. Pat. No. 5,631,360, incorporated by reference herein in its entirety).

During solid phase synthesis, each nucleotide is added sequentially (3'- to 5'-direction) to the solid support-bound oligonucleotide. The first nucleoside at the 3'-end of the chain is covalently attached to a solid support (e.g., controlled pore glass or polystyrene) using various linkers. The nucleotide precursor, a ribonucleoside phosphoramidite, and activator are combined resulting in the coupling of the second nucleoside phosphoramidite onto the 5'-end of the first nucleoside. The support is then washed and any unreacted 5'-hydroxyl groups are capped with a capping reagent such as acetic anhydride to yield inactive 5'-acetyl moieties. The trivalent phosphorus linkage is then oxidized to a more stable phosphate linkage. At the end of the nucleotide addition cycle, the 5'-O-protecting group is cleaved under suitable conditions (e.g., acidic conditions for trityl-based groups and Fluoride for silyl-based groups). The cycle is repeated for each subsequent nucleotide.

Modification of synthesis conditions can be used to optimize coupling efficiency, for example by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Usman et al., U.S. Pat. Nos. 5,831,071, 6,353,098, 6,437,117, and Bellon et al., U.S. Pat. Nos. 6,054, 576, 6,162,909, 6,303,773, or Scaringe supra, incorporated by reference herein in their entireties. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 6

RNAi In Vitro Assay to Assess siNA Activity

An in vitro assay that recapitulates RNAi in a cell-free system is used to evaluate siNA constructs targeting GAB2 RNA targets. The assay comprises the system described by Tuschl et al., 1999, *Genes and Development*, 13, 3191-3197 and Zamore et al., 2000, *Cell*, 101, 25-33 adapted for use with GAB2 target RNA. A *Drosophila* extract derived from syncytial blastoderm is used to reconstitute RNAi activity in vitro. Target RNA is generated via in vitro transcription from an appropriate GAB2 expressing plasmid using T7 RNA polymerase or via chemical synthesis as described herein. Sense and antisense siNA strands (for example 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol]lysis buffer containing siNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which siNA is omitted from the reaction.

Alternately, internally-labeled target RNA for the assay is prepared by in vitro transcription in the presence of [alpha-$^{32}_P$] CTP, passed over a G50 Sephadex column by spin chromatography and used as target. RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without siNA and the cleavage products generated by the assay.

In one embodiment, this assay is used to determine target sites in the GAB2 RNA target for siNA mediated RNAi cleavage, wherein a plurality of siNA constructs are screened for RNAi mediated cleavage of the GAB2 RNA target, for example, by analyzing the assay reaction by electrophoresis of labeled target RNA, or by Northern blotting, as well as by other methodology well known in the art.

Example 7

Nucleic Acid Inhibition of GAB2 Target RNA siNA molecules targeted to the human GAB2 RNA are designed and synthesized as described above. These nucleic acid molecules can be tested for cleavage activity in vivo, for example, using the following procedure. The target sequences and the nucleotide location within the GAB2 RNA are given in Tables II and III.

Two formats are used to test the efficacy of siNAs targeting GAB2. First, the reagents are tested in cell culture using, for example, cultured human mast cells or 293T cells, to determine the extent of RNA and protein inhibition. siNA reagents (e.g.; see Tables II and III) are selected against the GAB2 target as described herein. RNA inhibition is measured after delivery of these reagents by a suitable transfection agent to, for example, cultured human mast cells or 293T cells. Relative amounts of target RNA are measured versus actin using real-time PCR monitoring of amplification (e.g., ABI 7700 TAQMAN®). A comparison is made to a mixture of oligonucleotide sequences made to unrelated targets or to a randomized siNA control with the same overall length and chemistry, but randomly substituted at each position. Primary and secondary lead reagents are chosen for the target and optimization performed. After an optimal transfection agent concentration is chosen, a RNA time-course of inhibition is performed with the lead siNA molecule. In addition, a cell-plating format can be used to determine RNA inhibition.

Delivery of siNA to Cells

Cells (e.g., cultured human mast cells or 293T cells) are seeded, for example, at 1×10$^5$ cells per well of a six-well dish in EGM-2 (BioWhittaker) the day before transfection. siNA (final concentration, for example 20 nM) and cationic lipid (e.g., final concentration 2 µg/ml) are complexed in EGM basal media (Bio Whittaker) at 37° C. for 30 minutes in polystyrene tubes. Following vortexing, the complexed siNA is added to each well and incubated for the times indicated. For initial optimization experiments, cells are seeded, for example, at 1×10$^3$ in 96 well plates and siNA complex added as described. Efficiency of delivery of siNA to cells is determined using a fluorescent siNA complexed with lipid. Cells in 6-well dishes are incubated with siNA for 24 hours, rinsed with PBS and fixed in 2% paraformaldehyde for 15 minutes at room temperature. Uptake of siNA is visualized using a fluorescent microscope.

TAQMAN® (Real-Time PCR Monitoring of Amplification) and Lightcycler Quantification of mRNA Total RNA is prepared from cells following siNA delivery, for example, using Qiagen RNA purification kits for 6-well or Rneasy extraction kits for 96-well assays. For TAQMAN® analysis (real-time PCR monitoring of amplification), dual-labeled probes are synthesized with the reporter dye, FAM or JOE, covalently linked at the 5'-end and the quencher dye TAMRA conjugated to the 3'-end. One-step RT-PCR amplifications are performed on, for example, an ABI PRISM 7700 Sequence Detector using 50 µl reactions consisting of 10 µl total RNA, 100 nM forward primer, 900 nM reverse primer, 100 nM probe, 1× TaqMan PCR reaction buffer (PE-Applied Biosystems), 5.5 mM MgCl$_2$, 300 µM each dATP, dCTP, dGTP, and dTTP, IOU RNase Inhibitor (Promega), 1.25U AMPLITAQ GOLD® (DNA polymerase) (PE-Applied Biosystems) and IOU M-MLV Reverse Transcriptase (Promega). The thermal cycling conditions can consist of 30 minutes at 48° C., 10 minutes at 95° C., followed by 40 cycles of 15 seconds at 95° C. and 1 minute at 60° C. Quantitation of mRNA levels is determined relative to standards generated from serially diluted total cellular RNA (300, 100, 33, 11 ng/rxn) and normalizing to 6-actin or GAPDH mRNA in parallel TAQMAN® reactions (real-time PCR monitoring of amplification). For each gene of interest an upper and lower primer and a fluorescently labeled probe are designed. Real time incorporation of SYBR Green I dye into a specific PCR product can be measured in glass capillary tubes using a lightcyler. A standard curve is generated for each primer pair using control cRNA. Values are represented as relative expression to GAPDH in each sample.

Western Blotting

Nuclear extracts can be prepared using a standard micro preparation technique (see for example Andrews and Faller, 1991, *Nucleic Acids Research*, 19, 2499). Protein extracts from supernatants are prepared, for example using TCA precipitation. An equal volume of 20% TCA is added to the cell supernatant, incubated on ice for 1 hour and pelleted by centrifugation for 5 minutes. Pellets are washed in acetone, dried and resuspended in water. Cellular protein extracts are run on a 10% Bis-Tris NuPage (nuclear extracts) or 4-12% Tris-Glycine (supernatant extracts) polyacrylamide gel and transferred onto nitro-cellulose membranes. Non-specific binding can be blocked by incubation, for example, with 5% non-fat milk for 1 hour followed by primary antibody for 16 hour at 4° C. Following washes, the secondary antibody is applied, for example (1:10,000 dilution) for 1 hour at room temperature and the signal detected with SuperSignal reagent (Pierce).

Example 8

Models Useful to Evaluate the Down-Regulation of GAB2 Gene Expression

Cell Culture

There are numerous cell culture systems that can be used to analyze reduction of GAB2 levels either directly or indirectly by measuring downstream effects. For example, cultured human mast cells or A549 cells can be used in cell culture experiments to assess the efficacy of nucleic acid molecules of the invention. As such, cultured human mast cells or A549 cells treated with nucleic acid molecules of the invention (e.g., siNA) targeting GAB2 RNA would be expected to have decreased GAB2 expression capacity compared to matched control nucleic acid molecules having a scrambled or inactive sequence. In a non-limiting example, human cultured human mast cells or A549 cells are cultured and GAB2 expression is quantified, for example, by time-resolved immuno fluorometric assay. GAB2 messenger-RNA expression is quantitated with RT-PCR in cultured cells. Untreated cells are compared to cells treated with siNA molecules transfected with a suitable reagent, for example, a cationic lipid such as lipofectamine, and GAB2 protein and RNA levels are quantitated. Dose response assays are then performed to establish dose dependent inhibition of GAB2 expression.

In several cell culture systems, cationic lipids have been shown to enhance the bioavailability of oligonucleotides to cells in culture (Bennet, et al., 1992, *Mol. Pharmacology*, 41, 1023-1033). In one embodiment, siNA molecules of the invention are complexed with cationic lipids for cell culture experiments. siNA and cationic lipid mixtures are prepared in serum-free DMEM immediately prior to addition to the cells. DMEM plus additives are warmed to room temperature (about 20-25° C.) and cationic lipid is added to the final desired concentration and the solution is vortexed briefly. siNA molecules are added to the final desired concentration and the solution is again vortexed briefly and incubated for 10 minutes at room temperature. In dose response experiments, the RNA/lipid complex is serially diluted into DMEM following the 10 minute incubation.

Animal Models

Evaluating the efficacy of anti-GAB2 agents in animal models is an important prerequisite to human clinical trials. Gu et al., 2002, *Nature*, 412, 186-190, have described an animal model of allergic response via GAB2. In this study, GAB2 (−/−) mice were used to elucidate the role of GAB2 in the allergic response. GAB2 (−/−) mice were viable and generally healthy; however, the response of GAB2 (−/−) mast cells to stimulation of the high affinity immunoglobulin-E (IgE) receptor FcER1 (e.g., degranulation and cytokine gene expression) was found to be defective in GAB2 (−/−) mice. Accordingly, allergic reactions such as passive cutaneous and systemic anaphylaxis are markedly impaired in the GAB2 (−/−) mice. Biochemical analyses revealed that signalling pathways dependent on PI(3)K, a critical component of FcER1 signalling, are defective in GAB2 (−/−) mast cells. Furthermore, GAB2 was identified as the principal activator of PI(3)K in response to FcER1 activation, thereby providing genetic evidence that Dos/Gab family scaffolds regulate the PI(3)K pathway in VIVO.

Furthermore, bone marrow myeloid progenitors from Gab2 (−/−) mice are resistant to transformation by BCR/ABL, whereas lymphoid transformation is diminished as a consequence of markedly increased apoptosis. BCR/ABL-evoked PI3K/Akt and Ras/Erk activation also are impaired in GAB2 (−/−) primary myeloid and lymphoid cells. Because these results identify Gab2 and its associated proteins as key determinants of the lineage and severity of BCR/ABL transformation (Sattler et al., 2002, Cancer Cell., 1, 479-492), the mouse model described by Gu et al., 2002 supra, can be used to study the effect of nucleic acid molecules of the invention toward therapeutic use in treating BCR/ABL induced cancers, such as chronic myelogenous leukemia (CML).

A such, these mouse models are useful tools for identifying compounds that modulate the activity and/or expression of GAB2 and can be used to identify nucleic acid molecules of the invention that modulate GAB2 gene expression and gene function toward therapeutic use in treating allergic conditions and various cancers, including breast cancer and chronic myelogenous leukemia.

Example 9

RNAi Mediated Inhibition of GAB2 Expression siNA constructs (Table III) are tested for efficacy in reducing GAB2 RNA expression in, for example, A549 or 293T cells. Cells are plated approximately 24 hours before transfection in 96-well plates at 5,000-7,500 cells/well, 100 µl/well, such that at the time of transfection cells are 70-90% confluent. For transfection, annealed siNAs are mixed with the transfection reagent (Lipofectamine 2000, Invitrogen) in a volume of 50 µl/well and incubated for 20 minutes at room temperature. The siNA transfection mixtures are added to cells to give a final siNA concentration of 25 nM in a volume of 150 µl. Each siNA transfection mixture is added to 3 wells for triplicate siNA treatments. Cells are incubated at 37° for 24 hours in the continued presence of the siNA transfection mixture. At 24 hours, RNA is prepared from each well of treated cells. The supernatants with the transfection mixtures are first removed and discarded, then the cells are lysed and RNA prepared from each well. Target gene expression following treatment is evaluated by RT-PCR for the target gene and for a control gene (36B4, an RNA polymerase subunit) for normalization. The triplicate data is averaged and the standard deviations determined for each treatment. Normalized data are graphed and the percent reduction of target mRNA by active siNAs in comparison to their respective inverted control siNAs is determined.

Figure 22:
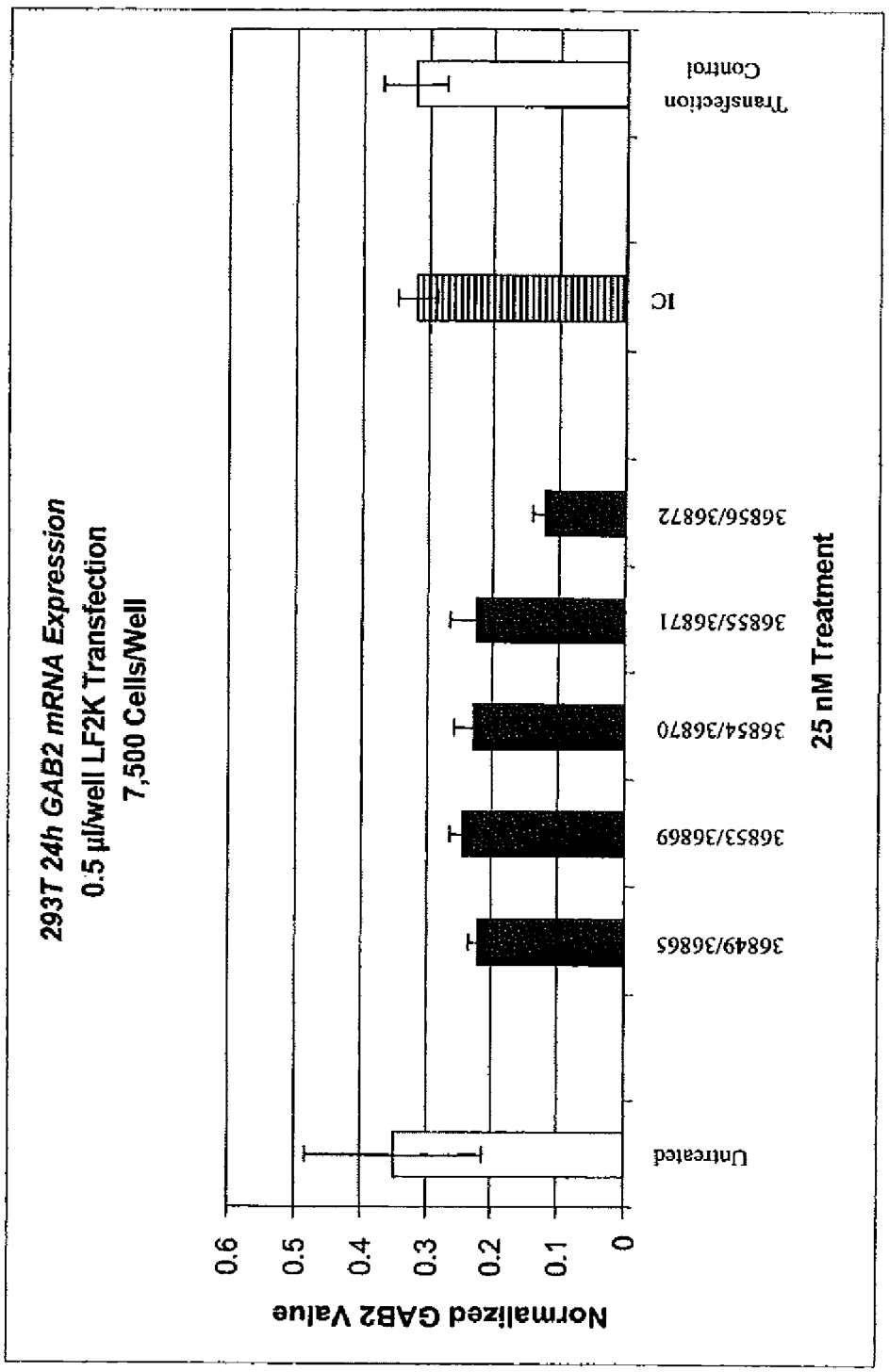
FIG. 22 shows a non-limiting example of reduction of GAB2 mRNA in 293T cells mediated by siNAs that target GAB2 mRNA. 293T cells were transfected with 0.25 ug/well of lipid complexed with 25 nM siNA. Chemically modified siNA constructs (see Table III) comprising Stab 9/22 chemistry (see Table IV) were compared to untreated cells, a matched chemistry irrelevant siNA control construct (IC), and cells transfected with lipid alone (transfection control). As shown in the figure, the siNA constructs reduce GAB2 RNA expression.

In another non-limiting example, chemically modified siNA constructs (Table III) were tested for efficacy as described above in reducing GAB2 RNA expression in 293T cells. Active siNAs were evaluated compared to untreated cells, a matched chemistry inverted control (IC), and a transfection control. Results are summarized in FIG. 22 FIG. 22 shows results for Stab 9/22 (Table IV) siNA constructs targeting various sites in GAB2 mRNA. As shown in FIG. 22, the active siNA constructs provide significant inhibition of ERG2 gene expression in cell culture experiments as determined by levels of GAB2 mRNA when compared to appropriate controls.

Example 10

Indications

Particular degenerative and disease states that can be associated with modulation of GAB2 gene expression include, but are not limited to, allergic conditions, including allergy induced asthma; allergic rhinitis; allergic dermatitis; allergic conjuctivitis; cancer, including malignant blood diseases, such as lymphomas (e.g., non-Hodgkins and Hodgkins lymphomas); leukemias (e.g., chronic myeloid leukemia, CML; acute myeloid leukemias, AML; secondary leukemias, acute lymphoblastic leukemias, ALL; chronic lymphoid leukemia; CLL); polycytemia vera; idiopathic myelofibrosis; essential thrombocythemia; myelodysplastic syndromes; autoimmune disease (e.g., multiple sclerosis, lupus, rheumatoid arthritis, insulin dependent diabetes, encephalitis, Rasmussen's encephalitis, thyroiditis, Crohn's disease, fibromyalgia, Grave's disease, Guillain Barre syndrome, chronic fatigue syndrome, autoimmune hepatitis, Meniere's disease, Myasthenia Gravis, cardiomyopathy, polymyalgia, Psoriasis, ulcerative collitis, etc.); viral infection (e.g., HIV, HCV, HBV, RSV, CMV, HSV, influenza, rhinovirus etc.); and any other diseases or conditions that are related to the levels of GAB2 in a cell or tissue, alone or in combination with other therapies. The reduction of GAB2 expression (specifically GAB2 RNA levels) and thus reduction in the level of the respective protein relieves, to some extent, the symptoms of the disease or condition.

Antihistamines, epinephrin, tyrosine kinase inhibitors, such as STI 571 (Imatinib), and chemotherapeutics, such as Gemcytabine and cyclophosphamide, are non-limiting examples of chemotherapeutic agents that can be combined with or used in conjunction with the nucleic acid molecules of the instant invention. Those skilled in the art will recognize that other drugs, such as anti-cancer compounds and therapies, can be similarly be readily combined with the nucleic acid molecules of the instant invention (e.g. siNA) and are hence within the scope of the instant invention. Such compounds and therapies are well known in the art (see for example *Cancer: Principles and Practice of Oncology*, Volumes 1 and 2, eds Devita, V. T., Hellman, S., and Rosenberg, S. A., J. B. Lippincott Company, Philadelphia, USA; incorporated herein by reference) and include, without limitations, antifolates; fluoropyrimidines; cytarabine; purine analogs; adenosine analogs; amsacrine; topoisomerase I inhibitors; anthrapyrazoles; retinoids; antibiotics such as bleomycin, anthacyclins, mitomycin C, dactinomycin, and mithramycin; hexamethylmelamine; dacarbazine; 1-asperginase; platinum analogs; alkylating agents such as nitrogen mustard, melphalan, chlorambucil, busulfan, ifosfamide, 4-hydroperoxy-cyclophosphamide, nitrosoureas, thiotepa; plant derived compounds such as vinca alkaloids, epipodophyllotoxins, taxol; Tamoxifen; radiation therapy; surgery; nutritional supplements; gene therapy; radiotherapy, such as 3D-CRT; immunotoxin therapy such as ricin, monoclonal antibodies herceptin; and the like. For combination therapy, the nucleic acids of the invention are prepared in one of two ways. First, the agents are physically combined in a preparation of nucleic acid and chemotherapeutic agent, such as a mixture of a nucleic acid of the invention encapsulated in liposomes and ifosfamide in a solution for intravenous administration, wherein both agents are present in a therapeutically effective concentration (e.g., ifosfamide in solution to deliver 1000-1250 mg/m2/day and liposome-associated nucleic acid of the invention in the same solution to deliver 0.1-100 mg/kg/day). Alternatively, the agents are administered separately but simultaneously in their respective effective doses (e.g., 1000-1250 mg/m2/d ifosfamide and 0.1 to 100 mg/kg/day nucleic acid of the invention).

Example 11

Diagnostic Uses

The siNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of siNA molecules involves utilizing reconstituted RNAi systems, for example, using cellular lysates or partially purified cellular lysates. siNA molecules of this invention can be used as diagnostic tools to examine genetic drift and mutations within diseased cells or to detect the presence of endogenous or exogenous, for example viral, RNA in a cell. The close relationship between siNA activity and the structure of the target RNA allows the detection of mutations in any region of the molecule, which alters the base-pairing and three-dimensional structure of the target RNA. By using multiple siNA molecules described in this invention, one can map nucleotide changes, which are important to RNA structure and function in vitro, as well as in cells and tissues. Cleavage of target RNAs with siNA molecules can be used to inhibit gene expression and define the role of specified gene products in the progression of disease or infection. In this manner, other genetic targets can be defined as important mediators of the disease. These experiments will lead to better treatment of the disease progression by affording the possibility of combination therapies (e.g., multiple siNA molecules targeted to different genes, siNA molecules coupled with known small molecule inhibitors, or intermittent treatment with combinations siNA molecules and/or other chemical or biological molecules). Other in vitro uses of siNA molecules of this invention are well known in the art, and include detection of the presence of mRNAs associated with a disease, infection, or related condition. Such RNA is detected by determining the presence of a cleavage product after treatment with an siNA using standard methodologies, for example, fluorescence resonance emission transfer (FRET).

In a specific example, siNA molecules that cleave only wild-type or mutant forms of the target RNA are used for the assay. The first siNA molecules (i.e., those that cleave only wild-type forms of target RNAi are used to identify wild-type RNA present in the sample and the second siNA molecules (i.e., those that cleave only mutant forms of target RNA) are used to identify mutant RNA in the sample. As reaction controls, synthetic substrates of both wild-type and mutant RNA are cleaved by both siNA molecules to demonstrate the relative siNA efficiencies in the reactions and the absence of cleavage of the "non-targeted" RNA species. The cleavage products from the synthetic substrates also serve to generate size markers for the analysis of wild-type and mutant RNAs in the sample population. Thus, each analysis requires two siNA molecules, two substrates and one unknown sample, which is combined into six reactions. The presence of cleavage products is determined using an RNase protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., disease related or infection related) is adequate to establish risk. If probes of comparable specific activity are used for both transcripts, then a qualitative comparison of RNA levels is adequate and decreases the cost of the initial diagnosis. Higher mutant form to wild-type ratios are correlated with higher risk whether RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying siNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

TABLE I

GAB2 Accession Numbers

NM_012296 *Homo sapiens* GRB2-associated binding protein 2 (GAB2), transcript variant 2, mRNA
NM_080491 *Homo sapiens* GRB2-associated binding protein 2 (GAB2), transcript variant 1, mRNA

TABLE II

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 3 | AAUUUUGAGAAGUGGUGGG | 1 | 3 | AAUUUUGAGAAGUGGUGGG | 1 | 25 | CCCACCACUUCUCAAAAUU | 337 |
| 21 | GAUGAAGAAGAUCCCUGAA | 2 | 21 | GAUGAAGAAGAUCCCUGAA | 2 | 43 | UUCAGGGAUCUUCUUCAUC | 338 |
| 39 | GAUGAAGAAGAUCCCUGAA | 3 | 39 | AGAGAGGAGUAACUGAGAC | 3 | 61 | GUCUCAGUUACUCCUCUCU | 339 |
| 57 | CAAAGGCGAGGCUAGCAAU | 4 | 57 | CAAAGGCGAGGCUAGCAAU | 4 | 79 | AUUGCUAGCCUCGCCUUUG | 340 |
| 75 | UAGAGAGACAAGUGAGGGA | 5 | 75 | UAGAGAGACAAGUGAGGGA | 5 | 97 | UCCCUCACUUGUCUCUCUA | 341 |
| 93 | AAUUAGACCUUUGGUAUCA | 6 | 93 | AAUUAGACCUUUGGUAUCA | 6 | 115 | UGAUACCAAAGGUCUAAUU | 342 |
| 111 | AUCAUGAAAAGGCCUGGAA | 7 | 111 | AUCAUGAAAAGGCCUGGAA | 7 | 133 | UUCCAGGCCUUUUCAUGAU | 343 |
| 129 | AGAAACGCUGGUUUAUCCU | 8 | 129 | AGAAACGCUGGUUUAUCCU | 8 | 151 | AGGAUAAACCAGCGUUUCU | 344 |
| 147 | UGCGGAGUGGCCGGAUGAG | 9 | 147 | UGCGGAGUGGCCGGAUGAG | 9 | 169 | CUCAUCCGGCCACUCCGCA | 345 |
| 165 | GCGGUGACCCAGAUGUUCU | 10 | 165 | GCGGUGACCCAGAUGUUCU | 10 | 187 | AGAACAUCUGGGUCACCGC | 346 |
| 183 | UGGAAUACUACAAGAACGA | 11 | 183 | UGGAAUACUACAAGAACGA | 11 | 205 | UCGUUCUUGUAGUAUUGCA | 347 |
| 201 | AUCACUCCAAGAAGCCUCU | 12 | 201 | AUCACUCCAAGAAGCCUCU | 12 | 223 | AGAGGCUUCUUGGAGUGAU | 348 |
| 219 | UGCGGAUCAUCAACCUGAA | 13 | 219 | UGCGGAUCAUCAACCUGAA | 13 | 241 | UUCAGGUUGAUGAUCCGCA | 349 |
| 237 | ACUUCUGUGAGCAGGUAGA | 14 | 237 | ACUUCUGUGAGCAGGUAGA | 14 | 259 | UCUACCUGCUCACAGAAGU | 350 |
| 255 | AUGCAGGCCUGACCUUUAA | 15 | 255 | AUGCAGGCCUGACCUUUAA | 15 | 277 | UUAAAGGUCAGGCCUGCAU | 351 |
| 273 | ACAAGAAGGAGCUGCAGGA | 16 | 273 | ACAAGAAGGAGCUGCAGGA | 16 | 295 | UCCUGCAGCUCCUUCUUGU | 352 |
| 291 | AUAGUUUUGUGUUUGACAU | 17 | 291 | AUAGUUUUGUGUUUGACAU | 17 | 313 | AUGUCAAACACAAAACUAU | 353 |
| 309 | UCAAGACCAGUGAACGCAC | 18 | 309 | UCAAGACCAGUGAACGCAC | 18 | 331 | GUGCGUUCACUGGUCUUGA | 354 |
| 327 | CCUUUUACCUGGUGGCUGA | 19 | 327 | CCUUUUACCUGGUGGCUGA | 19 | 349 | UCAGCCACCAGGUAAAAGG | 355 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 345 | AGACAGAAGAGGACAUGAA | 20 | 345 | AGACAGAAGAGGACAUGAA | 20 | 367 | UUCAUGUCCUCUUCUGUCU | 356 |
| 363 | AUAAGUGGGUCCAGAGCAU | 21 | 363 | AUAAGUGGGUCCAGAGCAU | 21 | 385 | AUGCUCUGGACCCACUUAU | 357 |
| 381 | UCUGCCAGAUCUGUGGCUU | 22 | 381 | UCUGCCAGAUCUGUGGCUU | 22 | 403 | AAGCCACAGAUCUGGCAGA | 358 |
| 399 | UCAAUCAGGCUGAGGAGAG | 23 | 399 | UCAAUCAGGCUGAGGAGAG | 23 | 421 | CUCUCCUCAGCCUGAUUGA | 359 |
| 417 | GCACAGACUCCCUGAGAAA | 24 | 417 | GCACAGACUCCCUGAGAAA | 24 | 439 | UUUCUCAGGGAGUCUGUGC | 360 |
| 435 | AUGUUUCCUCAGCCGGUCA | 25 | 435 | AUGUUUCCUCAGCCGGUCA | 25 | 457 | UGACCGGCUGAGGAAACAU | 361 |
| 453 | AUGGCCCCCGCUCUUCUCC | 26 | 453 | AUGGCCGCCGCUCUUCUCC | 26 | 475 | GGAGAAGAGCGGGGGCCAU | 362 |
| 471 | CAGCUGAGCUCAGCAGCUC | 27 | 471 | CAGCUGAGCUCAGCAGCUC | 27 | 493 | GAGCUGCUGAGCUCAGCUG | 363 |
| 489 | CUAGCCAGCACCUUCUCCG | 28 | 489 | CUAGCCAGCACCUUCUCCG | 28 | 511 | CGGAGAAGGUGCUGGCUAG | 364 |
| 507 | GAGAGCGCAAGUCCUCAGC | 29 | 507 | GAGAGCGCAAGUCCUCAGC | 29 | 529 | GCUGAGGACUUGCGCUCUC | 365 |
| 525 | CCCCAUCACACUCCAGCCA | 30 | 525 | CCCCAUCACACUCCAGCCA | 30 | 547 | UGGCUGGAGUGUGAUGGGG | 366 |
| 543 | AGCCAACUCUGUUCACGUU | 31 | 543 | AGCCAACUCUGUUCACGUU | 31 | 565 | AACGUGAACAGAGUUGGCU | 367 |
| 561 | UUGAACCCCUGUGUCAAA | 32 | 561 | UUGAACCCCCUGUGUCAAA | 32 | 583 | UUUGACACAGGGGGUUCAA | 368 |
| 579 | ACCACAUGCAGCCCACCUU | 33 | 579 | ACCACAUGCAGCCCACCUU | 33 | 601 | AAGGUGGGCUGCAUGUGGU | 369 |
| 597 | UGUCCACCAGCGCACCUCA | 34 | 597 | UGUCCACCAGCGCACCUCA | 34 | 619 | UGAGGUGCGCUGGUGGACA | 370 |
| 615 | AGGAGUAUCUCUACUUGCA | 35 | 615 | AGGAGUAUCUCUACUUGCA | 35 | 637 | UGCAAGUAGAGAUACUCCU | 371 |
| 633 | ACCAGUGCAUAAGCCGAAG | 36 | 633 | ACCAGUGCAUAAGCCGAAG | 36 | 655 | CUUCGGCUUAUGCACUGGU | 372 |
| 651 | GAGCAGAAAAUGCAAGGAG | 37 | 651 | GAGCAGAAAAUGCAAGGAG | 37 | 673 | CUCCUUGCAUUUUCUGCUC | 373 |
| 669 | GUGCCAGCUUCUCUCAGGG | 38 | 669 | GUGCCAGCUUCUCUCAGGG | 38 | 691 | CCCUGAGAGAAGCUGGCAC | 374 |
| 687 | GCACCAGAGCCUCUUUUCU | 39 | 687 | GCACCAGAGCCUCUUUUCU | 39 | 709 | AGAAAAGAGGCUCUGGUGC | 375 |
| 705 | UCAUGAGGAGUGACACAGC | 40 | 705 | UCAUGAGGAGUGACACAGC | 40 | 727 | GCUGUGUCACUCCUCAUGA | 376 |
| 723 | CUGUACAAAAACUUGCCCA | 41 | 723 | CUGUACAAAAACUUGCCCA | 41 | 745 | UGGGCAAGUUUUUGUACAG | 377 |
| 741 | AGGGCAAUGGACACUGUGU | 42 | 741 | AGGGCAAUGGACACUGUGU | 42 | 763 | ACACAGUGUCCAUUGCCCU | 378 |
| 759 | UCAACGGGAUCAGUGGUCA | 43 | 759 | UCAACGGGAUCAGUGGUCA | 43 | 781 | UGACCACUGAUCCCGUUGA | 379 |
| 777 | AAGUCCAUGGCUUCUAUAG | 44 | 777 | AAGUCCAUGGCUUCUAUAG | 44 | 799 | CUAUAGAAGCCAUGGACUU | 380 |
| 795 | GCCUUCCCAAGCCGAGCCG | 45 | 795 | GCCUUCCCAAGCCGAGCCG | 45 | 817 | CGGCUCGGCUUGGGAAGGC | 381 |
| 813 | GGCACAAUACAGAAUUCAG | 46 | 813 | GGCACAAUACAGAAUUCAG | 46 | 835 | CUGAAUUCUGUAUUGUGCC | 382 |
| 831 | GAGACAGUACCUACGACCU | 47 | 831 | GAGACAGUACCUACGACCU | 47 | 853 | AGGUGGUAGGUACUGUCUC | 383 |
| 849 | UCCCCGCAGCCUGGCUC | 48 | 849 | UCCCCCGCAGCCUGGCCUC | 48 | 871 | GAGGCCAGGCUGCGGGGA | 384 |
| 867 | CCCAUGGCCACACCAAGGG | 49 | 867 | CCCAUGGCCACACCAAGGG | 49 | 889 | CCCUUGGUGUGGCCAUGGG | 385 |
| 885 | GCAGCCUCACAGGCUCCGA | 50 | 885 | GCAGCCUCACAGGCUCCGA | 50 | 907 | UCGGAGCCUGUGAGGCUGC | 386 |
| 903 | AGACAGAUAAUGAGGAUGU | 51 | 903 | AGACAGAUAAUGAGGAUGU | 51 | 925 | ACAUCCUCAUUAUCUGUCU | 387 |
| 921 | UGUACACCUUCAAGACGCC | 52 | 921 | UGUACACCUUCAAGACGCC | 52 | 943 | GGCGUCUUGAAGGUGUACA | 388 |
| 939 | CCAGCAACACCCUGUGCAG | 53 | 939 | CCAGCAACACCCUGUGCAG | 53 | 961 | CUGCACAGGGUGUUGCUGG | 389 |
| 957 | GGGAGUUCGGGGACCUCCU | 54 | 957 | GGGAGUUCGGGGACCUCCU | 54 | 979 | AGGAGGUCCCCGAACUCCC | 390 |
| 975 | UGGUAGACAAUAUGGAUGU | 55 | 975 | UGGUAGACAAUAUGGAUGU | 55 | 997 | ACAUCCAUAUUGUCUACCA | 391 |
| 993 | UUCCGGCCACCCCACUCUC | 56 | 993 | UUCCGGCCACCCCACUCUC | 56 | 1015 | GAGAGUGGGGUGGCCGGAA | 392 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 1011 | CAGCCUACCAGAUCCCUAG | 57 | 1011 | CAGCCUACCAGAUCCCUAG | 57 | 1033 | CUAGGGAUCUGGUAGGCUG | 393 |
| 1029 | GGACAUUCACUCUGGACAA | 58 | 1029 | GGACAUUCACUCUGGACAA | 58 | 1051 | UUGUCCAGAGUGAAUGUCC | 394 |
| 1047 | AAAACCACAAUGCCAUGAC | 59 | 1047 | AAAACCACAAUGCCAUGAC | 59 | 1069 | GUCAUGGCAUUGUGGUUUU | 395 |
| 1065 | CAGUGGCCACUCCUGGGGA | 60 | 1065 | CAGUGGCCACUCCUGGGGA | 60 | 1087 | UCCCCAGGAGUGGCCACUG | 396 |
| 1083 | ACUCAGCCAUAGCUCCCCC | 61 | 1083 | ACUCAGCCAUAGCUCCCCC | 61 | 1105 | GGGGGAGCUAUGGCUGAGU | 397 |
| 1101 | CACCCCGCCCCCCCAAGCC | 62 | 1101 | CACCCCGCCCCCCCAAGCC | 62 | 1123 | GGCUUGGGGGGCGGGGUG | 398 |
| 1119 | CAAGUCAGGCAGAAACACC | 63 | 1119 | CAAGUCAGGCAGAAACACC | 63 | 1141 | GGUGUUUCUGCCUGACUUG | 399 |
| 1137 | CUCGAUGGGGCAGUCCUCA | 64 | 1137 | CUCGAUGGGGCAGUCCUCA | 64 | 1159 | UGAGGACUGCCCCAUCGAG | 400 |
| 1155 | AGCAGAGACCGCCAAUCAG | 65 | 1155 | AGCAGAGACCGCCAAUCAG | 65 | 1177 | CUGAUUGGCGGUCUCUGCU | 401 |
| 1173 | GUGAAAAUAGCAGAUCUGU | 66 | 1173 | GUGAAAAUAGCAGAUCUGU | 66 | 1195 | ACAGAUCUGCUAUUUUCAC | 402 |
| 1191 | UCGCUGCCAGCAUCCCCAG | 67 | 1191 | UCGCUGCCACCAUCCCCAG | 67 | 1213 | CUGGGGAUGGUGGCAGCGA | 403 |
| 1209 | GACGCAACACCCUCCCUGC | 68 | 1209 | GACGCAACACCCUCCCUGC | 68 | 1231 | GCAGGGAGGGUGUUGCGUC | 404 |
| 1227 | CAAUGGACAACAGCCGACU | 69 | 1227 | CAAUGGACAACAGCCGACU | 69 | 1249 | AGUCGGCUGUUGUCCAUUG | 405 |
| 1245 | UUCACCGAGCUUCUUCCUG | 70 | 1245 | UUCACCGAGCUUCUUCCUG | 70 | 1267 | CAGGAAGAAGCUCGGUGAA | 406 |
| 1263 | GUGAGACCUACGAGUACCC | 71 | 1263 | GUGAGACCUACGAGUACCC | 71 | 1285 | GGGUACUCGUAGGUCUCAC | 407 |
| 1281 | CACAGCGUGGUGGAGAGAG | 72 | 1281 | CACAGCGUGGUGGAGAGAG | 72 | 1303 | CUCUCUCCACCACGCUGUG | 408 |
| 1299 | GUGCAGGCCGGUCUGCUGA | 73 | 1299 | GUGCAGGCCGGUCUGCUGA | 73 | 1321 | UCAGCAGACCGGCCUGCAC | 409 |
| 1317 | AAUCCAUGAGUGAUGGAGU | 74 | 1317 | AAUCCAUGAGUGAUGGAGU | 74 | 1339 | ACUCCAUCACUCAUGGAUU | 410 |
| 1335 | UUGGCUCUUUCCUGCCAGG | 75 | 1335 | UUGGCUCUUUCCUGCCAGG | 75 | 1357 | CCUGGCAGGAAAGAGCCAA | 411 |
| 1353 | GGAAAAUGAUUGUGGGCCG | 76 | 1353 | GGAAAAUGAUUGUGGGCCG | 76 | 1375 | CGGCCCACAAUCAUUUUCC | 412 |
| 1371 | GAUCGGACAGCACCAAUUC | 77 | 1371 | GAUCGGACAGCACCAAUUC | 77 | 1393 | GAAUUGGUGCUGUCCGAUC | 413 |
| 1389 | CUGAAGACAACUAUGUGCC | 78 | 1389 | CUGAAGACAACUAUGUGCC | 78 | 1411 | GGCACAUAGUUGUCUUCAG | 414 |
| 1407 | CCAUGAAUCCAGGUUCUUC | 79 | 1407 | CCAUGAAUCCAGGUUCUUC | 79 | 1429 | GAAGAACCUGGAUUCAUGG | 415 |
| 1425 | CCACCCUGUUGGCCAUGGA | 80 | 1425 | CCACCCUGUUGGCCAUGGA | 80 | 1447 | UCCAUGGCCAACAGGGUGG | 416 |
| 1443 | AACGAGCAGGUGAUAAUUC | 81 | 1443 | AACGAGCAGGUGAUAAUUC | 81 | 1465 | GAAUUAUCACCUGCUCGUU | 417 |
| 1461 | CCCAGAGCGUCUACAUCCC | 82 | 1461 | CCCAGAGCGUCUACAUCCC | 82 | 1483 | GGGAUGUAGACGCUCUGGG | 418 |
| 1479 | CAAUGAGCCCAGGGGCCCA | 83 | 1479 | CAAUGAGCCCAGGGGCCCA | 83 | 1501 | UGGGCCCCUGGGCUCAUUG | 419 |
| 1497 | AUCACUUUGACUCACUUGG | 84 | 1497 | AUCACUUUGACUCACUUGG | 84 | 1519 | CCAAGUGAGUCAAAGUGAU | 420 |
| 1515 | GCUACCCAUCAACAACCCU | 85 | 1515 | GCUACCCAUCAACAACCCU | 85 | 1537 | AGGGUUGUUGAUGGGUAGC | 421 |
| 1533 | UUCCUGUGCACCGAGGCCC | 86 | 1533 | UUCCUGUGCACCGAGGCCC | 86 | 1555 | GGGCCUCGGUGCACAGGAA | 422 |
| 1551 | CCAGCAGAGGAAGUGAAU | 87 | 1551 | CCAGCAGAGGAAGUGAGAU | 87 | 1573 | AUCUCACUUCCUCUGCUGG | 423 |
| 1569 | UUCAGCCACCCCCUGUCAA | 88 | 1569 | UUCAGCCACCCCCUGUCAA | 88 | 1591 | UUGACAGGGGGUGGCUGAA | 424 |
| 1587 | ACCGCAACCUCAAACCUGA | 89 | 1587 | ACCGCAACCUCAAACCUGA | 89 | 1609 | UCAGGUUUGAGGUUGCGGU | 425 |
| 1605 | AUCGGAAAGCAAAGCCAAC | 90 | 1605 | AUCGGAAAGCAAAGCCAAC | 90 | 1627 | GUUGGCUUUGCUUUCCGAU | 426 |
| 1623 | CACCACUUGACCUGAGGAA | 91 | 1623 | CACCACUUGACCUGAGGAA | 91 | 1645 | UUCCUCAGGUCAAGUGGUG | 427 |
| 1641 | ACAACACCGUCAUCGAUGA | 92 | 1641 | ACAACACCGUCAUCGAUGA | 92 | 1663 | UCAUCGAUGACGGUGUUGU | 428 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 1659 | AACUCCCCUUCAAGUCACC | 93 | 1659 | AACUCCCCUUCAAGUCACC | 93 | 1681 | GGUGACUUGAAGGGGAGUU | 429 |
| 1677 | CUAUCACCAAGUCUUGGUC | 94 | 1677 | CUAUCACCAAGUCUUGGUC | 94 | 1699 | GACCAAGACUUGGUGAUAG | 430 |
| 1695 | CUAGGGCCAACCACACCUU | 95 | 1695 | CUAGGGCCAACCACACCUU | 95 | 1717 | AAGGUGUGGUUGGCCCUAG | 431 |
| 1713 | UCAACUCCAGCUCCUCCCA | 96 | 1713 | UCAACUCCAGCUCCUCCCA | 96 | 1735 | UGGGAGGAGCUGGAGUUGA | 432 |
| 1731 | AGUACUGCCGCCCCAUCUC | 97 | 1731 | AGUACUGCCGCCCCAUCUC | 97 | 1753 | GAGAUGGGGCGGCAGUACU | 433 |
| 1749 | CCACCCAGAGCAUCACCAG | 98 | 1749 | CCACCCAGAGCAUCACCAG | 98 | 1771 | CUGGUGAUGCUCUGGGUGG | 434 |
| 1767 | GCACAGACUCAGGAGACAG | 99 | 1767 | GCACAGACUCAGGAGACAG | 99 | 1789 | CUGUCUCCUGAGUCUGUGC | 435 |
| 1785 | GCGAAGAGAACUAUGUCCC | 100 | 1785 | GCGAAGAGAACUAUGUCCC | 100 | 1807 | GGGACAUAGUUCUCUUCGC | 436 |
| 1803 | CUAUGCAAAACCCAGUGUC | 101 | 1803 | CUAUGCAAAACCCAGUGUC | 101 | 1825 | GACACUGGGUUUUGCAUAG | 437 |
| 1821 | CUGCAUCUCCCGUUCCCAG | 102 | 1821 | CUGCAUCUCCCGUUCCCAG | 102 | 1843 | CUGGGAACGGGAGAUGCAG | 438 |
| 1839 | GUGGCACGAACAGUCCUGC | 103 | 1839 | GUGGCACGAACAGUCCUGC | 103 | 1861 | GCAGGACUGUUCGUGCCAC | 439 |
| 1857 | CCCCUAAGAAGAGCACCGG | 104 | 1857 | CCCCUAAGAAGAGCACCGG | 104 | 1879 | CCGGUGCUCUUCUUAGGGG | 440 |
| 1875 | GCAGCGUUGAUUAUCUGG | 105 | 1875 | GCAGCGUUGAUUAUCUGG | 105 | 1897 | GCCAGAUAAUCAACGCUGC | 441 |
| 1893 | CCCUGGACUUCCAGCCGAG | 106 | 1893 | CCCUGGACUUCCAGCCGAG | 106 | 1915 | CUCGGCUGGAAGUCCAGGG | 442 |
| 1911 | GCUCCCCAAGCCCCCACCG | 107 | 1911 | GCUCCCCAAGCCCCCACCG | 107 | 1933 | CGGUGGGGGCUUGGGGAGC | 443 |
| 1929 | GCAAGCCAUCUACUUCAUC | 108 | 1929 | GCAAGCCAUCUACUUCAUC | 108 | 1951 | GAUGAAGUAGAUGGCUUGC | 444 |
| 1947 | CCGUCACCUCUGAUGAGAA | 109 | 1947 | CCGUCACCUCUGAUGAGAA | 109 | 1969 | UUCUCAUCAGAGGUGACGG | 445 |
| 1965 | AGGUGGACUACGUUCAGGU | 110 | 1965 | AGGUGGACUACGUUCAGGU | 110 | 1987 | ACCUGAACGUAGUCCACCU | 446 |
| 1983 | UGGACAAGGAGAAGACCCA | 111 | 1983 | UGGACAAGGAGAAGACCCA | 111 | 2005 | UGGGUCUUCUCCUUGUCCA | 447 |
| 2001 | AGGCCCUGCAGAACACCAU | 112 | 2001 | AGGCCCUGCAGAACACCAU | 112 | 2023 | AUGGUGUUCUGCAGGGCCU | 448 |
| 2019 | UGCAGGAGUGGACAGACGU | 113 | 2019 | UGCAGGAGUGGACAGACGU | 113 | 2041 | ACGUCUGUCCACUCCUGCA | 449 |
| 2037 | UGCGGCAGUCCUCAGAGCC | 114 | 2037 | UGCGGCAGUCCUCAGAGCC | 114 | 2059 | GGCUCUGAGGACUGCCGCA | 450 |
| 2055 | CUUCCAAGGGUGCCAAGCU | 115 | 2055 | CUUCCAAGGGUGCCAAGCU | 115 | 2077 | AGCUUGGCACCCUUGGAAG | 451 |
| 2073 | UGUGAUGAGAGGGCCACCG | 116 | 2073 | UGUGAUGAGAGGGCCACCG | 116 | 2095 | CGGUGGCCCUCUCAUCACA | 452 |
| 2091 | GCAGAGCCCAGGAGGCAGC | 117 | 2091 | GCAGAGCCCAGGAGGCAGC | 117 | 2113 | GCUGCCUCCUGGGCUCUGC | 453 |
| 2109 | CAUCUCCAGAGCUGGCCCU | 118 | 2109 | CAUCUCCAGAGCUGGCCCU | 118 | 2131 | AGGGCCAGCUCUGGAGAUG | 454 |
| 2127 | UUCCCAUCUCCCCUCUCCC | 119 | 2127 | UUCCCAUCUCCCCUCUCCC | 119 | 2149 | GGGAGAGGGGAGAUGGGAA | 455 |
| 2145 | CCUCUCCCGUUCUUCCUCC | 120 | 2145 | CCUCUCCCGUUCUUCCUCC | 120 | 2167 | GGAGGAAGAACGGGAGAGG | 456 |
| 2163 | CCAUCCACCUCCUCUCUAC | 121 | 2163 | CCAUCCACCUCCUCUCUAC | 121 | 2185 | GUAGAGAGGAGGUGGAUGG | 457 |
| 2181 | CUCUGCCAGUCUCAGCCUU | 122 | 2181 | CUCUGCCAGUCUCAGCCUU | 122 | 2203 | AAGGCUGAGACUGGCAGAG | 458 |
| 2199 | UCAAAGCACUUGACAUCAG | 123 | 2199 | UCAAAGCACUUGACAUCAG | 123 | 2221 | CUGAUGUCAAGUGCUUUGA | 459 |
| 2217 | GGGACCCUGAACCCUUCCC | 124 | 2217 | GGGACCCUGAACCCUUCCC | 124 | 2239 | GGGAAGGGUUCAGGGUCCC | 460 |
| 2235 | CCUGGGAGGUGAGGGCCUG | 125 | 2235 | CCUGGGAGGUGAGGGCCUG | 125 | 2257 | CAGGCCCUCACCUCCCAGG | 461 |
| 2253 | GAUCAAGGCACCUCCUCUG | 126 | 2253 | GAUCAAGGCACCUCCUCUG | 126 | 2275 | CAGAGGAGGUGCCUUGAUC | 462 |
| 2271 | GCCCACUCGGGGCCCAGCU | 127 | 2271 | GCCCACUCGGGGCCCAGCU | 127 | 2293 | AGCUGGGCCCCGAGUGGGC | 463 |
| 2289 | UGUGAUUUUAUCAGUAAU | 128 | 2289 | UGUGAUUUUAUCAGUAAU | 128 | 2311 | AUUACUGAUAAAAAUCACA | 464 |
| 2307 | UGGCCAUGCCUCCACCCAC | 129 | 2307 | UGGCCAUGCCUCCACCCAC | 129 | 2329 | GUGGGUGGAGGCAUGGCCA | 465 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 2325 | CCUUAGUUAGGAGCUACUU | 130 | 2325 | CCUUAGUUAGGAGCUACUU | 130 | 2347 | AAGUAGCUCCUAACUAAGG | 466 |
| 2343 | UCCAAAAAGCAUCCUUCAG | 131 | 2343 | UCCAAAAAGCAUCCUUCAG | 131 | 2365 | CUGAAGGAUGCUUUUUGGA | 467 |
| 2361 | GCCUCUUCCUGUCCUUUAG | 132 | 2361 | GCCUCUUCCUGUCCUUUAG | 132 | 2383 | CUAAAGGACAGGAAGAGGC | 468 |
| 2379 | GACCUGACUCUCUACCAGA | 133 | 2379 | GACCUGACUCUCUACCAGA | 133 | 2401 | UCUGGUAGAGAGUCAGGUC | 469 |
| 2397 | AUGUUUGGAGGGAAGGGCU | 134 | 2397 | AUGUUUGGAGGGAAGGGCU | 134 | 2419 | AGCCCUUCCCUCCAAACAU | 470 |
| 2415 | UGGGGCUCUGAGCCAGAUU | 135 | 2415 | UGGGGCUCUGAGCCAGAUU | 135 | 2437 | AAUCUGGCUCAGAGCCCCA | 471 |
| 2433 | UCCACACCUCACGUUCAGU | 136 | 2433 | UCCACACCUCACGUUCAGU | 136 | 2455 | ACUGAACGUGAGGUGUGGA | 472 |
| 2451 | UCACAGCCCUCAGCUAUCU | 137 | 2451 | UCACAGCCCUCAGCUAUCU | 137 | 2473 | AGAUAGCUGAGGGCUGUGA | 473 |
| 2469 | UUCCCUCCGGCCACUGGGC | 138 | 2469 | UUCCCUCCGGCCACUGGGC | 138 | 2491 | GCCCAGUGGCCGGAGGGAA | 474 |
| 2487 | CUACCUCUCCUUCAGUCCC | 139 | 2487 | CUACCUCUCCUUCAGUCCC | 139 | 2509 | GGGACUGAAGGAGAGGUAG | 475 |
| 2505 | CAGAAGACAAGUCUCACCA | 140 | 2505 | CAGAAGACAAGUCUCACCA | 140 | 2527 | UGGUGAGACUUGUCUUCUG | 476 |
| 2523 | AACCCAGGGAGUCAAGGAC | 141 | 2523 | AACCCAGGGAGUCAAGGAC | 141 | 2545 | GUCCUUGACUCCCUGGGUU | 477 |
| 2541 | CCAGCAAACCAAAGUGGAU | 142 | 2541 | CCAGCAAACCAAAGUGGAU | 142 | 2563 | AUCCACUUUGGUUUGCUGG | 478 |
| 2559 | UAAUGGACUUUUUCAUUCC | 143 | 2559 | UAAUGGACUUUUUCAUUCC | 143 | 2581 | GGAAUGAAAAAGUCCAUUA | 479 |
| 2577 | CUGUUUUUCUUGGCAGGAG | 144 | 2577 | CUGUUUUUCUUGGCAGGAG | 144 | 2599 | CUCCUGCCAAGAAAAACAG | 480 |
| 2595 | GAGAAGCAAGGCCACUAAA | 145 | 2595 | GAGAAGCAAGGCCACUAAA | 145 | 2617 | UUUAGUGGCCUUGCUUCUC | 481 |
| 2613 | AAGAGGAGAUGGUGGAGAC | 146 | 2613 | AAGAGGAGAUGGUGGAGAC | 146 | 2635 | GUCUCCACCAUCUCCUCUU | 482 |
| 2631 | CGGAGGCUCAGCAGUGGUC | 147 | 2631 | CGGAGGCUCAGCAGUGGUC | 147 | 2653 | GACCACUGCUGAGCCUCCG | 483 |
| 2649 | CUUGAGGGGUAAAGGACUU | 148 | 2649 | CUUGAGGGGUAAAGGACUU | 148 | 2671 | AAGUCCUUUACCCCUCAAG | 484 |
| 2667 | UAGAUGCCCAGAUGAAGAG | 149 | 2667 | UAGAUGCCCAGAUGAAGAG | 149 | 2689 | CUCUUCAUCUGGGCAUCUA | 485 |
| 2685 | GGGAAAGCUGACAUCUGCA | 150 | 2685 | GGGAAAGCUGACAUCUGCA | 150 | 2707 | UGCAGAUGUCAGCUUUCCC | 486 |
| 2703 | AGGGAACCCACUUUGAGGC | 151 | 2703 | AGGGAACCCACUUUGAGGC | 151 | 2725 | GCCUCAAAGUGGGUUCCCU | 487 |
| 2721 | CUGAGGCCAUGGCAGGACA | 152 | 2721 | CUGAGGCCAUGGCAGGACA | 152 | 2743 | UGUCCUGCCAUGGCCUCAG | 488 |
| 2739 | AGCUGCUGUGGGGUGCAGA | 153 | 2739 | AGCUGCUGUGGGGUGCAGA | 153 | 2761 | UCUGCACCCCACAGCAGCU | 489 |
| 2757 | AGGCAGAAGAUGAAGGACA | 154 | 2757 | AGGCAGAAGAUGAAGGACA | 154 | 2779 | UGUCCUUCAUCUUCUGCCU | 490 |
| 2775 | AAAAGGAAGGGAAAACUGA | 155 | 2775 | AAAAGGAAGGGAAAACUGA | 155 | 2797 | UCAGUUUUCCCUUCCUUUU | 491 |
| 2793 | AUGGCCAACCUAGAGCAGC | 156 | 2793 | AUGGCCAACCUAGAGCAGC | 156 | 2815 | GCUGCUCUAGGUUGGCCAU | 492 |
| 2811 | CAAGGAGCAGGGCUUGGAG | 157 | 2811 | CAAGGAGCAGGGCUUGGAG | 157 | 2833 | CUCCAAGCCCUGCUCCUUG | 493 |
| 2829 | GCUCGGGUGGUGGAGAUGA | 158 | 2829 | GCUCGGGUGGUGGAGAUGA | 158 | 2851 | UCAUCUCCACCACCCGAGC | 494 |
| 2847 | ACAAGGACACUGUGGGGUC | 159 | 2847 | ACAAGGACACUGUGGGGUC | 159 | 2869 | GACCCCACAGUGUCCUUGU | 495 |
| 2865 | CUGGGUCCCCAGAACUCUG | 160 | 2865 | CUGGGUCCCCAGAACUCUG | 160 | 2887 | CAGAGUUCUGGGGACCCAG | 496 |
| 2883 | GGAGCUACAGGCCACUCUA | 161 | 2883 | GGAGCUACAGGCCACUCUA | 161 | 2905 | UAGAGUGGCCUGUAGCUCC | 497 |
| 2901 | AGGCCCAAGGGCUAGUCCU | 162 | 2901 | AGGCCCAAGGGCUAGUCCU | 162 | 2923 | AGGACUAGCCCUUGGGCCU | 498 |
| 2919 | UCUUCCCCAGUCCCCUCAG | 163 | 2919 | UCUUCCCCAGUCCCCUCAG | 163 | 2941 | CUGAGGGGACUGGGGAAGA | 499 |
| 2937 | GAGGCCCCCGCCAGCCCCA | 164 | 2937 | GAGGCCCCCGCCAGCCCCA | 164 | 2959 | UGGGGCUGGCGGGGCCUC | 500 |
| 2955 | ACCUUGAAAGCAGCAUACA | 165 | 2955 | ACCUUGAAAGCAGCAUACA | 165 | 2977 | UGUAUGCUGCUUUCAAGGU | 501 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 2973 | AGGGGAAGGGUUGGACCAA | 166 | 2973 | AGGGGAAGGCUUGGACGAA | 166 | 2995 | UUGGUCCAAGCCUUCCCCU | 502 |
| 2991 | AGCUGGGCGACCAAGCACA | 167 | 2991 | AGCUGGGCGACCAAGCACA | 167 | 3013 | UGUGCUUGGUCGCCCAGCU | 503 |
| 3009 | AUGGGGCAGGAACACAUGG | 168 | 3009 | AUGGGGCAGGAACACAUGG | 168 | 3031 | CCAUGUGUUCCUGCCCCAU | 504 |
| 3027 | GUAAAGGGGUGGGGAAUAU | 169 | 3027 | GUAAAGGGGUGGGGAAUAU | 169 | 3049 | AUAUUCCCCACCCCUUUAC | 505 |
| 3045 | UGGGAGGGAGUGUGGUGUG | 170 | 3045 | UGGGAGGGAGUGUGGUGUG | 170 | 3067 | CACACCACACUCCCUCCCA | 506 |
| 3063 | GGAUGGGGUGAUGCAGGG | 171 | 3063 | GGAUGGGGUGAUGCAGGG | 171 | 3085 | CCCUGCAUCACCCCCAUCC | 507 |
| 3081 | GACUGAGGGGAACCCUGGG | 172 | 3081 | GACUGAGGGGAACCCUGGG | 172 | 3103 | CCCAGGGUUCCCCUCAGUC | 508 |
| 3099 | GACAGGCACAGGCUGGGCA | 173 | 3099 | GACAGGCACAGGCUGGGCA | 173 | 3121 | UGCCCAGCCUGUGCCUGUC | 509 |
| 3117 | AGAGGCACAGGGCAGUGCA | 174 | 3117 | AGAGGCACAGGGCAGUGCA | 174 | 3139 | UGCACUGCCCUGUGCCUCU | 510 |
| 3135 | AGGGGACUCUGCAGUGGGG | 175 | 3135 | AGGGGACUCUGCAGUGGGG | 175 | 3157 | CCCCACUGCAGAGUCCCCU | 511 |
| 3153 | GUCGGGAAGUGAGUUUCUU | 176 | 3153 | GUCGGGAAGUGAGUUUCUU | 176 | 3175 | AAGAAACUCACUUCCCGAC | 512 |
| 3171 | UUGCAGUGAGCAGUGCAGU | 177 | 3171 | UUGCAGUGAGCAGUGCAGU | 177 | 3193 | ACUGCACUGCUCACUGCAA | 513 |
| 3189 | UGGAAGUCGGGCACAGAGG | 178 | 3189 | UGGAAGUCGGGCACAGAGG | 178 | 3211 | CCUCUGUGCCCGACUUCCA | 514 |
| 3207 | GUAGCAGACAGAUGUGAAG | 179 | 3207 | GUAGCAGACAGAUGUGAAG | 179 | 3229 | CUUCACAUCUGUCUGCUAC | 515 |
| 3225 | GCAGUGGUGAAGGCCAUGU | 180 | 3225 | GCAGUGGUGAAGGCCAUGU | 180 | 3247 | ACAUGGCCUUCACCACUGC | 516 |
| 3243 | UAGCAAGUGGGGAAAUACA | 181 | 3243 | UAGCAAGUGGGGAAAUACA | 181 | 3265 | UGUAUUUCCCCACUUGCUA | 517 |
| 3261 | AUCCAAAGGGCCUGGGAGU | 182 | 3261 | AUCCAAAGGGCCUGGGAGU | 182 | 3283 | ACUCCCAGGCCCUUUGGAU | 518 |
| 3279 | UUGGGGGGUGCCCAACGCA | 183 | 3279 | UUGGGGGGUGCCCAACGCA | 183 | 3301 | UGCGUUGGGCACCCCCCAA | 519 |
| 3297 | AAUCCUUGGGGGUGCAGGG | 184 | 3297 | AAUCCUUGGGGGUGCAGGG | 184 | 3319 | CCCUGCACCCCCAAGGAUU | 520 |
| 3315 | GUGGAGCAGAAAGUGAAGG | 185 | 3315 | GUGGAGCAGAAAGUGAAGG | 185 | 3337 | CCUUCACUUUCUGCUCCAC | 521 |
| 3333 | GAGGGACACGUGCAAGAGU | 186 | 3333 | GAGGGACACGUGCAAGAGU | 186 | 3355 | ACUCUUGCACGUGUCCCUC | 522 |
| 3351 | UGGUGUGCAUGGUGGUGUG | 187 | 3351 | UGGUGUGGAUGGUGGUGUG | 187 | 3373 | CACACCACCAUGCACACCA | 523 |
| 3369 | GACAUGAGGACCGUUCCUA | 188 | 3369 | GACAUGAGGACCGUUCCUA | 188 | 3391 | UAGGAACGGUCCUCAUGUC | 524 |
| 3387 | AGGAUGGGACAGUGGGUCA | 189 | 3387 | AGGAUGGGACAGUGGGUCA | 189 | 3409 | UGACCCACUGUCCCAUCCU | 525 |
| 3405 | AGGCAGGACAAGGAGAAAG | 190 | 3405 | AGGCAGGACAAGGAGAAAG | 190 | 3427 | CUUUCUCCUUGUCCUGCCU | 526 |
| 3423 | GCAGGGCAGAAUGAUGCCU | 191 | 3423 | GCAGGGCAGAAUGAUGCCU | 191 | 3445 | AGGCAUCAUUCUGCCCUGC | 527 |
| 3441 | UAGAGGACCACAUCAGGCA | 192 | 3441 | UAGAGGACCACAUCAGGCA | 192 | 3463 | UGCCUGAUGUGGUCCUCUA | 528 |
| 3459 | AUGGCUGACAGCUUGUGCC | 193 | 3459 | AUGGCUGACAGCUUGUGCC | 193 | 3481 | GGCACAAGCUGUCAGCCAU | 529 |
| 3477 | CCAUGGGCUGUGGCGUAUG | 194 | 3477 | GCAUGGGCUGUGGCGUAUG | 194 | 3499 | CAUACGCCACAGGCGAUGG | 530 |
| 3495 | GUCAGAUCGCAGGGUAGGA | 195 | 3495 | GUCAGAUCGCAGGGUAGGA | 195 | 3517 | UCCUACCOUGCGAUCUGAC | 531 |
| 3513 | AACGAGUCUGGCCUGGUGC | 196 | 3513 | AACGAGUCUGGCCUGGUGC | 196 | 3535 | GCACCAGGCCAGACUCGUU | 532 |
| 3531 | CCGGCCCAGUGUUUCCUCA | 197 | 3531 | CCGGCCCAGUGUUUCCUCA | 197 | 3553 | UGAGGAAACACUGGGCCGG | 533 |
| 3549 | AGCUCAUCCGCCCUCUGUU | 198 | 3549 | AGCUCAUCCGCCCUCUGUU | 198 | 3571 | AACAGAGGGCGGAUGAGCU | 534 |
| 3567 | UGCUCCCUAGCAUUCCAGG | 199 | 3567 | UGCUCCCUAGCAUUCCAGG | 199 | 3589 | CCUGGAAUGCUAGGGAGCA | 535 |
| 3585 | GAGCCAUCUUGGACUCUCC | 200 | 3585 | GAGCCAUCUUGGACUCUCC | 200 | 3607 | GGAGAGUCCAAGAUGGCUC | 536 |
| 3603 | CUCCCCAGGUUUGAAAGGC | 201 | 3603 | CUCCCCAGGUUUGAAAGGC | 201 | 3625 | GCCUUUCAAACCUGGGGAG | 537 |
| 3621 | CCAUCAGAUUAGCAGGGAC | 202 | 3621 | CCAUCAGAUUAGCAGGGAC | 202 | 3643 | GUCCCUGCUAAUCUGAUGG | 538 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 3639 | CGGGGUGUAGGGCAUCACC | 203 | 3639 | CGGGGUGUAGGGCAUCACC | 203 | 3661 | GGUGAUGCCCUACACCCCG | 539 |
| 3657 | CCAAGGUUCCUUCUCUUAA | 204 | 3657 | CCAAGGUUCCUUCUCUUAA | 204 | 3679 | UUAAGAGAAGGAACCUUGG | 540 |
| 3675 | AACUAAGGGUGGGGGAUCU | 205 | 3675 | AACUAAGGGUGGGGGAUCU | 205 | 3697 | AGAUCCCCACCCUUAGUU | 541 |
| 3693 | UGAAUGUUUUAUGUUGAC | 206 | 3693 | UGAAUGUUUUUAUGUUGAC | 206 | 3715 | GUCAACAUAAAAACAUUCA | 542 |
| 3711 | CUGUUCUUGACUAAAUUUU | 207 | 3711 | CUGUUCUUGACUAAAUUUU | 207 | 3733 | AAAAUUUAGUCAAGAACAG | 543 |
| 3729 | UCAAGAGUUUCAGAAGCAA | 208 | 3729 | UCAAGAGUUUCAGAAGCAA | 208 | 3751 | UUGCUUCUGAAACUCUUGA | 544 |
| 3747 | ACAGGACAGACCAGACGUU | 209 | 3747 | AOAGGACAGACCAGACGUU | 209 | 3769 | AACGUCGGUCUGUCCUGU | 545 |
| 3765 | UUCAUUCUACCCUGGGGCG | 210 | 3765 | UUCAUUCUACCCUGGGGCG | 210 | 3787 | CGCCCCAGGGUAGAAUGAA | 546 |
| 3783 | GAACAGAACUUCUUCCUCC | 211 | 3783 | GAACAGAACUUCUUCCUCC | 211 | 3805 | GGAGGAAGAAGUUCUGUUC | 547 |
| 3801 | CCAAACAAUGACUUCCUGC | 212 | 3801 | CCAAACAAUGACUUCCUGC | 212 | 3823 | GCAGGAAGUCAUUGUUUGG | 548 |
| 3819 | CCAUGUUUGAUGGGGACAG | 213 | 3819 | CCAUGUUUGAUGGGGACAG | 213 | 3841 | CUGUCCCCAUCAAACAUGG | 549 |
| 3837 | GCUACCACUGUCCUCUGCC | 214 | 3837 | GCUACCACUGUCCUCUGCC | 214 | 3859 | GGCAGAGGACAGUGGUAGC | 550 |
| 3855 | CCCCAUUCCCCUUUCAGCU | 215 | 3855 | CCCCAUUCCCCUUUCAGCU | 215 | 3877 | AGCUGAAAGGGGAAUGGGG | 551 |
| 3873 | UCCCAUGAGCAUGCAUAGU | 216 | 3873 | UCCCAUGAGCAUGCAUAGU | 216 | 3895 | ACUAUGGAUGCUCAUGGGA | 552 |
| 3891 | UUCACCAGACCAAUGGCCU | 217 | 3891 | UUCACCAGACCAAUGGCCU | 217 | 3913 | AGGCCAUUGGUCUGGUGAA | 553 |
| 3909 | UAGCCAUUCUCUAAGUCCC | 218 | 3909 | UAGCCAUUCUCUAAGUCCC | 218 | 3931 | GGGACUUAGAGAAUGGCUA | 554 |
| 3927 | CAUCCUGGAAGAAGUUAUU | 219 | 3927 | CAUCCUGGAAGAAGUUAUU | 219 | 3949 | AAUAACUUCUUCCAGGAUG | 555 |
| 3945 | UUCUUCAAGAGCUGCACCU | 220 | 3945 | UUCUUCAAGAGCUGCACCU | 220 | 3967 | AGGUGCAGCUCUUGAAGAA | 556 |
| 3963 | UCUCCUCCUAGCAUUAGUU | 221 | 3963 | UCUCCUCCUAGCAUUAGUU | 221 | 3985 | AACUAAUGCUAGGAGGAGA | 557 |
| 3981 | UUAGAUCAACUCAAGGAGU | 222 | 3981 | UUAGAUCAACUOAAGGAGU | 222 | 4003 | ACUCCUUGAGUUGAUCUAA | 558 |
| 3999 | UAUUUAUUAAUGGCUGCUG | 223 | 3999 | UAUUUAUUAAUGGCUGCUG | 223 | 4021 | CAGCAGCCAUUAAUAAAUA | 559 |
| 4017 | GUCUCCAGUUUCUGGGGUU | 224 | 4017 | GUCUGCAGUUUGUGGGGUU | 224 | 4039 | AACCCCAGAAACUGGAGAC | 560 |
| 4035 | UAAGCACUAAGGACACAAG | 225 | 4035 | UAAGCACUAAGGACACAAG | 225 | 4057 | CUUGUGUCCUUAGUGCUUA | 561 |
| 4053 | GAAUCAAUCAGACCUUCUC | 226 | 4053 | GAAUCAAUCAGACCUUCUC | 226 | 4075 | GAGAAGGUCUGAUUGAUUC | 562 |
| 4071 | CCCUGAACUUAAGAUAGCC | 227 | 4071 | CCCUGAACUUAAGAUAGCC | 227 | 4093 | GGCUAUCUUAAGUUCAGGG | 563 |
| 4089 | CACAAUCAGAAAAGGACA | 228 | 4089 | CACAAUCAGAAAAAGGACA | 228 | 4111 | UGUCCUUUUUCUGAUUGUG | 564 |
| 4107 | AAGGACAUGAGACAGUGGU | 229 | 4107 | AAGGACAUGAGACAGUGGU | 229 | 4129 | ACCACUGUCUCAUGUCCUU | 565 |
| 4125 | UGAUGGCCAUCAGACAGAG | 230 | 4125 | UGAUGGCCAUCAGACAGAG | 230 | 4147 | CUCUGUCUGAUGGCCAUCA | 566 |
| 4143 | GACUUCAAAUGCUGAUGGA | 231 | 4143 | GACUUCAAAUGCUGAUGGA | 231 | 4165 | UCCAUCAGCAUUUGAAGUC | 567 |
| 4161 | AGGGCAGAGGAAGUACUUA | 232 | 4161 | AGGGCAGAGGAAGUACUUA | 232 | 4183 | UAAGUACUUCCUCUGCCCU | 568 |
| 4179 | AGGGAGGUUGGUGUCAGAG | 233 | 4179 | AGGGAGGUUGGUGUCAGAG | 233 | 4201 | CUCUGACACCAACCUCCCU | 569 |
| 4197 | GGCAGGAGUGGGGGAUCAG | 234 | 4197 | GGCAGGAGUGGGGGAUCAG | 234 | 4219 | CUGAUCCCCACUCCUGCC | 570 |
| 4215 | GGGAAGGUGGAUUCUAGGA | 235 | 4215 | GGGAAGGUGGAUUCUAGGA | 235 | 4237 | UCCUAGAAUCCACCUUCCC | 571 |
| 4233 | AAAAGGGAGUGCCUGAGGU | 236 | 4233 | AAAAGGGAGUGCCUGAGGU | 236 | 4255 | ACCUCAGGCACUCCCUUUU | 572 |
| 4251 | UAGGCCUUAGAAGGGGAUG | 237 | 4251 | UAGGCCUUAGAAGGGGAUG | 237 | 4273 | CAUCCCCUUCUAAGGCCUA | 573 |
| 4269 | GAGUCAGAUUUUUACAGAG | 238 | 4269 | GAGUCAGAUUUUUACAGAG | 238 | 4291 | CUCUGUAAAAAUCUGACUC | 574 |

TABLE II-continued

GAB2 siNA AND TARGET SEQUENCES
GAB2|NM_012296.2

| Pos Seq | Seq ID | UPos | Upper seq | Seq ID | LPos | Lower seq | Seq ID |
|---|---|---|---|---|---|---|---|
| 4287 GGAGGAGGGCAGGGCUUGG | 239 | 4287 | GGAGGAGGGCAGGGCUUGG | 239 | 4309 | CCAAGCCCUGCCCUCCUCC | 575 |
| 4305 GGUCCAGUGGAGGAAGAAG | 240 | 4305 | GGUCCAGUGGAGGAAGAAG | 240 | 4327 | CUUCUUCCUCCACUGGACC | 576 |
| 4323 GGAAGGAGAGGCUUGGAAA | 241 | 4323 | GGAAGGAGAGGCUUGGAAA | 241 | 4345 | UUUCCAAGCCUCUCCUUCC | 577 |
| 4341 AGCCUUGUGUCUUGGGAAA | 242 | 4341 | AGCCUUGUGUCUUGGGAAA | 242 | 4363 | UUUCCCAAGACACAAGGCU | 578 |
| 4359 AAAAAGGCCUUUGAGCAUA | 243 | 4359 | AAAAAGGCCUUUGAGCAUA | 243 | 4381 | UAUGCUCAAAGGCCUUUUU | 579 |
| 4377 AUGGGUCCAGCCACUCAGA | 244 | 4377 | AUGGGUCCAGCCACUCAGA | 244 | 4399 | UCUGAGUGGCUGGACCCAU | 580 |
| 4395 AAGUGCAGGGGCCAUGCCU | 245 | 4395 | AAGUGCAGGGGCCAUGCCU | 245 | 4417 | AGGCAUGGCCCCUGCACUU | 581 |
| 4413 UUGGUGUUCCAAUAAGUGA | 246 | 4413 | UUGGUGUUCCAAUAAGUGA | 246 | 4435 | UCACUUAUUGGAACACCAA | 582 |
| 4431 AAUGGAAGCAGUGGUGGUA | 247 | 4431 | AAUGGAAGCAGUGGUGGUA | 247 | 4453 | UACCACCACUGCUUCCAUU | 583 |
| 4449 AGCUACACUGGGCAGAGUU | 248 | 4449 | AGCUACACUGGGCAGAGUU | 248 | 4471 | AACUCUGCCCAGUGUAGCU | 584 |
| 4467 UGGCAGGGUGCUGGUUCAC | 249 | 4467 | UGGCAGGGUGCUGGUUCAC | 249 | 4489 | GUGAACCAGCACCCUGCCA | 585 |
| 4485 CUCUGCCCAGCCCUGAAUG | 250 | 4485 | CUCUGCCCAGCCCUGAAUG | 250 | 4507 | CAUUCAGGGCUGGGCAGAG | 586 |
| 4503 GUGUGCCUUAAAGGCCCCC | 251 | 4503 | GUGUGCCUUAAAGGCCCCC | 251 | 4525 | GGGGGCCUUUAAGGCACAC | 587 |
| 4521 CUACAAGGGGCCCCAUACG | 252 | 4521 | CUACAAGGGGCCCCAUACG | 252 | 4543 | CGUAUGGGGCCCCUUGUAG | 588 |
| 4539 GACAGAGCUUUUAACUGGU | 253 | 4539 | GACAGAGCUUUUAACUGGU | 253 | 4561 | ACCAGUUAAAAGCUCUGUC | 589 |
| 4557 UGCCUUCCCUGUACCCGCA | 254 | 4557 | UGCCUUCCCUGUACCCGCA | 254 | 4579 | UGCGGGUACAGGGAAGGCA | 590 |
| 4575 AGCAGCCACAAGUGGGCCC | 255 | 4575 | AGCAGCCACAAGUGGGCCC | 255 | 4597 | GGGCCCACUUGUGGCUGCU | 591 |
| 4593 CAGACUAUUGCAGCCUCCC | 256 | 4593 | CAGACUAUUGCAGCCUCCC | 256 | 4615 | GGGAGGCUGCAAUAGUCUG | 592 |
| 4611 CAUAAACAUGUGAGCAUGU | 257 | 4611 | CAUAAACAUGUGAGGAUGU | 257 | 4633 | ACAUGCUCACAUGUUUAUG | 593 |
| 4629 UUCUGAGUGUGCCAUGAUG | 258 | 4629 | UUCUGAGUGUGCCAUGAUG | 258 | 4651 | CAUCAUGGCACACUCAGAA | 594 |
| 4647 GUGAGUGGACCUGGCUGGA | 259 | 4647 | GUGAGUGGACCUGGCUGGA | 259 | 4669 | UCCAGCCAGGUCCACUCAC | 595 |
| 4665 AAUCUUCGGAGAGCGACUG | 260 | 4665 | AAUCUUCGGAGAGCGACUG | 260 | 4687 | CAGUCGCUCUCCGAAGAUU | 596 |
| 4683 GAGGUGUUCAAAUCGAAUC | 261 | 4683 | GAGGUGUUCAAAUCGAAUC | 261 | 4705 | GAUUCGAUUUGAACACCUC | 597 |
| 4701 CUCCCAGGAGGCUUCCUUC | 262 | 4701 | CUCCGAGGAGGCUUCCUUC | 262 | 4723 | GAAGGAAGCCUCCUGGGAG | 598 |
| 4719 CCAGCCCCUAUUCUGGUA | 263 | 4719 | CCAGCCCCUAUUCUGGUA | 263 | 4741 | UACCAGAAUAGGGGCUGG | 599 |
| 4737 AACUACCAGGAGGCUUCCU | 264 | 4737 | AACUACCAGGAGGCUUCCU | 264 | 4759 | AGGAAGCCUCCUGGUAGUU | 600 |
| 4755 UUCCAGCCCCUAUUCUGG | 265 | 4755 | UUCCAGCCCCUAUUCUGG | 265 | 4777 | CCAGAAUAGGGGCUGGAA | 601 |
| 4773 GUAACUACCAAAAUCCCUC | 266 | 4773 | GUAACUACCAAAAUCCCUC | 266 | 4795 | GAGGGAUUUUGGUAGUUAC | 602 |
| 4791 CGGGUGCAAGUGUAGGGGU | 267 | 4791 | CGGGUGCAAGUGUAGGGGU | 267 | 4813 | ACCCCUACACUUGCACCCG | 603 |
| 4809 UAGAGAUGGAAGGAUGAGA | 268 | 4809 | UAGAGAUGGAAGGAUGAGA | 268 | 4831 | UCUCAUCCUUCCAUCUCUA | 604 |
| 4827 AGGUGAAAUUGACCUUUUG | 269 | 4827 | AGGUGAAAUUGACCUUUUG | 269 | 4849 | CAAAAGGUCAAUUUCACCU | 605 |
| 4845 GAAAGCAAAGCUCUGGCUC | 270 | 4845 | GAAAGCAAAGCUCUGGCUC | 270 | 4867 | GAGCCAGAGCUUUGCUUUC | 606 |
| 4863 CACAGGCCCCAAACUACCA | 271 | 4863 | CACAGGCCCCAAACUACCA | 271 | 4885 | UGGUAGUUUGGGGCCUGUG | 607 |
| 4881 AGCCGUAUCUAGCAUAUCC | 272 | 4881 | AGCCGUAUCUAGCAUAUCC | 272 | 4903 | GGAUAUGCUAGAUACGGCU | 608 |
| 4899 CCCACCCUCCACCCACUAC | 273 | 4899 | CCCACCCUCCACCCACUAC | 273 | 4921 | GUAGUGGGUGGAGGGUGGG | 609 |
| 4917 CCUCCUCCAACAAAGGAGU | 274 | 4917 | CCUCCUGCAACAAAGGAGU | 274 | 4939 | ACUCCUUUGUUGGAGGAGG | 610 |
| 4935 UCAACUCAGUUGAAAAAAC | 275 | 4935 | UCAACUCAGUUGAAAAAAC | 275 | 4957 | GUUUUUUCAACUGAGUUGA | 611 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 4953 | CUGGUCCUUUGGCCUAUCC | 276 | 4953 | CUGGUCCUUUGGCCUAUCC | 276 | 4975 | GGAUAGGCCAAAGGACCAG | 612 |
| 4971 | CAUGGGUCAAAGUCCACCU | 277 | 4971 | CAUGGGUCAAAGUCCACCU | 277 | 4993 | AGGUGGACUUUGACCCAUG | 613 |
| 4989 | UCUCCUGGGGGCCUGGAGA | 278 | 4989 | UCUCCUGGGGGCCUGGAGA | 278 | 5011 | UCUCCAGGCCCCCAGGAGA | 614 |
| 5007 | AGGACUGAGCCUACGGAAA | 279 | 5007 | AGGACUGAGCCUACGGAAA | 279 | 5029 | UUUCCGUAGGCUCAGUCCU | 615 |
| 5025 | AGGGGAUACCUUCCCACUC | 280 | 5025 | AGGGGAUACCUUCCCACUC | 280 | 5047 | GAGUGGGAAGGUAUCCCCU | 616 |
| 5043 | CAGCACUGCUUCACACAGG | 281 | 5043 | CAGCACUGCUUCACACAGG | 281 | 5065 | CCUGUGUGAAGCAGUGCUG | 617 |
| 5061 | GCCCCUGCCUGGGGCUCU | 282 | 5061 | GCCCCCUGCCUGGGGCUCU | 282 | 5083 | AGAGCCCCAGGCAGGGGC | 618 |
| 5079 | UCCAAGGAGCCUUCUUCAC | 283 | 5079 | UCCAAGGAGCCUUCUUCAC | 283 | 5101 | GUGAAGAAGGCUCCUUGGA | 619 |
| 5097 | CCCACUUCCAGCUCCACUU | 284 | 5097 | CCCACUUCCAGCUCCACUU | 284 | 5119 | AAGUGGAGCUGGAAGUGGG | 620 |
| 5115 | UCUGCAAGGUUAAGUCAAG | 285 | 5115 | UCUGCAAGGUUAAGUCAAG | 285 | 5137 | CUUGACUUAACCUUGCAGA | 621 |
| 5133 | GUGAGAACGAUGAGAAAUA | 286 | 5133 | GUGAGAACGAUGAGAAAUA | 286 | 5155 | UAUUUCUCAUCGUUCUCAC | 622 |
| 5151 | AGGGAGAUGGUGUCUCCUU | 287 | 5151 | AGGGAGAUGGUGUCUCCUU | 287 | 5173 | AAGGAGACACCAUCUCCCU | 623 |
| 5169 | UAAGUCCUUGAUCUGCCUG | 288 | 5169 | UAAGUCCUUGAUCUGCCUG | 288 | 5191 | CAGGCAGAUCAAGGACUUA | 624 |
| 5187 | GUCUGUGGAAUGGGAGGUU | 289 | 5187 | GUCUGUGGAAUGGGAGGUU | 289 | 5209 | AACCUCCCAUUCCACAGAC | 625 |
| 5205 | UGGAUUAGCUGCGCUGAGG | 290 | 5205 | UGGAUUAGCUGCGCUGAGG | 290 | 5227 | CCUCAGCGCAGCUAAUCCA | 626 |
| 5223 | GUCCCAUCCACAGCUGGUG | 291 | 5223 | GUCCCAUCCACAGCUGGUG | 291 | 5245 | CACCAGCUGUGGAUGGGAC | 627 |
| 5241 | GCUCAGCUGCUUGAAGGGG | 292 | 5241 | GCUCAGCUGCUUGAAGGGG | 292 | 5263 | CCCCUUCAAGCAGCUGAGC | 628 |
| 5259 | GAGACUCCCUCCUCUGUAA | 293 | 5259 | GAGACUCCCUCCUCUGUAA | 293 | 5281 | UUACAGAGGAGGGAGUCUC | 629 |
| 5277 | ACUUCUUUCUGGGGGAUUG | 294 | 5277 | ACUUCUUUCUGGGGGAUUG | 294 | 5299 | CAAUCCCCCAGAAAGAAGU | 630 |
| 5295 | GGGGUGGGCAGUACCUAUC | 295 | 5295 | GGGGUGGGCAGUACCUAUC | 295 | 5317 | GAUAGGUACUGCCCACCCC | 631 |
| 5313 | CCCCAGUCCCCUCCUAGCU | 296 | 5313 | CCCCAGUCCCCUCCUAGCU | 296 | 5335 | AGCUAGGAGGGGACUGGGG | 632 |
| 5331 | UUGACUUUAGUGGUUUCCA | 297 | 5331 | UUGACUUUAGUGGUUUCCA | 297 | 5353 | UGGAAACCACUAAAGUCAA | 633 |
| 5349 | AAUGUAGAAGUUAACAAAG | 298 | 5349 | AAUGUAGAAGUUAACAAAG | 298 | 5371 | CUUUGUUAACUUCUACAUU | 634 |
| 5367 | GUAUGCCCCAUUCCUGUGA | 299 | 5367 | GUAUGCCCCAUUCCUGUGA | 299 | 5389 | UCACAGGAAUGGGGCAUAC | 635 |
| 5385 | ACAAAAGCACAACCAUUCU | 300 | 5385 | ACAAAAGCACAACCAUUCU | 300 | 5407 | AGAAUGGUUGUGCUUUUGU | 636 |
| 5403 | UGAAGUUACUGGAGCAUGG | 301 | 5403 | UGAAGUUACUGGAGCAUGG | 301 | 5425 | CCAUGCUCCAGUAACUUCA | 637 |
| 5421 | GGCUCAGCUCAUCCUCCCU | 302 | 5421 | GGCUCAGGUCAUCCUCCCU | 302 | 5443 | AGGGAGGAUGAGCUGAGGC | 638 |
| 5439 | UCUGGCCCCUUCUCCCAUG | 303 | 5439 | UCUGGCCCCUUCUCCCAUG | 303 | 5461 | CAUGGGAGAAGGGGCCAGA | 639 |
| 5457 | GGGGACAUCUCGGCCCAGC | 304 | 5457 | GGGGACAUCUCGGCCCAGC | 304 | 5479 | GCUGGGCCGAGAUGUCCCC | 640 |
| 5475 | CACCCCUAUCCCAUUUCCA | 305 | 5475 | CACCCCUAUCCCAUUUCCA | 305 | 5497 | UGGAAAUGGGAUAGGGGUG | 641 |
| 5493 | AGAGUUCUUCCUUCCCAU | 306 | 5493 | AGAGUUCUUCCUUCCCAU | 306 | 5515 | AUGGGGAAGGAAGAACUCU | 642 |
| 5511 | UCUGGGCCUUCAUAAAAUG | 307 | 5511 | UCUGGGCCUUGAUAAAAUG | 307 | 5533 | CAUUUUAUGAAGGCCCAGA | 643 |
| 5529 | GCAGGGGAAGCCAGACUGG | 308 | 5529 | GCAGGGGAAGCCAGACUGG | 308 | 5551 | CCAGUCUGGCUUCCCCUGC | 644 |
| 5547 | GUCUCAGGAGCGCUAAAGC | 309 | 5547 | GUCUCAGGAGCGCUAAAGC | 309 | 5569 | GCUUUAGCGCUCCUGAGAC | 645 |
| 5565 | CCCUUCCGUGGGGGGUCGU | 310 | 5565 | CCCUUCCGUGGGGGGUCGU | 310 | 5587 | ACGACCCCCCACGGAAGGG | 646 |
| 5583 | UCUUUCUGGGACUAGCCCU | 311 | 5583 | UCUUUCUGGGACUAGCCCU | 311 | 5605 | AGGGCUAGUCCCAGAAAGA | 647 |

TABLE II-continued

GAB2 siNA AND TARGET SEQUENCES
GAB2|NM_012296.2

| Pos | Seq | Seq ID | UPos | Upper seq | Seq ID | LPos | Lower seq | Seq ID |
|---|---|---|---|---|---|---|---|---|
| 5601 | UGCUGUUUAGGACCUGGGA | 312 | 5601 | UGCUGUUUAGGACCUGGGA | 312 | 5623 | UCCCAGGUCCUAAACAGCA | 648 |
| 5619 | ACCACAAUGGGGUACCUGC | 313 | 5619 | ACCACAAUGGGGUACCUGC | 313 | 5641 | GCAGGUACCCCAUUGUGGU | 649 |
| 5637 | CCGAGGGGUCCCCAAGAG | 314 | 5637 | CCGAGGGGUCCCCAAGAG | 314 | 5659 | CUCUUGGGGACCCCCUCGG | 650 |
| 5655 | GAUCCAGGCUGUCAUGUGA | 315 | 5655 | GAUCCAGGCUGUCAUGUGA | 315 | 5677 | UCACAUGACAGCUGGAUC | 651 |
| 5673 | AUUUAUGGUGGCAUGUGUU | 316 | 5673 | AUUUAUGGUGGCAUGUGUU | 316 | 5695 | AACACAUGCCACCAUAAAU | 652 |
| 5691 | UGUGUAUUUGUUGGCUACU | 317 | 5691 | UGUGUAUUUGUUGGCUACU | 317 | 5713 | AGUAGCCAACAAAUACACA | 653 |
| 5709 | UUGUGUCUUGAAAUCUAGA | 318 | 5709 | UUGUGUCUUGAAAUCUAGA | 318 | 5731 | UCUAGAUUUCAAGACACAA | 654 |
| 5727 | AAUUAUUUCACGCAGAAUU | 319 | 5727 | AAUUAUUUCACGCAGAAUU | 319 | 5749 | AAUUCUGCGUGAAAUAAUU | 655 |
| 5745 | UGUCACUGUUUGUCAGGAA | 320 | 5745 | UGUCACUGUUUGUCAGGAA | 320 | 5767 | UUCCUGACAAACAGUGACA | 656 |
| 5763 | AGAGAAAAUGGGCUAGUGG | 321 | 5763 | AGAGAAAAUGGGCUAGUGG | 321 | 5785 | CCACUAGCCCAUUUUCUCU | 657 |
| 5781 | GAAGCCCAGUCUUGAGUUC | 322 | 5781 | GAAGCCCAGUCUUGAGUUC | 322 | 5803 | GAACUCAAGACUGGGCUUC | 658 |
| 5799 | CUUGUCUUGUUACCAUUUA | 323 | 5799 | CUUGUCUUGUUACCAUUUA | 323 | 5821 | UAAAUGGUAACAAGACAAG | 659 |
| 5817 | AAAAUUGACAUUUAAUUUU | 324 | 5817 | AAAAUUGACAUUUAAUUUU | 324 | 5839 | AAAAUUAAAUGUCAAUUUU | 660 |
| 5835 | UCAAAUCACUGUUGGUGCC | 325 | 5835 | UCAAAUCACUGUUGGUGCC | 325 | 5857 | GGCACCAACAGUGAUUUGA | 661 |
| 5853 | CUAAUCACUUAAGUUAUUA | 326 | 5853 | CUAAUCACUUAAGUUAUUA | 326 | 5875 | UAAUAACUUAAGUGAUUAG | 662 |
| 5871 | AAUUUAUUCUGUUGUAUUC | 327 | 5871 | AAUUUAUUCUGUUGUAUUC | 327 | 5893 | GAAUACAACAGAAUAAAUU | 663 |
| 5889 | CUUUUUUUUAAAUUGUAAC | 328 | 5889 | CUUUUUUUUAAAUUGUAAC | 328 | 5911 | GUUACAAUUUAAAAAAAAG | 664 |
| 5907 | CAUAUUUAUCCGGUGGGUG | 329 | 5907 | CAUAUUUAUCCGGUGGGUG | 329 | 5929 | CACCCACCGGAUAAAUAUG | 665 |
| 5925 | GGGACAGGAGUGUGUUCAA | 330 | 5925 | GGGACAGGAGUGUGUUCAA | 330 | 5947 | UUGAACACACUCCUGUCCC | 666 |
| 5943 | AGUGGGUCAUGUUUUUGCU | 331 | 5943 | AGUGGGUCAUGUUUUUGCU | 331 | 5965 | AGCAAAAACAUGACCCACU | 667 |
| 5961 | UGUGGUGACACAUGGUACA | 332 | 5961 | UGUGGUGACACAUGGUACA | 332 | 5983 | UGUACCAUGUGUCACCACA | 668 |
| 5979 | AGGCUUGGAGCUUGCAGGU | 333 | 5979 | AGGCUUGGAGCUUGCAGGU | 333 | 6001 | ACCUGCAAGCUCCAAGCCU | 669 |
| 5997 | UCCCUUUCUACUGUGGUGU | 334 | 5997 | UCCCUUUCUACUGUGGUGU | 334 | 6019 | ACACCACAGUAGAAAGGGA | 670 |
| 6015 | UUGGAGCAGGACAAUAAAG | 335 | 6015 | UUGGAGCAGGACAAUAAAG | 335 | 6037 | CUUUAUUGUCCUGCUCCAA | 671 |
| 6033 | GUCCACUAGAAAUGGAGCC | 336 | 6033 | GUCCACUAGAAAUGCACCC | 336 | 6055 | GGGUGCAUUUCUAGUGGAC | 672 |

The 3'-ends of the Upper sequence and the Lower sequence of the siNA construct can include an overhang sequence, for example about 1, 2, 3, or 4 nucleotides in length, preferably 2 nucleotides in length, wherein the overhanging sequence of the lower sequence is optionally complementary to a portion of the target sequence.
The upper sequence is also referred to as the sense strand, whereas the lower sequence is also referred to as the antisense strand. The upper and lower sequences in the Table can further comprise a chemical modification having Formulae I-VII or any combination thereof.

TABLE III

GAB2 Synthetic Modified siNA Constructs

| Target Pos | Target | Seq ID | Cmpd # | Aliases | Sequence | Seq ID |
|---|---|---|---|---|---|---|
| 2679 | UGAAGAGGGAAAGCUGACAUCUG | 673 | 31541 | GAB2:2681U21 sense siNA | AAGAGGGAAAGCUGACAUCTT | 682 |
| 3651 | CAUCACCCAAGGUUCCUUCUCUU | 674 | | GAB2:3653U21 sense siNA | UCACCCAAGGUUCCUUCUCTT | 683 |

TABLE III-continued

GAB2 Synthetic Modified siNA Constructs

| Target Pos | Target | Seq ID | Cmpd # | Aliases | Sequence | Seq ID |
|---|---|---|---|---|---|---|
| 3888 | UAGUUCACCAGACCAAUGGCCUA | 675 | | GAB2:3890U21 sense siNA | GUUCACCAGACCAAUGGCCTT | 684 |
| 4546 | CUUUUAACUGGUGCCUUCCCUGU | 676 | | GAB2:4548U21 sense siNA | UUUAACUGGUGCCUUCCCUTT | 685 |
| 5004 | GAGAGGACUGAGCCUACGGAAAG | 677 | 31543 | GAB2:5006U21 sense siNA | GAGGACUGAGCCUACGGAATT | 686 |
| 5171 | AGUCCUUGAUCUGCCUGUCUGUG | 678 | | GAB2:5173U21 sense siNA | UCCUUGAUCUGCCUGUCUGTT | 687 |
| 5939 | UUCAAGUGGGUCAUGUUUUUGCU | 679 | | GAB2:5941U21 sense siNA | CAAGUGGGUCAUGUUUUUGTT | 688 |
| 5956 | UUUGCUGUGGUGACACAUGGUAC | 680 | 31544 | GAB2:5958U21 sense siNA | UGCUGUGGUGACACAUGGUTT | 689 |
| 2679 | UGAAGAGGGAAAGCUGACAUCUG | 673 | 31545 | GAB2:2699L21 antisense siNA (2681C) | GAUGUCAGCUUUCCCUCUUTT | 690 |
| 3651 | CAUCACCCAAGGUUCCUUCUCUU | 674 | | GAB2:3671L21 antisense siNA (3653C) | GAGAAGGAACCUUGGGUGATT | 691 |
| 3888 | UAGUUCACCAGACCAAUGGCCUA | 675 | | GAB2:3908L21 antisense siNA (3890C) | GGCCAUUGGUCUGGUGAACTT | 692 |
| 4546 | CUUUUAACUGGUGCCUUCCCUGU | 676 | | GAB2:4566L21 antisense siNA (4548C) | AGGGAAGGCACCAGUUAAATT | 693 |
| 5004 | GAGAGGACUGAGCCUACGGAAAG | 677 | 31547 | GAB2:5024L21 antisense siNA (5006C) | UUCCGUAGGCUCAGUCCUCTT | 694 |
| 5171 | AGUCCUUGAUCUGCCUGUCUGUG | 678 | | GAB2:5191L21 antisense siNA (5173C) | CAGACAGGCAGAUCAAGGATT | 695 |
| 5939 | UUCAAGUGGGUCAUGUUUUUGCU | 679 | | GAB2:5959L21 antisense siNA (5941C) | CAAAAACAUGACCCACUUGTT | 696 |
| 5956 | UUUGCUGUGGUGACACAUGGUAC | 680 | 31548 | GAB2:5976L21 antisense siNA (5958C) | ACCAUGUGUCACCACAGCATT | 697 |
| 2679 | UGAAGAGGGAAAGCUGACAUCUG | 673 | | GAB2:2681U21 sense siNA stab04 | B AAGAGGGAAAGcuGAcAucTT B | 698 |
| 3651 | CAUCACCCAAGGUUCCUUCUCUU | 674 | | GAB2:3653U21 sense siNA stab04 | B ucAcccAAGGuuccuucucTT B | 699 |
| 3888 | UAGUUCACCAGACCAAUGGCCUA | 675 | | GAB2:3890U21 sense siNA stab04 | B GuucAccAGAccAAuGGccTT B | 700 |
| 4546 | CUUUUAACUGGUGCCUUCCCUGU | 676 | | GAB2:4548U21 sense siNA stab04 | B uuuAAcuGGuGccuucccuTT B | 701 |
| 5004 | GAGAGGACUGAGCCUACGGAAAG | 677 | | GAB2:5006U21 sense siNA stab04 | B GAGGAcuGAGccuAcGGAATT B | 702 |
| 5171 | AGUCCUUGAUCUGCCUGUCUGUG | 678 | | GAB2:5173U21 sense siNA stab04 | B uccuuGAucuGccuGucuGTT B | 703 |

TABLE III-continued

GAB2 Synthetic Modified siNA Constructs

| Target Pos | Target | Seq ID | Cmpd # | Aliases | Sequence | Seq ID |
|---|---|---|---|---|---|---|
| 5939 | UUCAAGUGGGUCAUGUUUUUGCU | 679 | | GAB2:5941U21 sense siNA stab04 | B cAAGuGGGucAuGuuuuuGTT B | 704 |
| 5956 | UUUGCUGUGGUGACACAUGGUAC | 680 | | GAB2:5958U21 sense siNA stab04 | B uGcuGuGGuGAcAcAuGGuTT B | 705 |
| 2679 | UGAAGAGGGAAAGCUGACAUCUG | 673 | | GAB2:2699L21 antisense siNA (2681C) stab05 | GAuGucAGcuuucccucuuTsT | 706 |
| 3651 | CAUCACCCAAGGUUCCUUCUCUU | 674 | | GAB2:3671L21 antisense siNA (3653C) stab05 | GAGAAGGAAccuuGGGuGATsT | 707 |
| 3888 | UAGUUCACCAGAGCAAUGGCCUA | 675 | | GAB2:3908L21 antisense siNA (3890C) stab05 | GGccAuuGGucuGGuGAAcTsT | 708 |
| 4546 | CUUUUAACUGGUGCCUUCCCUGU | 676 | | GAB2:4566L21 antisense siNA (4548C) stab05 | AGGGAAGGcAccAGuuAAATsT | 709 |
| 5004 | GAGAGGACUGAGCCUACGGAAAG | 677 | | GAB2:5024L21 antisense siNA (5006C) stab05 | uuccGuAGGcucAGucucTsT | 710 |
| 5171 | AGUCCUUGAUCUGCCUGUCUGUG | 678 | | GAB2:5191L21 antisense siNA (5173C) stab05 | cAGAcAGGcAGAucAAGGATsT | 711 |
| 5939 | UUCAAGUGGGUCAUGUUUUUGCU | 679 | | GAB2:5959L21 antisense siNA (5941C) stab05 | cAAAAAcAuGAcccAcuuGTsT | 712 |
| 5956 | UUUGCUGUGGUGACACAUGGUAC | 680 | | GAB2:5976L21 antisense siNA (5958C) stab05 | AccAuGuGucAccAcAGcATsT | 713 |
| 2679 | UGAAGAGGGAAAGCUGACAUCUG | 673 | | GAB2:2681U21 sense siNA stab07 | B AAGAGGGAAAGcuGAcAucTT B | 714 |
| 3651 | CAUCACCCAAGGUUCCUUCUCUU | 674 | | GAB2:3653U21 sense siNA stab07 | B ucAcccAAGGuuccuucucTT B | 715 |
| 3888 | UAGUUCACCAGACCAAUGGCCUA | 675 | | GAB2.3890U21 sense siNA stab07 | B GuucAccAGAccAAuGGccTT B | 716 |
| 4546 | CUUUUAACUGGUGCCUUCCCUGU | 676 | | GAB2:4548U21 sense siNA stab07 | B uuuAAcuGGuGccuucccuTT B | 717 |
| 5004 | GAGAGGACUGAGCCUACGGAAAG | 677 | | GAB2:5006U21 sense siNA stab07 | B GAGGAcuGAGccuAcGGAATT B | 718 |
| 5171 | AGUCCUUGAUCUGCCUGUCUGUG | 678 | | GAB2:5173U21 sense siNA stab07 | B uccuuGAucuGccuGucuGTT B | 719 |
| 5939 | UUCAAGUGGGUCAUGUUUUUGCU | 679 | | GAB2:5941U21 sense siNA stab07 | B cAAGuGGGucAuGuuuuuGTT B | 720 |
| 5956 | UUUGCUGUGGUGACACAUGGUAC | 680 | 31868 | GAB2:5958U21 sense siNA stab07 | B uGcuGuGGuGAcAcAuGGuTT B | 721 |

TABLE III-continued

GAB2 Synthetic Modified siNA Constructs

| Target Pos | Target | Seq ID | Cmpd # | Aliases | Sequence | Seq ID |
|---|---|---|---|---|---|---|
| 2679 | UGAAGAGGGAAAGCUGACAUCUG | 673 | | GAB2:2699L21 antisense siNA (2681C) stab11 | GAuGucAGcuuucccucuuTsT | 722 |
| 3651 | CAUCACCCAAGGUUCCUUCUCUU | 674 | | GAB2:3671L21 antisense siNA (3653C) stab11 | GAGAAGGAAccuuGGGuGATsT | 723 |
| 3888 | UAGUUCACCAGACCAAUGGCCUA | 675 | | GAB2:3908L21 antisense siNA (3890C) stab11 | GGccAuuGGucuGGuGAAcTsT | 724 |
| 4546 | CUUUUAACUGGUGCCUUCCCUGU | 676 | | GAB2:4566L21 antisense siNA (4548C) stab11 | AGGGAAGGcAccAGuuAAATsT | 725 |
| 5004 | GAGAGGACUGAGCCUACGGAAAG | 677 | | GAB2:5024L21 antisense siNA (5006C) stab11 | uuccGuAGGcucAGuccucTsT | 726 |
| 5171 | AGUCCUUGAUCUGCCUGUCUGUG | 678 | | GAB2:5191L21 antisense siNA (5173C) stab11 | cAGAcAGGcAGAucAAGGATsT | 727 |
| 5939 | UUCAAGUGGGUCAUGUUUUUGCU | 679 | | GAB2:5959L21 antisense siNA (5941C) stab11 | cAAAAAcAuGAcccAcuuGTsT | 728 |
| 5956 | UUUGCUGUGGUGACACAUGGUAC | 680 | | GAB2:5976L21 antisense siNA (5958C) stab11 | AccAuGuGucAccAcAGcATsT | 729 |
| 2679 | UGAAGAGGGAAAGCUGACAUCUG | 673 | | GAB2:2681U21 sense siNA stab18 | B AAGAGGGAAAGcuGAcAucTT B | 730 |
| 3651 | CAUCACCCAAGGUUCCUUCUCUU | 674 | | GAB2:3653U21 sense siNA stab18 | B ucAcccAAGGuuccuucucTT B | 731 |
| 3888 | UAGUUCACCAGACCAAUGGCCUA | 675 | | GAB2:3890U21 sense siNA stab18 | B GuucAccAGAccAAuGGccTT B | 732 |
| 4546 | CUUUUAACUGGUGCCUUCCCUGU | 676 | | GAB2:4548U21 sense siNA stab18 | B uuuAAcuGGuGccuucccuTT B | 733 |
| 5004 | GAGAGGACUGAGCCUACGGAAAG | 677 | | GAB2:5006U21 sense siNA stab18 | B GAGGAcuGAGccuAcGGAATT B | 734 |
| 5171 | AGUCCUUGAUCUGCCUGUCUGUG | 678 | | GAB2:5173U21 sense siNA stab18 | B uccuuGAucuGccuGucuGTT B | 735 |
| 5939 | UUCAAGUGGGUCAUGUUUUUGCU | 679 | | GAB2:5941U21 sense siNA stab18 | B cAAGuGGGucAuGuuuuuGTT B | 736 |
| 5956 | UUUGCUGUGGUGACACAUGGUAC | 680 | | GAB2:5958U21 sense siNA stab18 | B uGcuGuGGuGAcAcAuGGuU B | 737 |
| 2679 | UGAAGAGGGAAAGCUGACAUCUG | 673 | | GAB2:2699L21 antisense siNA (2681C) stab08 | GAuGucAGcuuucccucuuTsT | 738 |
| 3651 | CAUCACCCAAGGUUCCUUCUCUU | 674 | | GAB2:3671L21 antisense siNA (3653C) stab08 | GAGAAGGAAccuuGGGuGATsT | 739 |

TABLE III-continued

GAB2 Synthetic Modified siNA Constructs

| Target Pos | Target | Seq ID | Cmpd # | Aliases | Sequence | Seq ID |
|---|---|---|---|---|---|---|
| 3888 | UAGUUCACCAGACCAAUGGCCUA | 675 | | GAB2:3908L21 antisense siNA (3890C) stab08 | GGccAuuGGucuGGuGAAcTsT | 740 |
| 4546 | GUUUUAACUGGUGCCUUCCCUGU | 676 | | GAB2:4566L21 antisense siNA (4548C) stab08 | AGGGAAGGcAccAGuuAAATsT | 741 |
| 5004 | GAGAGGACUGAGCCUACGGAAAG | 677 | | GAB2:5024L21 antisense siNA (5006C) stab08 | uuccGuAGGcucAGuccucTsT | 742 |
| 5171 | AGUCCUUGAUCUGCCUGUCUGUG | 678 | | GAB2:5191L21 antisense siNA (5173C) stab08 | cAGAcAGGcAGAucAAGGATsT | 743 |
| 5939 | UUCAAGUGGGUGAUGUUUUUGCU | 679 | | GAB2:5959L21 antisense siNA (5941C) stab08 | cAAAAAcAuGAcccAcuuGTsT | 744 |
| 5956 | UUUGCUGUGGUGACACAUGGUAG | 680 | 31874 | GAB2:5976L21 antisense siNA (5958C) stab08 | AccAuGuGucAccAcAGcATsT | 745 |
| 2679 | UGAAGAGGGAAAGCUGACAUCUG | 673 | 36849 | GAB2:2681U21 sense siNA stab09 | B AAGAGGGAAAGCUGACAUCTT B | 746 |
| 3651 | CAUCACCCAAGGUUCCUUCUCUU | 674 | 36850 | GAB2:3653U21 sense siNA stab09 | B UCACCCAAGGUUCCUUCUCTT B | 747 |
| 3888 | UAGUUCACCAGACCAAUGGCCUA | 675 | 36851 | GAB2:3890U21 sense siNA stab09 | B GUUCACCAGACCAAUGGCCTT B | 748 |
| 4546 | OUUUUAACUGGUGCCUUCCCUGU | 676 | 36852 | GAB2:4548U21 sense siNA stab09 | B UUUUAACUGGUGCCUUCCCTT B | 749 |
| 5004 | GAGAGGACUGAGCCUACGGAAAG | 677 | 36853 | GAB2:5006U21 sense siNA stab09 | B GAGGACUGAGCCUACGGAATT B | 750 |
| 5171 | AGUCCUUGAUCUGCCUGUCUGUG | 678 | 36854 | GAB2:5173U21 sense siNA stab09 | B UCCUUGAUCUGCCUGUCUGTT B | 751 |
| 5939 | UUCAAGUGGGUCAUGUUUUUGCU | 679 | 36855 | GAB2:5941U21 sense siNA stab09 | B CAAGUGGGUCAUGUUUUUGTT B | 752 |
| 5956 | UUCAAGUGGGUCAUGUUUUUGCU | 680 | 36856 | GAB2:5958U21 sense siNA stab09 | B UGCUGUGGUGACACAUGGUTT B | 753 |
| 2679 | UGAAGAGGGAAAGCUGACAUCUG | 673 | | GAB2:2699L21 antisense siNA (2681C) stab10 | GAUGUCAGCUUUCCCUCUUTsT | 754 |
| 3651 | CAUCACCCAAGGUUCCUUCUCUU | 674 | | GAB2:3671L21 antisense siNA (3653C) stab10 | GAGAAGGAACCUUGGGUGATsT | 755 |
| 3888 | UAGUUCACCAGACCAAUGGCCUA | 675 | | GAB2:3908L21 antisense siNA (3890C) stab10 | GGCCAUUGGUCUGGUGAACTsT | 756 |
| 4546 | CUUUUAACUGGUGCCUUCCCUGU | 676 | | GAB2:4566L21 antisense siNA (4548C) stab10 | AGGGAAGGCACCAGUUAAATsT | 757 |

TABLE III-continued

GAB2 Synthetic Modified siNA Constructs

| Target Pos | Target | Seq ID | Cmpd # | Aliases | Sequence | Seq ID |
|---|---|---|---|---|---|---|
| 5004 | GAGAGGACUGAGCCUACGGAAAG | 677 | | GAB2:5024L21 antisense siNA (5006C) stab10 | UUCCGUAGGCUCAGUCCUCTsT | 758 |
| 5171 | AGUCCUUGAUCUGCCUGUCUGUG | 678 | | GAB2:5191L21 antisense siNA (5173C) stab10 | CAGACAGGCAGAUCAAGGATsT | 759 |
| 5939 | UUCAAGUGGGUCAUGUUUUUGCU | 679 | | GAB2:5959L21 antisense siNA (5941C) stab10 | CAAAAACAUGACCCACUUGTsT | 760 |
| 5956 | UUUGCUGUGGUGACACAUGGUAC | 680 | | GAB2:5976L21 antisense siNA (5958C) stab10 | ACCAUGUGUCACCACAGCATsT | 761 |
| 2679 | UGAAGAGGGAAAGCUGACAUCUG | 673 | 36857 | GAB2:2699L21 antisense siNA (2681C) stab19 | GAuGucAGcuuucccucuuTT B | 762 |
| 3651 | CAUCACCCAAGGUUCCUUCUCUU | 674 | 36858 | GAB2:3671L21 antisense siNA (3653C) stab19 | GAGAAGGAAccuuGGGuGATT B | 763 |
| 3888 | UAGUUCACCAGACCAAUGGCCUA | 675 | 36859 | GAB2:3908L21 antisense siNA (3890C) stab19 | GGccAuuGGucuGGuGAAcTT B | 764 |
| 4546 | CUUUUAACUGGUGCCUUCCCUGU | 676 | 36860 | GAB2:4566L21 antisense siNA (4548C) stab19 | AGGGAAGGcAccAGuuAAATT B | 765 |
| 5004 | GAGAGGACUGAGCCUACGGAAAG | 677 | 36861 | GAB2:5024L21 antisense siNA (5006C) stab19 | uuccGuAGGcucAGuccucTT B | 766 |
| 5171 | AGUCCUUGAUCUGCCUGUCUGUG | 678 | 36862 | GAB2:5191L21 antisense siNA (5173C) stab19 | cAGAcAGGcAGAucAAGGATT B | 767 |
| 5939 | UUCAAGUGGGUCAUGUUUUUGCU | 679 | 36863 | GAB2:5959L21 antisense siNA (5941C) stab19 | cAAAAAcAuGAcccAcuuGTT B | 768 |
| 5956 | UUUGCUGUGGUGACACAUGGUAC | 680 | 36864 | GAB2:5976L21 antisense siNA (5958C) stab19 | AccAuGuGucAccAcAGcATT B | 769 |
| 2679 | UGAAGAGGGAAAGCUGACAUCUG | 673 | 36865 | GAB2:2699L21 antisense siNA (2681C) stab22 | GAUGUCAGCUUUCCCUCUUTT B | 770 |
| 3651 | CAUCACCCAAGGUUCCUUCUCUU | 674 | 36866 | GAB2:3671L21 antisense siNA (3653C) stab22 | GAGAAGGAACCUUGGGUGATT B | 771 |
| 3888 | UAGUUCACCAGACCAAUGGCCUA | 675 | 36867 | GAB2:3908L21 antisense siNA (3890C) stab22 | GGCCAUUGGUCUGGUGAACTT B | 772 |
| 4546 | CUUUUAACUGGUGCCUUCCCUGU | 676 | 36868 | GAB2:4566L21 antisense siNA (4548C) stab22 | AGGGAAGGCACCAGUUAAATT B | 773 |
| 5004 | GAGAGGACUGAGCCUACGGAAAG | 677 | 36869 | GAB2:5024L21 antisense siNA (5006C) stab22 | UUCCGUAGGCUCAGUCCUCTT B | 774 |
| 5171 | AGUCCUUGAUCUGCCUGUCUGUG | 678 | 36870 | GAB2:5191L21 antisense siNA (5173C) stab22 | CAGACAGGCAGAUCAAGGATT B | 775 |

TABLE III-continued

GAB2 Synthetic Modified siNA Constructs

| Target Pos | Target | Seq ID | Cmpd # | Aliases | Sequence | Seq ID |
|---|---|---|---|---|---|---|
| 5939 | UUCAAGUGGGUCAUGUUUUUGCU | 679 | 36871 | GAB2:5959L21 antisense siNA (5941C) stab22 | CAAAAACAUGACCCACUUGTT B | 776 |
| 5956 | UUUGCUGUGGUGACACAUGGUAC | 680 | 36872 | GAB2:5976L21 antisense siNA (5958C) stab22 | ACCAUGUGUCACCACAGCATT B | 777 |
| 4316 | GAGGAAGAAGGAAGGAGAGGCUU | 681 | 31542 | GAB2:4316U21 sense siNA | GGAAGAAGGAAGGAGAGGCTT | 778 |
| 4316 | GAGGAAGAAGGAAGGAGAGGCUU | 681 | 31546 | GAB2:4334L21 antisense siNA (4316C) | GCCUCUCCUUCCUUCUUCCTT | 779 |
| 5958 | UUUGCUGUGGUGACACAUGGUAC | 680 | 31892 | GAB2:5958U21 sense siNA inv stab07 | B u*GGu*Ac*Ac*AGu*GGu*Guc*GuTT B | 780 |
| 5958 | UUUGCUGUGGUGACACAUGGUAC | 680 | 31898 | GAB2:5976L21 antisense siNA (5958C) inv stab08 | Ac*GAc*Acc*Acu*Gu*Gu*Acc*ATsT | 781 |

Uppercase = ribonucleotide
u,c = 2'-deoxy-2'-fluoro U,C
T = thymidine
B = inverted deoxy abasic
s = phosphorothioate linkage
A = deoxy Adenosine
G = deoxy Guanosine
*G* = 2'-O-methyl Guanosine
*A* = 2'-O-methyl Adenosine

TABLE IV

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | — | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S/AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | — | Usually S |
| "Stab 13" | 2'-fluoro | LNA | — | 1 at 3'-end | Usually AS |
| "Stab 14" | 2'-fluoro | 2'-deoxy | — | 2 at 5'-end 1 at 3'-end | Usually AS |
| "Stab 15" | 2'-deoxy | 2'-deoxy | — | 2 at 5'-end 1 at 3'-end | Usually AS |
| "Stab 16" | Ribo | 2'-O-Methyl | 5' and 3'-ends | — | Usually S |
| "Stab 17" | 2'-O-Methyl | 2'-O-Methyl | 5' and 3'-ends | — | Usually S |
| "Stab 18" | 2'-fluoro | 2'-O-Methyl | 5' and 3'-ends | — | Usually S |
| "Stab 19" | 2'-fluoro | 2'-O-Methyl | 3'-end | — | S/AS |
| "Stab 20" | 2'-fluoro | 2'-deoxy | 3'-end | — | Usually AS |
| "Stab 21" | 2'-fluoro | Ribo | 3'-end | — | Usually AS |
| "Stab 22" | Ribo | Ribo | 3'-end | — | Usually AS |
| "Stab 23" | 2'-fluoro* | 2'-deoxy* | 5' and 3'-ends | — | Usually S |
| "Stab 24" | 2'-fluoro* | 2'-O-Methyl* | — | 1 at 3'-end | S/AS |
| "Stab 25" | 2'-fluoro* | 2'-O-Methyl* | — | 1 at 3'-end | S/AS |
| "Stab 26" | 2'-fluoro* | 2'-O-Methyl* | — | — | S/AS |

TABLE IV-continued

Non-limiting examples of Stabilization Chemistries for chemically modified siNA constructs

| Chemistry | pyrimidine | Purine | cap | p = S | Strand |
|---|---|---|---|---|---|
| "Stab 27" | 2'-fluoro* | 2'-O-Methyl* | 3'-end | | S/AS |
| "Stab 28" | 2'-fluoro* | 2'-O-Methyl* | 3'-end | | S/AS |
| "Stab 29" | 2'-fluoro* | 2'-O-Methyl* | | 1 at 3'-end | S/AS |
| "Stab 30" | 2'-fluoro* | 2'-O-Methyl* | | | S/AS |
| "Stab 31" | 2'-fluoro* | 2'-O-Methyl* | 3'-end | | S/AS |
| "Stab 32" | 2'-fluoro | 2'-O-Methyl | | | S/AS |

CAP = any terminal cap, see for example FIG. 10.
All Stab 00-32 chemistries can comprise 3'-terminal thymidine (TT) residues
All Stab 00-32 chemistries typically comprise about 21 nucleotides, but can vary as described herein.
S = sense strand
AS = antisense strand
*Stab 23 has a single ribonucleotide adjacent to 3'-CAP
*Stab 24 and Stab 28 have a single ribonucleotide at 5'-terminus
*Stab 25, Stab 26, and Stab 27 have three ribonucleotides at 5'-terminus
*Stab 29, Stab 30, and Stab 31, any purine at first three nucleotide positions from 5'-terminus are ribonucleotides
p = phosphorothioate linkage

TABLE V

A. 2.5 μmol Synthesis Cycle ABI 394 Instrument

| Reagent | Equivalents | Amount | Wait Time* DNA | Wait Time* 2'-O-methyl | Wait Time*RNA |
|---|---|---|---|---|---|
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

B. 0.2 μmol Synthesis Cycle ABI 394 Instrument

| Reagent | Equivalents | Amount | Wait Time* DNA | Wait Time* 2'-O-methyl | Wait Time*RNA |
|---|---|---|---|---|---|
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

C. 0.2 μmol Synthesis Cycle 96 well Instrument

| Reagent | Equivalents: DNA/2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

Wait time does not include contact time during delivery.
Tandem synthesis utilizes double coupling of linker molecule

What we claim is:

1. A chemically modified nucleic acid molecule, wherein:
   (a) the nucleic acid molecule comprises a sense strand having SEQ ID NO:682 and a separate antisense strand having SEQ ID NO:690; and
   (b) each strand of the nucleic acid molecule is independently 18 to 27 nucleotides in length.

2. The nucleic acid molecule of claim 1, wherein one or more nucleotides comprise a 2'-sugar modification.

3. The nucleic acid molecule of claim 2, wherein the 2'-sugar modification is selected from the group consisting of 2'-deoxy-2'-fluoro, 2'-O-methyl, and 2'-deoxy.

4. The nucleic acid of claim 3, wherein the 2'-deoxy-2'-fluoro sugar modification is a pyrimidine modification.

5. The nucleic acid of claim 3, wherein the 2'-deoxy sugar modification is a pyrimidine modification.

6. The nucleic acid molecule of claim 3, wherein the 2'-O-methyl sugar modification is a pyrimidine modification.

7. The nucleic acid molecule of claim 4, wherein said pyrimidine modification is in the sense strand, the antisense strand, or both the sense strand and antisense strand.

8. The nucleic acid molecule of claim 6, wherein said pyrimidine modification is in the sense strand, the antisense strand, or both the sense strand and antisense strand.

9. The nucleic acid molecule of claim 3, wherein the 2'-deoxy sugar modification is a purine modification.

10. The nucleic acid molecule of claim 3, wherein the 2'-O-methyl sugar modification is a purine modification.

11. The nucleic acid molecule of claim 9, wherein the purine modification is in the sense strand.

12. The nucleic acid molecule of claim 10, wherein the purine modification is in the antisense strand.

13. The nucleic acid molecule of claim 1, wherein the nucleic acid molecule comprises ribonucleotides.

14. The nucleic acid molecule of claim 1, wherein the sense strand includes a terminal cap moiety at the 5'-end, the 3'-end, or both of the 5'- and 3'-ends.

15. The nucleic acid molecule of claim 14, wherein the terminal cap moiety is an inverted deoxy abasic moiety.

16. The nucleic acid molecule of claim 1, wherein said nucleic acid molecule includes one or more phosphorothioate internucleotide linkages.

17. The nucleic acid molecule of claim 16, wherein one of the phosphorothioate internucleotide linkages is at the 3'-end of the antisense strand.

18. The nucleic acid molecule of claim 1, wherein the 5'-end of the antisense strand includes a terminal phosphate group.

19. A composition comprising the nucleic acid molecule of claim 1, in a pharmaceutically acceptable carrier or diluent.

* * * * *